United States Patent
Layton et al.

(10) Patent No.: US 9,273,040 B2
(45) Date of Patent: Mar. 1, 2016

(54) BENZOXAZOLINONE COMPOUNDS WITH SELECTIVE ACTIVITY IN VOLTAGE-GATED SODIUM CHANNELS

(71) Applicants: Mark E. Layton, Harleysville, PA (US); Joseph E. Pero, Harleysville, PA (US); Hannah Fiji, Boyertown, PA (US); Michael J. Kelly, III, Wayne, PA (US); Pablo de Leon, Philadelphia, PA (US); Michael A. Rossi, Limerick, PA (US); Kevin F. Gilbert, Barto, PA (US); Anthony J. Roecker, North Wales, PA (US); Zhijian Zhao, Wilmington, DE (US); Swati I P. Mercer, Philadelphia, PA (US); Scott Wolkenberg, Wyndmoor, PA (US); James Mulhearn, Elkins Park, PA (US); Lianyun Zhao, Shanghai (CN); Dansu Li, Warrington, PA (US)

(72) Inventors: Mark E. Layton, Harleysville, PA (US); Joseph E. Pero, Harleysville, PA (US); Hannah Fiji, Boyertown, PA (US); Michael J. Kelly, III, Wayne, PA (US); Pablo de Leon, Philadelphia, PA (US); Michael A. Rossi, Limerick, PA (US); Kevin F. Gilbert, Barto, PA (US); Anthony J. Roecker, North Wales, PA (US); Zhijian Zhao, Wilmington, DE (US); Swati I P. Mercer, Philadelphia, PA (US); Scott Wolkenberg, Wyndmoor, PA (US); James Mulhearn, Elkins Park, PA (US); Lianyun Zhao, Shanghai (CN); Dansu Li, Warrington, PA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 14/353,488

(22) PCT Filed: Oct. 26, 2012

(86) PCT No.: PCT/US2012/062207
§ 371 (c)(1),
(2) Date: Apr. 22, 2014

(87) PCT Pub. No.: WO2013/063459
PCT Pub. Date: May 2, 2013

(65) Prior Publication Data
US 2014/0303143 A1 Oct. 9, 2014

Related U.S. Application Data

(60) Provisional application No. 61/552,885, filed on Oct. 28, 2011.

(51) Int. Cl.
*A61K 31/00* (2006.01)
*C07D 417/12* (2006.01)
*C07D 417/14* (2006.01)
*C07D 451/02* (2006.01)
*C07D 471/04* (2006.01)
*C07D 491/107* (2006.01)
*C07D 493/10* (2006.01)

(52) U.S. Cl.
CPC ............ *C07D 417/12* (2013.01); *C07D 417/14* (2013.01); *C07D 451/02* (2013.01); *C07D 471/04* (2013.01); *C07D 491/107* (2013.01); *C07D 493/10* (2013.01)

(58) Field of Classification Search
None
See application file for complete search history.

(56) References Cited

U.S. PATENT DOCUMENTS

| | | | |
|---|---|---|---|
| 6,080,774 | A | 6/2000 | Murugesan et al. |
| 7,408,067 | B2 | 8/2008 | Astiles et al. |
| 2009/0023740 | A1 | 1/2009 | Fulp et al. |
| 2009/0156640 | A1 | 6/2009 | Sun et al. |
| 2010/0048629 | A1 | 2/2010 | Gage |
| 2011/0082117 | A1 | 4/2011 | Martinborough et al. |

FOREIGN PATENT DOCUMENTS

| | | |
|---|---|---|
| WO | WO0034248 | 6/2000 |
| WO | WO2009012242 | 1/2009 |
| WO | WO2010079443 | 7/2010 |
| WO | WO 2010129596 A1 * | 11/2010 |
| WO | WO2006133459 | 12/2014 |

OTHER PUBLICATIONS

Bergman et al., Identification of a Potent, State-Dependent inhibitor of Nav1.7 with Oral Efficacy in the Formalin Model of Persistant Pain, J. Med, Chem., 2011, vol. 54(13), pp. 4427-4445.
International Preliminary Examination Report for PCT/US2012/06026.

(Continued)

*Primary Examiner* — Heidi Reese
(74) *Attorney, Agent, or Firm* — H. Eric Fischer; John C. Todaro

(57) ABSTRACT

Disclosed are compounds of Formula (A) or a salt thereof, wherein "Het", $R^a$, and $R^b$ are defined herein, which have properties for blocking $Na_v$ 1.7 ion channels found in peripheral and sympathetic neurons. Also described are pharmaceutical formulations comprising the compounds of Formula (A) or their salts, and methods of treating neuropathic pain disorders using the same.

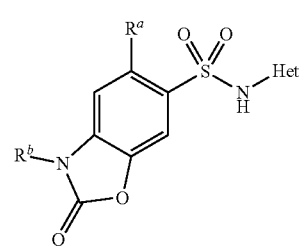

(A)

22 Claims, No Drawings

(56) References Cited

OTHER PUBLICATIONS

Database Registry Chemical Abstracts Service, Columbus, OH, US, Jun. 5, 2011, XP002738596, Database Accession No. 1305422-68-7.
Database registry Chemical Abstracts Service, Columbus, Ohio, US: Aug. 7, 2006, XP002738597, Database Accession No. 899395-23-4.
Database Registry Chemical Abstracts Service, Columbus, Ohio, US; Jul. 14, 2006, XP002738602, Database Accession No. 892699-21-7.
Database Registry Chemical Abstracts Service, Columbus, Ohio, US; Aug. 17, 2006, XP002738599, Database Accession No. 902495-46-9.
Database Registry Chemical Abstracts Service, Columbus, Ohio, US; Aug. 6, 2006, XP002738598, Database Accession No. 898913-54-7.
Database Registry Chemical Abstracts Service, Columbus, Ohio, US; Feb. 3, 2009, XP002738603, Database Accession No. 1099929-23-3.
Database Registry Chemical Abstracts Service, Columbus, Ohio, US; Jul. 7, 2011, XP002738604, Database Accession No. 1311765-05-5.
Database Registry, Chemical Abstracts Service, Columbus Ohio, US; Apr. 2, 2010, XP002738601, Database Accession No. 1215613-18-5.
Database Registry, Chemical Abstracts Service, Columbus, Ohio, US; Apr. 4, 2010, XP002738600, Database Accession No. 1216558-88-1.
EP Search Report and Written Opinion for Application No. 12843015.4-1462.
Zuliani et al., Sodium Channel Blockers: A Patent Review (2010-2014), Expert Opinion, 2015, pp. 279-290, 25.

* cited by examiner

BENZOXAZOLINONE COMPOUNDS WITH SELECTIVE ACTIVITY IN VOLTAGE-GATED SODIUM CHANNELS

CROSS-REFERENCE TO RELATED APPLICATIONS

This application is the national stage entry of International Patent Application Serial No. PCT/US2012/06207, filed Oct. 26, 2012, which in turn claims the priority of U.S. provisional application Ser. No. 61/552,885 filed Oct. 28, 2011, which applications are incorporated herein in their entirety by reference thereto.

BACKGROUND

Voltage-gated sodium channels play a central role in initiating and propagating action potentials in electrically excitable cells, see for example Yu and Catterall, Genome Biology 4:207 (2003) and references therein. Voltage-gated sodium channels are multimeric complexes characterized by an Alpha-subunit which encompasses an ion-conducting aqueous pore, and is the site of the essential features of the channel, and at least one Beta-subunit that modifies the kinetics and voltage-dependence of the channel gating. These structures are ubiquitous in the central and peripheral nervous system and are believed to play a central role in initiation and propagation of electrical signals in the nervous system.

It has been shown in human patients as well as in animal models of neuropathic pain that damage to primary afferent sensory neurons can lead to neuroma formation and spontaneous activity, as well as evoked activity in response to normally innocuous stimuli. [Carter, G. T. and Galer, B. S., Advances in the Management of Neuropathic Pain, Physical Medicine and Rehabilitation Clinics of North America, 2001, 12(2): pp 447 to 459]. Injuries of the peripheral nervous system often result in neuropathic pain persisting long after an initial injury resolves. Examples of neuropathic pain include, for example, post herpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. The ectopic activity of normally silent sensory neurons is thought to contribute to the generation and maintenance of neuropathic pain, which is generally assumed to be associated with an increase in sodium channel activity in the injured nerve. [Baker, M. D. and Wood, J. N., Involvement of Na Channels in Pain Pathways, TRENDS is Pharmacological Sciences, 2001, 22(1): pp 27 to 31.

Nine different Alpha-subunits have been identified and characterized in mammalian voltage-gated sodium channels. These structures are designated $Na_v$ 1.X sodium channels (X=1 to 9) in accordance with currently accepted nomenclature practice, designating their ion selectivity (Na), the physiological regulator ('v', potential, i.e. voltage), and the gene subfamily encoding them (1.), with the number designator X (1 to 9) being assigned for the alpha subunit present in the structure (see Aoldin et al., Neuron, 28:365-368 (2000)). $Na_v$1.7 voltage-gated sodium ion channels (herein designated "Nav 1.7 channels" in some instances for convenience) are expressed primarily in sensory and sympathetic neurons, and are believed to play a role in nociception, and in particular have a central role in inflammatory pain perception, (see Wood et al. J. Neurobiol. 61: pp 55-71 (2004) and Nassar et al., Proc. Nat. Acad. Sci. 101(34): pp 12706-12711 (2004)). Accordingly it is believed that identification and administration of agents which interact to block $Na_v$ 1.7 voltage-gated sodium ion channels represents a rational approach for providing treatment or therapy for nociception disorders stemming from dysfunction of $Na_v$1.7 voltage-gated sodium ion channels (see Clare et al., Drug Discovery Today, 5: pp 506-520 (2000)).

Because voltage gated sodium ion channels are ubiquitous in the central and peripheral nervous system and conservation of structures in the various Alpha-subunits characterizing voltage-gated sodium ion channels implicates the potential for producing serious side effects when utilizing therapeutic agents that target blocking voltage-gated sodium ion channels, therapeutic agents suitable for use in addressing nociception disorders require specificity in their action, particularly in discriminating between action upon $Na_v$1.5 sodium ion channels, thought to be important in regulation of cardiac function and action upon $Na_v$1.7 sodium ion channels, thought to be central in inflammatory nociception and disorders arising from dysfunctional $Na_v$ 1.7 sodium ion channels.

Published international application no. WO09/012242 (the '242 publication) describes compounds having the structure of Formula PA:

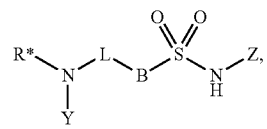

Formula PA wherein R* is a proton, alkyl or heteroalkyl, aryl, or heteroaryl group, Y is an aryl group or a 5 or 6 member-ring heteroaryl group, L is either not present or is a cyclic structure containing nitrogen or substituted with nitrogen, B is a cycloalkyl, heterocycloalkyl, aryl or heteroaryl moiety, and Z is a five or six-member ring heteroaryl moiety, and optionally R*, N, and Y form a cyclic structure which may be a heteroaryl moiety, for example, the compound of Formula PB:

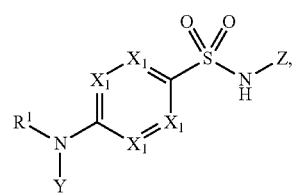

Formula PB wherein $R^1$, Y, and Z are as defined for the compound of Formula PA, and wherein each $X_1$ is independently N or unsaturated carbon optionally substituted with hydrogen, halogen, CN, OH, alkyl or substituted alkyl. These compounds are said to have activity as Nav 1.7 channel and Nav 1.3 channel blockers but are not shown to have selectivity as specific Nav 1.7 channel blockers.

Recently compounds described in published international application WO 2010/079443 (the '443 publication) having the structure of Formula PC:

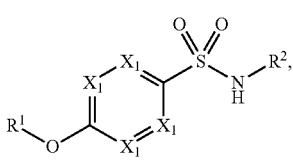

Formula PC wherein $X_1$ is N or C—$R^3$ ($R^3$ is a wide number of substituents including halogen), $R^1$ is an aryl or heteroaryl moiety and $R^2$ is a heteroaryl moiety, for example, the compound of Formula PD:

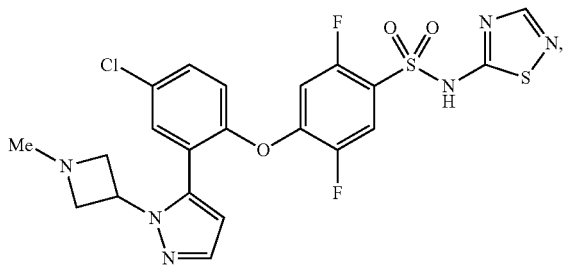

Formula PD have apparently shown high affinity for Nav 1.7 sodium channels and low affinity for other $Na_v$ 1.X sodium channels. However, the compounds described in the '443 publication are limited to aryl/heteroaryl-sulfonamide aryl/heteroaryl-ethers. There remains a need for additional compounds having high potency for $Na_v$ 1.7 sodium channels, are highly selective over $Na_v$1.5 sodium channels, and that offer a variety of cores to facility rational development of therapeutic agents for use as selective $Na_v$ 1.7 sodium ion channel blockers.

SUMMARY OF THE INVENTION

In one aspect, the invention provides compounds having selective activity as $Na_v$ 1.7 sodium ion channel blockers which have the structure of Formula A:

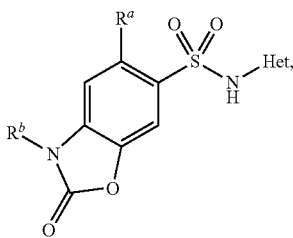

Formula A wherein:

$R^a$ is H, $C_{1-6}$ alkyl, $C_{1-6}$ alkoxy, —CN or halogen, and when selected to be a halogen is preferably —F;

"Het" is a heteroaryl moiety as defined herein, preferably a 5 member heteroaryl moiety comprising up to three heteroatoms selected from N, S, and O, bonded through any ring-atom of the aryl moiety available for bonding and optionally substituted with one or more "ring-system substitutes";

$R^b$ is: (i) a $C_{1-8}$ alkyl, $C_{1-14}$ heteroarylalkyl-, wherein the heteroaryl portion is optionally substituted with a "ring-system" substituent as defined herein, or $C_{1-14}$ arlyalkyl-, wherein the aryl portion is optionally substituted with a "ring-system" substituent as defined herein.

In some embodiments, "Het" is a moiety of Formula AD1:

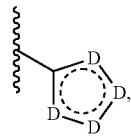

Formula AD1 wherein "D" is =CH—; =CF—; =C($C_{1-4}$ alkyl)-; =N—; —S—; or —O—.

In some embodiments where "Het" is a moiety of Formula AD1, preferably "Het" is a moiety of Formula AD1-a or AD1-b:

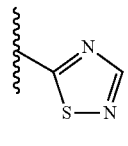

Formula AD1-a

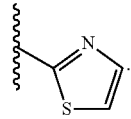

Formula AD1-b

In some embodiments it is preferred for $R^b$ to be a moiety of Formula A1:

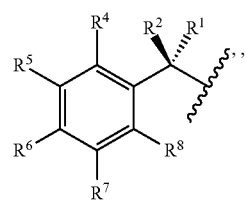

Formula A1 or a salt thereof,
wherein:

$R^1$ and $R^2$ are independently: (i) —H; (ii) $C_{1-8}$ alkyl, preferably methyl, ethyl, propyl, or cyclopropyl, more preferably methyl or cyclopropyl, wherein the alkyl moiety is optionally substituted with hydroxyl, halogen, —(C=O)—O—($C_{1-6}$ alkyl), $C_{3-6}$ cycloalkyl moiety, preferably cyclopropyl; (iii) $C_{1-4}$ alkenyl, preferably —$CH_2$—CH=$CH_2$; or (iv) a five or six member heteroaryl moiety, preferably oxazole;

$R^4$ and $R^5$ are independently: (i) $C_{1-4}$ alkyl, optionally substituted by one or more: (a) halogen atoms, preferably fluorine; (b) —$NH_2$, or (c) —$NR'^a{}_2$, wherein $R'^a$ is independently for each occurrence: linear or cyclic —($Y^a$)$_x$-alkyl, wherein, x=0, 1, and if present (x=1), $Y^a$ is: —$SO_2$—; —C(O)—; or —(C=O)O—, and the alkyl portion of the moiety is $C_{1-6}$-linear alkyl or $C_{3-6}$-cycloalkyl; (ii) $C_{1-4}$ alkenyl, optionally substituted by one or more: (a) halogen atoms, preferably fluorine; (b) —$NH_2$, or (c) —$NR'^a{}_2$, wherein $R'^a$ is as previously defined; (iii) a piperidine moiety which is bonded to the aryl ring through any of the atoms of the piperidine ring; (iv) a dihydropyridine, bonded through any of the atoms of the pyridine ring; (v) a tetrahydropyridine moiety bonded through any of the atoms of the pyridine ring; (vi) a pyridine moiety bonded to the aryl ring through any of the atoms of the pyridine ring, wherein the pyridine is optionally substituted on any other available ring atom with a heterocycle or an —$C_{1-3}$-alkyl-N-heterocycle, wherein preferably said heterocycle portion of the moiety is piperidine; (vii) an aryl moiety which is optionally substituted with a heterocycle moiety bonded to any available carbon atom of the aryl ring through any atom of the heterocycle ring, wherein, if present, preferably the heterocycle moiety is piperazine; (viii) a tetrahydroquinoline moiety bonded through any of the carbon atoms of the aromatic ring optionally substituted on any available carbon atom with halogen, —CN, $C_{1-6}$-alkyl or $C_{1-6}$-alkoxy; (ix) a tetrahydroisoquinoline moiety bonded through any of the carbon atoms of the aromatic ring optionally substituted on any available carbon atom with halogen, —CN, $C_{1-6}$-alkyl or $C_{1-6}$-alkoxy, and where the N-moiety in said isoquinoline is optionally substituted with —$SO_2$—$C_{1-6}$-alkyl; (x) an azabicyclo-moiety of the structure:

(xi) $C_{1-4}$-alkynyl optionally substituted with one or more of: $C_{1-4}$-alkyl; amino; or halogen moieties; or (xii) heteroaryl; or $R^4$ and $R^5$ together with the aryl ring to which they are bonded form a 10 to 12-member heteroaryl-aryl or heteroalkyl-aryl bicyclic moiety, in some embodiments wherein $R^4$ and $R^5$ together with the aryl moiety to which they are bonded form a heteroalkyl-aryl moiety, preferably they form a tetrahydroquinoline or tetrahydroisoquinoline moiety; and $R^6$, $R^7$, and $R^8$ are independently for each occurrence: hydrogen; CN; alkyl; alkoxy; or halogen, and when selected to be a halogen, preferably the halogen is chlorine.

In some embodiments where $R^b$ is a heteroarylalkyl moiety, $R^b$ is a moiety of Formula AE-1:

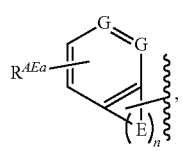

Formula AE-1 wherein:
one of "G" is —HC= and the other is —HC= or —N=; $R^{AEa}$ is a substituent defined below, "n" is an integer of 3 to 6 and "E" is independently for each occurrence: (a) —C$(R^{AEb})_2$—, wherein "$R^{AEb}$" is independently: (i) —H; (ii) halogen; (iii) $C_{1-6}$-alkyl; (iv) N$(R^{AEd})_2$, wherein "$R^{AEd}$" is independently —H, $C_{1-6}$-alkyl-C(O)—, $C_{1-6}$-alkyl-C(O)—O—, $C_{1-6}$-alkyl-SO$_2$—, $C_{1-6}$-alkyl, which alkyl is optionally substituted by one or more halogen, hydroxyl or alkoxy moiety; or two $R^{AEd}$ together form a $C_{1-6}$-cycloalkyl moiety which is optionally substituted on any suitable carbon atom thereof by a halogen, alkoxy, hydroxy or alkyl moiety; (v) two $R^{AEb}$ together form a $C_{2-6}$-cycloalkyl moiety or a $C_{2-6}$-cycloheteroalkyl moiety comprising additionally up to three heteroatoms, which cycloalkyl or heterocycloalkyl moiety is optionally substituted on any suitable carbon atom thereof by a halogen, alkoxy, hydroxy or alkyl moiety; (b) —O—; (c) —N($R^{AEc}$)—, wherein "$R^{AEc}$" is: (i) —H; or (ii) $C_{1-6}$-alkyl-SO2-; or (iii) $C_{1-6}$-alkyl; and wherein the nitrogen of the benzoxazolinone portion of the compound may be bonded to said moiety through any "E" which is a suitable carbon atom.

In some embodiments where $R^b$ is a heteroarylalkyl moiety, $R^b$ is a moiety of Formula AF-1:

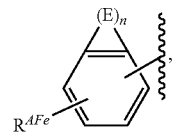

Formula AF-1 wherein $R^{AFe}$ is a substituent defined below, "n" is an integer of 3 to 6 and "E" is independently for each occurrence: (a) —C$(R^{AFb})_2$—, wherein "$R^{AFb}$" is independently: (i) —H; (ii) halogen; (iii) $C_{1-6}$-alkyl; (iv) N$(R^{AFd})_2$, wherein "$R^{AFd}$" is independently —H, $C_{1-6}$-alkyl-C(O)—, $C_{1-6}$-alkyl-C(O)—O—, $C_{1-6}$-alkyl, which alkyl is optionally substituted by one or more halogen, hydroxyl or alkoxy moiety; or two $R^{AFd}$ together form a $C_{1-6}$-cycloalkyl moiety which is optionally substituted on any suitable carbon atom thereof by a halogen, alkoxy, hydroxy or alkyl moiety; (v) two $R^{AFb}$ together form a $C_{1-6}$-cycloalkyl moiety which is optionally substituted on any suitable carbon atom thereof by a halogen, alkoxy, hydroxy or alkyl moiety; (b) —O—; (c) —N($R^{AFc}$)—, wherein "$R^{AFc}$" is: (i) —H; (ii) $C_{1-6}$-alkyl-SO2-; or (iii) $C_{1-6}$-alkyl; and wherein the nitrogen of the benzoxazolinone portion of the compound may be bonded to the aryl portion of said moiety through available carbon atom on the ring in place of a hydrogen atom otherwise residing there.

With reference to the moieties of Formulae AE-1 and AF-1, $R^{AEa}$ and $R^{AFe}$ are independently for each occurrence:
(a) $C_{1-6}$-alkyl which is optionally substituted with halogen, hydroxy, alkoxy or N$(R^{AGd})_2$, wherein "$R^{AGd}$" is independently —H, $C_{1-6}$-alkyl-C(O)—, $C_{1-6}$-alkyl-C(O)—O—, $C_{1-6}$-alkyl-SO$_2$—, $C_{1-6}$-alkyl, which alkyl is optionally substituted by one or more halogen, hydroxyl or alkoxy moiety or two $R^{AGd}$ together form a $C_{1-6}$-cycloalkyl moiety which is optionally substituted on any suitable carbon atom thereof by a halogen, alkoxy, hydroxy or alkyl moiety;
(b) N$(R^{AHd})_2$, wherein "$R^{AHd}$" is independently —H, $C_{1-6}$-alkyl-C(O)—, $C_{1-6}$-alkyl-C(O)—O—, $C_{1-6}$-alkyl-SO$_2$—, $C_{1-6}$-alkyl, which alkyl is optionally substituted by one or more halogen, hydroxyl or alkoxy moiety or two $R^{AHd}$ together form a $C_{1-6}$-cycloalkyl moiety which is optionally substituted on any suitable carbon atom thereof by a halogen, alkoxy, hydroxy or alkyl moiety;
(c) halogen;
(d) —H; or
(e) a 4 to 6-member heterocycle moiety which may optionally be substituted with $C_{1-4}$-alkyl, said heterocycle moiety comprising one or more heteroatoms which are: (i) —O—; (ii) —N($R^{AJa}$)—, wherein "$R^{AJa}$" is independently for each occurrence —H or $C^{1-4}$-alkyl; or (iii) —N=.

In one aspect the invention provides a pharmaceutical composition comprising at least one compound of Formula A and at least one pharmaceutically acceptable excipient adapted for administration to a patient via oral, intravenous, subcutaneous, transcutaneous, intramuscular, intradermal, transmucosal, or intramucosal routes of administration.

This invention also provides a pharmaceutical composition comprising a pharmaceutical carrier, an effective amount of at least one compound of Formula A or a salt thereof, and an effective amount of at least one other pharmaceutically active ingredient which is: (i) an opiate agonist or antagonist; (ii) a calcium channel antagonist; (iii) an NMDA receptor agonist or antagonist; (iv) a COX-2 selective inhibitor; or (v) an NSAID (non-steroidal anti-inflammatory drug).

In one aspect the invention provides a method of treatment, management, alleviation or amelioration of conditions or disease states which can be treated, managed, alleviated or ameliorated by specific blocking of Nav 1.7 channel activity, the method comprising administering to a patient in need thereof a composition comprising at least one compound of Formula A in an amount providing a serum level of at least one said compound which sufficient to effect said treatment, management, alleviation or amelioration of the condition or disease state. Preferably the condition to be treated, managed, alleviated or ameliorated is a chronic pain disorder

DETAILED DESCRIPTION OF THE INVENTION

As mentioned above, the invention provides compounds having selective activity as $Na_v$ 1.7 sodium ion channel blockers which have the structure of Formula A:

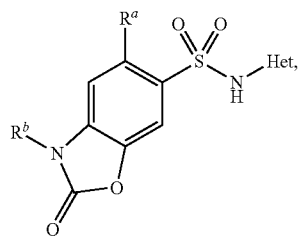

Formula A or a salt thereof,
where $R^a$, $R^b$, and "Het" are defined herein.

Compounds suitable for use in formulations of the invention, comprise the core structure of Formula A, and surprisingly have potent activity for blocking Nav 1.7 channels with high specificity when evaluated using IonWorks® or PatchXperss® assay techniques described in more detail herein. Accordingly, compounds of the invention and compounds comprising formulations of the invention are believed to be useful in providing treatment, management, alleviation or amelioration of conditions or disease states which can be treated, managed, alleviated or ameliorated by specific blocking of Nav 1.7 channel activity. Examples of disease states which can be desirably affected using such therapy include, but are not limited to, chronic, visceral, inflammatory or neuropathic pain.

With reference to Formula A, in some embodiments, preferably $R^a$ is —H, $C_{1-6}$ alkyl, $C_{1-6}$ alkoxy, —CN or halogen, and when selected to be a halogen is preferably —F;

preferably "Het" is a heteroaryl moiety as defined herein, more preferably a 5 member heteroaryl moiety comprising up to three heteroatoms selected from N, S, and O, bonded through any ring-atom of the aryl moiety available for bonding and optionally substituted with one or more "ring-system substitutes", and more preferably "Het" is a thiadiazole; and preferably $R^b$ is (i) a $C_{1-8}$ alkyl or arylalkyl-substituent, which moiety is optionally substituted with a halogen or an amino moiety; (ii) a benzyl moiety optionally substituted with a "ring-system substituent" as defined herein; or (iii) a heteroaryl-alkyl-moiety, optionally substituted with a "ring-system substituent" as defined herein; or (iv) a heteroalkylaryl-moiety which is optionally substituted as described herein.

In some embodiments, compounds of the invention preferably have the structure of Formula B:

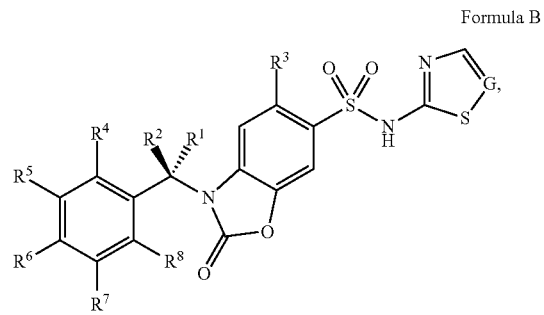

Formula B or a salt thereof,
wherein:
"G" is —HC= or —N=
$R^1$ and $R^2$ are independently: (i) —H; (ii) $C_{1-8}$ alkyl, preferably methyl, ethyl, propyl, or cyclopropyl, more preferably methyl or cyclopropyl, wherein the alkyl moiety is optionally substituted with hydroxyl, halogen, —(C=O)—O—($C_{1-6}$ alkyl), $C_{3-6}$ cycloalkyl moiety, preferably cyclopropyl; (iii) $C_{1-4}$ alkenyl, preferably —$CH_2$—CH=$CH_2$; or (iv) a five or six member heteroaryl moiety, preferably oxazole;

$R^3$ is —H, $C_{1-6}$ alkyl, $C_{1-6}$ alkoxy, —CN or halogen, and when selected to be a halogen is preferably —F;

$R^4$ and $R^5$ are independently: (i) $C_{1-4}$ alkyl, optionally substituted by one or more: (a) halogen atoms, preferably fluorine; (b) —$NH_2$, or (c) —$NR'^a{}_2$, wherein $R'^a$ is independently for each occurrence: linear or cyclic —$(Y^a)_x$— alkyl, wherein, x=0, 1, and if present (x=1), $Y^a$ is —$SO_2$ or —C(O)— or —(C=O)O—, and the alkyl portion of the moiety is $C_{1-6}$-linear alkyl or $C_{3-6}$-cycloalkyl; (ii) $C_{1-4}$ alkenyl, optionally substituted by one or more: (a) halogen atoms, preferably fluorine; (b) —$NH_2$, or (c) —$NR'^a{}_2$, wherein $R'^a$ is as previously defined; (iii) a piperidine moiety which is bonded to the aryl ring through any of the atoms of the piperidine ring; (iv) a dihydropyridine, bonded through any of the atoms of the pyridine ring; (v) a tetrahydropyridine moiety bonded through any of the atoms of the pyridine ring; (vi) a pyridine moiety bonded to the aryl ring through any of the atoms of the pyridine ring, wherein the pyridine is optionally substituted on any other available ring atom with a heterocycle or an —$C_{1-3}$-alkyl-N-heterocycle, wherein preferably said heterocycle portion of the moiety is piperidine; (vii) an aryl moiety which is optionally substituted with a heterocycle moiety bonded to any available carbon atom of the aryl ring through any atom of the heterocycle ring, wherein, if present, preferably the heterocycle moiety is piperazine; (viii) a tetrahydroquinoline moiety bonded through any of the carbon atoms of the aromatic ring optionally substituted on any available carbon atom with halogen, —CN, $C_{1-6}$-alkyl or $C_{1-6}$-alkoxy; (ix) a tetrahydroisoquinoline moiety bonded through any of the carbon atoms of the aromatic ring optionally substituted on any available carbon atom with halogen, —CN, $C_{1-6}$-alkyl or $C_{1-6}$-alkoxy and where the N-moiety in said isoquinoline is optionally substituted with —$SO_2$—$C_{1-6}$-alkyl; or (x) an azabicyclo-moiety of the structure:

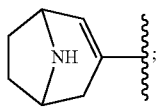

(xi) $C_{1-4}$ alkenyl, optionally substituted by one or more: (a) halogen atoms, preferably fluorine; (b) —$NH_2$, or (c) —$NR'^a_2$, wherein $R'^a$ is as previously defined; or (xii) heteroaryl; or $R^4$ and $R^5$ together with the aryl ring to which they are bonded form a 10 to 12-member heteroaryl-aryl or heteroalkyl-aryl bicyclic moiety, in some embodiments wherein $R^4$ and $R^5$ together with the aryl moiety to which they are bonded form a heteroalkyl-aryl moiety, preferably they form a tetrahydroquinoline or tetrahydroisoquinoline moiety; and $R^6$, $R^7$, and $R^8$ are independently selected from hydrogen, CN, alkyl, alkoxy or halogen, and when selected to be a halogen, preferably the halogen is chlorine.

In some embodiments, compounds of the invention preferably have the structure of Formula C:

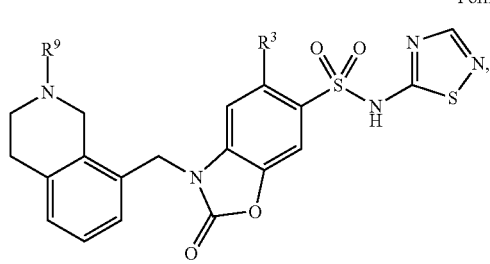

Formula C or a salt thereof,
wherein:

$R^3$ is —F or —H, and $R^9$ is: (i) —H; (ii) $C_{1-3}$-alkyl, preferably methyl or cyclopropyl; (iii) $C_{3-5}$ cycloalkyl; (iv) alkylcarbonyl, preferably —C(O)—$CH_3$ or —C(O)-cyclopropyl; or (v) alkylsulfonyl, preferably methylsulfonyl.

In some embodiments compounds of the invention preferably have the structure of Formula D:

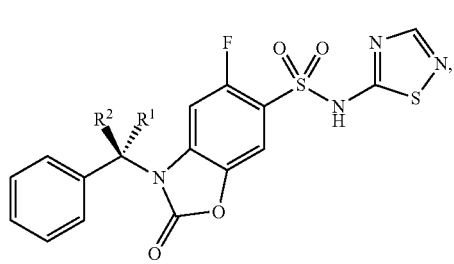

Formula D or a salt thereof
wherein one of $R^1$ and $R^2$ is —H and the other of $R^1$ and $R^2$ is —H or $C_{1-3}$ alkyl, and when one of $R^1$ or $R^2$ is selected to be a $C_{1-3}$ alkyl, preferably it is methyl.

In some embodiments it is preferred for compounds of the invention have the structure of Formula I:

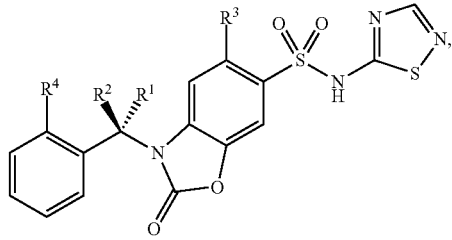

Formula I or a salt thereof
wherein $R^1$, $R^2$, $R^3$, and $R^4$ are defined in Table I.

TABLE I

| Comp. | $R^1$ | $R^2$ | $R^3$ | $R^4$ |
|---|---|---|---|---|
| 13-4 | —$CH_3$ | —H | —F | —H |
| 13-3 | —H | —$CH_3$ | —F | —H |
| 11-7 | —H | —H | —F | —H |
| 13-5 | Racemic —H and -cyclopropyl | | —F | —H |
| 12-3 | —H | —H | —F | $H_2N$—$CH_2CH$=CH— |
| 4-13 | Racemic —H and —$CH_2CH$=$CH_2$ | | —H | —H |
| 4-7 | —H | —$CH_3$ | —H | —H |
| 4-6 | Racemic —H and —$CH_3$ | | —H | —H |
| 4-12 | Racemic —H and -cyclopropyl | | —H | —H |
| 4-9 | Racemic —H and —$CH_3$ | | —H | —$CF_3$ |
| 4-10 | Racemic —H and ![oxazole] | | —H | —H |
| 4-8 | —$CH_3$ | —H | —H | —H |

In some embodiments it is preferred for a compound of the invention to have the structure of Formula E:

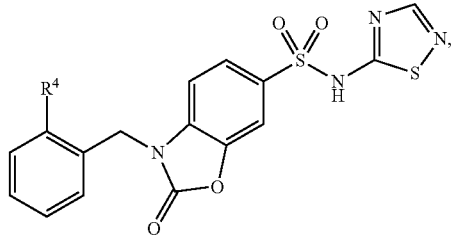

Formula E or a salt thereof,
wherein $R^4$ is hydrogen; a tetrahydroquinoline bonded to the aryl ring in the compound of Formula E through any carbon of the aryl ring in the tetrahydroquinoline substituent; a tetrahydroisoquinoline bonded to the aryl ring in the compound of Formula E through any carbon of the aryl ring in the tetrahydroisoquinoline substituent; a tetrahydropyridine moiety bonded to the aryl ring in the compound of Formula E through any carbon atom of the tetrahydropyridine moiety; or an alkylamino moiety bonded to the aryl ring of the compound of Formula E via a $C_{1-3}$ alkyl chain terminated with an amino-functional group.

In some embodiments, it is preferred for the compound of the invention to be a compound of Formula II:
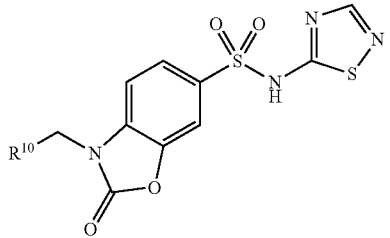
Formula II, or a salt thereof,
wherein $R^{10}$ is as shown in Table II
TABLE II
| Compound | $R^{10}$ |
|---|---|
| 3-4 | |
| 3-13 | |
| 3-12 | |
| 3-14 | |
| 3-3 | |
| 3-5 | |
TABLE II-continued
| Compound | $R^{10}$ |
|---|---|
| 3-17 | |
| 1-14 | |
| 3-6 | |
| 3-15 | |
| 3-16 | |
| 3-7 | |
| 3-18 | |
| 3-8 | |

TABLE II-continued
| Compound | R¹⁰ |
|---|---|
| 1-11 | 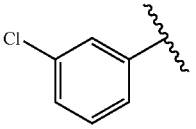 [SMILES: *c1cccc(Cl)c1] |
| 6-1 | 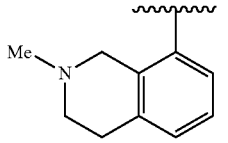 [SMILES: *c1cccc2c1CN(C)CC2] |
| 6-2 | 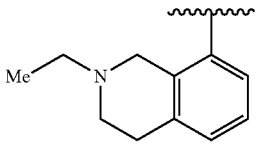 [SMILES: *c1cccc2c1CN(CC)CC2] |
| 6-3 | 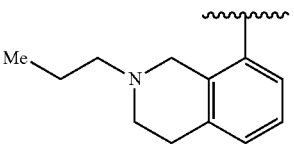 [SMILES: *c1cccc2c1CN(CCC)CC2] |
| 1-12 | 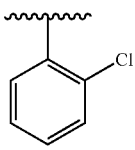 [SMILES: *c1ccccc1Cl] |
| 1-9 | 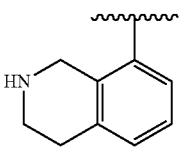 [SMILES: *c1cccc2c1CNCC2] |
| 6-4 | 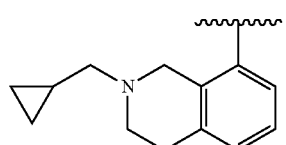 |
| 8-4 | 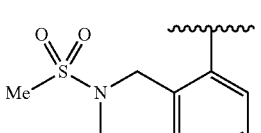 |
| 3-9 | 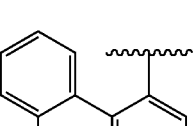 |
TABLE II-continued
| Compound | R¹⁰ |
|---|---|
| 3-11 | 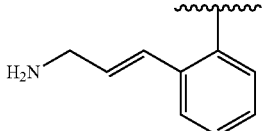 |
| 1-15 |  |
| 9-1 | 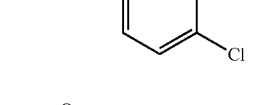 |
| 10-1 | 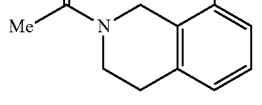 |
| 1-10 | 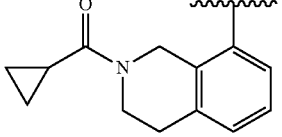 [SMILES: *c1cccc2c1CN(CC1CC1)CC2] |
| 1-13 | 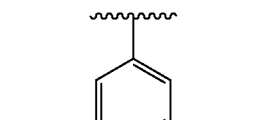 |
| 1-16 | 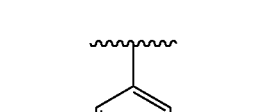 |
| 3-10 | 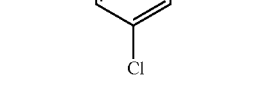 |
In some embodiments, it is preferred for the compound of the invention to be a compound of Formula IIa:

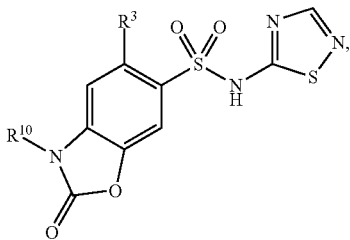

Formula IIa or a salt thereof,
wherein —R³ and —R¹⁰ᵃ is as shown in Table III

TABLE III

| Compound | R¹⁰ᵃ | R³ |
|---|---|---|
| 11-5 | 1,2,3,4-tetrahydroisoquinolin-8-ylmethyl | —F |
| 4-14 | 1-(1,2,3,4-tetrahydroisoquinolin-8-yl)ethyl | —H |
| 4-4 | 1-(1,2,3,4-tetrahydroisoquinolin-8-yl)ethyl | —H |
| 4-15 | 1-(1,2,3,4-tetrahydroisoquinolin-8-yl)ethyl | —H |
| 13-2 | 1-(1,2,3,4-tetrahydroisoquinolin-8-yl)ethyl | —F |
| 4-11 | 4-phenylbutan-2-yl | —H |

In some embodiments, it is preferred for the compound of the invention to be the following compound:

3-(isoquinolin-8-ylmethyl)-2-oxo-N-1,2,4-thiadiazol-5-yl-2,3-dihydro-1,3-benzoxazole-6-sulfonamide;

3-(2,3-dihydro-1H-isoindol-4-ylmethyl)-2-oxo-N-1,2,4-thiadiazol-5-yl-2,3-dihydro-1,3-benzoxazole-6-sulfonamide;

3-(diphenylmethyl)-2-oxo-N-1,2,4-thiadiazol-5-yl-2,3-dihydro-1,3-benzoxazole-6-sulfonamide;

2-oxo-3-(1-phenylpropyl)-N-1,2,4-thiadiazol-5-yl-2,3-dihydro-1,3-benzoxazole-6-sulfonamide;

3-benzyl-5-fluoro-2-oxo-N-1,2,4-thiadiazol-5-yl-2,3-dihydro-1,3-benzoxazole-6-sulfonamide;

5-fluoro-3-{[(1R,2S)-2-iodocyclopropyl]methyl}-2-oxo-N-1,2,4-thiadiazol-5-yl-2,3-dihydro-1,3-benzoxazole-6-sulfonamide;

5-fluoro-2-oxo-3-[(2-phenylcyclopropyl)methyl]-N-1,2,4-thiadiazol-5-yl-2,3-dihydro-1,3-benzoxazole-6-sulfonamide;

5-fluoro-3-[(2-methyl-2H-indazol-7-yl)methyl]-2-oxo-N—N-1,2,4-thiadiazol-5-yl-2,3-dihydro-1,3-benzoxazole-6-sulfonamide;

5-fluoro-3-(imidazo[1,5-a]pyridin-5-ylmethyl)-2-oxo-N-1,2,4-thiadiazol-5-yl-2,3-dihydro-1,3-benzoxazole-6-sulfonamide;

3-(1a,7b-dihydro-1H-cyclopropa[a]naphthalen-7-ylmethyl)-5-fluoro-2-oxo-N-1,2,4-thiadiazol-5-yl-2,3-dihydro-1,3-benzoxazole-6-sulfonamide;

(R)-3-(1-(isoquinolin-8-yl)ethyl)-2-oxo-N-(1,2,4-thiadiazol-5-yl)-2,3-dihydrobenzo[d]oxazole-6-sulfonamide;

5-fluoro-3-[(1R)-1-isoquinolin-8-ylethyl]-2-oxo-N—N-1,2,4-thiadiazol-5-yl-2,3-dihydro-1,3-benzoxazole-6-sulfonamide;

3-[(1S)-1-isoquinolin-8-ylethyl]-2-oxo-N-1,2,4-thiadiazol-5-yl-2,3-dihydro-1,3-benzoxazole-6-sulfonamide;

5-fluoro-3-[(1S)-1-isoquinolin-8-ylethyl]-2-oxo-N-1,2,4-thiadiazol-5-yl-2,3-dihydro-1,3-benzoxazole-6-sulfonamide;

(R)-5-Fluoro-3-(1-(imidazo[1,5-a]pyridin-5-yl)ethyl)-2-oxo-N-(1,2,4-thiadiazol-5-yl)-2,3-dihydrobenzo[d]oxazole-6-sulfonamide;

5-fluoro-3-[(1S)-1-imidazo[1,5-a]pyridin-5-ylethyl]-2-oxo-N-1,2,4-thiadiazol-5-yl-2,3-dihydro-1,3-benzoxazole-6-sulfonamide;

(R)-5-Fluoro-3-(1-(2-iodophenyl)ethyl)-2-oxo-N-(1,2,4-thiadiazol-5-yl)-2,3-dihydrobenzo[d]oxazole-6-sulfonamide;

(R)-5-Fluoro-2-oxo-3-(1-(2-(1,2,3,6-tetrahydropyridin-4-yl)phenyl)ethyl)-N-(1,2,4-thiadiazol-5-yl)-2,3-dihydrobenzo[d]oxazole-6-sulfonamide;

5-fluoro-2-oxo-3-{(1R)-1-[2-(1,2,5,6-tetrahydropyridin-3-yl)phenyl]ethyl}-N-1,2,4-thiadiazol-5-yl-2,3-dihydro-1,3-benzoxazole-6-sulfonamide;

5-fluoro-2-oxo-3-{(1R)-1-[2-(2,5,6,7-tetrahydro-1H-azepin-4-yl)phenyl]ethyl}-N-1,2,4-thiadiazol-5-yl-2,3-dihydro-1,3-benzoxazole-6-sulfonamide;

(R)-3-(1-(2-((1-aminocyclopropyl)ethynyl)phenyl)ethyl)-5-fluoro-2-oxo-N-(1,2,4-thiadiazol-5-yl)-2,3-dihydrobenzo[d]oxazole-6-sulfonamide;

5-fluoro-3-{(1R)-1-[2-(3-morpholin-4-ylprop-1-yn-1-yl)phenyl]ethyl}-2-oxo-N-1,2,4-thiadiazol-5-yl-2,3-dihydro-1,3-benzoxazole-6-sulfonamide;

5-fluoro-3-[(1R)-1-{2-[(1-hydroxycyclopentyl)ethynyl]phenyl}ethyl]-2-oxo-N-1,2,4-thiadiazol-5-yl-2,3-dihydro-1,3-benzoxazole-6-sulfonamide;

5-fluoro-3-{(1R)-1-[2-(4-hydroxybut-1-yn-1-yl)phenyl]ethyl}-2-oxo-N-1,2,4-thiadiazol-5-yl-2,3-dihydro-1,3-benzoxazole-6-sulfonamide;

3-[(1R)-1-{2-[3-(1,1-dioxidothiomorpholin-4-yl)prop-1-yn-1-yl]phenyl}ethyl]-5-fluoro-2-oxo-N-1,2,4-thiadiazol-5-yl-2,3-dihydro-1,3-benzoxazole-6-sulfonamide;

3-{(1R)-1-[2-(3-ethyl-3-hydroxypent-1-yn-1-yl)phenyl]ethyl}-5-fluoro-2-oxo-N-1,2,4-thiadiazol-5-yl-2,3-dihydro-1,3-benzoxazole-6-sulfonamide;

5-fluoro-3-[(1R)-1-{2-[(3R)-3-hydroxybut-1-yn-1-yl]phenyl}ethyl]-2-oxo-N-1,2,4-thiadiazol-5-yl-2,3-dihydro-1,3-benzoxazole-6-sulfonamide;

5-fluoro-3-[(1R)-1-{2-[(1-methyl-1H-imidazol-5-yl)ethynyl]phenyl}ethyl]-2-oxo-N-1,2,4-thiadiazol-5-yl-2,3-dihydro-1,3-benzoxazole-6-sulfonamide;

5-fluoro-3-{(1R)-1-[2-(3-hydroxyprop-1-yn-1-yl)phenyl]ethyl}-2-oxo-N-1,2,4-thiadiazol-5-yl-2,3-dihydro-1,3-benzoxazole-6-sulfonamide;

3-{(1R)-1-[2-(3-amino-3-methylbut-1-yn-1-yl)phenyl]ethyl}-5-fluoro-2-oxo-N-1,2,4-thiadiazol-5-yl-2,3-dihydro-1,3-benzoxazole-6-sulfonamide;

5-fluoro-3-[(1R)-1-{2-[3-(methylamino)prop-1-yn-1-yl]phenyl}ethyl]-2-oxo-N-1,2,4-thiadiazol-5-yl-2,3-dihydro-1,3-benzoxazole-6-sulfonamide;

5-fluoro-3-[(1R)-1-{2-[(3S)-3-hydroxybut-1-yn-1-yl]phenyl}ethyl]-2-oxo-N-1,2,4-thiadiazol-5-yl-2,3-dihydro-1,3-benzoxazole-6-sulfonamide;

5-fluoro-2-oxo-3-{(1R)-1-[2-(3-pyrrolidin-2-ylprop-1-yn-1-yl)phenyl]ethyl}-N-1,2,4-thiadiazol-5-yl-2,3-dihydro-1,3-benzoxazole-6-sulfonamide;

5-fluoro-2-oxo-3-{(1R)-1-[2-(pyrrolidin-3-ylethynyl)phenyl]ethyl}-N-1,2,4-thiadiazol-5-yl-2,3-dihydro-1,3-benzoxazole-6-sulfonamide;

3-{(1R)-1-[2-(4-amino-4-methylpent-1-yn-1-yl)phenyl]ethyl}-5-fluoro-2-oxo-N-1,2,4-thiadiazol-5-yl-2,3-dihydro-1,3-benzoxazole-6-sulfonamide;

3-{(1R)-1-[2-(azetidin-3-ylethynyl)phenyl]ethyl}-5-fluoro-2-oxo-N-1,2,4-thiadiazol-5-yl-2,3-dihydro-1,3-benzoxazole-6-sulfonamide;

5-fluoro-2-oxo-3-[(1R)-1-{2-[(2S)-pyrrolidin-2-ylethynyl]phenyl}ethyl]-N-1,2,4-thiadiazol-5-yl-2,3-dihydro-1,3-benzoxazole-6-sulfonamide;

3-{(1R)-1-[2-(3-azetidin-1-ylprop-1-yn-1-yl)phenyl]ethyl}-5-fluoro-2-oxo-N-1,2,4-thiadiazol-5-yl-2,3-dihydro-1,3-benzoxazole-6-sulfonamide;

3-{(1R)-1-[2-(3-aminobut-1-yn-1-yl)phenyl]ethyl}-5-fluoro-2-oxo-N-1,2,4-thiadiazol-5-yl-2,3-dihydro-1,3-benzoxazole-6-sulfonamide;

3-{(1R)-1-[2-(3-aminoprop-1-yn-1-yl)phenyl]ethyl}-5-fluoro-2-oxo-N-1,2,4-thiadiazol-5-yl-2,3-dihydro-1,3-benzoxazole-6-sulfonamide;

5-fluoro-2-oxo-3-[(1R)-1-{2-[(2R)-pyrrolidin-2-ylethynyl]phenyl}ethyl]-N-1,2,4-thiadiazol-5-yl-2,3-dihydro-1,3-benzoxazole-6-sulfonamide;

5-fluoro-2-oxo-3-{(1R)-1-[2-(piperidin-2-ylethynyl)phenyl]ethyl}-N-1,2,4-thiadiazol-5-yl-2,3-dihydro-1,3-benzoxazole-6-sulfonamide;

3-[(1R)-1-{2-[(1-aminocyclohexyl)ethynyl]phenyl}ethyl]-5-fluoro-2-oxo-N-1,2,4-thiadiazol-5-yl-2,3-dihydro-1,3-benzoxazole-6-sulfonamide;

(R)-5-fluoro-2-oxo-3-(1-(2-(pyrrolidin-1-ylmethyl)phenyl)ethyl)-N-(1,2,4-thiadiazol-5-yl)-2,3-dihydrobenzo[d]oxazole-6-sulfonamide;

3-[(1R)-1-{2-[(3,3-difluoropyrrolidin-1-yl)methyl]phenyl}ethyl]-5-fluoro-2-oxo-N-1,2,4-thiadiazol-5-yl-2,3-dihydro-1,3-benzoxazole-6-sulfonamide;

5-fluoro-3-[(1R)-1-{2-[(3-fluoropyrrolidin-1-yl)methyl]phenyl}ethyl]-2-oxo-N-1,2,4-thiadiazol-5-yl-2,3-dihydro-1,3-benzoxazole-6-sulfonamide;

3-[(1R)-1-{2-[(dimethylamino)methyl]phenyl}ethyl]-5-fluoro-2-oxo-N-1,2,4-thiadiazol-5-yl-2,3-dihydro-1,3-benzoxazole-6-sulfonamide;

3-((7-(3,3-difluoroazetidin-1-yl)-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide hydrochloride;

3-((7-amino-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide;

5-fluoro-3-((7-hydroxy-5,6,7,8-tetrahydronaphthalen-1-yl)methyl)-2-oxo-N-(1,2,4-thiadiazol-5-yl)-2,3-dihydrobenzo[d]oxazole-6-sulfonamide;

N-(8-((6-(N-(1,2,4-thiadiazol-5-yl)sulfamoyl)-5-fluoro-2-oxobenzo[d]oxazol-3(2H)-yl)methyl)-1,2,3,4-tetrahydronaphthalen-2-yl)acetamide;

(8-((6-(N-(1,2,4-thiadiazol-5-yl)sulfamoyl)-5-fluoro-2-oxobenzo[d]oxazol-3(2H)-yl)methyl)-1,2,3,4-tetrahydronaphthalen-2-yl)carbamate;

(+/−)-3-[1-(3',4'-dihydro-1'H-spiro[1,3-dioxolane-2,2'-naphthalen]-8'-yl)ethyl]-N-(2,4-dimethoxybenzyl)-5-fluoro-2-oxo-N-1,2,4-thiadiazol-5-yl-2,3-dihydro-1,3-benzoxazole-6-sulfonamide;

(+/−)-3-[(6-amino-5,6,7,8-tetrahydronaphthalen-1-yl)methyl]-2-oxo-N-1,2,4-thiadiazol-5-yl-2,3-dihydro-1,3-benzoxazole-6-sulfonamide;

(R or S)-2-[(8-{[5-fluoro-2-oxo-6-(1,2,4-thiadiazol-5-ylsulfamoyl)-1,3-benzoxazol-3(2H)-yl]methyl}-1,2,3,4-tetrahydronaphthalen-2-yl)amino]-2-oxoethyl acetate;

(+/−)-3-{[7-(3,3-difluoropyrrolidin-1-yl)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide;

(R or S)-3-{[7-(1,1-dioxidothiomorpholin-4-yl)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide;

(+/−)-5-fluoro-2-oxo-N-1,2,4-thiadiazol-5-yl-3-({7-[(2,2,2-trifluoroethyl)amino]-5,6,7,8-tetrahydronaphthalen-1-yl}methyl)-2,3-dihydro-1,3-benzoxazole-6-sulfonamide;

(+/−)-3-[(6-amino-5,6,7,8-tetrahydronaphthalen-1-yl)methyl]-5-fluoro-2-oxo-N-1,2,4-thiadiazol-5-yl-2,3-dihydro-1,3-benzoxazole-6-sulfonamide;

(+/−)-3-[(2-amino-2,3-dihydro-1H-inden-4-yl)methyl]-2-oxo-N-1,2,4-thiadiazol-5-yl-2,3-dihydro-1,3-benzoxazole-6-sulfonamide;

(R or S)-3-[(7-amino-5,6,7,8-tetrahydronaphthalen-1-yl)methyl]-2-oxo-N-1,2,4-thiadiazol-5-yl-2,3-dihydro-1,3-benzoxazole-6-sulfonamide;

(+/−)-5-fluoro-2-oxo-N-1,2,4-thiadiazol-5-yl-3-({7-[2-(trifluoromethyl)pyrrolidin-1-yl]-5,6,7,8-tetrahydronaphthalen-1-yl}methyl)-2,3-dihydro-1,3-benzoxazole-6-sulfonamide;

(+/−)-3-{-[7-(3,3-difluoroazetidin-1-yl)-5,6,7,8-tetrahydronaphthalen-1-yl]ethyl}-5-fluoro-2-oxo-N-1,2,4-thiadiazol-5-yl-2,3-dihydro-1,3-benzoxazole-6-sulfonamide;

(+/−)-3-({7-[(2,2-difluoroethyl)amino]-5,6,7,8-tetrahydronaphthalen-1-yl}methyl)-5-fluoro-2-oxo-N-1,2,4-thiadiazol-5-yl-2,3-dihydro-1,3-benzoxazole-6-sulfonamide;

(S or R)-3-[(7-amino-5,6,7,8-tetrahydronaphthalen-1-yl)methyl]-2-oxo-N-1,2,4-thiadiazol-5-yl-2,3-dihydro-1,3-benzoxazole-6-sulfonamide;

(+/−) {[7-(dimethylamino)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide;

(+/−)-5-fluoro-3-[(7-morpholin-4-yl-5,6,7,8-tetrahydronaphthalen 1-yl)methyl]-2-oxo-N-1,2,4-thiadiazol-5-yl-2,3-dihydro-1,3-benzoxazole-6-sulfonamide;

(+/−)-3-[(2-amino-2,3-dihydro-1H-inden-4-yl)methyl]-5-fluoro-2-oxo-N-1,2,4-thiadiazol-5-yl-2,3-dihydro-1,3-benzoxazole-6-sulfonamide;

(+/−)-3-{[7-(methylamino)-5,6,7,8-tetrahydronaphthalen-1-yl]methyl}-2-oxo-N-1,2,4-thiadiazol-5-yl-2,3-dihydro-1,3-benzoxazole-6-sulfonamide;

(+/−)-3-[(7-azetidin-1-yl-5,6,7,8-tetrahydronaphthalen-1-yl)methyl]-5-fluoro-2-oxo-N-1,2,4-thiadiazol-5-yl-2,3-dihydro-1,3-benzoxazole-6-sulfonamide;

(+/−)-5-fluoro-2-oxo-3-[(7-pyrrolidin-1-yl-5,6,7,8-tetrahydronaphthalen-1-yl)methyl]-N-1,2,4-thiadiazol-5-yl-2,3-dihydro-1,3-benzoxazole-6-sulfonamide;

(+/−)-5-fluoro-3-({7-[(2-fluoroethyl)amino]-5,6,7,8-tetrahydronaphthalen-1-yl}methyl)-2-oxo-N-1,2,4-thiadiazol-5-yl-2,3-dihydro-1,3-benzoxazole-6-sulfonamide;

(+/−)-5-fluoro-3-({7-[(2-hydroxyethyl)amino]-5,6,7,8-tetrahydronaphthalen-1-yl}methyl)-2-oxo-N-1,2,4-thiadiazol-5-yl-2,3-dihydro-1,3-benzoxazole-6-sulfonamide;

(+/−)-3-{[7-(benzylamino)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide;

(R,R and S,R) or (R,S and S,S)-3-[1-(7-amino-5,6,7,8-tetrahydronaphthalen-1-yl)ethyl]-5-fluoro-2-oxo-N-1,2,4-thiadiazol-5-yl-2,3-dihydro-1,3-benzoxazole-6-sulfonamide;

(R or S)-3-[(1R)-1-(7-amino-5,6,7,8-tetrahydronaphthalen-1-yl)ethyl]-5-fluoro-2-oxo-N-1,2,4-thiadiazol-5-yl-2,3-dihydro-1,3-benzoxazole-6-sulfonamide;

(+/−)-5-fluoro-3-{[7-(methylamino)-5,6,7,8-tetrahydronaphthalen-1-yl]methyl}-2-oxo-N-1,2,4-thiadiazol-5-yl-2,3-dihydro-1,3-benzoxazole-6-sulfonamide;

(S or R)-3-[(7-amino-5,6,7,8-tetrahydronaphthalen-1-yl)methyl]-5-fluoro-2-oxo-N-1,2,4-thiadiazol-5-yl-2,3-dihydro-1,3-benzoxazole-6-sulfonamide;

5-fluoro-3-((4-fluoro-1,2,3,4-tetrahydroisoquinolin-8-yl)methyl)-2-oxo-N-(1,2,4-thiadiazol-5-yl)-2,3-dihydrobenzo[d]oxazole-6-sulfonamide hydrochloride;

3-((3-chloroisoquinolin-8-yl)methyl)-5-fluoro-2-oxo-N-(1,2,4-thiadiazol-5-yl)-2,3-dihydrobenzo[d]oxazole-6-sulfonamide;

3-((3-Aminoisoquinolin-5-yl)methyl)-5-fluoro-2-oxo-N-(1,2,4-thiadiazol-5-yl)-2,3-dihydrobenzo[d]oxazole-6-sulfonamide;

3-((3-aminoisoquinolin-8-yl)methyl)-5-fluoro-2-oxo-N-(1,2,4-thiadiazol-5-yl)-2,3-dihydrobenzo[d]oxazole-6-sulfonamide;

3-[(3-aminoisoquinolin-5-yl)methyl]-2-oxo-N-1,2,4-thiadiazol-5-yl-2,3-dihydro-1,3-benzoxazole-6-sulfonamide;

3-[(3-chloroisoquinolin-8-yl)methyl]-2-oxo-N-1,2,4-thiadiazol-5-yl-2,3-dihydro-1,3-benzoxazole;

(R)-3-(1-(3-(1-methyl-1H-pyrazol-3-yl)phenyl)ethyl)-2-oxo-N-(1,2,4-thiadiazol-5-yl)-2,3-dihydrobenzo[d]oxazole-6-sulfonamide;

5-fluoro-3-{(1R)-1-[3-(6-hydroxypyridin-3-yl)phenyl]ethyl}-2-oxo-N-1,2,4-thiadiazol-5-yl-2,3-dihydro-1,3-benzoxazole-6-sulfonamide;

5-fluoro-3-{(1R)-1-[3-(3-methyl-1H-pyrazol-4-yl)phenyl]ethyl}-2-oxo-N-1,2,4-thiadiazol-5-yl-2,3-dihydro-1,3-benzoxazole-6-sulfonamide;

5-fluoro-3-(1-{3-[2-(hydroxymethyl)pyridin-4-yl]phenyl}ethyl)-2-oxo-N-1,2,4-thiadiazol-5-yl-2,3-dihydro-1,3-benzoxazole-6-sulfonamide;

5-fluoro-2-oxo-3-[1-(3-pyridin-3-ylphenyl)ethyl]-N-1,2,4-thiadiazol-5-yl-2,3-dihydro-1,3-benzoxazole-6-sulfonamide;

(R)-3-(1-(3-(3-aminoprop-1-yn-1-yl)phenyl)ethyl)-5-fluoro-2-oxo-N-(1,2,4-thiadiazol-5-yl)-2,3-dihydrobenzo[d]oxazole-6-sulfonamide;

3-[(1R)-1-{3-[(1-aminocyclohexyl)ethynyl]phenyl}ethyl]-5-fluoro-2-oxo-N-1,2,4-thiadiazol-5-yl-2,3-dihydro-1,3-benzoxazole-6-sulfonamide;

(R)-3-(1-(2-(azetidin-3-yl)phenyl)ethyl)-5-fluoro-2-oxo-N-(1,2,4-thiadiazol-5-yl)-2,3-dihydrobenzo[d]oxazole-6-sulfonamide;

(R)-5-fluoro-3-(1-(2-(3-hydroxyazetidin-3-yl)phenyl)ethyl)-2-oxo-N-(1,2,4-thiadiazol-5-yl)-2,3-dihydrobenzo[d]oxazole-6-sulfonamide;

(R)-5-Fluoro-3-(1-(2-(3-fluoroazetidin-3-yl)phenyl)ethyl)-2-oxo-N-(1,2,4-thiadiazol-5-yl)-2,3-dihydrobenzo[d]oxazole-6-sulfonamide;

(R)-3-(1-(2-(3-Aminopropyl)phenyl)ethyl)-5-fluoro-2-oxo-N-(1,2,4-thiadiazol-5-yl)-2,3-dihydrobenzo[d]oxazole-6-sulfonamide;

3-{(1S)-1-[2-(3-aminopropyl)phenyl]ethyl}-5-fluoro-2-oxo-N—N-1,2,4-thiadiazol-5-yl-2,3-dihydro-1,3-benzoxazole-6-sulfonamide;

(R)-5-chloro-2-oxo-3-(1-(2-(1,2,3,6-tetrahydropyridin-4-yl)phenyl)ethyl)-N-(1,2,4-thiadiazol-5-yl)-2,3-dihydrobenzo[d]oxazole-6-sulfonamide hydrochloride;

(+/−)-5-chloro-2-oxo-3-[1-(1,2,3,4-tetrahydroisoquinolin-8-yl)ethyl]-N-1,2,4-thiadiazol-5-yl-2,3-dihydro-1,3-benzoxazole-6-sulfonamide;

3-{(1R)-1-[2-(3-aminoprop-1-yn-1-yl)phenyl]ethyl}-5-chloro-2-oxo-N-1,2,4-thiadiazol-5-yl-2,3-dihydro-1,3-benzoxazole-6-sulfonamide;

(R)-5-bromo-2-oxo-3-(1-(1,2,3,4-tetrahydroisoquinolin-8-yl)ethyl)-N-(1,2,4-thiadiazol-5-yl)-2,3-dihydrobenzo[d]oxazole-6-sulfonamide;

3-{(1R)-1-[2-(3-aminoprop-1-yn-1-yl)phenyl]ethyl}-5-bromo-2-oxo-N-1,2,4-thiadiazol-5-yl-2,3-dihydro-1,3-benzoxazole-6-sulfonamide;

(R)-5-chloro-3-(1-(2-(1-(methylsulfonyl)-1,2,3,6-tetrahydropyridin-4-yl)phenyl)ethyl)-2-oxo-N-(1,2,4-thiadiazol-5-yl)-2,3-dihydrobenzo[d]oxazole-6-sulfonamide;

(+/−)-5-chloro-3-{1-[2-(methylsulfonyl)-1,2,3,4-tetrahydroisoquinolin-8-yl]ethyl}-2-oxo-N-1,2,4-thiadiazol-5-yl-2,3-dihydro-1,3-benzoxazole-6-sulfonamide;

5-fluoro-3-[(1R)-1-{2-[1-(methylsulfonyl)-1,2,3,6-tetrahydropyridin-4-yl]phenyl}ethyl]-2-oxo-N-1,2,4-thiadiazol-5-yl-2,3-dihydro-1,3-benzoxazole-6-sulfonamide;

5-bromo-3-[(1R)-1-(2-{3-[(methylsulfonyl)amino]prop-1-yn-1-yl}phenyl)ethyl]-2-oxo-N-1,2,4-thiadiazol-5-yl-2,3-dihydro-1,3-benzoxazole-6-sulfonamide;

5-fluoro-3-{(1R)-1-[2-(methylsulfonyl)-1,2,3,4-tetrahydroisoquinolin-8-yl]ethyl}-2-oxo-N-1,2,4-thiadiazol-5-yl-2,3-dihydro-1,3-benzoxazole-6-sulfonamide;

5-chloro-3-[(1R)-1-(2-{3-[(methylsulfonyl)amino]prop-1-yn-1-yl}phenyl)ethyl]-2-oxo-N-1,2,4-thiadiazol-5-yl-2,3-dihydro-1,3-benzoxazole-6-sulfonamide;

5-fluoro-3-[(1R)-1-{7-[(methylsulfonyl)amino]-5,6,7,8-tetrahydronaphthalen-1-yl}ethyl]-2-oxo-N-1,2,4-thiadiazol-5-yl-2,3-dihydro-1,3-benzoxazole-6-sulfonamide;

(R)-3-(3-Fluoro-1-phenylpropyl)-2-oxo-N-(1,2,4-thiadiazol-5-yl)-2,3-dihydrobenzo[d]oxazole-6-sulfonamide;

5-ethyl-2-oxo-3-[(1R)-1-phenylethyl]-N-1,2,4-thiadiazol-5-yl-2,3-dihydro-1,3-benzoxazole-6-sulfonamide;

5-methyl-2-oxo-3-[(1R)-1-phenylethyl]-N-1,2,4-thiadiazol-5-yl-2,3-dihydro-1,3-benzoxazole-6-sulfonamide;
3-(7-amino-1,2,3,4-tetrahydronaphthalen-1-yl)-2-oxo-N-(1,2,4-thiadiazol-5-yl)-2,3-dihydrobenzo[d]oxazole-6-sulfonamide;
3-(3,4-dihydrospiro[chromene-2,3'-oxetan]-4-yl)-5-fluoro-2-oxo-N-1,2,4-thiadiazol-5-yl-2,3-dihydro-1,3-benzoxazole-6-sulfonamide;
5-fluoro-3-(5-methyl-1,2,3,4-tetrahydronaphthalen-1-yl)-2-oxo-N-1,2,4-thiadiazol-5-yl-2,3-dihydro-1,3-benzoxazole-6-sulfonamide;
3-(3,4-dihydro-2H-chromen-4-yl)-5-fluoro-2-oxo-N-1,2,4-thiadiazol-5-yl-2,3-dihydro-1,3-benzoxazole-6-sulfonamide;
3-(2,2-dimethyl-3,4-dihydro-2H-chromen-4-yl)-5-fluoro-2-oxo-N-1,2,4-thiadiazol-5-yl-2,3-dihydro-1,3-benzoxazole-6-sulfonamide;
3-(3,4-dihydro-1H-isochromen-4-yl)-5-fluoro-2-oxo-N-1,2,4-thiadiazol-5-yl-2,3-dihydro-1,3-benzoxazole-6-sulfonamide;
5-fluoro-3-[6-fluoro-1'-(phenylcarbonyl)-3,4-dihydrospiro[chromene-2,4'-piperidin]-4-yl]-2-oxo-N-1,2,4-thiadiazol-5-yl-2,3-dihydro-1,3-benzoxazole-6-sulfonamide;
5-fluoro-2-oxo-3-(1,2,3,4-tetrahydronaphthalen-1-yl)-N-1,2,4-thiadiazol-5-yl-2,3-dihydro-1,3-benzoxazole-6-sulfonamide;
3-(1'-benzyl-3,4-dihydrospiro[chromene-2,4'-piperidin]-4-yl)-5-fluoro-2-oxo-N-1,2,4-thiadiazol-5-yl-2,3-dihydro-1,3-benzoxazole-6-sulfonamide;
3-(4,4-dimethyl-1,2,3,4-tetrahydronaphthalen-1-yl)-5-fluoro-2-oxo-N-1,2,4-thiadiazol-5-yl-2,3-dihydro-1,3-benzoxazole-6-sulfonamide;
5-fluoro-3-(6-fluoro-3,4-dihydro-2H-chromen-4-yl)-2-oxo-N-1,2,4-thiadiazol-5-yl-2,3-dihydro-1,3-benzoxazole-6-sulfonamide;
3-[(4R)-3,4-dihydrospiro[chromene-2,1'-cyclobutan]-4-yl]-5-fluoro-2-oxo-N-1,2,4-thiadiazol-5-yl-2,3-dihydro-1,3-benzoxazole-6-sulfonamide;
5-fluoro-2-oxo-3-[(2S,4R)-2-phenyl-3,4-dihydro-2H-chromen-4-yl]-N-1,2,4-thiadiazol-5-yl-2,3-dihydro-1,3-benzoxazole-6-sulfonamide;
3-[(4S)-3,4-dihydrospiro[chromene-2,1'-cyclobutan]-4-yl]-5-fluoro-2-oxo-N-1,2,4-thiadiazol-5-yl-2,3-dihydro-1,3-benzoxazole-6-sulfonamide;
5-fluoro-3-[(4S)-6-fluoro-3,4-dihydrospiro[chromene-2,1'-cyclobutan]-4-yl]-2-oxo-N-1,2,4-thiadiazol-5-yl-2,3-dihydro-1,3-benzoxazole-6-sulfonamide;
N-(4-methyl-1,3-thiazol-2-yl)-2-oxo-3-(1-phenylethyl)-2,3-dihydro-1,3-benzoxazole-6-sulfonamide;
(R)-2-oxo-3-(1-phenylethyl)-N-(thiazol-2-yl)-2,3-dihydrobenzo[d]oxazole-6-sulfonamide;
2-oxo-3-[(1R)-1-phenylethyl]-N-1,3-thiazol-2-yl-2,3-dihydro-1,3-benzoxazole-6-sulfonamide;
2-oxo-3-(1-phenylethyl)-N-1,3-thiazol-2-yl-2,3-dihydro-1,3-benzoxazole-6-sulfonamide;
methyl(2S)-[2-oxo-6-(1,3-thiazol-2-ylsulfamoyl)-1,3-benzoxazol-3(2H)-yl](phenyl)ethanoate;
(R)-2-oxo-3-(1-(1,2,3,4-tetrahydroisoquinolin-8-yl)ethyl)-N-(thiazol-2-yl)-2,3-dihydrobenzo[d]oxazole-6-sulfonamide;
(R)-5-fluoro-2-oxo-3-(1-phenylethyl)-N-(thiazol-2-yl)-2,3-dihydrobenzo[d]oxazole-6-sulfonamide;
5-fluoro-2-oxo-3-(5,6,7,8-tetrahydroisoquinolin-8-yl)-N-1,3-thiazol-2-yl-2,3-dihydro-1,3-benzoxazole-6-sulfonamide;
5-fluoro-2-oxo-3-(5,6,7,8-tetrahydroquinolin-8-yl)-N-1,3-thiazol-2-yl-2,3-dihydro-1,3-benzoxazole-6-sulfonamide;
3-(2-chloro-5,6,7,8-tetrahydroquinolin-8-yl)-5-fluoro-2-oxo-N-1,3-thiazol-2-yl-2,3-dihydro-1,3-benzoxazole-6-sulfonamide;
3-(3-bromobenzyl)-5-fluoro-2-oxo-N-1,3-thiazol-2-yl-2,3-dihydro-1,3-benzoxazole-6-sulfonamide;
5-fluoro-3-(7-methyl-1,2,3,4-tetrahydronaphthalen-1-yl)-2-oxo-N-1,3-thiazol-2-yl-2,3-dihydro-1,3-benzoxazole-6-sulfonamide;
5-fluoro-3-(5-fluoro-1,2,3,4-tetrahydronaphthalen-1-yl)-2-oxo-N-1,3-thiazol-2-yl-2,3-dihydro-1,3-benzoxazole-6-sulfonamide;
5-fluoro-2-oxo-3-[(1R)-1-phenylethyl]-N-1,3-thiazol-2-yl-2,3-dihydro-1,3-benzoxazole-6-sulfonamide;
3-(5,7-difluoro-1,2,3,4-tetrahydronaphthalen-1-yl)-5-fluoro-2-oxo-N-1,3-thiazol-2-yl-2,3-dihydro-1,3-benzoxazole-6-sulfonamide;
3-(6-bromo-3,4-dihydrospiro[chromene-2,1'-cyclobutan]-4-yl)-5-fluoro-2-oxo-N-1,3-thiazol-2-yl-2,3-dihydro-1,3-benzoxazole-6-sulfonamide;
5-fluoro-3-(6-fluoro-3,4-dihydrospiro[chromene-2,1'-cyclobutan]-4-yl)-2-oxo-N-1,3-thiazol-2-yl-2,3-dihydro-1,3-benzoxazole-6-sulfonamide;
5-fluoro-3-(7-fluoro-1,2,3,4-tetrahydronaphthalen-1-yl)-2-oxo-N-1,3-thiazol-2-yl-2,3-dihydro-1,3-benzoxazole-6-sulfonamide;
3-(5-amino-1,2,3,4-tetrahydronaphthalen-1-yl)-5-fluoro-2-oxo-N-1,3-thiazol-2-yl-2,3-dihydro-1,3-benzoxazole-6-sulfonamide;
3-(7-amino-1,2,3,4-tetrahydronaphthalen-1-yl)-5-fluoro-2-oxo-N-1,3-thiazol-2-yl-2,3-dihydro-1,3-benzoxazole-6-sulfonamide;
5-fluoro-2-oxo-3-[(1R)-1-(1,2,3,4-tetrahydroisoquinolin-8-yl)ethyl]-N-1,3-thiazol-2-yl-2,3-dihydro-1,3-benzoxazole-6-sulfonamide;
3-(7-amino-1,2,3,4-tetrahydronaphthalen-1-yl)-5-fluoro-2-oxo-N-1,3-thiazol-2-yl-2,3-dihydro-1,3-benzoxazole-6-sulfonamide;
5-fluoro-3-[(1S)-1-imidazo[1,5-a]pyridin-5-ylethyl]-2-oxo-N-1,3-thiazol-2-yl-2,3-dihydro-1,3-benzoxazole-6-sulfonamide;
5-fluoro-3-[(1R)-1-imidazo[1,5-a]pyridin-5-ylethyl]-2-oxo-N-1,3-thiazol-2-yl-2,3-dihydro-1,3-benzoxazole-6-sulfonamide;
3-{(1R)-1-[2-(3-aminoprop-1-yn-1-yl)phenyl]ethyl}-5-fluoro-2-oxo-N-1,3-thiazol-2-yl-2,3-dihydro-1,3-benzoxazole-6-sulfonamide;
3-[(1S)-1-(2-azetidin-3-ylphenyl)ethyl]-5-fluoro-2-oxo-N—N-1,3-thiazol-2-yl-2,3-dihydro-1,3-benzoxazole-6-sulfonamide;
3-[(1R)-1-(2-azetidin-3-ylphenyl)ethyl]-5-fluoro-2-oxo-N-1,3-thiazol-2-yl-2,3-dihydro-1,3-benzoxazole-6-sulfonamide;
5-fluoro-3-{(1R)-1-[2-(3-hydroxyazetidin-3-yl)phenyl]ethyl}-2-oxo-N-1,3-thiazol-2-yl-2,3-dihydro-1,3-benzoxazole-6-sulfonamide;
5-fluoro-3-{(1R)-1-[2-(3-fluoroazetidin-3-yl)phenyl]ethyl}-2-oxo-N-1,3-thiazol-2-yl-2,3-dihydro-1,3-benzoxazole-6-sulfonamide;
5-fluoro-3-{(1R)-1-[3-(3-methyl-1H-pyrazol-4-yl)phenyl]ethyl}-2-oxo-N-1,3-thiazol-2-yl-2,3-dihydro-1,3-benzoxazole-6-sulfonamide;
5-fluoro-3-{(1R)-1-[3-(1-methyl-1H-pyrazol-3-yl)phenyl]ethyl}-2-oxo-N-1,3-thiazol-2-yl-2,3-dihydro-1,3-benzoxazole-6-sulfonamide;
(+/−)-5-fluoro-3-[(4-fluoro-1,2,3,4-tetrahydroisoquinolin-8-yl)methyl]-2-oxo-N—N-1,3-thiazol-2-yl-2,3-dihydro-1,3-benzoxazole-6-sulfonamide;

(R or S)-5-fluoro-3-[(4-fluoro-1,2,3,4-tetrahydroisoquinolin-8-yl)methyl]-2-oxo-N-1,3-thiazol-2-yl-2,3-dihydro-1,3-benzoxazole-6-sulfonamide;
(S or R)-5-fluoro-3-[(4-fluoro-1,2,3,4-tetrahydroisoquinolin-8-yl)methyl]-2-oxo-N-1,3-thiazol-2-yl-2,3-dihydro-1,3-benzoxazole-6-sulfonamide;
3-((4,4-Difluoro-1,2,3,4-tetrahydroisoquinolin-8-yl)methyl)-5-fluoro-2-oxo-N-(thiazol-2-yl)-2,3-dihydrobenzo[d]oxazole-6-sulfonamide hydrochloride;
5-fluoro-2-oxo-3-{[(1S,2S)-2-phenylcyclopropyl]methyl}-N-1,2,4-thiadiazol-5-yl-2,3-dihydro-1,3-benzoxazole-6-sulfonamide;
(R)-5-fluoro-3-(1-(2-(3-hydroxyazetidin-3-yl)phenyl)ethyl)-2-oxo-N-(1,2,4-thiadiazol-5-yl)-2,3-dihydrobenzo[d]oxazole-6-sulfonamide;
5-fluoro-3-(1-(3-(2-(hydroxymethyl)pyridin-4-yl)phenyl)ethyl)-2-oxo-N-(1,2,4-thiadiazol-5-yl)-2,3-dihydrobenzo[d]oxazole-6-sulfonamide;
(R)-5-fluoro-3-(1-(3-(1-methyl-1H-pyrazol-3-yl)phenyl)ethyl)-2-oxo-N-(1,2,4-thiadiazol-5-yl)-2,3-dihydrobenzo[d]oxazole-6-sulfonamide;
(R)-tert-butyl 1-((2-(1-(6-(N-1,2,4-thiadiazol-5-ylsulfamoyl)-5-fluoro-2-oxobenzo[d]oxazol-3(2H)-yl)ethyl)phenyl)ethynyl)cyclopropylcarbamate;
2-oxo-N-(1,3,4-thiadiazol-2-yl)-3-((2-(2,2,2-trifluoroethyl)-1,2,3,4-tetrahydroisoquinolin-8-yl)methyl)-2,3-dihydrobenzo[d]oxazole-6-sulfonamide;
5-fluoro-3-(2-iodobenzyl)-2-oxo-N-(1,2,4-thiadiazol-5-yl)-2,3-dihydrobenzo[d]oxazole-6-sulfonamide;
(S)-3-(1-(2-iodophenyl)ethyl)-2-oxo-N-(1,2,4-thiadiazol-5-yl)-2,3-dihydrobenzo[d]oxazole-6-sulfonamide;
5-fluoro-2-oxo-3-(1-(pyridin-2-yl)ethyl)-N-(1,2,4-thiadiazol-5-yl)-2,3-dihydrobenzo[d]oxazole-6-sulfonamide;
(R)-tert-butyl 8-(1-(6-(N-1,3,4-thiadiazol-2-ylsulfamoyl)-2-oxobenzo[d]oxazol-3(2H)-yl)ethyl)-3,4-dihydroisoquinoline-2(1H)-carboxylate;
3-(7-amino-1,2,3,4-tetrahydronaphthalen-1-yl)-5-fluoro-2-oxo-N-(thiazol-2-yl)-2,3-dihydrobenzo[d]oxazole-6-sulfonamide;
(R)-2-oxo-3-(1-(1,2,3,4-tetrahydroisoquinolin-8-yl)ethyl)-N-(thiazol-2-yl)-2,3-dihydrobenzo[d]oxazole-6-sulfonamide;
(R)-5-(1-methyl-1H-pyrazol-5-yl)-2-oxo-3-(1-phenylethyl)-N-(1,2,4-thiadiazol-5-yl)-2,3-dihydrobenzo[d]oxazole-6-sulfonamide; and
3-(5-amino-1,2,3,4-tetrahydronaphthalen-1-yl)-5-fluoro-2-oxo-N-(thiazol-2-yl)-2,3-dihydrobenzo[d]oxazole-6-sulfonamide.

As used herein, unless otherwise specified, the term "Na$_v$ 1.7 (equivalently, Nav 1.7) blocker" means a compound of the invention exhibiting a potency (IC$_{50}$) of less than about 2 µM when assayed in accordance with either the IonWorks® or PatchXpress® assays described herein. Preferred compounds exhibit at least 10-fold selectivity for Na$_v$ 1.7 sodium channels over Na$_v$ 1.5 sodium channels, more preferably at least 100-fold selectivity for Na$_v$ 1.7 sodium channels over Na$_v$ 1.5 sodium channels when functional potency for each channel are compared using either the PatchXpress® or IonWorks® assay systems described herein.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

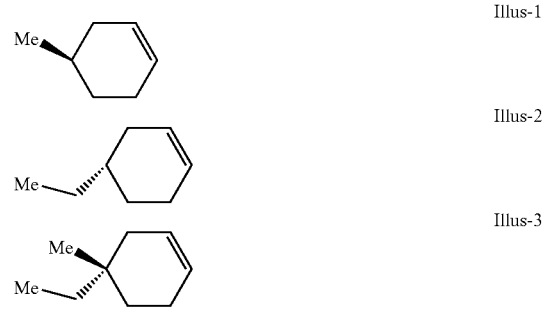

Illus-1

Illus-2

Illus-3

As is conventional, ordinary "stick" bonds or "wavy" bonds are used where there is a mixture of possible isomers present, including a racemic mixture of possible isomers As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present.

Components of a composition are typically aliquots of isolated pure material added to the composition, where the purity level of the isolated material added into the composition is the normally accepted purity level of a substance appropriate for pharmaceutical use.

"at least one" used in reference to substituents on a compound or moiety appended to the core structure of a compound means that one substituent of the group of substituents specified is present, and more than one substituent may be bonded to chemically accessible bonding points of the core.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of compound or of a composition comprising a compound of the present invention which is effective in treating or inhibiting the diseases or conditions described herein, and thus producing the desired therapeutic, ameliorative, inhibitory or preventative effect; thus, for example, in the methods of treating or neuropathic pain with one or more of the compounds described herein "effective amount" (or "therapeutically effective amount") means, for example, the amount of a compound of Formula A that results in therapeutic response of a neuropathic pain condition ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

"solvate" means a physical association of a compound of this invention with one or more solvent molecules; this physical association involves varying degrees of ionic and covalent bonding, including hydrogen bonding; in certain instances the solvate will be capable of isolation, for example when one or more solvent molecules are incorporated in the crystal lattice of the crystalline solid; "solvate" encompasses both solution-phase and isolatable solvates; non-limiting examples of suitable solvates include ethanolates, methanolates, and the like; "hydrate" is a solvate wherein the solvent molecule is $H_2O$.

The term "substituted" means that one or more of the enumerated substituents (or, where a list of substituents are not specifically enumerated, the default substituents specified in this "Definitions" section for the particular type of substrate which contains variable substituents) can occupy one or more of the bonding positions on the substrate typically occupied by "—H", provided that such substitution does not exceed the normal valency rules for the atom in the bonding configuration present in the substrate, and that the substitution ultimate provides a stable compound, e.g., mutually reactive substituents are not present geminal or vicinal to each other, and wherein such a compound is sufficiently robust to survive isolation to a useful degree of purity from a reaction mixture; when the text indicates optional substitution of a moiety (e.g. "optionally substituted") the term means "if present, one or more of the enumerated (or default substituents for the specified substrate) can be present on the substrate in a bonding position normally occupied by a hydrogen atom" in accordance with the definition of "substituted" presented herein;

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, the chemical term "acyl", defined below, is equivalently described herein by the term itself, or by typographical representations "R'—(C=O)—" or "R'—C(O)-", or by the structural representation:

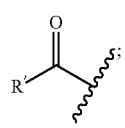

"acyl" means an R'—C(O)—, where R' is linear, branched or cyclic alkyl; linear, branched or cyclic alkenyl; or linear, branched or cyclic alkynyl moiety, each of which moieties can be substituted; wherein the acyl substituent is bonded through the carbonyl carbon to the substrate of which it is a substituent; non-limiting examples of suitable acyl groups include formyl, acetyl, propanoyl, 2-methylpropanoyl, butanoyl and cyclohexanoyl;

"alkenyl" means an aliphatic hydrocarbon moiety which is not aromatic but includes in its structure at least one constituent of the structure —(R'C=CR'$_2$) or —(R'C=CR')—, where R' is a defined substituent, for example —H or -alkyl; the alkenyl moiety can be incorporated into a linear hydrocarbon chain, or incorporated into a cyclic hydrocarbon chain (termed "cycloalkenyl") and can comprise further, linear, branched, or cyclic substituents depending from the carbon atoms of the chain, preferably the chain comprises about 2 to about 15 carbon atoms; more preferably from about 2 to about 12 carbon atoms; and more preferably chains comprise from about 2 to about 6 carbon atoms;

the term "substituted alkenyl", unless specified otherwise by a recitation of specific substituents defining the term where used, means that the alkenyl group is substituted by one or more substituents which are independently for each occurrence: Cilo-alkyl, as defined herein and aryl;

"alkoxy" means a moiety of the structure: alkyl-O— (i.e., the bond to the substrate moiety is through the ether oxygen), wherein the alkyl portion of the moiety is as defined below for alkyl; non-limiting examples of suitable alkoxy groups include methoxy, ethoxy, n-propoxy, isopropoxy, n-butoxy and heptoxy;

"alkoxycarbonyl" means a moiety of the structure alkyl-O—C(O)—, equivalently represented as [alkyl-O—(C=O)-] and also as R—O(C=O)—, where "R" is a defined alkyl moiety, (i.e., the bond to the parent moiety is through the carbonyl carbon) wherein the alkyoxy portion of the moiety is as previously defined; non-limiting examples of suitable alkoxycarbonyl groups include methoxycarbonyl and ethoxycarbonyl;

"alkyl" (including the alkyl portions of other moieties, such as trifluoromethyl-alkyl- and alkoxy-) means an aliphatic hydrocarbon chain comprising from about 1 to about 20 carbon atoms (that is, "$C_{1-20}$ alkyl"), preferably 1 to about 10 carbon atoms (herein "$C_{1-10}$ alkyl"), unless the term is modified by an indication that a shorter chain is contemplated, for example, an alkyl moiety of up to 8 carbon atoms (designated herein "$C_{1-8}$ alkyl"); the term "alkyl", unless specifically limited by another term, for example, "linear", "branched", or "cyclic", includes alkyl moieties which are linear (a hydrocarbon chain with no aliphatic hydrocarbon "branches" appended to it); branched (a main hydrocarbon chain comprising up to the maximum specified number of carbon atoms with a lower-alkyl chain appended to one or more carbon atoms comprising, but not terminating, the main hydrocarbon chain); and cyclic (the main hydrocarbon chain forms an cyclic aliphatic moiety of from 3 carbon atoms, the minimum number necessary to provide a cyclic moiety, up to the maximum number of specified carbon atoms), accordingly when unmodified, the term "$C_{1-x}$ alkyl" refers to linear, branched, or cyclic alkyl, and the "$C_{1-x}$" designation means: for a cyclic moiety a ring comprising at minimum 3 carbon atoms up to "X" carbon atoms; for a branched moiety, a main chain of at least 3 carbon atoms up to "X" carbon atoms with at least one linear or branched alkyl moiety bonded to a carbon atom which does not terminate the chain; and for a linear alkyl, a moiety comprising one carbon atom (i.e., -methyl), up to "X" carbon atoms; when the term "alkyl" is modified by "substituted" or "optionally substituted" it means an alkyl group having substituents in accordance with the relevant definitions appearing below; where use of the terms "substituted" or "optionally substituted" modify "alkyl" and substituent moieties are not specifically enumerated, the substituents bonded to the alkyl substrate are independently for each occurrence (in accordance with definitions appearing herein): $C_{1-20}$ alkyl; halogen; -alkoxy; —OH; —CN; alkylthio-; amino, —NH(alkyl), -alkyl), —N(alkyl)$_2$, —(C=O)—OH; —C(O)O-alkyl; —S(alkyl); or —S(O$_2$)-alkyl; or -aryl; cycloalkyl moieties may alternatively, or in addition, be substituted with one or more, "ring-system substituents" as that term is defined herein;

"lower alkyl" means a group comprising about 1 to about 6 carbon atoms in the chain (i.e. $C_{1-6}$); non-limiting examples of suitable alkyl groups include methyl (also abbreviated in the structures as "Me-"), ethyl, n-propyl, isopropyl, n-butyl, t-butyl, n-pentyl, heptyl, nonyl, decyl, fluoromethyl, trifluoromethyl and cyclopropylmethyl, where the term "alkyl" is indicated with two hyphens (i.e., "-alkyl-" it indicates that the alkyl moiety is bonded in a manner that the alkyl moiety connects a substrate with another moiety, for example, "-alkyl-OH" indicates an alkyl moiety connecting a hydroxyl moiety to a substrate;

"alkylaryl" (or alkaryl) means an alkyl-aryl- group (i.e., the bond to the parent moiety is through the aryl group) wherein the alkyl group is unsubstituted or substituted as defined above, and the aryl group is unsubstituted or substituted as defined below; preferred alkylaryl moieties comprise a lower alkyl group; non-limiting examples of suitable alkylaryl groups include o-tolyl, p-tolyl and xylyl;

as exemplified by the term "alkyl-aryl" defined above, in general, a substituent which is the called out by the combination of terms used to define two other substituent fragments indicates that the substituent called out by the last term used is bonded to the substrate whilst the preceding term called out is bonded in turn to the substituent fragment it precedes, proceeding right to left to understand the order in which the various fragments are bonded to the substrate;

"alkylsulfinyl" means an alkyl-S(O)— moiety (i.e., the moiety is bonded to a substrate through the sulfur atom of the sulfinyl moiety); "alkylthio" means an alkyl-S— group (i.e., the moiety is bonded to a substrate through the sulfur atom of the moiety); "alkylsulfonyl" means an alkyl-S(O$_2$)— group (i.e., the moiety is bonded to a substrate through the sulfur atom of the sulfonyl moiety), suitable alkyl groups can be unsubstituted or substituted as previously defined; preferred groups are those in which the alkyl group is lower alkyl;

"alkynyl" means an aliphatic hydrocarbon group (chain) comprising at least one moiety of the structure:

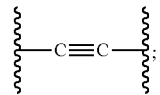 [SMILES: *C#C*]

or the structure:

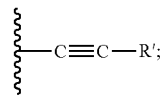

wherein R' is a defined substituent, the alkynyl moiety can be incorporated into a linear or branched hydrocarbon chain, or incorporated into a cyclic hydrocarbon chain (non-aromatic, termed "cycloalkynyl",); preferably hydrocarbon chains of an alkynyl moiety comprises about 2 to about 15 carbon atoms; more preferably alkynyl groups comprise about 2 to about 12 carbon atoms in the chain; and more preferably about 2 to about 4 carbon atoms in the chain;

"amino" means an —NR$_2$ group wherein R is selected independently for each occurrence from —H or alkyl, alkylamino means —NR'$_2$, wherein one R' is -alkyl and the other is —H or -alkyl selected independently for each occurrence, non-limiting examples of alkylamino moieties are —NH—CH$_3$ (methylamino-) and —N(CH$_3$)$_2$ (dimethylamino);

"ammonium ion" means —N$^+$R$_3$, wherein R is independently —H, alkyl, substituted alkyl, or the cationic portion of a dissociated acid capable of producing an ammonium ion from an amine; when not explicitly shown in representations herein the presence of an ammonium ion presumes that a charge-balancing anion is associated with the ammonium ion moiety, which anion is derived from the anionic portion of the acid used to provide said ammonium ion, it will be appreciated that many of the nitrogen atoms present in compounds of the invention can be converted to an ammonium ion thereby providing a salt of the parent compound, which is within the scope of the invention;

"aryl" (sometimes abbreviated "ar") means an aromatic monocyclic or multicyclic ring system comprising about 6 to about 14 carbon atoms (denoted herein also as "$C_{6-14}$-aryl"), preferably about 6 to about 10 carbon atoms ("$C_{6-10}$-aryl"); the aryl group can be optionally substituted with one or more independently selected "ring system substituents" (defined below).

Non-limiting examples of suitable aryl groups include:

phenyl

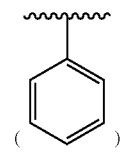

and naphthyl

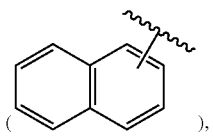

wherein bonding can be through any of the carbons in the aromatic ring, and wherein any ring carbon atoms not participating in a bond to the substrate may have bonded to it a substituent other than —H, independently selected in each instance from the list of "ring-system substituents" defined herein, or as defined in each instance where the term is used in conjunction with an enumerated list of substituents;

"aryloxy" means an aryl-O— group (i.e., the moiety is bonded to a substrate through the ether oxygen) wherein the aryl group is unsubstituted or substituted as defined above; non-limiting examples of suitable aryloxy groups include phenoxy and naphthoxy;

"aryloxycarbonyl" means an aryl-O—C(O)— group (i.e., the bond to a substrate is through the carbonyl carbon) wherein the aryl group is unsubstituted or substituted as previously defined; non-limiting examples of suitable aryloxycarbonyl groups include phenoxycarbonyl and naphthoxycarbonyl;

the term the terms "sulfinyl" means (—SO—), "sulfonyl" means (—S(O$_2$)—), and the term "thio" means (—S—), and in combination with any other substituent terms, mean the same thing, thus, for example: "arylsulfinyl" means an aryl-S(O)— group; "arylsulfonyl" means an aryl-S(O$_2$)— group; and "arylthio" means an aryl-S— group (i.e., the bond of the first-named substituent is to the substrate through the sulfur atom in each case) wherein aryl is unsubstituted or substituted as previously defined;

a "carboxylic acid" moiety means a substituent having the formula "—C(O)—OH", wherein the moiety is bonded to a substrate is through the carbonyl carbon;

"cycloalkyl" defined above with the "alkyl" definition, means a non-aromatic mono- or multicyclic ring system comprising about 3 to about 20 carbon atoms which may be substituted as defined herein; the term includes multicyclic cycloalkyls, for example, 1-decalin, norbornyl, adamantyl and the like;

"halogen" means fluorine, chlorine, bromine, or iodine; preferred halogens are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl means that all bonding positions not participating in bonding the alkyl substituent to a substrate are occupied by a halogen, for example, perfluoroalkyl, where alkyl is methyl, means —CF$_3$;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; preferred heteroaryl moieties comprise 5 ring atoms, for example, thiazole thiadiazole, imidazole, isothiazole, oxazole, oxadiazole, or pyrazole; the "heteroaryl" can be optionally substituted at chemically available ring atoms by one or more independently selected "ring system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can be optionally oxidized to the corresponding N-oxide; non-limiting examples of heteroaryl moieties include: tetrahydroquinolinyl- moiety

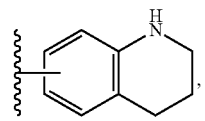

pyrdyl-

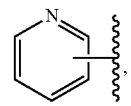

thiopenyl-

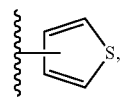

furanyl-

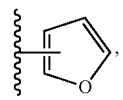

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, for example:

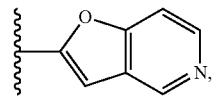

and the like (unless otherwise noted, bonded to the substrate through any available atom that results in a stable bonding arrangement);

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination; there are no adjacent oxygen and/or sulfur atoms present in the ring system; preferred heterocyclyl moieties contain about 5 to about 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide; non-limiting examples of suitable monocyclic heterocyclyl rings include piperidyl, pyrrolidinyl, piperazinyl, morpholinyl-

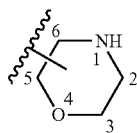

(where unless otherwise noted the moiety is bonded to the substrate through any of ring carbon atoms C2, C3, C5, or C6), thiomorpholinyl, thiomorpholinyl dione, thiazolidinyl, 1,3-dioxolanyl, 1,4-dioxanyl, tetrahydrofuranyl, tetrahydrothiophenyl, tetrahydrothiopyranyl, and the like;

"ring-system substituent" means a substituent attached to an aromatic or non-aromatic ring system that, for example, replaces a bonding position normally occupied by a hydrogen atom on the ring system; unless modified by exclusions or additions, the term "ring-system substituent" means one or more moieties independently selected from: alkyl, aryl, heteroaryl, aralkyl, alkylaryl, aralkenyl, heteroaralkyl, alkylheteroaryl, heteroaralkenyl, hydroxy (also termed "hydroxyl" when standing alone as a substituent moiety), hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently: hydrogen, alkyl, aryl, and aralkyl (as defined herein);

"tetrahydropyranyl" moiety means a 6-member cyclic ether of the formula:

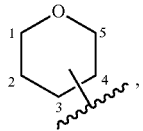

where, the bond line having an open end in the center of the structure and terminated at the other end with a wavy line indicates that the substituent is bonded to the substrate to which it is attached through any of carbon atoms 1 to 5, and wherein any of the bonding positions on carbons 1 to 5 normally occupied by a hydrogen atom, that is, the bonding positions on carbon atoms 1 to 5 which are not occupied by the bond to the substrate can optionally be occupied by specified or optional substituents;

"piperidinyl" means:

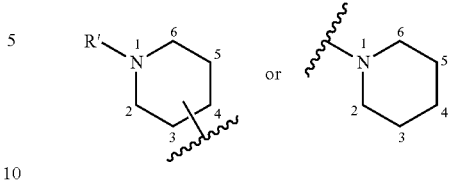

the open bond line terminated on one end with a wavy line indicates the ring atom through which the moiety is bonded to the substrate (i.e., any of carbon atoms 2 to 6 (left-hand structure) or the ring nitrogen atom (right-hand structure), and wherein any of the bonding positions on the nitrogen atom or on carbon atoms 2 to 6 not participating in a bond to the substrate and normally occupied by a hydrogen atom can be bonded to a specified or optional substituent, and wherein R', if present, is either —H or another specified substituent;

"pyridinyl" means:

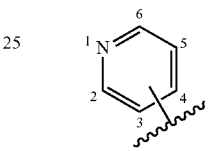

where, the bond-terminated-with-wavy-line indicates that the pyridinyl moiety is bonded to the substrate at any of carbon atoms 2 to 6, and wherein any of the bonding positions on carbons 2 to 6 normally occupied by a hydrogen atom, that is, any position on carbon 2 to 6 which is not the bond to the substrate, can optionally be occupied by a specified substituent;

"quinoline" means:

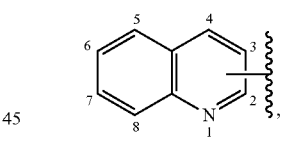

where, the bond-terminated-with-wavy-line indicates that the moiety is bonded to the substrate through any of carbon atoms 2 to 8, and wherein any of the bonding positions on carbon atoms 2 to 8 normally occupied by a hydrogen atom, that is, any bonding positions on carbon atoms 2 to 8 which are not bonded to the substrate, can optionally be occupied by one of a list of enumerated substituents;

for any of the foregoing ring-system moieties, bonding of the moiety through a specific ring carbon atom (or heteroatom) is sometimes described for convenience and "bonded through C—X to C—Y carbon atoms", where "X" and "Y" are integers referring to the carbon atoms, for example, as numbered in the examples above;

"hydroxyl moiety" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example

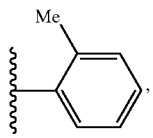 [SMILES: *c1ccccc1C]

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding, for example:

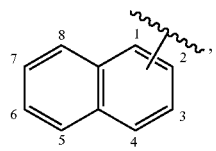

indicates that the naphthalene moiety may be bonded to the substrate through any of carbons 1 to 8.

Any carbon or heteroatom with unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit can contain fixed amounts of the afore-said "more than one pharmaceutically active agents". The bulk composition is material that has not yet been formed into individual dosage units.

This invention also includes the compounds of this invention in isolated and purified form. Polymorphic forms of the compounds of formula A1, and of the salts, solvates and prodrugs of the compounds of formula A1, are intended to be included in the present invention. Certain compounds of the invention may exist in different isomeric (e.g., enantiomers, diastereoisomers, atropisomers) forms. The invention contemplates all such isomers both in pure form and in admixture, including racemic mixtures. Enol forms are also included.

All stereoisomers (for example, geometric isomers, optical isomers and the like) of the present compounds (including prodrugs of compounds of the invention as well as the salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diasteromeric mixtures can be separated into their individual diastereomers on the basis of their physical chemical differences by methods well known to those skilled in the art, for example, by chiral chromatography and/or fractional crystallization. As is know, enantiomers can also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding enantiomers.

Where the compounds of the invention form salts by known, ordinary methods, these salts are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, for example, but not limited to, a nitrogen atom, for example, an amine, pyridine or imidazole, and an acidic moiety, for example, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the invention may be formed, for example, by reacting a compound of the invention with an amount of acid or base, for example, an equivalent amount, in a medium in which the salt precipitates or in an aqueous medium wherein the product is obtained by lyophilization. Acids (and bases) which are generally considered suitable for the formation of pharmaceutically useful salts from basic (or acidic) pharmaceutical compounds are discussed, for example, by S. Berge et al., *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference.

Exemplary acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. In some embodiments, HCl salts are preferred.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of the invention, their salts and solvates and prodrugs thereof, may exist in exist in different tautomeric forms. All such forms are embraced and included within the scope of the invention, for example, ketone/enol tautomeric forms, imine-enamine tautomeric forms, and for example heteroaromatic forms such as the following moieties:

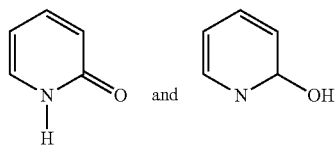 [SMILES: O=c1cccc[nH]1 ; OC1C=CC=CN1]

are considered equivalent in certain embodiments of this invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan A functional group in a compound termed "protected" means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When a variable (e.g., aryl, heterocycl, $R^3$, etc.) appears more than once in any moiety or in any compound of the invention, the selection of moieties defining that variable for each occurrence is independent of its definition at every other occurrence unless specified otherwise in the variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled compounds of the invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detection. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of The invention can generally be prepared by following procedures analogous to those disclosed in the Schemes and/or in the Examples herein below, by substituting an appropriate isotopically labeled reagent for a non-isotopically labeled reagent.

In one aspect, as mentioned above, the present invention provides pharmaceutical formulations (pharmaceutical compositions) suitable for use in selectively blocking $Na_v1.7$ sodium channels found in sensory and sympathetic neurons, comprising at least one compound of Formula A:

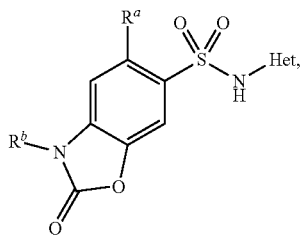

Formula A or a salt thereof,
where $R^a$, $R^b$, and "Het" are defined herein, and at least on pharmaceutically acceptable carrier (described below).

It will be appreciated that pharmaceutically formulations of the invention may comprise more than one compound of Formula A, for example, the combination of two or three compounds of Formula A, each present by adding to the formulation the desired amount of the compound in a pharmaceutically acceptably pure form. It will be appreciated that compositions of the invention may optionally comprise, in addition to one or more of the compounds of Formula A, one or more other compounds which also have pharmacological activity, for example, but not limited to: (i) an opiate agonist or antagonist; (ii) a calcium channel antagonist; (iii) an NMDA receptor agonist or antagonist; (iv) a COX-2 selective inhibitor; or (v) an NSAID (non-steroidal anti-inflammatory drug).

While formulations of the invention may be employed in bulk form, it will be appreciated that for most applications the inventive formulations will be incorporated into a dosage form suitable for administration to a patient, each dosage form comprising an amount of the selected formulation which contains an effective amount of said one or more compounds of Formula A. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachet or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions from the compounds described by this invention, generally pharmaceutically active compounds are combined with one or more pharmaceutically inactive excipients. These pharmaceutically inactive excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier".

Pharmaceutical compositions can be solid, semi-solid or liquid. Solid form preparations can be adapted to a variety of modes of administration and include powders, dispersible granules, mini-tablets, beads, and the like for example, for tableting, encapsulation, or direct administration. Typically formulations may comprise up to about 95 percent active ingredient, although formulations with greater amounts may be prepared.

Liquid form preparations include solutions, suspensions and emulsions. Examples of liquid forms of medicament include, but are not limited to, water or water/surfactant mixtures, for example a water-propylene glycol solution, which can be employed in the preparation of formulations intended, for example, for parenteral injection, for example, as a solvent or as a suspending medium for the preparation of suspensions and emulsions where a medicament comprises constituents which are insoluble in water or water/surfactant mixtures. Liquid form preparations may also include solutions for intranasal administration which may also include, for example, viscosity modifiers to adapt the formulation to target application of the formulation to particular mucosa tissues accessible via nasal administration.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension, solution, or a solution, for example, for oral or parenteral administration. Examples of such solid forms include freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20th Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In another embodiment the present invention provides for treatment, management, prevention, alleviation or amelioration of conditions or disease states which can be treated, managed, prevented, alleviated or ameliorated by specific blocking of Nav 1.7 channel activity, for example, blocking neuropathic pain, for example, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associate with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmennorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain.

In accordance with the present invention, treatment, alleviation, amelioration, or management of a disease state amenable to blocking $Na_v 1.7$ channel activity, for example a state of neuropathic pain, comprises administering to a patient in need thereof an effective amount of one or more compounds of Formula A, as defined herein, or a pharmaceutically acceptable salt of one or more compounds of Formula A, as defined herein. In some embodiments it is preferred to effect a state of neuropathic pain disease by administering to a patient in need thereof of at least one compound of any of Formulae B, C, D, E, as each is defined herein, or Formulae I (as defined in Table I), II (as defined in Table II), or IIa (as defined in Table III).

As mentioned above, administration of a compound of Formula A in accordance with the present invention is preferably accomplished by incorporating the compound into a pharmaceutical formulation incorporated into a dosage form, for example, one of the above-described dosage forms comprising an effective amount of at least one compound of Formula A (e.g., 1, 2 or 3, or 1 or 2, or 1, and usually 1 compound of Formula A), or a pharmaceutically acceptable salt thereof, for example. Methods for determining safe and effective administration of compounds which are pharmaceutically active, for example, a compound of Formula A, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the instant invention can be administered at a total daily dosage of up to 1,000 mg, which can be administered in one daily dose or can be divided into two to four doses per day.

In general, in what ever form administered, the dosage form administered will contain an amount of at least one compound of Formula A, or a salt thereof, which will provide a therapeutically effective serum level of the compound in some form for a period of at least 2 hours, preferably at least four hours, and preferably longer. In general, as is known in the art, dosages of a pharmaceutical composition providing a therapeutically effective serum level of a compound of the invention, e.g., a compound of Formula A, can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. Such additional therapeutic agents can include, for example, i) opiate agonists or antagonists, ii) calcium channel antagonists, iii) NMDA receptor agonists or antagonists, iv) COX-2 selective inhibitors, and v) non-steroidal anti-inflammatory drugs ("NSAID").

Those skilled in the art will appreciate that treatment protocols utilizing at least one compound of Formula A can be varied according to the needs of the patient. Thus, compounds of Formula A used in the methods of this invention can be administered in variations of the protocols described above. For example, the compounds of this invention can be administered discontinuously rather than continuously during the treatment cycle.

Other embodiments of this invention are directed to any one of the embodiments above of managing, ameliorating, alleviating or treating disease states, wherein the compound of Formula A administered is a compound of any of Formula I as defined in Table I, Formula II as defined in Table II, or Formulae B, C, D, or E as described and defined above.

The following examples are presented to further illustrate, but not limit the invention.

EXAMPLES

In general, compounds of the invention can be prepared by coupling an alcohol of Formula E-1 with an benzoxazolinone of Formula E-2 using Mitsunobu conditions, preferably wherein Mitsunobu coupling is carried out using di-tert-butyl azodicarboxylate (DTBAD) as the azide and $Ph_3P$ as the phosphine, followed by deprotection of the product, preferably by treatment with trifluoroacetic acid (TFA), to yield a compound of Formula E-3 in accordance with Scheme E-A:

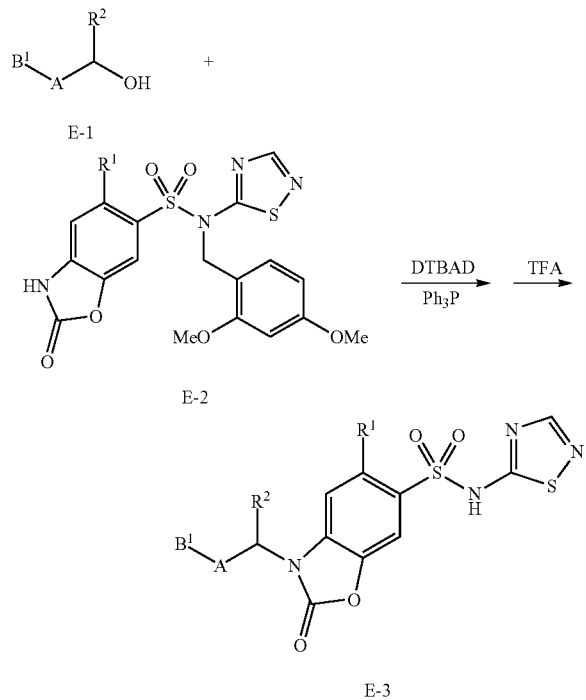

With reference to Scheme E-A, $R^1$ is hydrogen or fluorine, $R^2$ is $C_{1-6}$ alkyl, $C_{1-6}$ alkenyl, or an oxazole moiety, and A is an aryl, quinoline, or isoquinoline moiety, each of which may optionally have one or more substituents ($B^1$) as described herein. It will be appreciated that where at least one $B^1$ substituent is a halogen, alcohol E-1 can be derivatized, for example, via a Suzuki coupling using a boronic ester of Formula E-4:

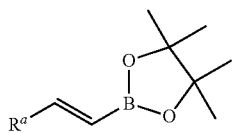

to provide the corresponding alkenyl substituted compound, wherein $R^a$ is an alkyl moiety, $R^a$ may optionally be substituted with one or more moieties as defined herein for alkyl or alkenyl substituents, for example, an amino-functional group. It will be appreciated that such derivatives may be prepared either before or after utilizing the E-1 alcohol in a Mitsunobu reaction, and if carried out after a Mitsunobu reaction, such a derivative is preferably prepared before performing the final deprotection step. Those of skill in the art will appreciate that other functional groups may additionally or alternatively be introduced into compounds of the invention by utilizing other known functional group transformations to prepare useful alcohol reagents before a Mitsunobu coupling has been carried out, or upon a functional group introduced into the product of a Mitsunobu coupling via an appropriately functionalized alcohol.

In some embodiments it is preferred to prepare the precursor compound of Formula E-2 via reaction of a sulfonyl chloride-derivative (E-2b) with the lithium salt of 2,4-dimethoxybenzyl-(1,2,4-thiadiazol-5-yl)azide (E-5) in accordance with Scheme E-B, wherein $R^1$ is hydrogen or fluorine. As shown in Scheme E-B also, E-2b may be prepared by reacting a commercially available benzoxazolinone of Formula E-2a with sulfonyl chloride or may be a benzoxazolinone sulfonyl chloride which is commercially available.

In the examples presented below, unless specified otherwise, experimental procedures were carried out at ambient temperature (18° C.-25° C.). Where air or moisture-sensitive reagents or intermediates were present, inert atmosphere was employed as a protective blanket in the reactor. In the processes described below, solvent was evaporated using a rotary evaporator under reduced pressure (600-4000 pascals: 4.5-30 mm Hg) and bath temperatures of up to 60° C. The course of reactions was followed by thin layer chromatography (TLC) or by high-pressure liquid chromatography-mass spectrometry (HPLC-MS). Structure and purity of all final products was confirmed by at least one of the following techniques: TLC, mass spectrometry, nuclear magnetic resonance (NMR) spectrometry or microanalytical data. When given, yields are indicative of the reaction presented but are not limiting. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. Broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The procedures described herein for synthesizing the compounds may include manipulation of protecting group(s), which are carried out in accordance with standard laboratory practices. Unless specifically described, where purification steps are indicated they may include conventional re-crystallization, distillation, column chromatography, flash chromatography, thin-layer chromatography (TLC), radial chromatography and/or high-pressure chromatography (HPLC), in accordance with standard laboratory practices. Where products are characterized, unless specified otherwise, they are characterized using well known techniques, for example, proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (HPLC-MS). Starting materials may be prepared and purified according to the following procedures or via known procedures.

It will be appreciated that the examples include precursor and starting materials, as well as products, which contain one or more reactive moieties appended thereto that can be manipulated prior to, during, or after the specified transformations to yield derivatives of the exemplified compounds. These derivatives are included in the scope of the application. It will also be appreciated that reactants and products with one or more stereocenter present represent reactions which may be carried out with the reactant compounds either as pure isomers, collections of various diastereomers or racemic mixtures, and in the same manner products may be prepared or isolated as pure isomers, collections of various diastereomers, or racemates and still be within the scope of the application.

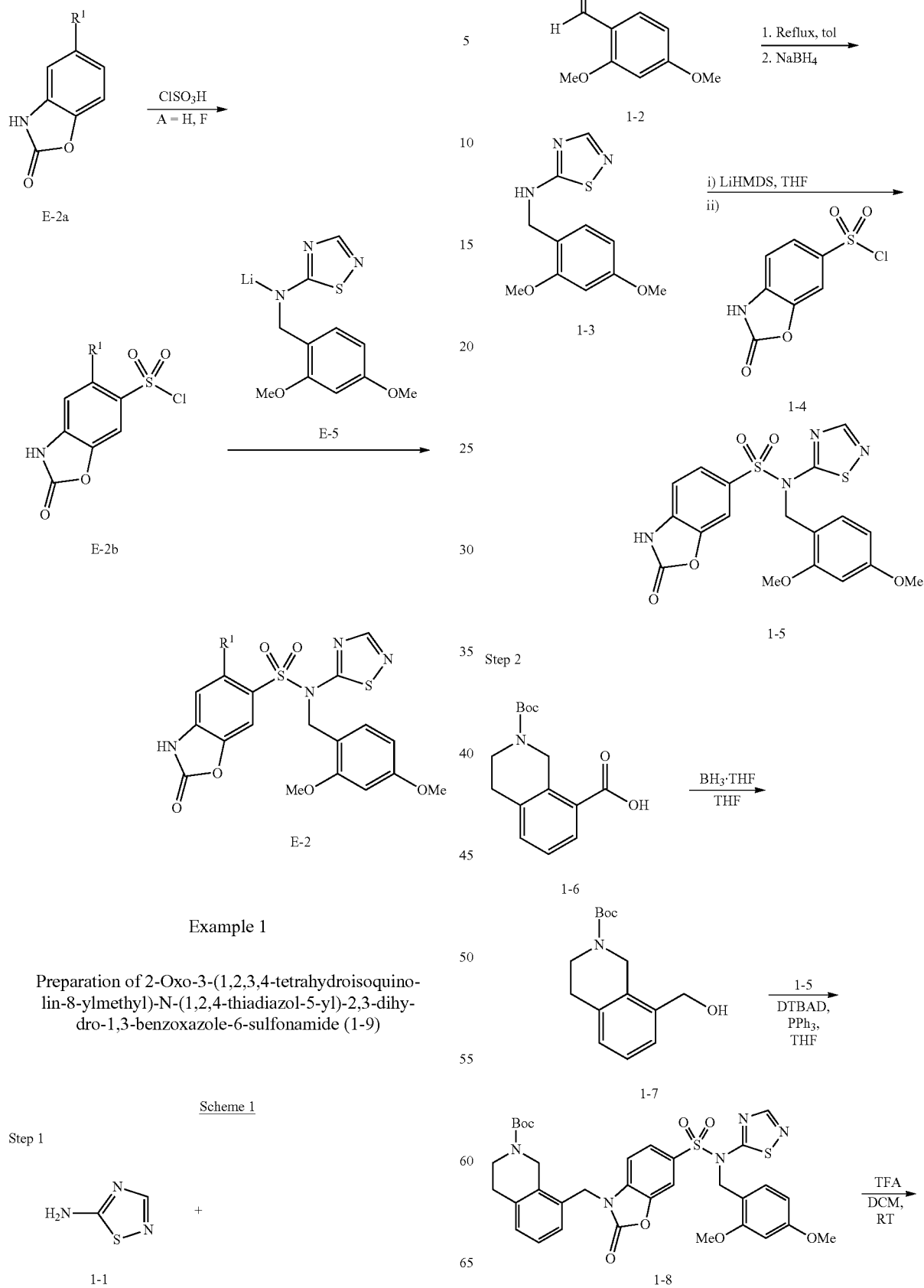

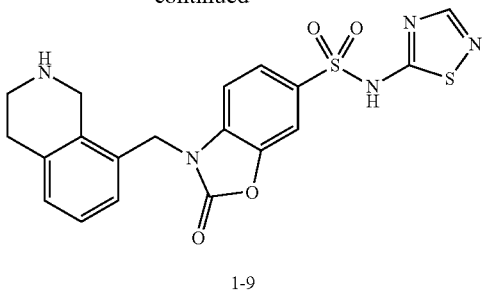

1-9

Step 1: Preparation of N-(2,4-Dimethoxybenzyl)-2-oxo-N-(1,2,4-thiadiazol-5-yl)-2,3-dihydro-1,3-benzoxazole-6-sulfonamide (1-5)

N-(2,4-Dimethoxybenzyl)-1,2,4-thiadiazol-5-amine (1-3)

A solution of 1-1 (3.3 g, 32.6 mmol) and 1-2 (5.96 g, 35.9 mmol) in toluene (9 9 mL) was refluxed under Dean-Stark conditions for 2 hours. Upon cooling to ambient temperature (RT, about 25° C.), the reaction was concentrated under reduced pressure to yield the corresponding imine, which was subsequently dissolved in methanol (82 mL) and cooled to 0° C. The reaction mixture was then treated with NaBH$_4$ (1.85 g, 48.9 mmol) portion wise. After stirring overnight the reaction was concentrated and treated with 100 mL of water and diluted with 100 mL of ethyl acetate. The layers were separated and the aqueous layer was back-extracted with EtOAc (2×150 mL). The combined organic layers were concentrated and purified by normal phase chromatography (20-66% EtOAc in hexane) to yield 1-3 as a white solid.

N-(2,4-Dimethoxybenzyl)-2-oxo-N-(1,2,4-thiadiazol-5-yl)-2,3-dihydro-1,3-benzoxazole-6-sulfonamide (1-5)

A solution of 1-3 (10.76 g, 42.8 mmol, previously prepared) in THF (171 mL) was cooled to −78° C. Lithium hexamethyldisilizane (LHMDS, 41.1 ml, 41.1 mmol, 1.0M in THF) was added and the reaction was allowed to warm to RT and stir for 30 minutes. Commercially-available, solid 1-4 (4 g, 17.12 mmol) was then added in portions, maintaining the temperature of the reaction mixture at −78° C. The reaction was allowed to slowly warm to RT. After reaching RT, the reaction was quenched with saturated ammonium chloride solution at 0° C. and extracted into EtOAc (3×100 mL). The combined organic layers were washed with brine, dried over sodium sulfate, filtered and concentrated. Purification by normal phase chromatography (0-50% EtOAc in hexane) yielded an oil. This oil was subsequently treated with dichloromethane to produce a white precipitate, which was filtered and dried to yield 1-5 as a white solid.

Step 2: Preparation of 2-Oxo-3-(1,2,3,4-tetrahydroisoquinolin-8-ylmethyl)-N-(1,2,4-thiadiazol-5-yl)-2,3-dihydro-1,3-benzoxazole-6-sulfonamide (1-9)

tert-Butyl 8-(hydroxymethyl)-3,4-dihydroisoquinoline-2(1H)-carboxylate (1-7)

A solution of commercially available 1-6 (3 g, 10.82 mmol) in THF (108 mL) cooled to 0° C. was treated with BH$_3$-THF (32.5 mL, 32.5 mmol). After stirring for 2 hours at 0° C., 50 mL of 1N NaOH was added. The reaction was stirred for 30 minutes, then diluted with EtOAc and the layers were separated. Aqueous layer was washed with EtOAc (2×100 mL). Combined organic layers were washed with brine, dried over sodium sulfate, then filtered and concentrated. The concentrated residue was purified by normal phase chromatography (0-50% EtOAc in hexane) to yield 1-7 as a white solid.

2-Oxo-3-(1,2,34-tetrahydroisoquinolin-8-yl-methyl)-N-(1,2,4-thiadiazol-5-yl)-2,3-dihydro-1,3-benzoxazole-6-sulfonamide (1-9)

Into 3.3 mL THF was dissolved 150 mg 1-5 (prepared above, 0.334 mmol) and 97 mg of 1-7 (prepared above, 0.368 mmol). This solution was cooled to 0° C. and treated with triphenylphosphine (175 mg, 0.669 mmol) followed by DTBAD (154 mg, 0.669 mmol). Reaction was filtered and concentrated after stirring for 2 hours at RT. Residue was taken up in 1 mL of DCM and treated with 0.25 mL TFA, removing the dimethoxymethyl benzene protecting group from the sulfonamide nitrogen. After stirring for 30 minutes at RT, the solvent and TFA was removed in vacuo. Purified by reverse phase chromatography (5-75% MeCN in water with 0.1% TFA, C18 column) to yield 1-9 as a white solid (TFA salt). $^1$H NMR δ (ppm)(DMSO-d): 9.06 (2H, s), 8.34 (1H, s), 7.75 (1H, s), 7.67 (1H, d, J=8.26 Hz), 7.23 (3H, dd, J=15.29, 7.61 Hz), 7.15 (1H, d, J=7.41 Hz), 5.06 (2H, s), 4.37 (2H, s), 3.17 (2H, s), 3.07-2.99 (2H, m). HRMS C19H17N5O4S2 [M+H] calc 444.0795, obs 444.0812.

The compounds listed in Table 1 were prepared from 1-5 and the appropriate alcohol using the synthetic sequence described in Step 2 of Scheme 1:

TABLE 1

| # | Structure | Name | HRMS |
|---|-----------|------|------|
| 1-10 | 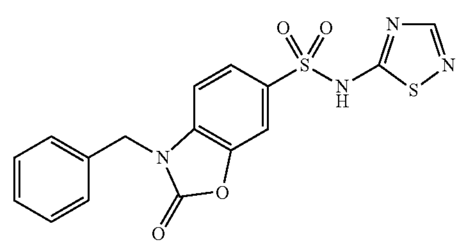 [SMILES: O=c1oc2cc(S(=O)(=O)Nc3ncns3)ccc2n1Cc1ccccc1] | 3-benzyl-2-oxo-N-1,2,4-thiadiazol-5-yl-2,3-dihydro-1,3-benzoxazole-6-sulfonamide | C16H12N4O4S2 [M + H] calc 389.0373 obs 389.0380 |

TABLE 1-continued

| # | Structure | Name | HRMS |
|---|---|---|---|
| 1-11 | 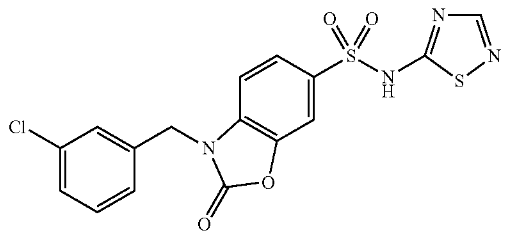 [SMILES: O=c1oc2cc(S(=O)(=O)Nc3ncns3)ccc2n1Cc1cccc(Cl)c1] | 3-(3-chlorobenzyl)-2-oxo-N-1,2,4-thiadiazol-5-yl-2,3-dihydro-1,3-benzoxazole-6-sulfonamide | C16H11ClN4O4S2 [M + H] calc 422.9983 obs 422.9993 |
| 1-12 | 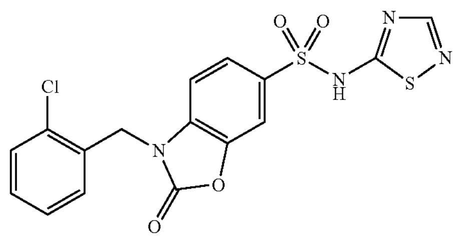 [SMILES: O=c1oc2cc(S(=O)(=O)Nc3ncns3)ccc2n1Cc1ccccc1Cl] | 3-(2-chlorobenzyl)-2-oxo-N-1,2,4-thiadiazol-5-yl-2,3-dihydro-1,3-benzoxazole-6-sulfonamide | C16H11ClN4O4S2 [M + H] calc 423.0000 obs 423.0000 |
| 1-13 | 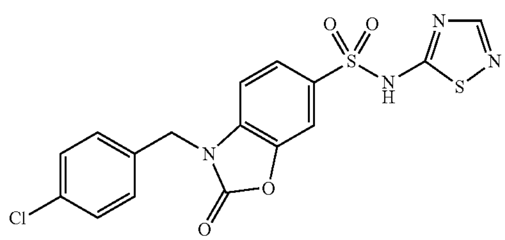 [SMILES: O=c1oc2cc(S(=O)(=O)Nc3ncns3)ccc2n1Cc1ccc(Cl)cc1] | 3-(4-chlorobenzyl)-2-oxo-N-1,2,4-thiadiazol-5-yl-2,3-dihydro-1,3-benzoxazole-6-sulfonamide | C16H11ClN4O4S2 [M + H] calc 422.9983 obs 422.9993 |
| 1-14 | 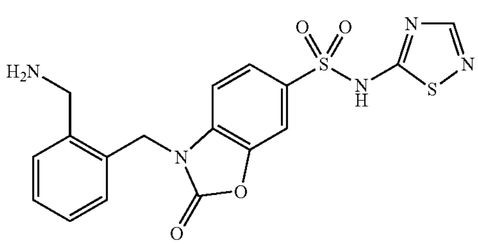 [SMILES: NCc1ccccc1Cn1c(=O)oc2cc(S(=O)(=O)Nc3ncns3)ccc21] | 3-[2-(aminomethyl)benzyl]-2-oxo-N-1,2,4-thiadiazol-5-yl-2,3-dihydro-1,3-benzoxazole-6-sulfonamide | C17H15N5O4S2 [M + H] calc 418.1000 obs 418.1000 |
| 1-15 | 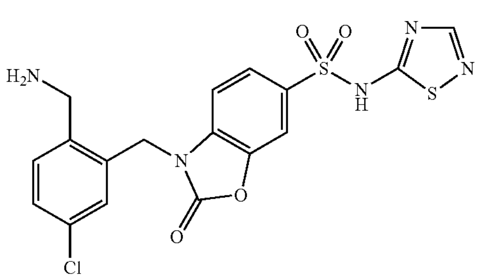 [SMILES: NCc1ccc(Cl)cc1Cn1c(=O)oc2cc(S(=O)(=O)Nc3ncns3)ccc21] | 3-[2-(aminomethyl)-5-chlorobenzyl]-2-oxo-N-1,2,4-thiadiazol-5-yl-2,3-dihydro-1,3-benzoxazole-6-sulfonamide | C17H14ClN5O4S2 [M + H] calc 452.0249 obs 452.0253 |

TABLE 1-continued

| # | Structure | Name | HRMS |
|---|---|---|---|
| 1-16 | 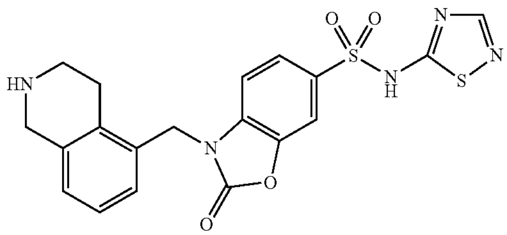 [SMILES: O=c1oc2cc(S(=O)(=O)Nc3ncns3)ccc2n1Cc1cccc2c1CCNC2] | 2-oxo-3-(1,2,3,4-tetrahydroisoquinolin-5-ylmethyl)-N-1,2,4-thiadiazol-5-yl-2,3-dihydro-1,3-benzoxazole-6-sulfonamide | C19H17N5O4S2 [M + H] calc 444.0795 obs 444.0811 |
| 1-17 | 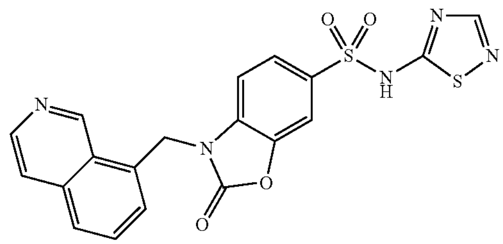 [SMILES: O=c1oc2cc(S(=O)(=O)Nc3ncns3)ccc2n1Cc1cccc2ccncc12] | 3-(isoquinolin-8-ylmethyl)-2-oxo-N-1,2,4-thiadiazol-5-yl-2,3-dihydro-1,3-benzoxazole-6-sulfonamide | Calc'd 440.0482, found 440.0474 |
| 1-18 | 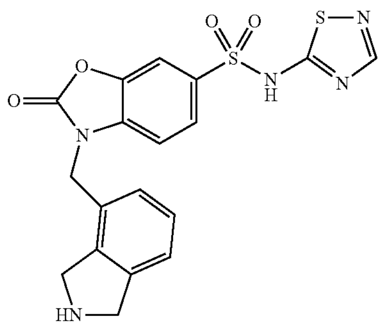 [SMILES: O=c1oc2cc(S(=O)(=O)Nc3ncns3)ccc2n1Cc1cccc2c1CNC2] | 3-(2,3-dihydro-1H-isoindol-4-ylmethyl)-2-oxo-N-1,2,4-thiadiazol-5-yl-2,3-dihydro-1,3-benzoxazole-6-sulfonamide | Calc'd 430.0638, found 430.0627 |

Example 2

Preparation of 3-{2-[(1E)-3-Aminoprop-1-en-1-yl]benzyl}-2-oxo-N-(1,2,4-thiadiazol-5-yl)-2,3-dihydro-1,3-benzoxazole-6-sulfonamide (3-3)

The reaction of Scheme 2 was carried out in accordance with the process of Example I, Step 2. Thus, as illustrated in Scheme 2, the compound of Formula 1-5 was reacted with the alcohol of Formula 2-1 to yield the compound of Formula 2-2.

Accordingly, a solution of 1-5 (150 mg, 0.334 mmol) and 2-1 (78 mg, 0.334 mmol) in THF (1.5 mL) at 0° C. was treated with triphenylphosphine (175 mg, 0.669 mmol), followed by DTBAD (154 mg, 0.669 mmol). The reaction was allowed to reach RT, then the reaction was filtered and concentrated before purification by normal phase chromatography (0-20% EtOAc in hexane) yielding the compound of Formula 2-2 (N-(2,4-Dimethoxybenzyl)-3-(2-iodobenzyl)-2-oxo-N-(1,2,4-thiadiazol-5-yl)-2,3-dihydro-1,3-benzoxazole-6-sulfonamide) as a white solid.

The compound of Formula 2-2 was deprotected in accordance with Scheme 3 to yield the compound of Formula 3-1, which was subsequently reacted in a Suzuki coupling reaction with the boronic ester of 3-2 to yield, after workup, the derivative compound of Formula 3-3.

Scheme 2

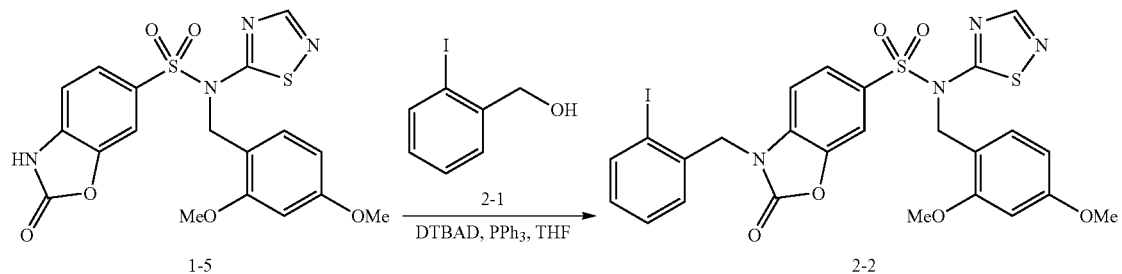

Scheme 3

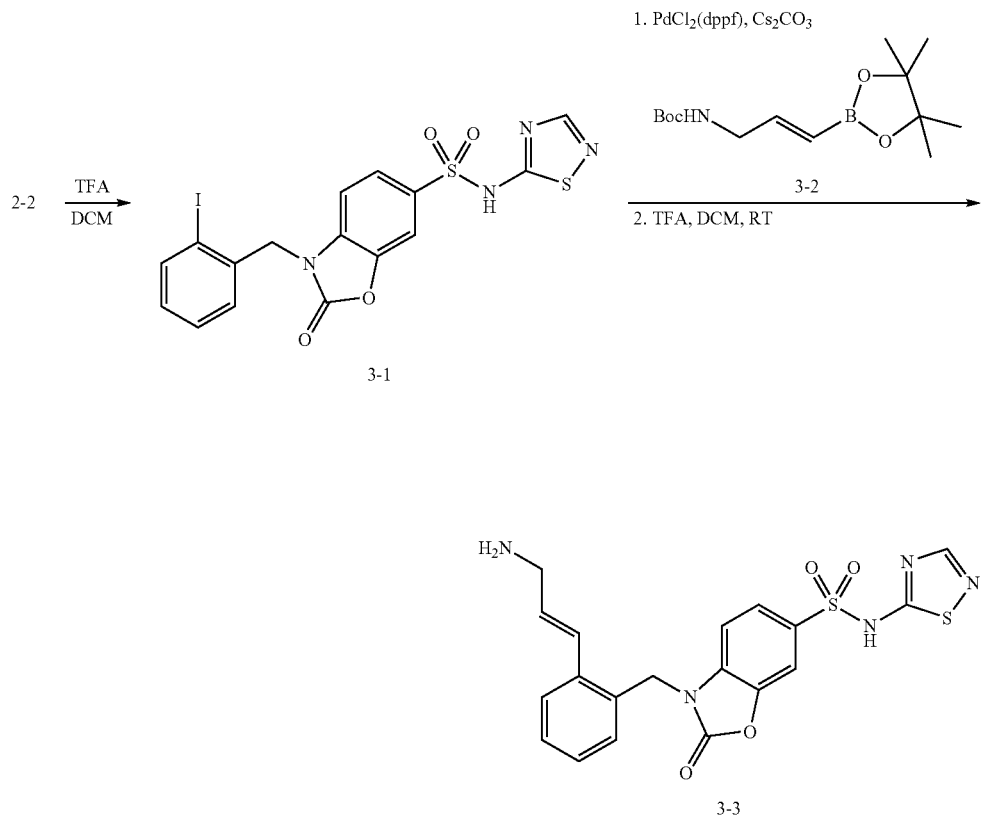

Accordingly A solution of 2-2 (94 mg, 0.141 mmol) in DCM (1 mL) was treated with TFA (283 μl). The reaction was stirred at RT for 30 minutes, after which the solvent and TFA were removed in vacuo. The mixture was purified by reverse phase chromatography (15-90% MeCN in water with 0.1% TFA, C18 column) to yield 3-1 (3-(2-iodobenzyl)-2-oxo-N-(1,2,4-thiadiazol-5-yl)-2,3-dihydro-1,3-benzoxazole-6-sulfonamide) as a white solid.

Subsequently, a solution of 3-1 (30 mg, 0.058 mmol), 3-2 (24.8 mg, 0.087 mmol), PdCl$_2$(dppf)-DCM adduct (9.5 mg, 0.012 mmol, prepared according to the literature) and Cs$_2$CO$_3$ (0.175 mL, 1M solution) in 1,4-dioxane (778 μl) was heated to 110° C. for 30 minutes in a microwave reactor. The dioxane layer was then decanted, filtered and concentrated. Residue dissolved in 1 mL of DCM and treated with 0.1 mL of TFA. After stirring for 30 minutes at RT, the solvent and TFA was removed in vacuo. Purified by reverse phase chromatography (20-95% MeCN in water with 0.1% TFA, C18 column) to yield 3-3 (3-{2-[(1E)-3-Aminoprop-1-en-1-yl]benzyl}-2-oxo-N-(1,2,4-thiadiazol-5-yl)-2,3-dihydro-1,3-benzoxazazole-6-sulfonamide) as the TFA salt, an off-white solid. $^1$H NMR δ (ppm)(DMSO-d☐): 8.45 (1H, s), 8.02 (3H, s), 7.78 (1H, d, J=1.67 Hz), 7.67 (1H, dd, J=8.29, 1.68 Hz), 7.53 (1H, d, J=7.73 Hz), 7.39-7.33 (1H, m), 7.32-7.25 (1H, m), 7.22 (1H, d, J=7.72 Hz), 7.17 (1H, d, J=8.32 Hz), 7.13 (1H, d, J=15.79 Hz), 6.20-6.12 (1H, m), 5.17 (2H, s), 3.64 (2H, m). HRMS C19H17N5O4S2 [M+H] calc 444.0795, obs 444.0798.

The compounds listed in Table 2 were prepared from 3-1 and the appropriate boronic ester in accordance with the process of Scheme 3:

TABLE 2

| # | Structure | Name | HRMS/LRMS |
|---|-----------|------|-----------|
| 3-4 | 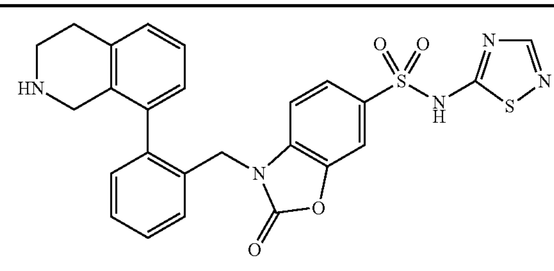 | 2-oxo-3-[2-(1,2,3,4-tetrahydroisoquinolin-8-yl)benzyl]-N-1,2,4-thiadiazol-5-yl-2,3-dihydro-1,3-benzoxazole-6-sulfonamide | C25H21N5O4S2 [M + H] calc 520.1108 obs 520.1077 |

TABLE 2-continued

| # | Structure | Name | HRMS/LRMS |
|---|---|---|---|
| 3-5 | 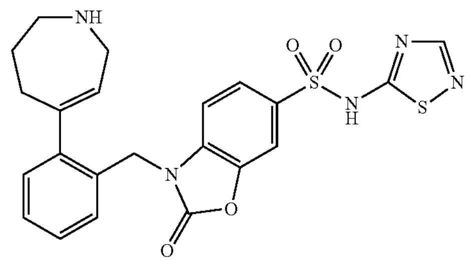 [SMILES: O=c1oc2cc(S(=O)(=O)Nc3ncns3)ccc2n1Cc1ccccc1C1=CCNCCC1] | 2-oxo-3-[2-(2,5,6,7-tetrahydro-1H-azepin-4-yl)benzyl]-N-1,2,4-thiadiazol-5-yl-2,3-dihydro-1,3-benzoxazole-6-sulfonamide | C22H21N5O4S2 [M + H] calc 484.1108 obs 484.1082 |
| 3-6 | 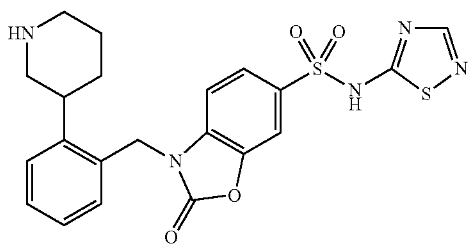 [SMILES: O=c1oc2cc(S(=O)(=O)Nc3ncns3)ccc2n1Cc1ccccc1C1CCCNC1] | 2-oxo-3-[2-(1,2,5,6-tetrahydropyridin-3-yl)benzyl]-N-1,2,4-thiadiazol-5-yl-2,3-dihydro-1,3-benzoxazole-6-sulfonamide | C21H19N5O4S2 [M + H] calc 470.0951 obs 470.0954 |
| 3-7 | 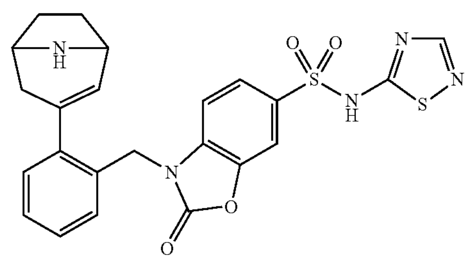 [SMILES: O=c1oc2cc(S(=O)(=O)Nc3ncns3)ccc2n1Cc1ccccc1C1=CC2CCC(C1)N2] | 3-[2-(8-azabicyclo[3.2.1]oct-2-en-3-yl)benzyl]-2-oxo-N-1,2,4-thiadiazol-5-yl-2,3-dihydro-1,3-benzoxazole-6-sulfonamide | C23H21N5O4S2 [M + H] calc 496.1108 obs 496.1081 |
| 3-8 | 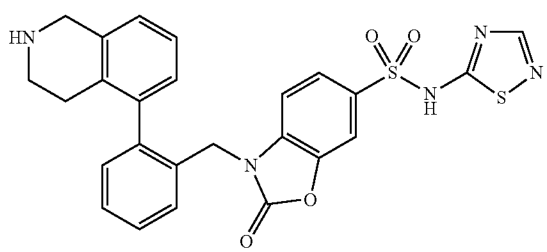 [SMILES: O=c1oc2cc(S(=O)(=O)Nc3ncns3)ccc2n1Cc1ccccc1-c1cccc2c1CCNC2] | 2-oxo-3-[2-(1,2,3,4-tetrahydroisoquinolin-5-yl)benzyl]-N-1,2,4-thiadiazol-5-yl-2,3-dihydro-1,3-benzoxazole-6-sulfonamide | C25H21N5O4S2 [M + H] calc 520.1108 obs 520.1082 |
| 3-9 | 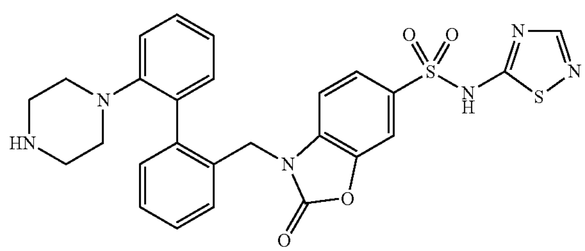 [SMILES: O=c1oc2cc(S(=O)(=O)Nc3ncns3)ccc2n1Cc1ccccc1-c1ccccc1N1CCNCC1] | 2-oxo-3-[(2'-piperazin-1-ylbiphenyl-2-yl)methyl]-N-1,2,4-thiadiazol-5-yl-2,3-dihydro-1,3-benzoxazole-6-sulfonamide | C26H24N6O4S2 [M + H] calc 549.1373 obs 549.1347 |
| 3-10 | 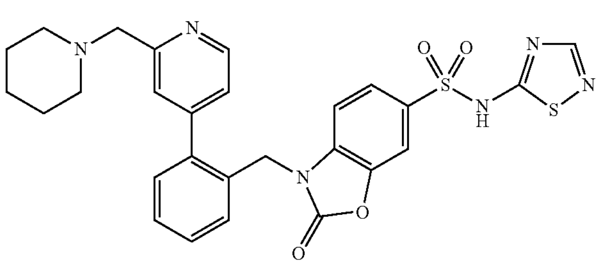 [SMILES: O=c1oc2cc(S(=O)(=O)Nc3ncns3)ccc2n1Cc1ccccc1-c1ccnc(CN2CCCCC2)c1] | 2-oxo-3-{2-[2-(piperidin-1-ylmethyl)pyridin-4-yl]benzyl}-N-1,2,4-thiadiazol-5-yl-2,3-dihydro-1,3-benzoxazole-6-sulfonamide | C27H26N6O4S2 [M + H] calc 563.1530 obs 563.1524 |

TABLE 2-continued

| # | Structure | Name | HRMS/LRMS |
|---|---|---|---|
| 3-11 | 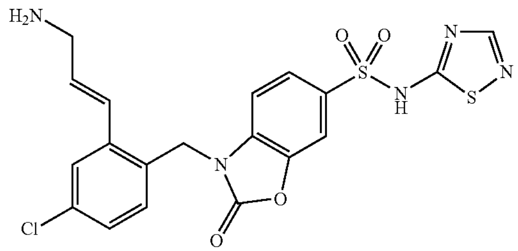 [SMILES: NC/C=C/c1cc(Cl)ccc1Cn1c(=O)oc2cc(S(=O)(=O)Nc3ncns3)ccc21] | 3-{2-[(1E)-3-aminoprop-1-en-1-yl]-4-chlorobenzyl}-2-oxo-N-1,2,4-thiadiazol-5-yl-2,3-dihydro-1,3-benzoxazole-6-sulfonamide | C19H16ClN5O4S2 [M + H] calc 478.0405 obs 478.0406 |
| 3-12 | 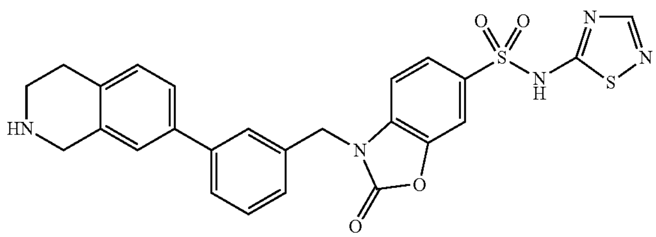 [SMILES: O=c1oc2cc(S(=O)(=O)Nc3ncns3)ccc2n1Cc1cccc(-c2ccc3c(c2)CNCC3)c1] | 2-oxo-3-[3-(1,2,3,4-tetrahydroisoquinolin-7-yl)benzyl]-N-1,2,4-thiadiazol-5-yl-2,3-dihydro-1,3-benzoxazole-6-sulfonamide | C25H21N5O4S2 [M + H] calc 520.1108 obs 520.1079 |
| 3-13 | 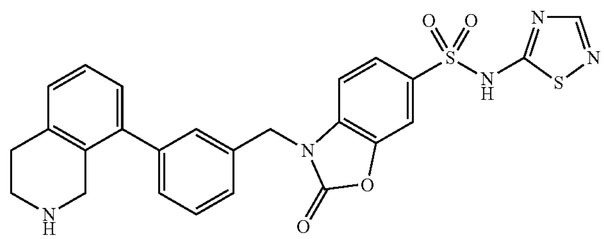 [SMILES: O=c1oc2cc(S(=O)(=O)Nc3ncns3)ccc2n1Cc1cccc(-c2cccc3c2CNCC3)c1] | 2-oxo-3-[3-(1,2,3,4-tetrahydroisoquinolin-8-yl)benzyl]-N-1,2,4-thiadiazol-5-yl-2,3-dihydro-1,3-benzoxazole-6-sulfonamide | C25H21N5O4S2 [M + H] calc 520.1108 obs 520.1079 |
| 3-14 | 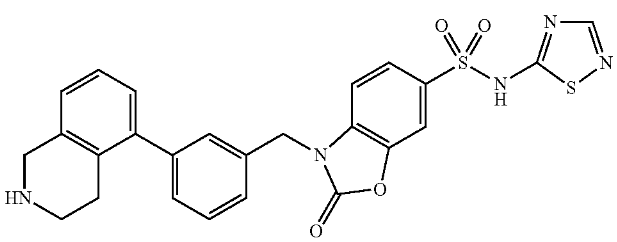 [SMILES: O=c1oc2cc(S(=O)(=O)Nc3ncns3)ccc2n1Cc1cccc(-c2cccc3c2CCNC3)c1] | 2-oxo-3-[3-(1,2,3,4-tetrahydroisoquinolin-5-yl)benzyl]-N-1,2,4-thiadiazol-5-yl-2,3-dihydro-1,3-benzoxazole-6-sulfonamide | C25H21N5O4S2 [M + H] calc 520.1108 obs 520.1081 |
| 3-15 | 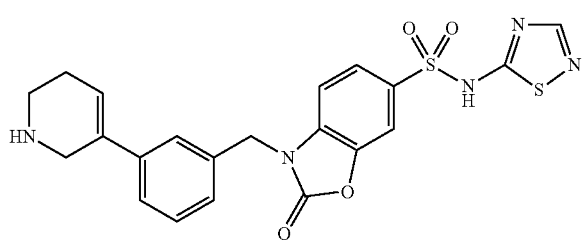 [SMILES: O=c1oc2cc(S(=O)(=O)Nc3ncns3)ccc2n1Cc1cccc(C2=CCCNC2)c1] | 2-oxo-3-[3-(1,2,5,6-tetrahydropyridin-3-yl)benzyl]-N-1,2,4-thiadiazol-5-yl-2,3-dihydro-1,3-benzoxazole-6-sulfonamide | C21H19N5O4S2 [M + H] calc 470.0951 obs 470.0926 |
| 3-16 | 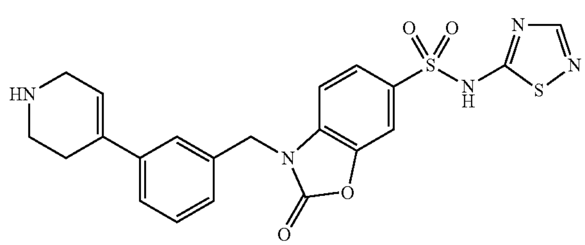 [SMILES: O=c1oc2cc(S(=O)(=O)Nc3ncns3)ccc2n1Cc1cccc(C2=CCNCC2)c1] | 2-oxo-3-[3-(1,2,3,6-tetrahydropyridin-4-yl)benzyl]-N-1,2,4-thiadiazol-5-yl-2,3-dihydro-1,3-benzoxazole-6-sulfonamide | C21H19N5O4S2 [M + H] calc 470.0951 obs 470.0927 |

TABLE 2-continued

| # | Structure | Name | HRMS/LRMS |
|---|---|---|---|
| 3-17 | 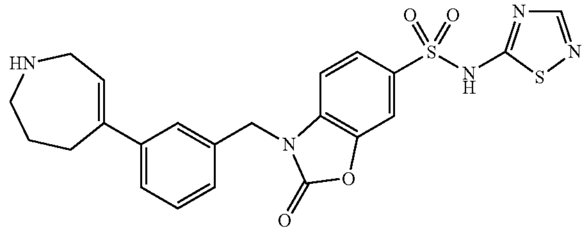 [SMILES: O=c1oc2cc(S(=O)(=O)Nc3ncns3)ccc2n1Cc1cccc(C2=CCNCCC2)c1] | 2-oxo-3-[3-(2,5,6,7-tetrahydro-1H-azepin-4-yl)benzyl]-N-1,2,4-thiadiazol-5-yl-2,3-dihydro-1,3-benzoxazole-6-sulfonamide | C22H21N5O4S2 [M + H] calc 484.1108 obs 484.1082 |
| 3-18 | 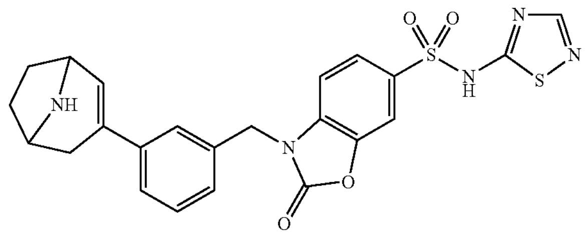 [SMILES: O=c1oc2cc(S(=O)(=O)Nc3ncns3)ccc2n1Cc1cccc(C2=CC3CCC(C2)N3)c1] | 3-[3-(8-azabicyclo[3.2.1]oct-2-en-3-yl)benzyl]-2-oxo-N-1,2,4-thiadiazol-5-yl-2,3-dihydro-1,3-benzoxazole-6-sulfonamide | C23H21N5O4S2 [M + H] calc 496.1108 obs 496.1082 |

Example 3

Preparation of 2-Oxo-3-[(1R)-1-(1,2,3,4-tetrahydroisoquinolin-8-yl)ethyl]-N-(1,2,4-thiadiazol-5-yl)-2,3-dihydro-1,3-benzoxazole-6-sulfonamide (4-4) and related compounds and preparation of 2-oxo-3-[(1R)-1-phenylethyl]-N-1,2,4-thiadiazol-5-yl-2,3-dihydro-1,3-benzoxazole-6-sulfonamide (4-5) and related compounds Scheme 4 illustrates that a Mitsunobu coupling reaction between a compound of Formula 1-5 and a secondary alcohol can be carried out according to the process of Example 1, Step 2 (illustrated above) with preparation of the compound of Formula 4-4.

Scheme 4

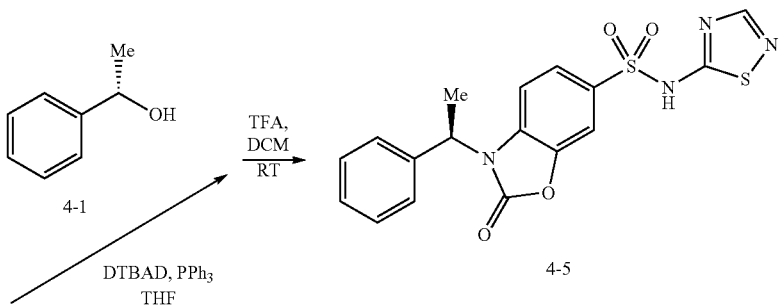

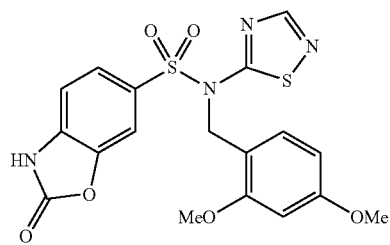

1-5

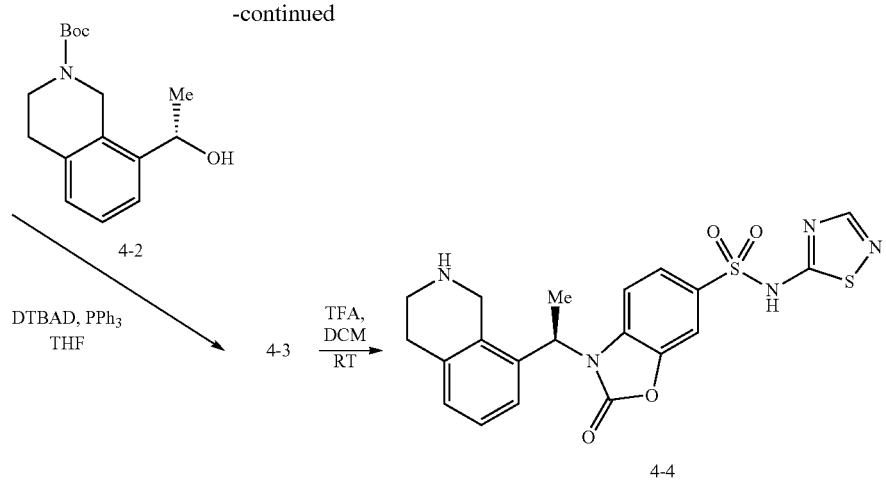

Preparation of 2-Oxo-3-[(1R)-1-(1,2,3,4-tetrahydroisoquinolin-8-yl)ethyl]-N-(1,2,4-thiadiazol-5-yl)-2,3-dihydro-1,3-benzoxazole-6-sulfonamide (4-4)

Step 1

Accordingly, the compound of Formula 4-3 (tert-Butyl 8-[(1R)-1-{6-[(2,4-dimethoxybenzyl)(1,2,4-thiadiazol-5-yl)sulfamoyl]-2-oxo-1,3-benzoxazol-3(2H)-yl}ethyl]-3,4-dihydroisoquinoline-2(1H)-carboxylate) was prepared from a solution provided by dissolving 48 mg of the compound of Formula 1-5 (0.107 mmol, prepared as described above) and 29.7 mg of the compound of Formula 4-2 (0.107 mmol, prepared as described herein) in 1 mL of THF. This solution was cooled to 0° C. and treated with resin-bound triphenylphosphine (56.1 mg, 0.214 mmol) followed by DTBAD (49.3 mg, 0.214 mmol). After stirring at 60 min, the reaction mixture was filtered through Celite and concentrated in vacuo. Purification by normal phase chromatography (0-50% EtOAc in hexane) yielded the compound of Formula 4-3 as a solid which was used as isolated.

A solution of the compound of Formula 4-3 was prepared by dissolving the entire amount previously prepared in 1 mL dichloromethane, and treating the resulting solution with trifluoroacetic acid (0.25 mL). After stirring for 30 minutes at RT, the solution was concentrated and purified by reverse phase HPLC (5-75% MeCN in water with 0.1% TFA, C18 column) to yield the compound of Formula 4-4 as the TFA salt, a white solid. The product was characterized by $^1$H NMR δ (ppm)(DMSO-$d_6$): 8.93 (2H, d, J=32.07 Hz), 8.42 (1H, s), 7.74-7.67 (2H, m), 7.58 (1H, d, J=8.45 Hz), 7.44-7.37 (1H, m), 7.26 (1H, d, J=7.67 Hz), 7.20 (1H, d, J=8.41 Hz), 5.64 (1H, m), 4.37 (1H, s), 4.07 (1H, d, J=15.91 Hz), 3.29 (2H, m), 3.00 (2H, m), 1.81 (3H, d, J=6.83 Hz). HRMS $C_{20}H_{19}N_5O_4S_2$ [M+H] calc 458.0951, obs 458.0943.

As illustrated in Scheme 4, the compound of Formula 4-5 can be prepared using the same process described for preparation of the compound of 4-4 by selecting the appropriate secondary alcohol (selecting 4-1 in lieu of 4-2). Additional compounds were prepared by reacting the compound of Formula 1-5 with the appropriate alcohol according to the process of Scheme 4, and are enumerated, along with characteristic HRMS data, in Table 3, below.

TABLE 3

| # | Structure | Name | HRMS |
|---|---|---|---|
| 4-6 | 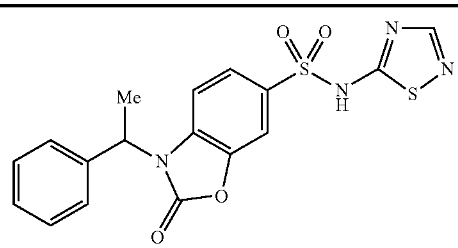 | 2-oxo-3-(1-phenylethyl)-N-1,2,4-thiadiazol-5-yl-2,3-dihydro-1,3-benzoxazole-6-sulfonamide | C17H14N4O4S2 [M + H] calc 403.0529 obs 403.0534 |
| 4-7 | 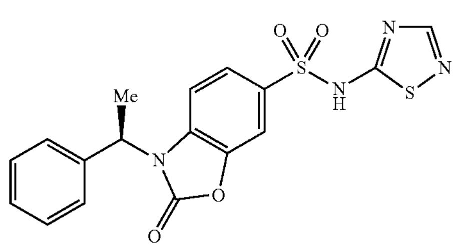 [SMILES: C[C@H](c1ccccc1)n1c(=O)oc2cc(S(=O)(=O)Nc3ncns3)ccc21] | 2-oxo-3-[(1R)-1-phenylethyl]-N-1,2,4-thiadiazol-5-yl-2,3-dihydro-1,3-benzoxazole-6-sulfonamide | C17H14N4O4S2 [M + H] calc 403.0529 obs 403.0537 |

TABLE 3-continued

| # | Structure | Name | HRMS |
|---|-----------|------|------|
| 4-8 | 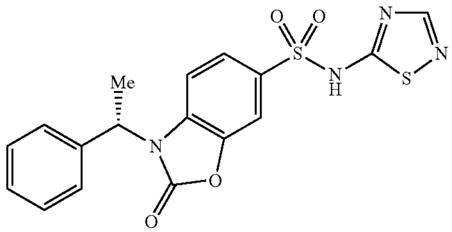 [SMILES: C[C@@H](c1ccccc1)n1c(=O)oc2cc(S(=O)(=O)Nc3ncns3)ccc21] | 2-oxo-3-[(1S)-1-phenylethyl]-N-1,2,4-thiadiazol-5-yl-2,3-dihydro-1,3-benzoxazole-6-sulfonamide | C17H14N4O4S2 [M + H] calc 403.0529 obs 403.0538 |
| 4-9 | 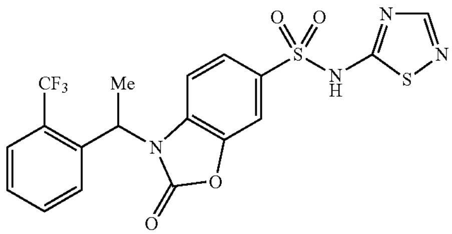 [SMILES: CC(c1ccccc1C(F)(F)F)n1c(=O)oc2cc(S(=O)(=O)Nc3ncns3)ccc21] | 2-oxo-N-1,2,4-thiadiazol-5-yl-3-{1-[2-(trifluoromethyl)phenyl]ethyl}-2,3-dihydro-1,3-benzoxazole-6-sulfonamide | C18H13F3N4O4S2 [M + H] calc 471.0403 obs 471.0404 |
| 4-10 | 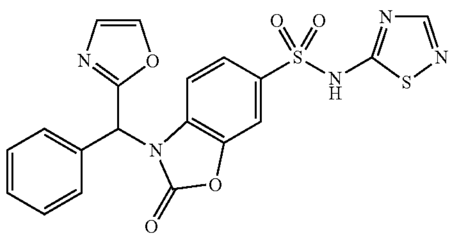 [SMILES: O=c1oc2cc(S(=O)(=O)Nc3ncns3)ccc2n1C(c1ccccc1)c1ncco1] | 3-[1,3-oxazol-2-yl(phenyl)methyl]-2-oxo-N-1,2,4-thiadiazol-5-yl-2,3-dihydro-1,3-benzoxazole-6-sulfonamide | C19H13N5O5S2 [M + H] calc 456.0431 obs 456.0435 |
| 4-11 | 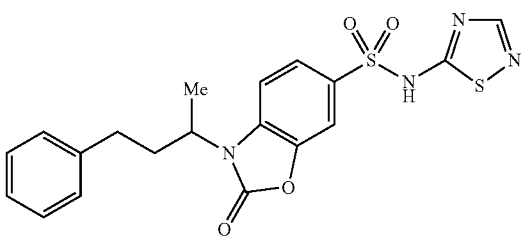 [SMILES: CC(CCc1ccccc1)n1c(=O)oc2cc(S(=O)(=O)Nc3ncns3)ccc21] | 3-(1-methyl-3-phenylpropyl)-2-oxo-N-1,2,4-thiadiazol-5-yl-2,3-dihydro-1,3-benzoxazole-6-sulfonamide | C19H18N4O4S2 [M + H] calc 431.0842 obs 431.0850 |
| 4-12 | 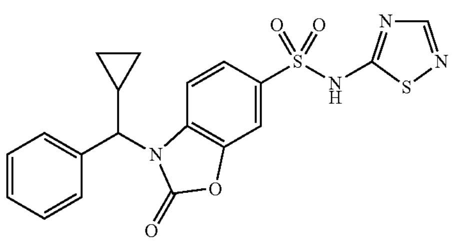 [SMILES: O=c1oc2cc(S(=O)(=O)Nc3ncns3)ccc2n1C(c1ccccc1)C1CC1] | 3-[cyclopropyl(phenyl)methyl]-2-oxo-N-1,2,4-thiadiazol-5-yl-2,3-dihydro-1,3-benzoxazole-6-sulfonamide | C19H16N4O4S2 [M + H] calc 429.0686 obs 429.0690 |
| 4-13 | 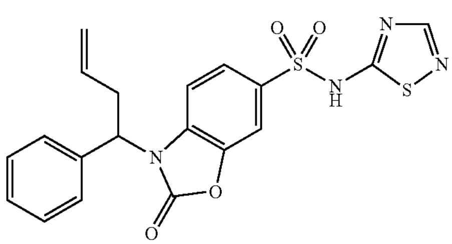 [SMILES: C=CCC(c1ccccc1)n1c(=O)oc2cc(S(=O)(=O)Nc3ncns3)ccc21] | 2-oxo-3-(1-phenylbut-3-en-1-yl)-N-1,2,4-thiadiazol-5-yl-2,3-dihydro-1,3-benzoxazole-6-sulfonamide | C19H16N4O4S2 [M + H] calc 429.0686 obs 429.0692 |

TABLE 3-continued

| # | Structure | Name | HRMS |
|---|-----------|------|------|
| 4-14 | 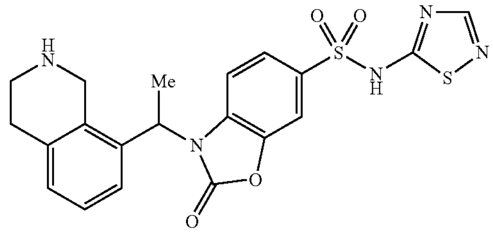 [SMILES: CC(c1cccc2c1CNCC2)n1c(=O)oc2cc(S(=O)(=O)Nc3ncns3)ccc21] | 2-oxo-3-[1-(1,2,3,4-tetrahydroisoquinolin-8-yl)ethyl]-N-1,2,4-thiadiazol-5-yl-2,3-dihydro-1,3-benzoxazole-6-sulfonamide | C20H19N5O4S2 [M + H] calc 458.0951 obs 458.0956 |
| 4-15 | 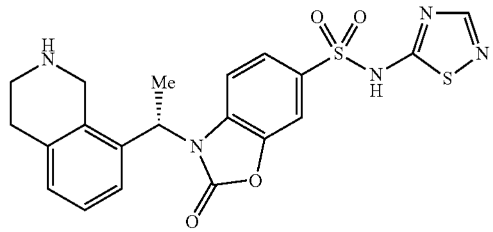 [SMILES: C[C@@H](c1cccc2c1CNCC2)n1c(=O)oc2cc(S(=O)(=O)Nc3ncns3)ccc21] | 2-oxo-3-[(1S)-1-(1,2,3,4-tetrahydroisoquinolin-8-yl)ethyl]-N-1,2,4-thiadiazol-5-yl-2,3-dihydro-1,3-benzoxazole-6-sulfonamide | C20H19N5O4S2 [M + H] calc 458.0951 obs 458.0939 |
| 4-16 | 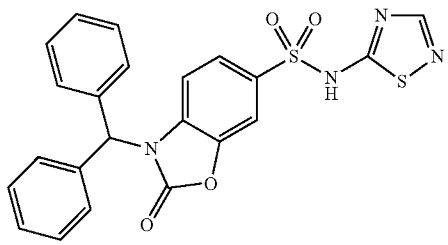 [SMILES: O=c1oc2cc(S(=O)(=O)Nc3ncns3)ccc2n1C(c1ccccc1)c1ccccc1] | 3-(diphenylmethyl)-2-oxo-N-1,2,4-thiadiazol-5-yl-2,3-dihydro-1,3-benzoxazole-6-sulfonamide | Calc'd 465.0686, found 465.0679 |
| 4-17 | 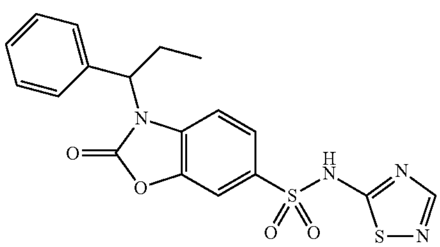 [SMILES: CCC(c1ccccc1)n1c(=O)oc2cc(S(=O)(=O)Nc3ncns3)ccc21] | 2-oxo-3-(1-phenylpropyl)-N-1,2,4-thiadiazol-5-yl-2,3-dihydro-1,3-benzoxazole-6-sulfonamide | Calc'd 417.0686, found 417.0695 |

Secondary alcohols suitable for use in the process of Scheme 4 may be prepared from the corresponding acid, illustrated in Scheme 5 with the preparation of the compound of Formula 4-2 (tert-Butyl 8-[(1S)-1-hydroxyethyl]-3,4-dihydroisoquinoline-2(1H)-carboxylate).

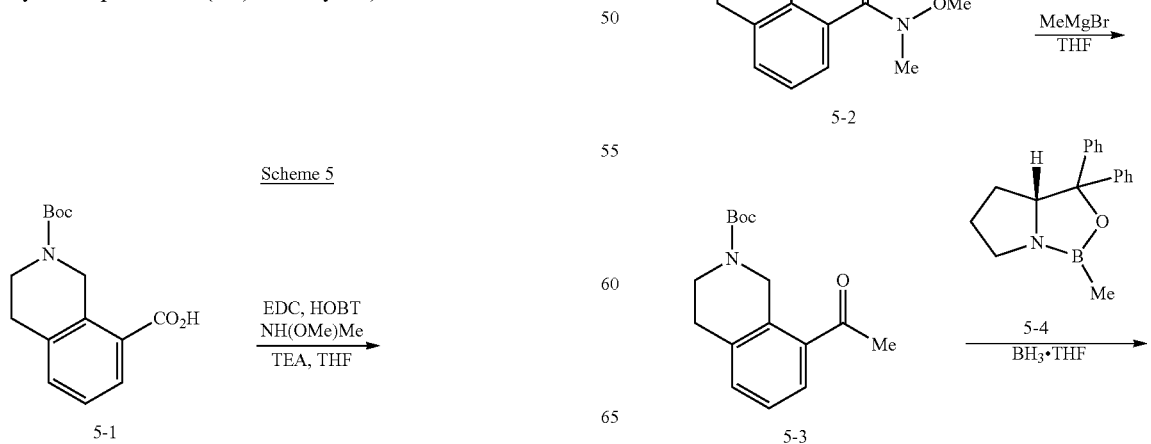

Scheme 5

-continued

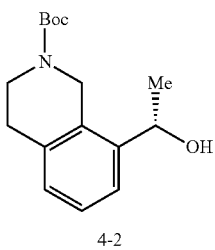

4-2

With reference to Scheme 5, 12.5 g of 5-1 (45.1 mmol, prepared from commercially available isoquinoline-8-carboxylic acid by literature methods) and 18.85 g triethylamine (135 mmol) were dissolved in 150 mL THF. This solution was treated with N,O-dimethylhydroxylamine hydrochloride (5.72 g, 58.6 mmol), followed by 1.726 g N-hydroxybenzotriazole (HOBT, 11.27 mmol) and 8.73 g ethyl-(N',N'-dimethylamino)propyl-carbodimide-hydrochloride (EDC, 45.5 mmol). The reaction was stirred overnight at RT. After removal of most of the solvent under reduced pressure, the residue was suspended in EtOAc (250 mL) and washed with 1N HCl (2×50 mL). The organic layer was washed with saturated sodium bicarbonate (2×50 mL), followed by brine. The organic layer was dried over sodium sulfate, filtered and concentrated. Purification by normal phase chromatography (0-50% EtOAc in hexane) yielded 5-2 (tert-butyl 8-[methoxy(methyl)-carbamoyl]-3,4-dihydroisoquinoline-2(1H)-carboxylate) as a clear light yellow oil The compound of Formula 5-2 previously prepared (1.26 g, 3.93 mmol) was dissolved in 39.3 mL THF and the solution was cooled to 0° C., then treated with a THF solution of methylmagnesium bromide (9.18 ml, 27.5 mmol). This reaction mixture was stirred at 0° C. for 4 hours, then quenched with saturated ammonium chloride (50 mL) and warmed to RT. The layers were split, the aqueous layer was back-extracted with EtOAc (3×75 mL) and the organic layers were combined, then washed with brine, dried over sodium sulfate, filtered and concentrated. The concentrate was purified by normal phase chromatography (0-50% EtOAc in hexane) yielding the compound of Formula 5-3 (tert-butyl 8-acetyl-3,4-dihydroisoquinoline-2(1H)-carboxylate) as a colorless oil, used without further purification in the next step.

Into an oven-dried 1-dram vial containing 224 microliters of anhydrous THF (RT) was added 24.7 mg of the compound of Formula 5-3 (previously prepared, 0.090 mmol) and 17.94 µl of (3aR)-1-methyl-3,3-diphenyltetrahydro-3H-pyrrolo[1,2-c][1,3,2]oxazaborole (5-4, 0.018 mmol). Into the reaction mixture thus provided was added (via 500 µL air-tight syringe) 90 µL BH$_3$-THF (0.090 mmol) in 224 µL anhydrous THF, dropwise over 20 min followed by a 50 µL anhydrous THF rinse. After an additional 30 min LCMS analysis showed complete consumption of starting material. The reaction mixture was cautiously quenched with 2M HCl (3 mL) and diluted with EtOAc (5 mL). The layers were separated and the aqueous layer was back-extracted with EtOAc (3×3 mL). The combined organics were dried over Na$_2$SO$_4$, filtered and concentrated to give a white solid. Chiral separation (ChiralPak AD-H) provided the compound of Formula 4-2 (tert-Butyl 8-[(1S)-1-hydroxyethyl]-3,4-dihydroisoquinoline-2(1H)-carboxylate) as a white solid. This material was used in the preparation of the compound of Formula 4-4, described above.

Example 4

Preparation of derivatives of 3-[(2-Methyl-1,2,3,4-tetrahydroisoquinolin-8-yl)methyl]-2-oxo-N-(1,2,4-thiadiazol-5-yl)-2,3-dihydro-1,3-benzoxazole-6-sulfonamide and related compounds (6-1) and 2-oxo-N-(1,2,4-thiadiazol-5-yl)-3-((2-(2,2,2-trifluoroethyl)-1,2,3,4 tetrahydroisoquinolin-8-yl)methyl)-2,3-dihydrobenzo[d]oxazole-6-sulfonamide (7-6)

Scheme 6

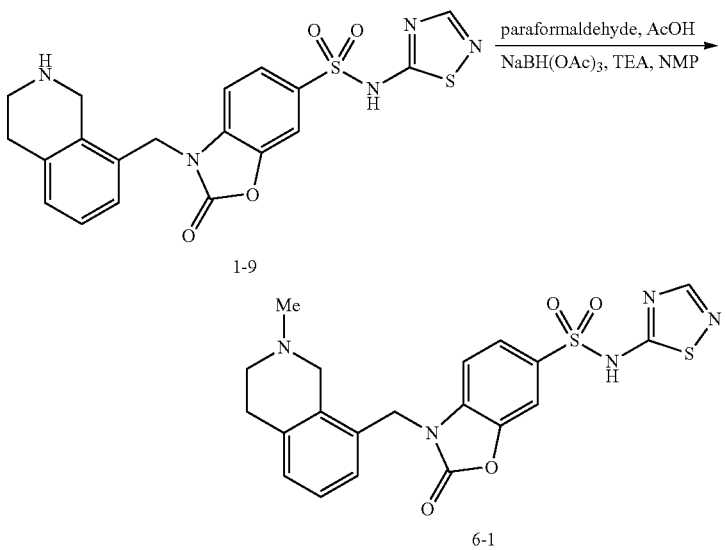

The compound of Formula 6-1 was prepared from the compound of Formula 1-9, prepared in Example 1, above, by dissolving 50 mg of 1-9 (0.090 mmol.) and 26.9 mg paraformaldehyde (0.897 mmol) in 897 µL of N-Methylpyrrolidone (NMP) and treating this solution with 25.00 μl trimethyl amine (TEA) (0.179 mmol) and 10.27 μl acetic acid (AcOH) (0.179 mmol) followed by 190 mg sodium triacetoxyborohydride (0.897 mmol). The reaction mixture was stirred overnight at RT, then filtered and purified by reverse phase chromatography (5-75% MeCN in water with 0.1% TFA, C18 column) to yield the compound of Formula 6-1 as the TFA salt, a white solid. HRMS C20H19N5O4S2 [M+H] calc 458.0951, obs 458.0946.

Additional derivatives of the compound of Formula 1-9 were prepared in accordance with the process of Scheme 6 by selecting the appropriate aldehyde. These compounds are enumerated in Table 4 along with characteristic mass spectroscopy data for each compound.

TABLE 4

| # | Structure | Name | HRMS |
|---|---|---|---|
| 6-2 | 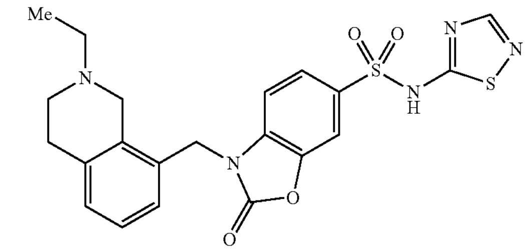 [SMILES: CCN1CCc2cccc(Cn3c(=O)oc4cc(S(=O)(=O)Nc5ncns5)ccc43)c2C1] | 3-[(2-ethyl-1,2,3,4-tetrahydroisoquinolin-8-yl)methyl]-2-oxo-N-1,2,4-thiadiazol-5-yl-2,3-dihydro-1,3-benzoxazole-6-sulfonamide | C21H21N5O4S2 [M + H] calc 472.1108 obs 472.1115 |
| 6-3 | 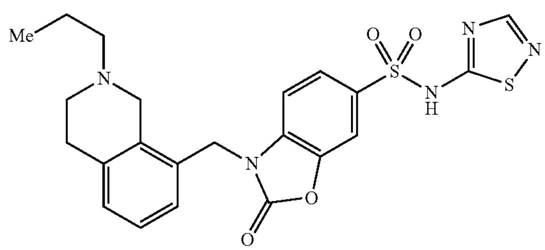 [SMILES: CCCN1CCc2cccc(Cn3c(=O)oc4cc(S(=O)(=O)Nc5ncns5)ccc43)c2C1] | 2-oxo-3-[(2-propyl-1,2,3,4-tetrahydroisoquinolin-8-yl)methyl]-N-1,2,4-thiadiazol-5-yl-2,3-dihydro-1,3-benzoxazole-6-sulfonamide | C22H23N5O4S2 [M + H] calc 486.1 obs 486.1000 |
| 6-4 | 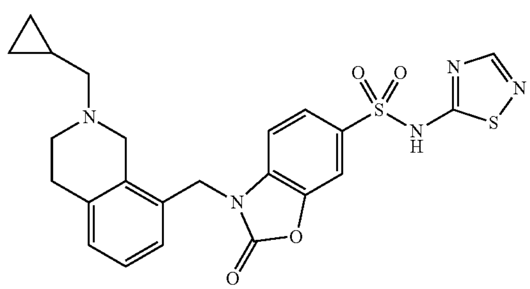 [SMILES: O=c1oc2cc(S(=O)(=O)Nc3ncns3)ccc2n1Cc1cccc2c1CN(CC1CC1)CC2] | 3-{[2-(cyclopropylmethyl)-1,2,3,4-tetrahydroisoquinolin-8-yl]methyl}-2-oxo-N-1,2,4-thiadiazol-5-yl-2,3-dihydro-1,3-benzoxazole-6-sulfonamide | C23H23N5O4S2 [M + H] calc 498.1264 obs 498.1259 |

Scheme 7

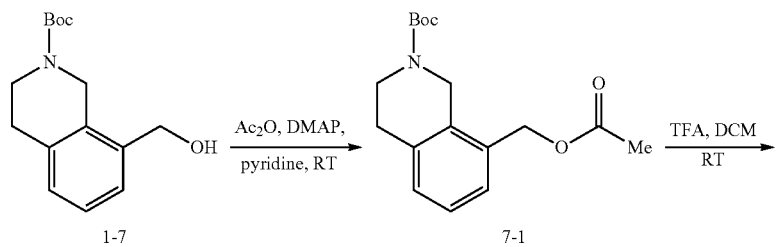

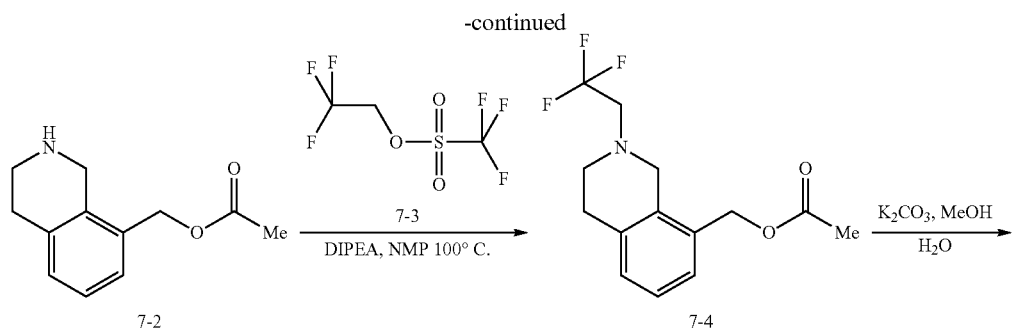

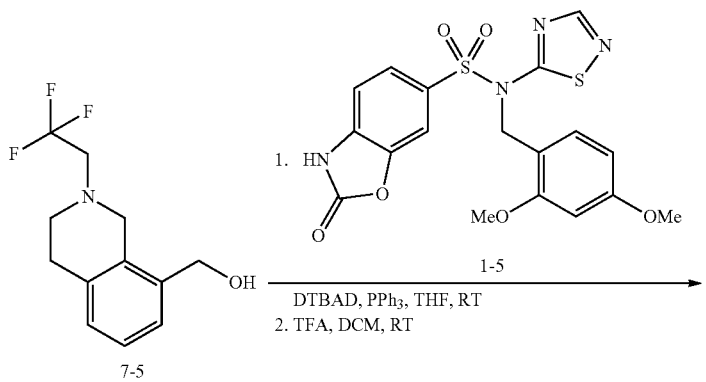

Preparation of tert-Butyl 8-(acetoxymethyl)-3,4-dihydroisoquinoline-2(1H)-carboxylate (7-1)

In a 10 dram vial, added 1-7 (300 mg, 0.795 mmol) to pyridine (3975 µl) followed by acetic anhydride (225 µl, 2.385 mmol) and DMAP (9.71 mg, 0.080 mmol). After 1 h, LCMS showed complete consumption of R1 desired product. Partitioned between 10 mL H$_2$O and 10 mL EtOAc, separated layers. Back-extracted aqueous with 1×5 mL EtOAc. Washed combined organics with 5×5 mL H$_2$O. Dried combined organics over Na$_2$SO$_4$, filtered, concentrated to give a pale yellow oil. Purification by normal-phase HPLC (40 g ISCO column, 0-50% EtOAc:Hexanes) gave 7-1 as a clear, colorless oil.

Preparation of (1,2,3,4-Tetrahydroisoquinolin-8-yl)methyl acetate (7-2)

In a 10 dram vial, added 7-1 (292.5 mg, 0.958 mmol) to DCM (3831 µl) and TFA (958 µl). After 30 min at RT, concentrated to give a clear, colorless oil. Carried crude material forward to subsequent step.

Preparation of (2-(2,2,2-Trifluoroethyl)-1,2,3,4-tetrahydroisoquinolin-8-yl)methyl acetate (7-4)

In an oven-dried 10 mL microwave vial, added crude 7-2 to NMP (3203 µl). Added DIPEA (1119 µl, 6.41 mmol) followed by 2,2,2-trifluoroethyl-trifluoromethanesulfonate (7-3). Heated to 100° C. in microwave for 10 min. Following this duration, LCMS showed complete consumption of SM to desired product. Concentrated in vacuo, purified by reverse-phase HPLC (C18 column, 2-80% 0.1% TFA/CH$_3$CN:0.1% TFA/H$_2$O) to give 7-4 as a white solid.

Preparation of (2-(2,2,2-Trifluoroethyl)-1,2,3,4-tetrahydroisoquinolin-8-yl)methanol (7-5)

In a 5 dram vial, added 7-4 (21.7 mg, 0.076 mmol) to methanol (504 µl) and water (252 µl). Added K$_2$CO$_3$ (52.2 mg, 0.378 mmol) and allowed to stir at RT. After 1 h at RT, LCMS showed complete consumption of SM to desired product. Partitioned reaction contents into 10 mL EtOAc+5 mL H$_2$O. Separated layers, back-extracted aqueous with 3×5 mL EtOAc. Dried combined organics over Na$_2$SO$_4$, filtered, concentrated to give 7-5 as a pale yellow oil. Carried crude material forward to subsequent step.

Preparation of 2-Oxo-N-(1,2,4-thiadiazol-5-yl)-3-((2-(2,2,2-trifluoroethyl)-1,2,3,4 tetrahydroisoquinolin-8-yl)methyl)-2,3-dihydrobenzo[d]oxazole-6-sulfonamide (7-6)

A solution of 1-5 (16.5 mg, 0.037 mmol) and 7-5 (9.02 mg, 0.037 mmol) in THF (368 µl) at RT was treated with PS-bound triphenylphosphine (1.84 mmol/g, 40.2 mg, 0.074 mmol), and DTBAD (16.94 mg, 0.074 mmol). After 30 min, LCMS showed complete consumption of SM. Filtered through Celite and concentrated in vacuo. Dissolved in 245 uL DCM, 123 uL TFA and stirred at RT. After 30 min, diluted with 1 mL MeOH, filtered through Celite and washed with 1 mL MeOH. Concentrated in vacuo and purified by reverse-phase HPLC (C18 column, 5-70% 0.1% TFA/CH$_3$CN:0.1% TFA/H$_2$O) to give 7-6 as an off-white solid. $^1$H NMR δ (ppm) (DMSO-d$_6$): 8.48 (1H, s), 7.78 (1H, d, J=1.69 Hz), 7.67 (1H, dd, J=8.28, 1.72 Hz), 7.25 (1H, d, J=8.33 Hz), 7.14-7.09 (2H, m), 6.92 (1H, d, J=6.83 Hz), 5.00 (2H, s), 3.99 (3H, s), 3.54 (3H, d, J=12.20 Hz), 2.90 (2H, s). HRMS C$_{21}$H$_{19}$F3N$_5$O$_4$S$_2$ [M+H] calc 526.0825, obs. 526.0806.

Example 5

Preparation of 3-{[2-(Methylsulfonyl)-1,2,3,4-tetrahydroisoquinolin-8-yl]methyl}-2-oxo-N-(1,2,4-thiadiazol-5-yl)-2,3-dihydro-1,3-benzoxazole-6-sulfonamide (8-4) and related compounds As shown in Scheme 8, Mitsunobu conditions can be employed to couple a mesylate-tetrahydroisoquinoline alcohol, for example, the compound of Formula 8-3 in Scheme 8, with a compound of Formula 1-5 in accordance with Step 1 of Example 1, above.

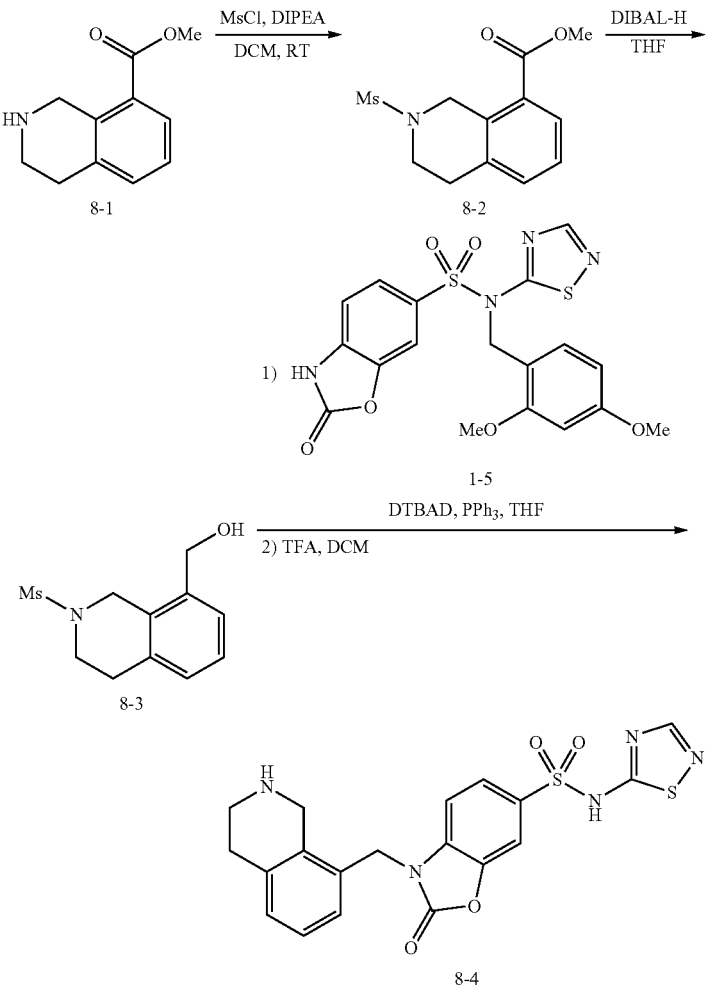

Accordingly, 100 mg of 8-1 (0.439 mmol) was dissolved in 2 mL of THF. This solution was treated with 0.307 mL diisopropylethylamine (DIPEA, 1.757 mmol) followed by 0.038 mL of methylsulfonyl chloride (MsCl, 0.483 mmol). The reaction mixture was filtered and purified by reverse phase chromatography (20-80% MeCN in water with 0.1% TFA, C18 column) to yield methyl 2-(methylsulfonyl)-1,2,3,4-tetrahydroisoquinoline-8-carboxylate (8-2).

The compound of Formula 8-2 (0.080 g, 0.297 mmol) was dissolved in 1.5 mL of THF and the solution was cooled to 0° C., then treated with 1.5 mL di-isobutyl aluminum hydride (DIBAl—H 1.5 mmol). The reaction mixture was stirred for 1 hour maintaining the temperature at 0° C., then quenched with 2N HCl and stirred at RT for 30 minutes additional. The reaction mixture was extracted into EtOAc three times. The combined organic layers were washed with brine, dried over sodium sulfate, filtered and concentrated in vacuo to yield 8-3 ([2-(methylsulfonyl)-1,2,3,4-tetrahydroisoquinolin-8-yl]methanol).

Into a vessel containing 780 µl of THF was dissolved 35 mg of the compound of Formula 8-3 (prepared in the previous step, 0.078 mmol) and 20.72 mg of the compound of Formula 1-5 (prepared in accordance with the procedures described in Example 1, 0.086 mmol). The solution was cooled to 0° C. and was treated with 40.9 mg triphenylphosphine (0.156 mmol), followed by 35.9 mg of DTBAD (0.156 mmol). After 2 hours the reaction mixture was filtered and concentrated in vacuo. The residue was taken up in 1 mL of DCM and treated with 0.25 mL TFA. After stirring for 30 minutes at RT, the solvent and TFA were removed in vacuo and the reaction mixture was filtered and purified by reverse phase chromatography (15-80% MeCN in water with 0.1% TFA, C18 column) to yield the compound of Formula 8-4 as the TFA salt, a white solid. HRMS $C_{20}H_{19}N_5O_6S3$ [M+H] calc 522.057, obs 522.0561.

Examples 6 and 7 illustrate the preparation of derivatives of the tetrahydro-isoquinoline moiety on compounds of the invention, for example, as shown in Schemes 9 and 10, a compound of Formula 1-9 prepared in Example 1, Step 2, is converted to the derivatives of 9-1 and 10-1 respectively Example 6

Preparation of 3-[(2-Acetyl-1,2,3,4-tetrahydroisoquinolin-8-yl)methyl]-2-oxo-N-(1,2,4-thiadiazol-5-yl)-2,3-dihydro-1,3-benzoxazole-6-sulfonamide
(9-1)

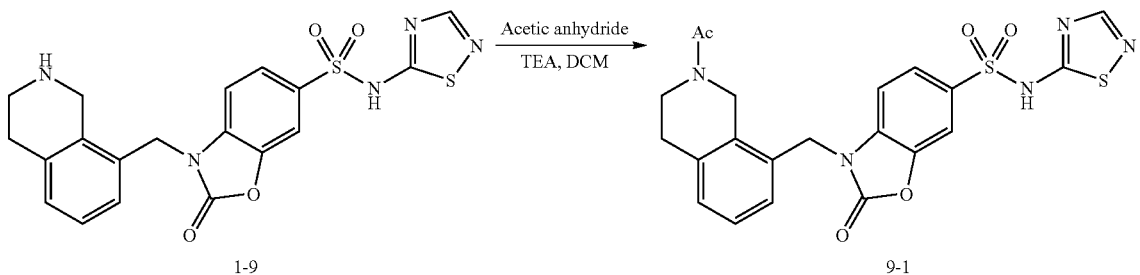

Scheme 9

In accordance with Scheme 9, 30 mg of 1-9 (0.054 mmol) and 15.00 µl TEA (0.108 mmol) were dissolved in 769 µL of DCM. This solution was treated with 5.58 µl of acetic anhydride (0.059 mmol). After stirring overnight at RT, the reaction mixture was concentrated in vacuo, purified by reverse phase chromatography (10-75% MeCN in water with 0.1% TFA, C18 column) to yield 9-1 as a white solid. HRMS $C_{21}H_{19}N_5O_5S_2$ [M+H] calc 486.0900, obs 486.0906.

Example 7

Preparation of 3-{[2-(Cyclopropylcarbonyl)-1,2,3,4-tetrahydroisoquinolin-8-yl]methyl}-2-oxo-N-1,2,4-thiadiazol-5-yl-2,3-dihydro-1,3-benzoxazole-6-sulfonamide (10-1)

Scheme 10

According to Scheme 10, 30 mg of 1-9 (the freebase of ExI-3-3, prepared in accordance with Example 1, Step 2, 0.054 mmol) and 9.26 mg cyclopropylcarboxylic acid (0.108 mmol) was dissolved in 538 μL DMF. This solution was treated with 22.50 μL TEA (0.161 mmol) followed by 8.24 mg HOBT (0.054 mmol) and 10.32 mg EDC (0.054 mmol). After stirring overnight at RT, the reaction was filtered and purified directly by reverse phase chromatography (10-75% MeCN in water with 0.1% TFA, C18 column) to yield 10-1 as a white solid. HRMS $C_{23}H_{21}N_5O_5S_2$ [M+H] calc 512.1057, obs 512.1059

Example 8 illustrates the preparation of compounds of Formula E-2, from Scheme E-B, wherein $R^1$ of E-2 is a Fluorine substituent.

Example 8

Preparation of 5-Fluoro-2-oxo-3-(1,2,3,4-tetrahydroisoquinolin-8-ylmethyl)-N-(1,2,4-thiadiazol-5-yl)-2,3-dihydro-1,3-benzoxazole-6-sulfonamide (11-5)

Scheme 11

Step 1

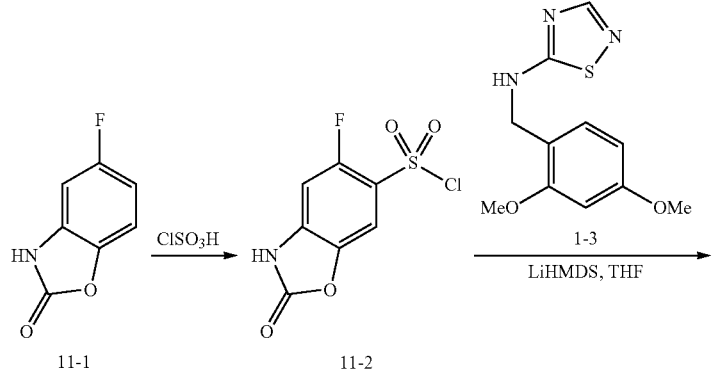

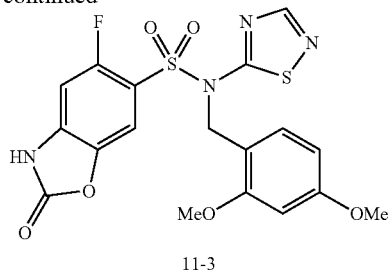

11-3

Step 2

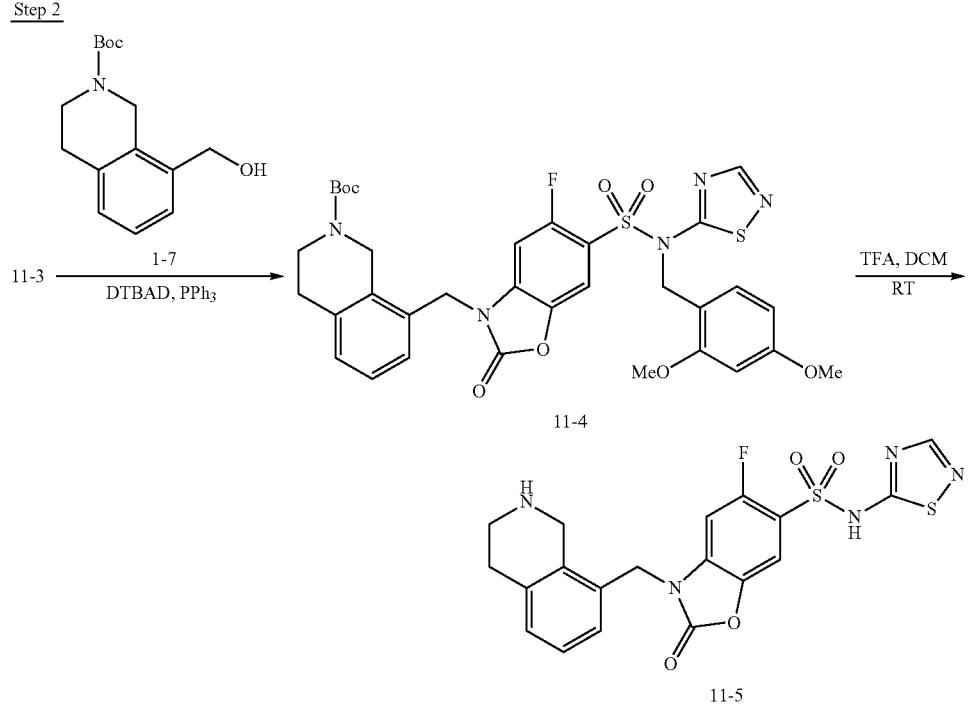

According to Scheme 11, a mixture of commercially-available 5-fluoro-1,3-benzoxazol-2(3H)-one (11-1, 1.02 g, 6.66 mmol) in DCM (66.6 ml) at RT was added chlorosulfonic acid (4.46 ml, 66.6 mmol). The suspension gradually became a solution and was stirred for 18 h at RT. Following this duration, LCMS showed complete consumption of starting material. The solution was cooled to 0° C. and carefully quenched with ice chips and then partitioned between water (100 mL) and EtOAc (100 mL). The layers were separated and the aqueous layer was back-extracted with 3×20 mL DCM and 2×20 mL EtOAc. The combined organic layers were washed with saturated aqueous NaHCO$_3$ (30 mL), dried over sodium sulfate and filtered. Concentration in vacuo to yield 11-2 (5-Fluoro-2-oxo-2,3-dihydro-1,3-benzoxazole-6-sulfonyl chloride) as a tan solid, which was used without purification.

A solution of LHMDS (1723 µl, 1.723 mmol, 1.0 M in THF) was added to 433 mg of the compound of Formula 1-3 (1.723 mmol) in anhydrous THF (3693 µl) which was maintained at −78° C. The reaction vessel was removed from the cooling bath and allowed to warm to RT. After 30 min, the reaction mixture was cooled to −78 C and a solution of 123.9 mg 11-2 (previously prepared, 0.492 mmol) in 123 µL of anhydrous THF was slowly added. This reaction mixture was warmed to RT over a period of 4 h at which time LCMS of the reaction mixture showed complete consumption of 11-2. The reaction was quenched with 3 mL saturated NH$_4$Cl and diluted with 10 mL EtOAc. The layers were separated, and the aqueous layer was back-extracted with 3×3 mL EtOAc. The combined organics were dried over Na$_2$SO$_4$, filtered and concentrated to give a yellow semi-solid. Purification by normal-phase chromatography (12 g ISCO column, 0-60% EtOAc: Hex) yielded 11-3 (N-(2,4-Dimethoxybenzyl)-5-fluoro-2-oxo-N-(1,2,4-thiadiazol-5-yl)-2,3-dihydro-1,3-benzoxazole-6-sulfonamide) as an off-white solid.

A reactor containing 2144 µL of THF was dissolved 100 mg of 11-3 prepared in the previous step (0.214 mmol) and 113 mg of 1-7 (0.429 mmol). The reaction mixture was cooled to 0° C. and treated sequentially with 112 mg triphenylphosphine (0.429 mmol) and 99 mg DTBAD (0.429 mmol). After 30 min maintaining the mixture at 0° C., LCMS showed consumption of 11-3. The reaction mixture was filtered through Celite and concentrated in vacuo to give an orange semi-solid. Purification by normal-phase chromatography (12 g ISCO column, 0-60% EtOAc:Hex) yielded 11-4 (tert-Butyl 8-({6-[(2,4-dimethoxybenzyl)(1,2,4-thiadiazol-5-yl)sulfamoyl]-5-fluoro-2-oxo-1,3-benzoxazol-3(2H)-yl}methyl)-3,4-dihydroisoquinoline-2(1H)-carboxylate) as a white solid.

Into a 1 dram vial containing 860 µL DCM and 215 µL TFA was added 153 mg of 11-4 (0.215 mmol). After 20 min at RT, LCMS showed complete consumption of 11-4. The reaction mixture was concentrated in vacuo, dissolved in 1 mL MeOH, filtered and purified by reverse-phase HPLC (5-60% MeCN in water with 0.1% TFA, C18 column) to yield 11-5 (5-Fluoro-2-oxo-3-(1,2,3,4-tetrahydroisoquinolin-8-ylmethyl)-N-(1,2,4-thiadiazol-5-yl)-2,3-dihydro-1,3-benzoxazole-6-sulfonamide) as a white solid. $^1$H NMR δ (ppm) (DMSO-$d_6$): 9.11 (1H, br s), 8.46 (1H, s), 7.80 (1H, d, J=5.35 Hz), 7.31 (1H, d, J=9.44 Hz), 7.28-7.19 (3H, m), 7.16 (1H, d, J=7.50 Hz), 5.03 (2H, s), 4.29 (2H, s), 3.35 (1H, s), 3.02 (3H, s). HRMS $C_{19}H_{17}FN_5O_4S_2$[M+H] calc 462.0701, obs 462.0687.

The process of Scheme 11 can be utilized to prepare additional compounds of the invention by reaction of 11-3 with an appropriate alcohol, for example, the compounds of Table 5:

TABLE 5

| # | Structure | Name | HRMS |
|---|---|---|---|
| 11-6 | 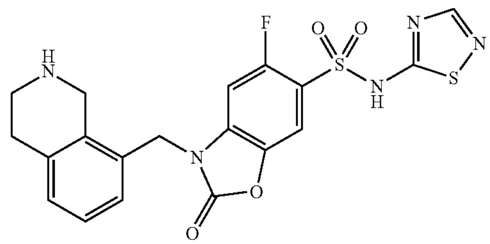 [SMILES: O=c1oc2cc(S(=O)(=O)Nc3ncns3)c(F)cc2n1Cc1cccc2c1CNCC2] | 5-fluoro-2-oxo-3-[(1S)-1-(1,2,3,4-tetrahydroisoquinolin-8-yl)ethyl]-N-1,2,4-thiadiazol-5-yl-2,3-dihydro-1,3-benzoxazole-6-sulfonamide | C20H18FN5O4S2 [M + H] calc 476.0857 obs 476.0847 |
| 11-7 | 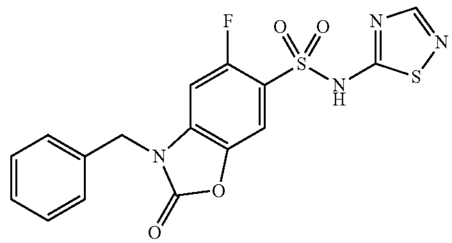 [SMILES: O=c1oc2cc(S(=O)(=O)Nc3ncns3)c(F)cc2n1Cc1ccccc1] | 3-benzyl-5-fluoro-2-oxo-N-1,2,4-thiadiazol-5-yl-2,3-dihydro-1,3-benzoxazole-6-sulfonamide | C16H11FN4O4S2 [M + H] calc 407.0279 obs 407.0268 |
| 11-8 | 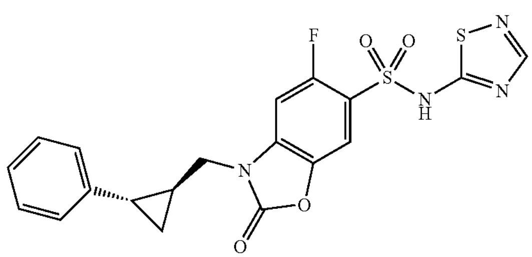 [SMILES: O=c1oc2cc(S(=O)(=O)Nc3ncns3)c(F)cc2n1C[C@H]1C[C@@H]1c1ccccc1] | 5-fluoro-2-oxo-3-{[(1S,2S)-2-phenylcyclopropyl]methyl}-N-1,2,4-thiadiazol-5-yl-2,3-dihydro-1,3-benzoxazole-6-sulfonamide | Calc'd 447.0592, found 447.0575 |
| 11-9 | 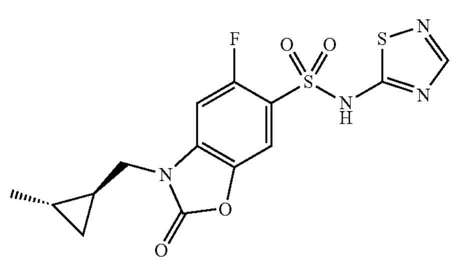 [SMILES: C[C@H]1C[C@@H]1Cn1c(=O)oc2cc(S(=O)(=O)Nc3ncns3)c(F)cc21] | 5-fluoro-3-{[(1R,2S)-2-iodocyclopropyl]methyl}-2-oxo-N-1,2,4-thiadiazol-5-yl-2,3-dihydro-1,3-benzoxazole-6-sulfonamide | Calc'd 496.9245, found 496.9228 |
| 11-10 | 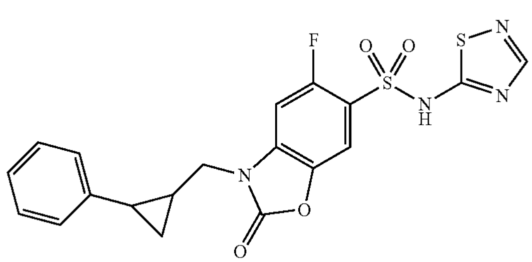 [SMILES: O=c1oc2cc(S(=O)(=O)Nc3ncns3)c(F)cc2n1CC1CC1c1ccccc1] | 5-fluoro-2-oxo-3-[(2-phenylcyclopropyl)methyl]-N-1,2,4-thiadiazol-5-yl-2,3-dihydro-1,3-benzoxazole-6-sulfonamide | Calc'd 447.0592, found 447.0575 |

TABLE 5-continued

| # | Structure | Name | HRMS |
|---|---|---|---|
| 11-11 | 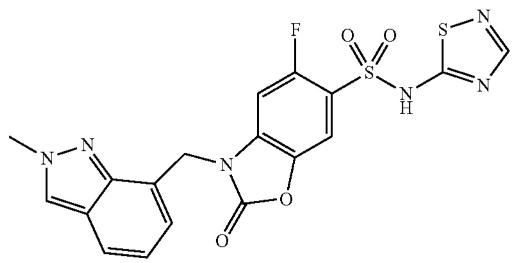 [SMILES: Cn1cc2cccc(Cn3c(=O)oc4cc(S(=O)(=O)Nc5ncns5)c(F)cc43)c2n1] | 5-fluoro-3-[(2-methyl-2H-indazol-7-yl)methyl]-2-oxo-N-1,2,4-thiadiazol-5-yl-2,3-dihydro-1,3-benzoxazole-6-sulfonamide | Calc'd 461.0496, found 461.0506 |
| 11-12 | 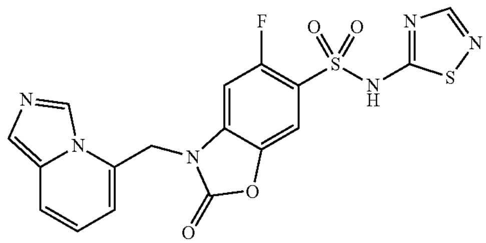 [SMILES: O=c1oc2cc(S(=O)(=O)Nc3ncns3)c(F)cc2n1Cc1cccc2cncn12] | 5-fluoro-3-(imidazo[1,5-a]pyridin-5-ylmethyl)-2-oxo-N-1,2,4-thiadiazol-5-yl-2,3-dihydro-1,3-benzoxazole-6-sulfonamide | Calc'd 447.034, found 447.0325 |
| 11-13 | 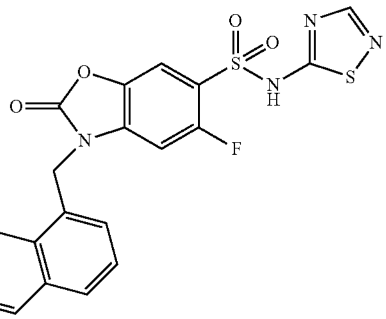 | 3-(1a,7b-dihydro-1H-cyclopropa[a]naphthalen-7-ylmethyl)-5-fluoro-2-oxo-N-1,2,4-thiadiazol-5-yl-2,3-dihydro-1,3-benzoxazole-6-sulfonamide | Calc'd 471.1, found 471.0 |

Example 9 illustrates the preparation of derived aryl alcohols using the Suzuki coupling of Scheme 3 which are suitable for use in preparing compounds of the invention via the process of Scheme 11, Step 2.

Example 9

3-{2-[(1E)-3-Aminoprop-1-en-1-yl]benzyl}-5-fluoro-2-oxo-N-(1,2,4-thiadiazol-5-yl)-2,3-dihydro-1,3-benzoxazole-6-sulfonamide (12-3)

Scheme 12

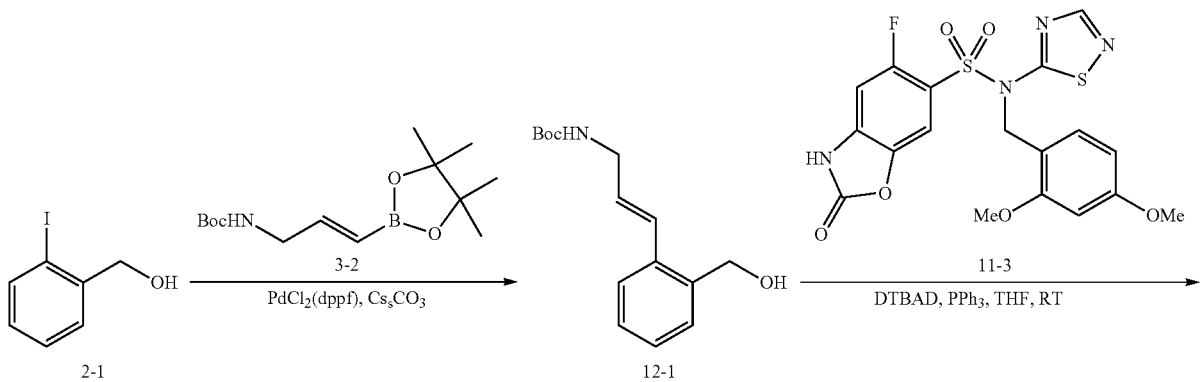

-continued

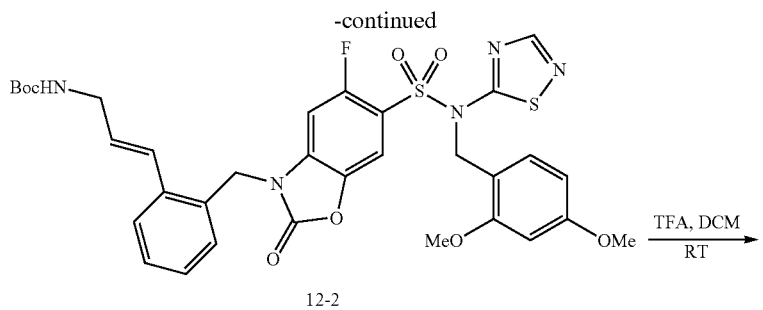

12-2

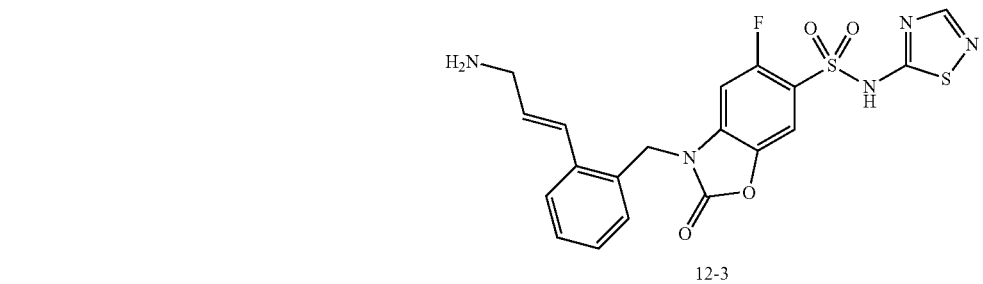

12-3

In accordance with Scheme 12, 1 g of 2-1 (2-Iodobenzyl alcohol, 4.27 mmol) and 1.425 g 3-2 (tert-butyl[(2E)-3-(4,4,5,5-tetramethyl-1,3,2-dioxaborolan-2-yl)prop-2-en-1-yl] carbamate, 5.13 mmol) were suspended in 9.50 mL degassed THF and 4.75 mL water. To this suspension was added 4.18 g cesium carbonate (12.82 mmol) and 0.313 g PdCl2(dppf) ([1,1-Bis(diphenylphosphino)ferrocene]dichloropalladium (II), 0.427 mmol). The resulting mixture was placed in a microwave emitter and heated to 120° C. After 10 min, LCMS showed complete consumption of 2-1. The reaction mixture was filtered through Celite, washed with 20 mL EtOAc and partitioned with 10 mL saturated aqueous NaHCO₃. The layers were separated and the aqueous layer was back-extracted with 3×10 mL EtOAc. The combined organics were dried over Na₂SO₄, filtered and concentrated in vacuo to give a dark oil. Purification by reverse-phase HPLC (5-80% MeCN in water with 0.1% TFA, C18 column) gave 12-1 as a dark semi-solid.

With further reference to Scheme 12, 81.8 mg of 11-3 (prepared in accordance with Example 8, Step 1, 0.175 mmol) and 92 mg of 12-1 prepared previously (0.351 mmol) were dissolved in 1754 μL THF cooled and maintained at 0° C. This solution was sequentially treated with 92 mg triphenylphosphine (0.351 mmol) and 81 mg DTBAD (0.351 mmol). After 30 min at 0° C., LCMS showed complete consumption of 11-4. The reaction contents were filtered through Celite and concentrated in vacuo to give an orange semi-solid. Purification by normal-phase chromatography (12 g ISCO column, 0-60% EtOAc:Hex) gave tert-butyl {(2E)-3-[2-({6-[(2,4-dimethoxybenzyl)(1,2,4-thiadiazol-5-yl)sulfamoyl]-5-fluoro-2-oxo-1,3-benzoxazol-3(2H)-yl}methyl)phenyl] prop-2-en-1-yl}carbamate (12-2) as a white solid.

The compound of Formula 12-2 thus prepared (125 mg, 0.176 mmol) was placed into a 1 dram vial containing 702 μL of DCM and 176 μL of TFA at ambient temperature (RT). After 20 minutes of stirring at RT, LCMS indicated complete consumption of was placed 125 mg of 12-2. The reaction mixture was concentrated in vacuo, dissolved in MeOH (1 mL), filtered and purified by reverse-phase HPLC (5-60% MeCN in water with 0.1% TFA, C18 column) to give 12-3 (3-{2-[(1E)-3-Aminoprop-1-en-1-yl]benzyl}-5-fluoro-2-oxo-N-(1,2,4-thiadiazol-5-yl)-2,3-dihydro-1,3-benzoxazole-6-sulfonamide) as a white solid. ¹H NMR δ (ppm) (DMSO-d₆): 8.40 (1H, s), 7.95 (2H, br s), 7.77 (1H, d, J=5.32 Hz), 7.50 (1H, d, J=7.71 Hz), 7.35 (1H, t, J=7.54 Hz), 7.28 (1H, t, J=7.56 Hz), 7.21 (3H, t, J=7.71 Hz), 7.09 (2H, d, J=12 Hz), 6.16-6.09 (2H, m), 5.12 (2H, s). HRMS C₁₉H₁₇FN₅O₄S₂ [M+H] calc 462.0701, obs 462.0706.

Example 10 (Scheme 13) illustrates that the Mitsunobu coupling utilized in reacting alcohols with unalkylated benzoxazolinones of the invention can be carried out between the derivatized alcohols provided in Example 3 (Scheme 4, for example the alcohol 4-2) and the fluorinated benzoxazolinone core 11-3.

Example 10

Preparation of 5-Fluoro-2-oxo-3-[(1R)-1-(1,2,3,4-tetrahydroisoquinolin-8-yl)ethyl]-N-(1,2,4-thiadiazol-5-yl)-2,3-dihydro-1,3-benzoxazole-6-sulfonamide (13-2) and related compounds Scheme 13

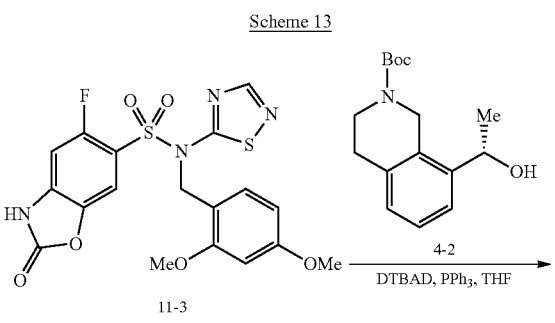

11-3

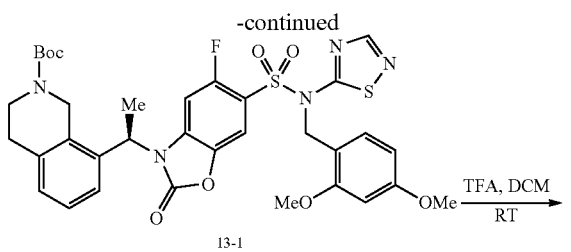

and 47.4 mg DTBAD (0.206 mmol). After 30 min at 0° C., LCMS showed consumption of 11-3. The reaction contents were filtered through Celite and concentrated in vacuo to give 13-1 (tert-Butyl 8-[(1R)-1-{6-[(2,4-dimethoxybenzyl)(1,2,4-thiadiazol-5-yl)sulfamoyl]-5-fluoro-2-oxo-1,3-benzoxazol-3(2H)-yl}ethyl]-3,4-dihydroisoquinoline-2(1H)-carboxylate) as an orange semi-solid. The crude material was carried forward without further purification.

The crude 13-1 thus prepared was dissolved in 1000 μL DCM and 250 μL TFA. After 30 min at RT, LCMS showed complete consumption of 13-1. The reaction mixture was concentrated in vacuo, dissolved in 1 mL MeOH, filtered and purified by reverse-phase HPLC (5-60% MeCN in water with 0.1% TFA, C18 column) yielding the compound of formula 13-2 (5-Fluoro-2-oxo-3-[(1R)-1-(1,2,3,4-tetrahydroisoquinolin-8-yl)ethyl]-N-(1,2,4-thiadiazol-5-yl)-2,3-dihydro-1,3-benzoxazole-6-sulfonamide) as a white solid, which was characterized: $^1$H NMR δ (ppm)(DMSO-$d_6$): 8.91 (2H, m), 8.42 (1H, s), 7.75-7.68 (2H, m), 7.43-7.37 (1H, m), 7.27 (1H, d, J=7.60 Hz), 7.18 (1H, d, J=9.65 Hz), 5.61 (1H, d, J=7.57 Hz), 4.38 (1H, m), 4.06 (1H, m), 3.26 (2H, m), 3.01 (2H, m), 1.80 (3H, d, J=6.83 Hz). HRMS $C_{20}H_{18}FN_5O_4S_2$ [M+H] calc 476.0857, obs. 476.0859

Thus, in accordance with Scheme 13, 48 mg 11-3 (0.103 mmol) and 28.5 mg of 4-2 (0.103 mmol) were dissolved in 1029 μL THF and the solution, cooled to 0° C., was sequentially treated with 54 mg triphenylphosphine (0.206 mmol)

The compounds of Table 6 were prepared by reacting the compound of Formula 11-3 with the appropriate alcohol in accordance with the process described in Scheme 13.

TABLE 6

| # | Structure | Name | HRMS |
|---|---|---|---|
| 13-3 | 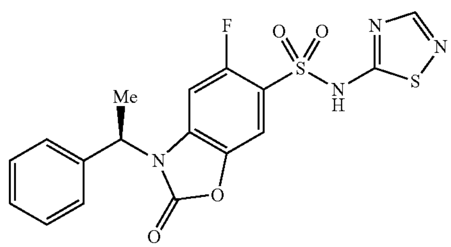 [SMILES: C[C@H](c1ccccc1)n1c(=O)oc2cc(S(=O)(=O)Nc3ncns3)c(F)cc21] | 5-fluoro-2-oxo-3-[(1R)-1-phenylethyl]-N-1,2,4-thiadiazol-5-yl-2,3-dihydro-1,3-benzoxazole-6-sulfonamide | C17H13FN4O4S2 [M + H] calc 421.0435 obs 421.10420 |
| 13-4 | 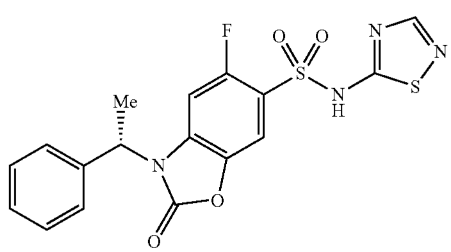 [SMILES: C[C@@H](c1ccccc1)n1c(=O)oc2cc(S(=O)(=O)Nc3ncns3)c(F)cc21] | 5-fluoro-2-oxo-3-[(1S)-1-phenylethyl]-N-1,2,4-thiadiazol-5-yl-2,3-dihydro-1,3-benzoxazole-6-sulfonamide | C17H13FN4O4S2 [M + H] calc 421.0435 obs 421.0422 |
| 13-5 | 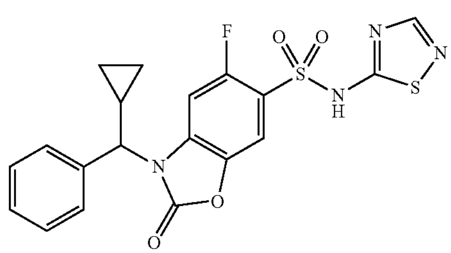 [SMILES: O=c1oc2cc(S(=O)(=O)Nc3ncns3)c(F)cc2n1C(c1ccccc1)C1CC1] | 3-[cyclopropyl(phenyl)methyl]-5-fluoro-2-oxo-N-1,2,4-thiadiazol-5-yl-2,3-dihydro-1,3-benzoxazole-6-sulfonamide | C19H15FN4O4S2 [M + H] calc 447.0592 obs 447.0597 |

TABLE 6-continued

| # | Structure | Name | HRMS |
|---|---|---|---|
| 13-6 | 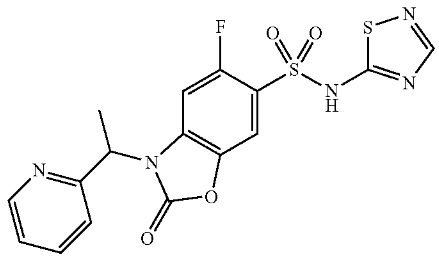 [SMILES: CC(c1ccccn1)n1c(=O)oc2cc(S(=O)(=O)Nc3ncns3)c(F)cc21] | 5-fluoro-2-oxo-3-(1-pyridin-2-ylethyl)-N-1,2,4-thiadiazol-5-yl-2,3-dihydro-1,3-benzoxazole-6-sulfonamide | Calc'd 422.0388, found 422.0400 |
| 13-7 | 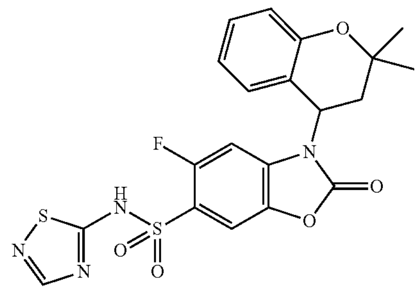 [SMILES: CC1(C)CC(n2c(=O)oc3cc(S(=O)(=O)Nc4ncns4)c(F)cc32)c2ccccc2O1] | 3-(2,2-dimethyl-3,4-dihydro-2H-chromen-4-yl)-5-fluoro-2-oxo-N-1,2,4-thiadiazol-5-yl-2,3-dihydro-1,3-benzoxazole-6-sulfonamide | Calc'd 477.1, found 477.0 |
| 13-8 | 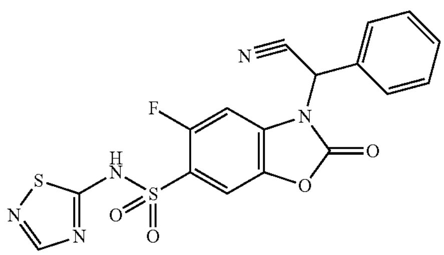 [SMILES: N#CC(c1ccccc1)n1c(=O)oc2cc(S(=O)(=O)Nc3ncns3)c(F)cc21] | 3-[cyano(phenyl)methyl]-5-fluoro-2-oxo-N-1,2,4-thiadiazol-5-yl-2,3-dihydro-1,3-benzoxazole-6-sulfonamide | Calc'd 432.0, found 431.9 |
| 13-9 | 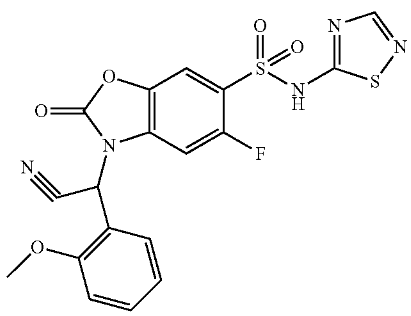 [SMILES: COc1ccccc1C(C#N)n1c(=O)oc2cc(S(=O)(=O)Nc3ncns3)c(F)cc21] | 3-[cyano(2-methoxyphenyl)methyl]-5-fluoro-2-oxo-N-1,2,4-thiadiazol-5-yl-2,3-dihydro-1,3-benzoxazole-6-sulfonamide | Calc'd 462.0, found 462.0 |
| 13-10 | 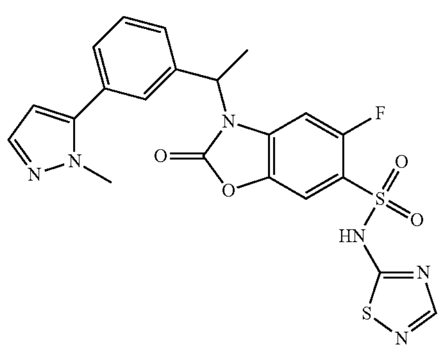 [SMILES: CC(c1cccc(-c2ccnn2C)c1)n1c(=O)oc2cc(S(=O)(=O)Nc3ncns3)c(F)cc21] | 5-fluoro-3-{1-[3-(1-methyl-1H-pyrazol-5-yl)phenyl]ethyl}-2-oxo-N-1,2,4-thiadiazol-5-yl-2,3-dihydro-1,3-benzoxazole-6-sulfonamide | Calc'd 501.0809, found 501.0917 |

TABLE 6-continued

| # | Structure | Name | HRMS |
|---|---|---|---|
| 13-11 | 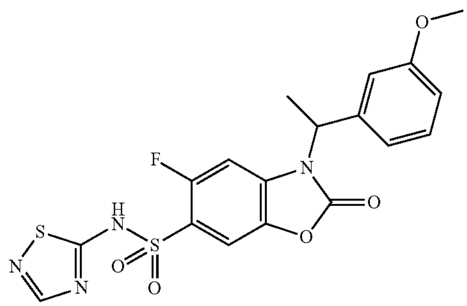 [SMILES: COc1cccc(C(C)n2c(=O)oc3cc(S(=O)(=O)Nc4ncns4)c(F)cc32)c1] | 5-fluoro-3-[1-{3-methoxyphenyl)ethyl]-2-oxo-N-1,2,4-thiadiazol-5-yl-2,3-dihydro-1,3-benzoxazole-6-sulfonamide | Calc'd 451.054, found 451.0 |
| 13-12 | 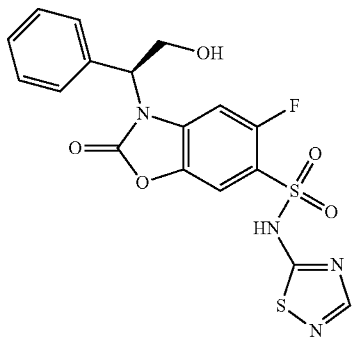 [SMILES: O=c1oc2cc(S(=O)(=O)Nc3ncns3)c(F)cc2n1[C@H](CO)c1ccccc1] | 5-fluoro-3-[(1S)-2-hydroxy-1-phenylethyl]-2-oxo-N-1,2,4-thiadiazol-5-yl-2,3-dihydro-1,3-benzoxazole-6-sulfonamide | Calc'd 437.0384, found 437.0364 |
| 13-13 | 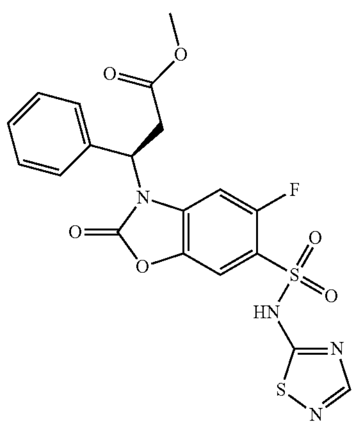 [SMILES: COC(=O)C[C@H](c1ccccc1)n1c(=O)oc2cc(S(=O)(=O)Nc3ncns3)c(F)cc21] | methyl (3R)-3-[5-fluoro-2-oxo-6-{1,2,4-thiadiazol-5-ylsulfamoyl)-1,3-benzoxazol-3(2H)-yl]-3-phenylpropanoate | Calc'd 479.0490, found 479.0499 |

Example 10

Preparation of (R)-3-(1-(isoquinolin-8-yl)ethyl)-2-oxo-N-(1,2,4-thiadiazol-5-yl)-2,3-dihydrobenzo[d]oxazole-6-sulfonamide (14-7)

Scheme 14

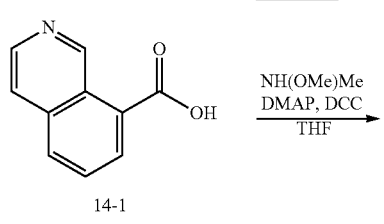

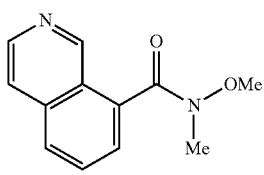

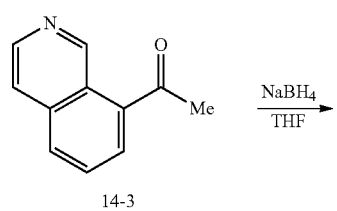

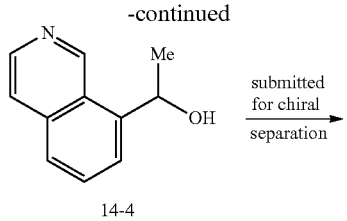

14-4

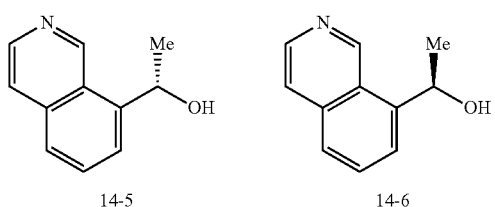

14-5          14-6

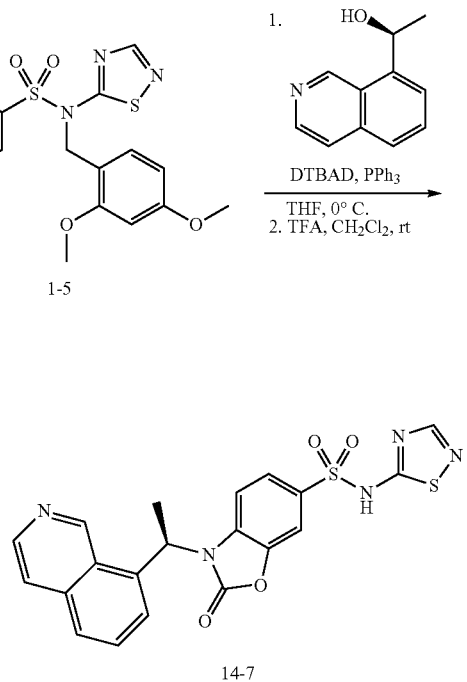

14-7

Preparation of N-Methoxy-N-methylisoquinoline-8-carboxamide (14-2)

Commercially available isoquinoline-8-carboxylic acid (0.4 g, 2.31 mmol), N,O-dimethylhydroxylamine hydrochloride (0.45 g, 4.62 mmol), DMAP (0.28 g, 2.31 mmol), and polymer-supported DCC (0.71 g, 3.46 mmol) were charged in a 50 mL round bottom flask. Then anhydrous THF (23 mL) was added. The reaction was stirred overnight at RT. The reaction mixture was filtered and filtrate was concentrated. Purification by normal phase chromatography (0-50% EtOAc in hexane) yielded N-methoxy-N-methylisoquinoline-8-carboxamide (14-2).

Preparation of 1-(Isoquinolin-8-yl)ethanone (14-3)

A solution of N-methoxy-N-methylisoquinoline-8-carboxamide (1.04 g, 4.81 mmol) in THF (40.1 ml) at 0° C. was treated with methylmagnesium bromide (11.22 ml, 33.7 mmol) in THF. Reaction was stirred at 0° C. for 1 hours before quenching with a saturated ammonium chloride solution (5 mL). After reaching RT, solution extracted with EtOAc (3×75 mL). Combined organic layers were washed with brine, dried over sodium sulfate, filtered and concentrated. Purified by normal phase chromatography (0-50% EtOAc in hexane) to yield 1-(isoquinolin-8-yl)ethanone as an oil.

Preparation of (S)-1-(Isoquinolin-8-yl)ethanol (14-6)

1-(isoquinolin-8-yl)ethanone (0.64 g, 3.74 mmol) in EtOH (37 mL) was added with sodium borohydride (2.26 g, 59.8 mmol). The reaction mixture was stirred overnight. The reaction mixture was quenched with 1M NaOH and extracted with DCM. Purified by normal phase chromatography (10-60% EtOAc in hexane) to yield 1-(isoquinolin-8-yl)ethanol as an oil. Chiral separation (ChiralPak AD-H) provided (S)-1-(isoquinolin-8-yl)ethanol and (R)-1-(isoquinolin-8-yl)ethanol.

Preparation of (R)-3-(1-(Isoquinolin-8-yl)ethyl)-2-oxo-N-(1,2,4-thiadiazol-5-yl)-2,3-dihydrobenzo[d]oxazole-6-sulfonamide (14-7)

A solution of N-(2,4-dimethoxybenzyl)-2-oxo-N-(1,2,4-thiadiazol-5-yl)-2,3-dihydrobenzo[d]oxazole-6-sulfonamide (100 mg, 0.214 mmol) and (S)-1-(isoquinolin-8-yl)ethanol (74.3 mg, 0.429 mmol) in THF (1072 µl) at 0° C. was treated with PS-triphenylphosphine (112 mg, 0.429 mmol) (0.233 g resin-bound PPh$_3$, 1.84 mmol PPh$_3$/g of resin), and (E)-di-tert-butyl diazene-1,2-dicarboxylate (99 mg, 0.429 mmol). Reaction mixtured was monitored at 0° C. After stirring at 0° C. for 2 h, the reaction was filtered and concentrated in vacuo. Residue was dissolved in 1 mL of DCM and treated with 0.25 mL of TFA. After stirring at RT for 30 minutes, the solvent and TFA were removed in vacuo. Purified by reverse phase chromatography (10-95% MeCN in water w/0.1% TFA, C18 column) to yield 14-7. $^1$H NMR δ (ppm)(CH$_3$OH-d$_4$): 9.86 (1H, s), 8.61 (1H, d, J=6.42 Hz), 8.47 (2H, dd, J=14.05, 6.52 Hz), 8.32-8.24 (2H, m), 8.14 (1H, s), 7.64-7.57 (2H, m), 7.29 (1H, d, J=8.39 Hz), 6.64-6.55 (1H, m), 2.15 (3H, d, J=7.05 Hz). HRMS [M+H]C$_{20}$H$_{15}$N$_5$O$_4$S$_2$ calc'd 454.0638. Found 454.0633.

The following compounds were prepared from 1-5 or 11-3 and 14-5 or 14-6 analogously to the synthetic sequence depicted in Scheme HF-1:

TABLE 7

| # | Structure | Name | HRMS |
|---|---|---|---|
| 14-8 | 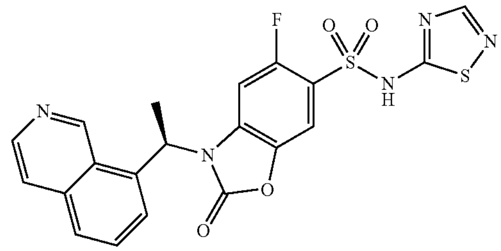 [SMILES: C[C@H](c1cccc2ccncc12)n1c(=O)oc2cc(S(=O)(=O)Nc3ncns3)c(F)cc21] | 5-fluoro-3-[(1R)-1-isoquinolin-8-ylethyl]-2-oxo-N-1,2,4-thiadiazol-5-yl-2,3-dihydro-1,3-benzoxazole-6-sulfonamid | Calc'd 472.0544, found 472.0534 |
| 14-9 | 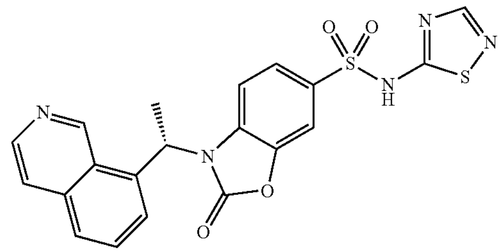 [SMILES: C[C@@H](c1cccc2ccncc12)n1c(=O)oc2cc(S(=O)(=O)Nc3ncns3)ccc21] | 3-[(1S)-1-isoquinolin-8-ylethyl]-2-oxo-N-1,2,4-thiadiazol-5-yl-2,3-dihydro-1,3-benzoxazole-6-sulfonamide | Calc'd 454.064, found 454.0632 |
| 14-10 | 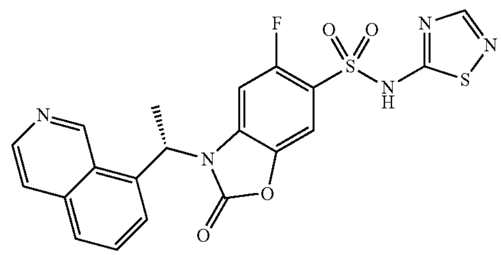 [SMILES: C[C@@H](c1cccc2ccncc12)n1c(=O)oc2cc(S(=O)(=O)Nc3ncns3)c(F)cc21] | 5-fluoro-3-[(1S)-1-isoquinolin-8-ylethyl]-2-oxo-N-1,2,4-thiadiazol-5-yl-2,3-dihydro-1,3-benzoxazole-6-sulfonamide | Calc'd 472.0544, found 472.0534 |

Example 12

Preparation of (R)-5-Fluoro-3-(1-(imidazo[1,5-a]pyridin-5-yl)ethyl)-2-oxo-N-(1,2,4-thiadiazol-5-yl)-2,3-dihydrobenzo[d]oxazole-6-sulfonamide (15-3)

Scheme 15

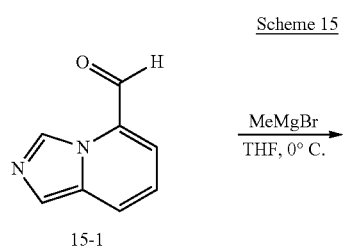

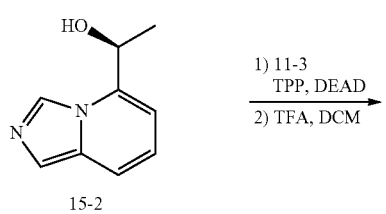

-continued

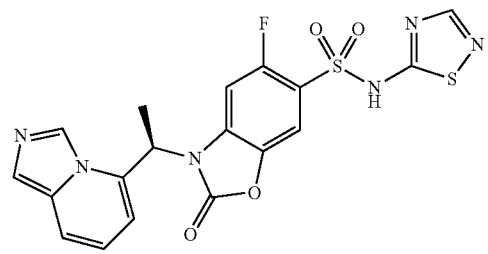

Preparation of(S)-1-(Imidazo[1,5-a]pyridin-5-yl)ethanol (15-2)

A solution of commercial 15-1 (0.4 g, 2.74 mmol) in THF (13.68 ml) was treated with methylmagnesium bromide (4.1 ml, 12.3 mmol, 3M in diethyl ether) at 0° C. After stirring at 0° C. for 2 hours, the reaction was quenched with NH₄Cl solution (5 mL). Extracted into EtOAc (3×50 mL). Combined organic layers were dried with Sodium sulfate, filtered and concentrated under reduced pressure. Purified by normal phase chromatography (0-10% MeOH in EtOAc). Chiral separation of isolated material (ChiralPak OJ-H) provided 15-2.

Preparation of (R)-5-Fluoro-3-(1-(imidazo[1,5-a]pyridin-5-yl)ethyl)-2-oxo-N-(1,2,4-thiadiazol-5-yl)-2,3-dihydrobenzo[d]oxazole-6-sulfonamide (15-3)

A solution of 11-3 (100 mg, 0.214 mmol) in THF (1 mL) was treated with DEAD (67.9 μl, 0.429 mmol) followed by triphenylphosphine (112 mg, 0.429 mmol) and 15-2 (34.8 mg, 0.214 mmol). After stirring overnight at RT, the reaction was concentrated under reduced pressure. Purified by normal phase chromatography (0-100% EtOAc in hexane). Isolated material was taken up in 2 mL of DCM and treated with 0.3 mL of TFA. After stirring for 30 minutes at RT, the solvent and TFA were removed under reduced pressure. Purified by reverse phase chromatography (5-75% MeCN in water with 0.1% TFA, C18 column) to yield 15-3 as a solid. $^1$H NMR δ (ppm)(DMSO-d$_6$): 8.47 (1H, s), 7.78-7.73 (3H, m), 7.47 (1H, s), 7.45-7.41 (2H, m), 7.09-7.04 (1H, m), 6.07-6.03 (1H, m), 1.95 (3H, d, J=6.96 Hz). HRMS C18H13FN6O4S2 [M+H] calc 461.0496, obs. 461.0488

The following compound was prepared from 11-3 and ent-15-2 analogously to the synthetic sequence depicted in Scheme 15:

TABLE 8

| # | Structure | Name | Exact Mass [M + H]+ |
|---|---|---|---|
| 15-4 | 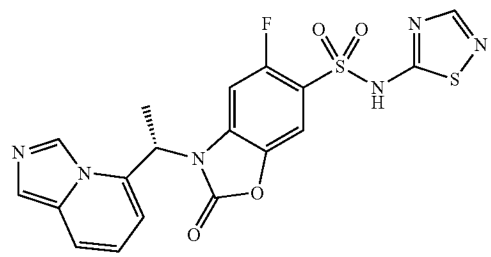 [SMILES: C[C@@H](c1cccc2cncn12)n1c(=O)oc2cc(S(=O)(=O)Nc3ncns3)c(F)cc21] | 5-fluoro-3-[(1S)-1-imidazo[1,5-a]pyridin-5-ylethyl]-2-oxo-N-1,2,4-thiadiazol-5-yl-2,3-dihydro-1,3-benzoxazole-6-sulfonamide | Calc'd 461.0496, found 461.0503 |

Example 13

Preparation of (R)-5-Fluoro-2-oxo-3-(1-(2-(1,2,3,6-tetrahydropyridin-4-yl)phenyl)ethyl)-N-(1,2,4-thiadiazol-5-yl)-2,3-dihydrobenzo[d]oxazole-6-sulfonamide (16-4)

Scheme 16

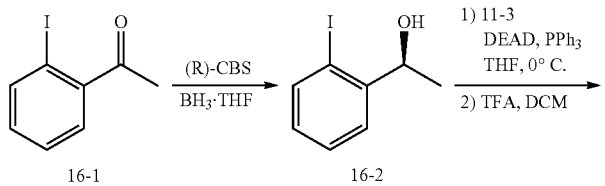

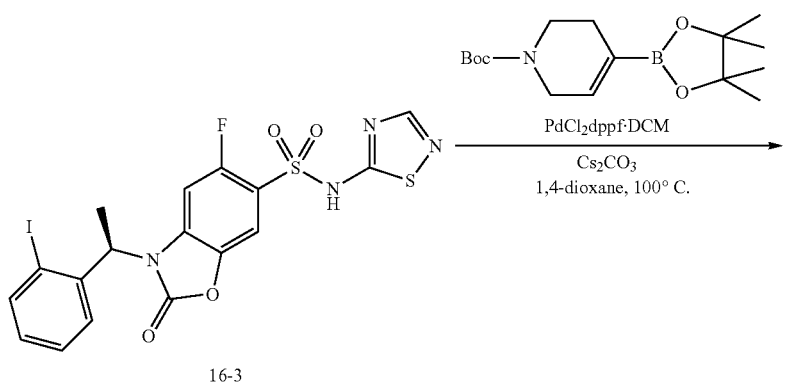

16-3

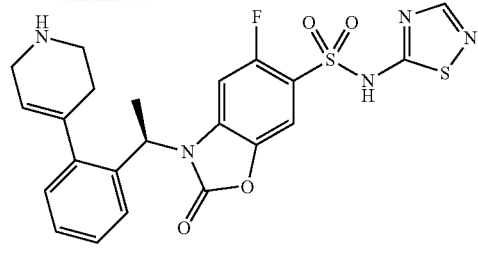

16-4

Preparation of (S)-1-(2-Iodophenyl)ethanol (16-2)

A solution of (R)-CBS (20.32 ml, 20.32 mmol) and 16-1 (5 g, 20.32 mmol) in THF (102 ml) was treated with $BH_3 \cdot THF$ (20.32 ml, 20.32 mmol, 1M in THF) that was diluted with an additional 50 mL of THF, and delivered via syringe pump at 75 mL/hr. Quenched with 2N HCl (50 mL), extracted into EtOAc (150 mL) and dried over Sodium sulfate before concentrating in vacuo. Material was taken up in dichloromethane and filtered. Filtrate was purified by normal phase chromatography (0-30% EtOAc in hexane). Isolated material chiral separated (ChiralPak AD-H) to yield 16-2 as a white solid.

(R)-5-Fluoro-3-(1-(2-iodophenyl)ethyl)-2-oxo-N-(1,2,4-thiadiazol-5-yl)-2,3-dihydrobenzo[d]oxazole-6-sulfonamide (16-3)

A solution of 11-3 and DEAD (1.154 ml, 7.29 mmol) in THF (18.22 ml) was treated with triphenylphosphine (1.912 g, 7.29 mmol) followed by 16-2 (0.949 g, 3.83 mmol) addition at 0° C. After stirring overnight at RT, the reaction was concentrated in vacuo. Purified by normal phase chromatography (0-40% EtOAc in hexane). Isolated material was taken up in DCM (10 ml) and was treated with TFA (2 ml). After stirring for 30 minutes at ambient temperature, the solvent was removed in vacuo. Purified by reverse phase chromatography (15-95% MeCN in water w/0.1% TFA, C18 column) to yield 16-3 as a solid.

(R)-5-Fluoro-2-oxo-3-(1-(2-(1,2,3,6-tetrahydropyridin-4-yl)phenyl)ethyl)-N-(1,2,4-thiadiazol-5-yl)-2,3-dihydrobenzo[d]oxazole-6-sulfonamide (16-4)

A solution of 16-3 (30 mg, 0.06 mmol), commercial tert-butyl 4-(4,4,5,5-tetramethyl-1,3,2-dioxaborolan-2-yl)-5,6-dihydropyridine-1(2H)-carboxylate (19 mg, 0.06 mmol), $PdCl_2dppf$ DCM adduct (9 mg, 0.011 mmol), and $Cs_2CO_3$ (0.165 mL, 1M in water, 0.165 mmol) in 1,4-Dioxane (0.5 mL) was degassed with nitrogen and heated in a microwave reactor for 30 minutes at 100° C. Purified by reverse phase chromatography (5-70% MeCN in water w/0.1% TFA, C18 column) to yield 16-4 as the TFA salt. $^1H$ NMR δ (ppm) (DMSO-$d_6$): 8.79 (2H, s), 8.44 (1H, s), 7.78-7.71 (2H, m), 7.46-7.36 (2H, m), 7.08 (1H, d, J=7.42 Hz), 7.02 (1H, d, J=9.77 Hz), 5.71-5.64 (1H, m), 5.42 (1H, s), 2.61-2.50 (1H, m), 2.17-2.07 (1H, m), 1.82 (3H, d, J=7.08 Hz). Note: some proton peaks were obscured by $H_2O$ peak in NMR spectrum. HRMS C22H20FN5O4S2 [M+H] calc: 502.1014, obs: 502.1004.

The following compounds were prepared from 16-3 and the appropriate boronic ester by analogy to the synthetic sequence described in Scheme 16:

TABLE 9

| # | Structure | Name | Exact Mass [M + H]+ |
|---|---|---|---|
| 16-5 | 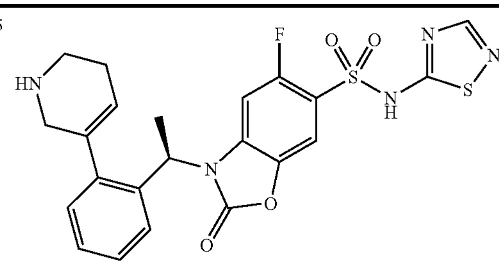 | 5-fluoro-2-oxo-3-{(1R)-1-[2-(1,2,5,6-tetrahydropyridin-3-yl)phenyl]ethyl}-N-1,2,4-thiadiazol-5-yl-2,3-dihydro-1,3-benzoxazole-6-sulfonamide | Calc'd 502.1014, found 502.1014 |
| 16-6 | 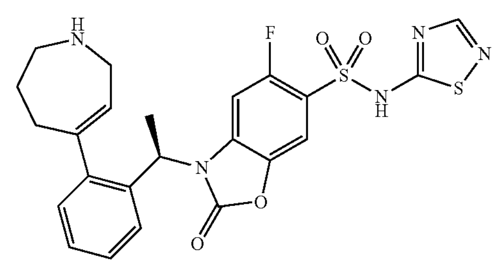 [SMILES: C[C@H](c1ccccc1C1=CCNCCC1)n1c(=O)oc2cc(S(=O)(=O)Nc3ncns3)c(F)cc21] | 5-fluoro-2-oxo-3-{(1R)-1-[2-(2,5,6,7-tetrahydro-1H-azepin-4-yl)phenyl]ethyl}-N-1,2,4-thiadiazol-5-yl-2,3-dihydro-1,3-benzoxazole-6-sulfonamide | Calc'd 516.1170, found 516.1164 |

Example 14

Preparation of (R)-3-(1-(2-((1-aminocyclopropyl)ethynyl)phenyl)ethyl)-5-fluoro-2-oxo-N-(1,2,4-thiadiazol-5-yl)-2,3-dihydrobenzo[d]oxazole-6-sulfonamide (17-1)

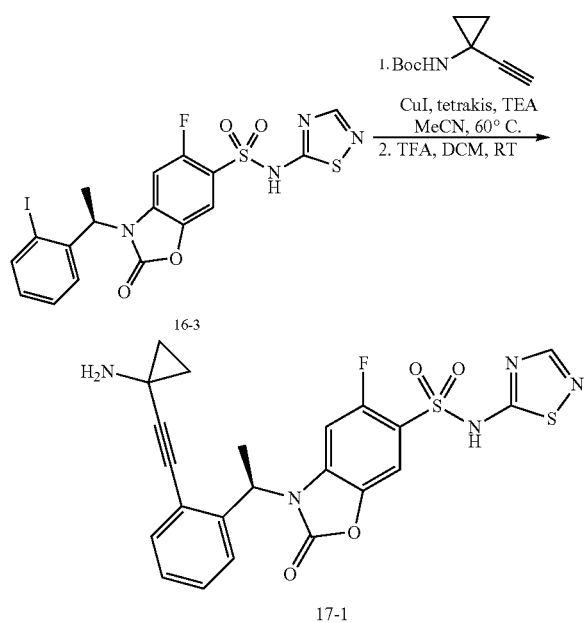

Scheme 17

A solution of 16-3 (20 mg, 0.037 mmol), commercial tert-butyl (1-ethynylcyclo-propyl)carbamate (13.27 mg, 0.073 mmol), Copper (I) iodide (2.092 mg, 10.98 µmol), Tetrakis (4.23 mg, 3.66 mol), and triethylamine (255 µl, 1.830 mmol) in degassed MeCN (400 µl) was heated to 60° C. for 1 hour. Purified by reverse phase chromatography (10-95% MeCN in water w/0.1% TFA, C18 column). Collected fractions were diluted with 25 mL of EtOAc and washed with bicarbonate solution (10 mL). Organic layer was dried over sodium sulfate, filtered and concentrated in vacuo to yield (R)-tert-butyl (1-((2-(1-(6-(N-(1,2,4-thiadiazol-5-yl)sulfamoyl)-5-fluoro-2-oxobenzo[d]oxazol-3(2H)-yl)ethyl)phenyl)ethynyl)cyclopropyl)-carbamate, TFA as a solid. The isolated material was then treated with 1 mL of DCM and 0.2 mL of TFA. After stirring at RT for 30 minutes, the solvent was removed in vacuo. Purified by reverse phase chromatography (5-70% MeCN in water w/0.1% TFA)(C18 column) to yield 17-1 (6 mg, 9.78 mol, 26.7% yield) as a solid. $^1$H NMR δ (ppm) (DMSO-$d_6$): 8.48 (1H, s), 7.77 (2H, t, J=5.77 Hz), 7.54 (1H, t, J=7.62 Hz), 7.51-7.41 (2H, m), 6.90 (1H, d, J=9.69 Hz), 5.72-5.65 (1H, m), 1.82 (3H, d, J=7.10 Hz), 1.36-1.18 (4H, m). HRMS C22H18FN5O4S2 [M+H] calc 500.0857, obs. 500.0850.

Table 10 describes additional compounds prepared from 16-3 and the appropriate alkyne using the reaction conditions described in Scheme 17:

TABLE 10

| # | Structure | Name | Exact Mass [M + H]+ |
|---|---|---|---|
| 17-2 | 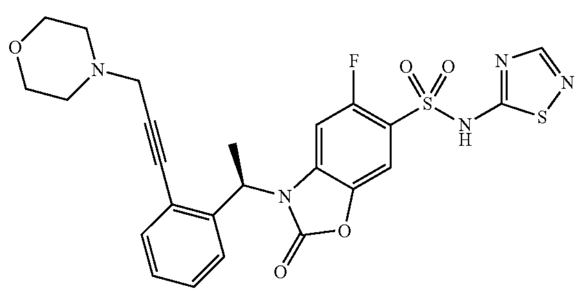 [SMILES: C[C@H](c1ccccc1C#CCN1CCOCC1)n1c(=O)oc2cc(S(=O)(=O)Nc3ncns3)c(F)cc21] | 5-fluoro-3-{(1R)-1-[2-(3-morpholin-4-ylprop-1-yn-1-yl)phenyl]ethyl}-2-oxo-N-1,2,4-thiadiazol-5-yl-2,3-dihydro-1,3-benzoxazole-6-sulfonamide | Calc'd 544.1119, found 544.1111 |
| 17-3 | 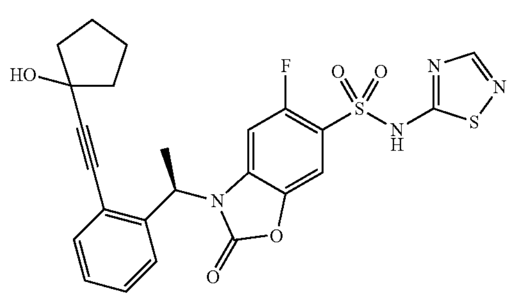 [SMILES: C[C@H](c1ccccc1C#CC1(O)CCCC1)n1c(=O)oc2cc(S(=O)(=O)Nc3ncns3)c(F)cc21] | 5-fluoro-3-[(1R)-1-{2-[(1-hydroxycyclopentyl)ethynyl]phenyl}ethyl]-2-oxo-N-1,2,4-thiadiazol-5-yl-2,3-dihydro-1,3-benzoxazole-6-sulfonamide | Calc'd 529.6, found 529.3 |

TABLE 10-continued

| # | Structure | Name | Exact Mass [M + H]+ |
|---|---|---|---|
| 17-4 | 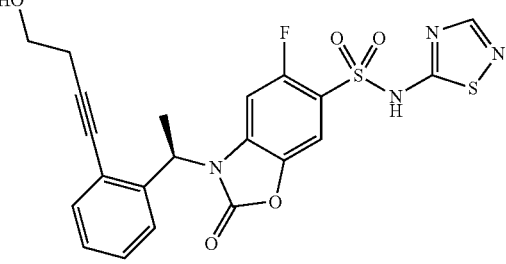 | 5-fluoro-3-{(1R)-1-[2-(4-hydroxybut-1-yn-1-yl)phenyl]ethyl}-2-oxo-N-1,2,4-thiadiazol-5-yl-2,3-dihydro-1,3-benzoxazole-6-sulfonamide | Calc'd 489.0697, found 489.0689 |
| 17-5 | 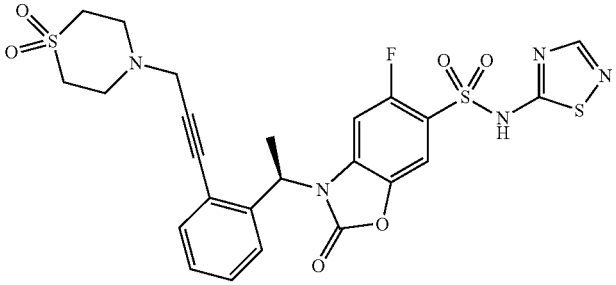 [SMILES: C[C@H](c1ccccc1C#CCN1CCS(=O)(=O)CC1)n1c(=O)oc2cc(S(=O)(=O)Nc3ncns3)c(F)cc21] | 3-[(1R)-1-{2-[3-(1,1-dioxidothiomorpholin-4-yl)prop-1-yn-1-yl]phenyl}ethyl)-5-fluoro-2-oxo-N-1,2,4-thiadiazol-5-yl-2,3-dihydro-1,3-benzoxazole-6-sulfonamide | Calc'd 592.0789, found 592.0776 |
| 17-6 | 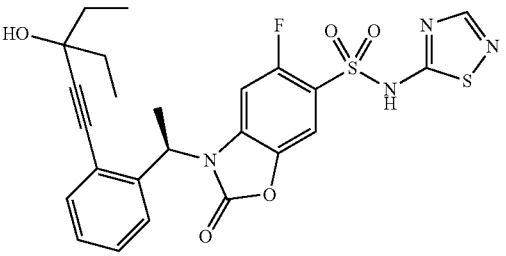 [SMILES: CCC(O)(C#Cc1ccccc1[C@@H](C)n1c(=O)oc2cc(S(=O)(=O)Nc3ncns3)c(F)cc21)CC] | 3-{(1R)-1-[2-(3-ethyl-3-hydroxypent-1-yn-1-yl)phenyl]ethyl}-5-fluoro-2-oxo-N-1,2,4-thiadiazol-5-yl-2,3-dihydro-1,3-benzoxazole-6-sulfonamide | Calc'd 531.6, found 531.2 |
| 17-7 | 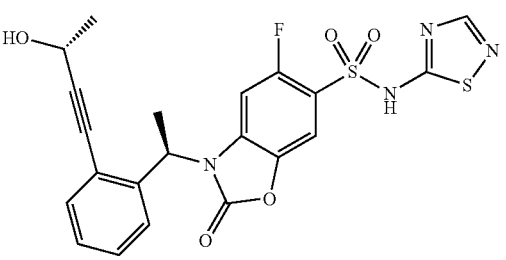 [SMILES: C[C@H](c1ccccc1C#C[C@@H](C)O)n1c(=O)oc2cc(S(=O)(=O)Nc3ncns3)c(F)cc21] | 5-fluoro-3-[(1R)-1-{2-[(3R)-3-hydroxybut-1-yn-1-yl]phenyl}ethyl]-2-oxo-N-1,2,4-thiadiazol-5-yl-2,3-dihydro-1,3-benzoxazole-6-sulfonamide | Calc'd 489.0697, found 489.0681 |
| 17-8 | 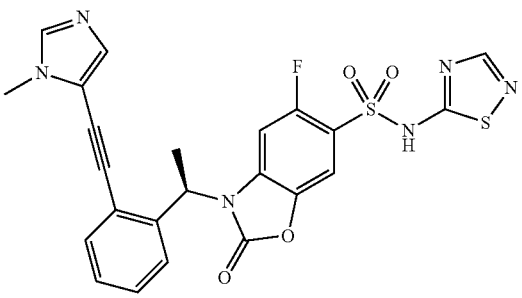 [SMILES: C[C@H](c1ccccc1C#Cc1cncn1C)n1c(=O)oc2cc(S(=O)(=O)Nc3ncns3)c(F)cc21] | 5-fluoro-3-[(1R)-1-{2-[(1-methyl-1H-imidazol-5-yl)ethynyl]phenyl}ethyl]-2-oxo-N-1,2,4-thiadiazol-5-yl-2,3-dihydro-1,3-benzoxazole-6-sulfonamide | Calc'd 525.0809, found 525.0802 |

TABLE 10-continued

| # | Structure | Name | Exact Mass [M + H]+ |
|---|---|---|---|
| 17-9 | 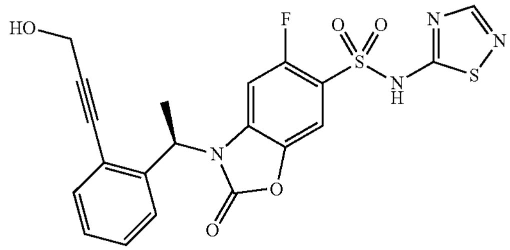 [SMILES: C[C@H](c1ccccc1C#CCO)n1c(=O)oc2cc(S(=O)(=O)Nc3ncns3)c(F)cc21] | 5-fluoro-3-{(1R)-1-[2-(3-hydroxyprop-1-yn-1-yl)phenyl]ethyl}-2-oxo-N-1,2,4-thiadiazol-5-yl-2,3-dihydro-1,3-benzoxazole-6-sulfonamide | Calc'd 475.0541, found 475.0534 |
| 17-10 | 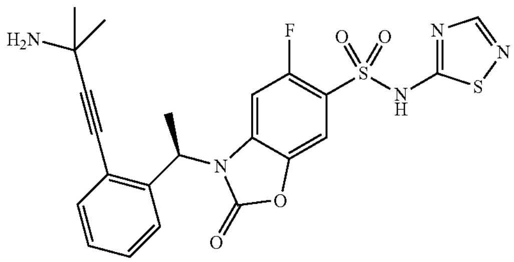 [SMILES: C[C@H](c1ccccc1C#CC(C)(C)N)n1c(=O)oc2cc(S(=O)(=O)Nc3ncns3)c(F)cc21] | 3-{(1R)-1-[2-(3-amino-3-methylbut-1-yn-1-yl)phenyl]ethyl}-5-fluoro-2-oxo-N-1,2,4-thiadiazol-5-yl-2,3-dihydro-1,3-benzoxazole-6-sulfonamide | Calc'd 502.1014, found 502.1006 |
| 17-11 | 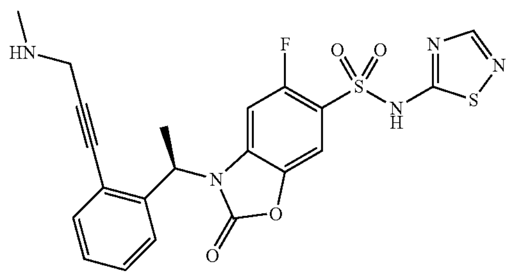 [SMILES: CNCC#Cc1ccccc1[C@@H](C)n1c(=O)oc2cc(S(=O)(=O)Nc3ncns3)c(F)cc21] | 5-fluoro-3-[(1R)-1-{2-[3-(methylamino)prop-1-yn-1-yl]phenyl}ethyl]-2-oxo-N-1,2,4-thiadiazol-5-yl-2,3-dihydro-1,3-benzoxazole-6-sulfonamide | Calc'd 488.0857, found 488.0855 |
| 17-12 | 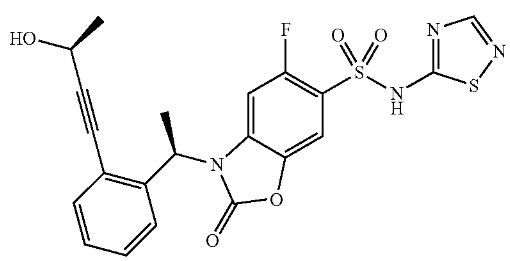 [SMILES: C[C@H](O)C#Cc1ccccc1[C@@H](C)n1c(=O)oc2cc(S(=O)(=O)Nc3ncns3)c(F)cc21] | 5-fluoro-3-[(1R)-1-{2-[(3S)-3-hydroxybut-1-yn-1-yl]phenyl}ethyl]-2-oxo-N-1,2,4-thiadiazol-5-yl-2,3-dihydro-1,3-benzoxazole-6-sulfonamide | Calc'd 489.0697, found 489.0680 |
| 17-13 | 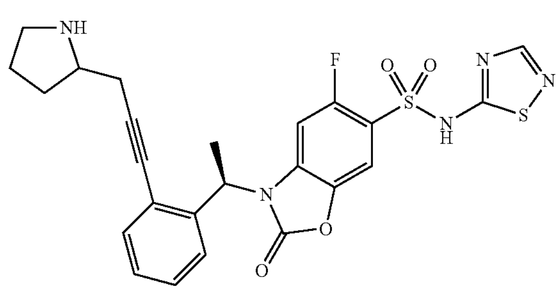 [SMILES: C[C@H](c1ccccc1C#CCC1CCCN1)n1c(=O)oc2cc(S(=O)(=O)Nc3ncns3)c(F)cc21] | 5-fluoro-2-oxo-3-{(1R)-1-[2-(3-pyrrolidin-2-ylprop-1-yn-1-yl)phenyl]ethyl}-N-1,2,4-thiadiazol-5-yl-2,3-dihydro-1,3-benzoxazole-6-sulfonamide | Calc'd 528.1170, found 528.1164 |

TABLE 10-continued

| # | Structure | Name | Exact Mass [M + H]+ |
|---|---|---|---|
| 17-14 | 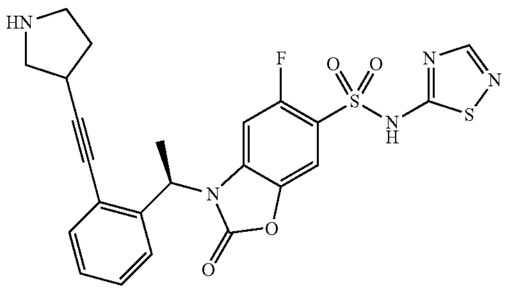 [SMILES: C[C@H](c1ccccc1C#CC1CCNC1)n1c(=O)oc2cc(S(=O)(=O)Nc3ncns3)c(F)cc21] | 5-fluoro-2-oxo-3-{(1R)-1-[2-(pyrrolidin-3-ylethynyl)phenyl]ethyl}-N-1,2,4-thiadiazol-5-yl-2,3-dihydro-1,3-benzoxazole-6-sulfonamide | Calc'd 514.1014, found 514.1009 |
| 17-15 | 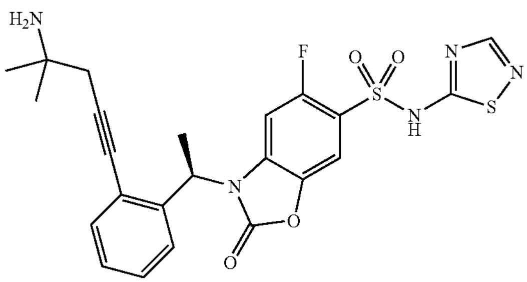 [SMILES: C[C@H](c1ccccc1C#CCC(C)(C)N)n1c(=O)oc2cc(S(=O)(=O)Nc3ncns3)c(F)cc21] | 3-{(1R)-1-[2-(4-amino-4-methylpent-1-yn-1-yl)phenyl]ethyl}-5-fluoro-2-oxo-N-1,2,4-thiadiazol-5-yl-2,3-dihydro-1,3-benzoxazole-6-sulfonamide | Calc'd 516.117, found 516.1164 |
| 17-16 | 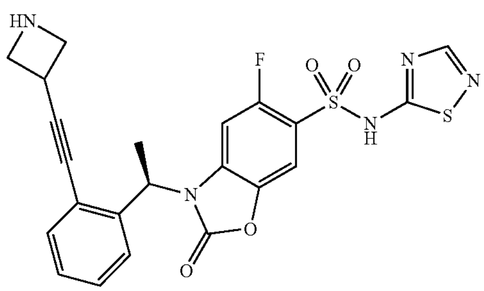 [SMILES: C[C@H](c1ccccc1C#CC1CNC1)n1c(=O)oc2cc(S(=O)(=O)Nc3ncns3)c(F)cc21] | 3-{(1R)-1-[2-(azetidin-3-ylethynyl)phenyl]ethyl}-5-fluoro-2-oxo-N-1,2,4-thiadiazol-5-yl-2,3-dihydro-1,3-benzoxazole-6-sulfonamide | Calc'd 500.0857, found 500.0852 |
| 17-17 | 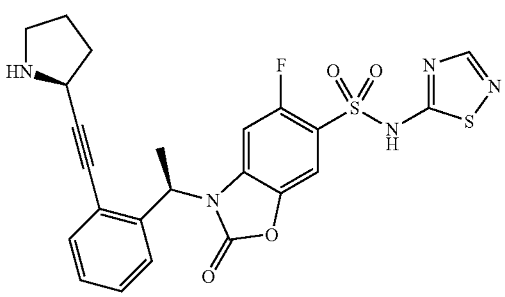 [SMILES: C[C@H](c1ccccc1C#C[C@@H]1CCCN1)n1c(=O)oc2cc(S(=O)(=O)Nc3ncns3)c(F)cc21] | 5-fluoro-2-oxo-3-[(1R)-1-{2-[(2S)-pyrrolidin-2-ylethynyl]phenyl}ethyl]-N-1,2,4-thiadiazol-5-yl-2,3-dihydro-1,3-benzoxazole-6-sulfonamide | Calc'd 514.1014, found 514.1010 |
| 17-18 | 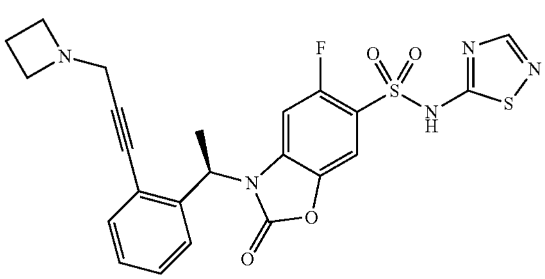 [SMILES: C[C@H](c1ccccc1C#CCN1CCC1)n1c(=O)oc2cc(S(=O)(=O)Nc3ncns3)c(F)cc21] | 3-{(1R)-1-[2-(3-azetidin-1-ylprop-1-yn-1-yl)phenyl]ethyl}-5-fluoro-2-oxo-N-1,2,4-thiadiazol-5-yl-2,3-dihydro-1,3-benzoxazole-6-sulfonamide | Calc'd 514.1014, found 514.1004 |

TABLE 10-continued

| # | Structure | Name | Exact Mass [M + H]+ |
|---|---|---|---|
| 17-19 | 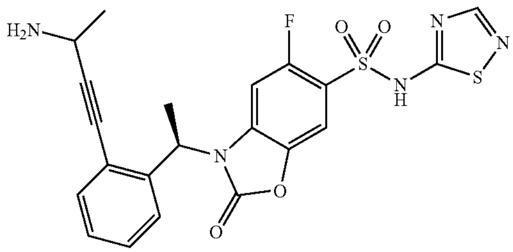 [SMILES: CC(N)C#Cc1ccccc1[C@@H](C)n1c(=O)oc2cc(S(=O)(=O)Nc3ncns3)c(F)cc21] | 3-{(1R)-1-[2-(3-aminobut-1-yn-1-yl)phenyl]ethyl}-5-fluoro-2-oxo-N-1,2,4-thiadiazol-5-yl-2,3-dihydro-1,3-benzoxazole-6-sulfonamide | Calc'd 488.0857, found 488.0848 |
| 17-20 | 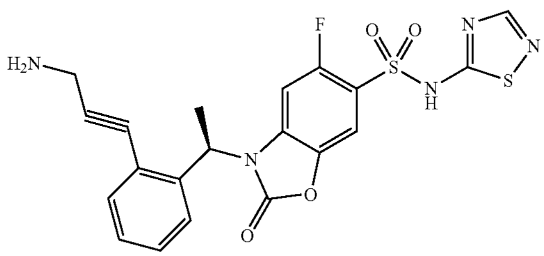 [SMILES: C[C@H](c1ccccc1C#CCN)n1c(=O)oc2cc(S(=O)(=O)Nc3ncns3)c(F)cc21] | 3-{(1R)-1-[2-(3-aminoprop-1-yn-1-yl)phenyl]ethyl}-5-fluoro-2-oxo-N-1,2,4-thiadiazol-5-yl-2,3-dihydro-1,3-benzoxazole-6-sulfonamide | Calc'd 474.0701, found 474.0688 |
| 17-21 | 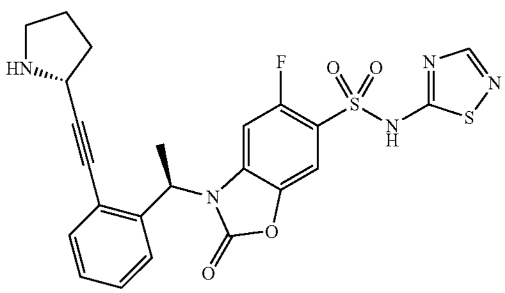 [SMILES: C[C@H](c1ccccc1C#C[C@H]1CCCN1)n1c(=O)oc2cc(S(=O)(=O)Nc3ncns3)c(F)cc21] | 5-fluoro-2-oxo-3-[(1R)-1-{2-[(2R)-pyrrolidin-2-ylethynyl]phenyl}ethyl]-N-1,2,4-thiadiazol-5-yl-2,3-dihydro-1,3-benzoxazole-6-sulfonamide | Calc'd 514.1014, found 514.1011 |
| 17-22 | 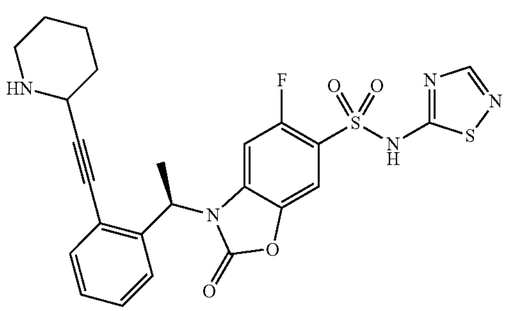 [SMILES: C[C@H](c1ccccc1C#CC1CCCCN1)n1c(=O)oc2cc(S(=O)(=O)Nc3ncns3)c(F)cc21] | 5-fluoro-2-oxo-3-{(1R)-1-[2-(piperidin-2-ylethynyl)phenyl]ethyl}-N-1,2,4-thiadiazol-5-yl-2,3-dihydro-1,3-benzoxazole-6-sulfonamide | Calc'd 528.117, found 528.1158 |
| 17-23 | 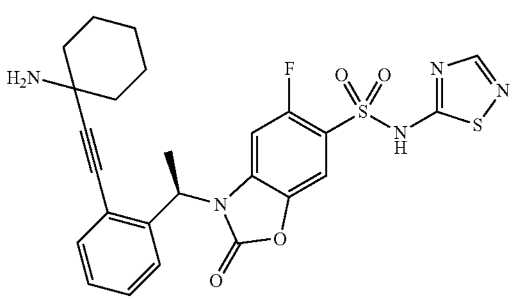 [SMILES: C[C@H](c1ccccc1C#CC1(N)CCCCC1)n1c(=O)oc2cc(S(=O)(=O)Nc3ncns3)c(F)cc21] | 3-[(1R)-1-{2-[(1-aminocyclohexyl)ethynyl]phenyl}ethyl]-5-fluoro-2-oxo-N-1,2,4-thiadiazol-5-yl-2,3-dihydro-1,3-benzoxazole-6-sulfonamide | Calc'd 542.1327, found 542.1323 |

Example 15

Preparation of (R)-5-fluoro-2-oxo-3-(1-(2-(pyrrolidin-1-ylmethyl)phenyl)ethyl)-N-(1,2,4-thiadiazol-5-yl)-2,3-dihydrobenzo[d]oxazole-6-sulfonamide (18-2)

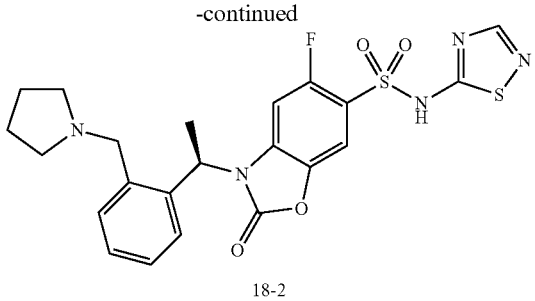

18-2

Scheme 18

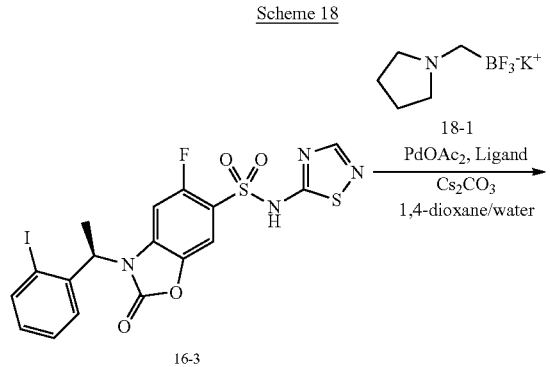

A solution of 16-3 (20 mg, 0.037 mmol), potassium trifluoroborate 18-1 (13.99 mg, 0.073 mmol), $Cs_2CO_3$ (35.8 mg, 0.110 mmol), Palladium (II) Acetate (0.822 mg, 3.66 mol), and butyldi-1-adamantylphosphine (2.63 mg, 7.32 mol) in degassed 1,4-Dioxane (305 µl) and Water (61.0 µl) was heated to 85° C. overnight under an atmosphere of nitrogen. Upon cooling to RT, the organic layer was decanted and diluted with DMSO (1.5 ml). Purified by reverse phase chromatography (5-70% MeCN in water w/0.1% TFA, C18 column) to yield 18-2 as a tan solid. $^1$H NMR δ (ppm)(DMSO-$d_6$): 9.73 (1H, s), 8.42 (1H, s), 7.92 (1H, d, J=7.77 Hz), 7.74 (1H, d, J=5.57 Hz), 7.59-7.52 (2H, m), 7.53-7.47 (1H, m), 7.22 (1H, d, J=9.73 Hz), 5.89-5.84 (1H, m), 4.49-4.42 (1H, m), 4.39-4.32 (1H, m), 2.08 (2H, br s), 1.88-1.83 (5H, m). Note: some proton peaks were obscured by $H_2O$ peak in NMR spectrum. HRMS C22H22FN5O4S2 [M+H] calc: 504.1170, obs: 504.1157.

The compounds defined in Table 11 were prepared in accordance with Example 15.

TABLE 11

| # | Structure | Name | Exact Mass [M + H]+ |
|---|---|---|---|
| 18-3 | 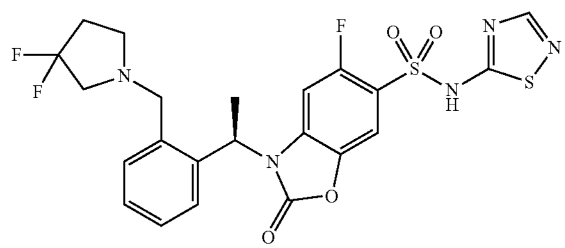 [SMILES: C[C@H](c1ccccc1CN1CCC(F)(F)C1)n1c(=O)oc2cc(S(=O)(=O)Nc3ncns3)c(F)cc21] | 3-[(1R)-1-{2-[(3,3-difluoropyrrolidin-1-yl)methyl]phenyl}ethyl]-5-fluoro-2-oxo-N-1,2,4-thiadiazol-5-yl-2,3-dihydro-1,3-benzoxazole-6-sulfonamide | Calc'd 540.0982, found 540.0955 |
| 18-4 | 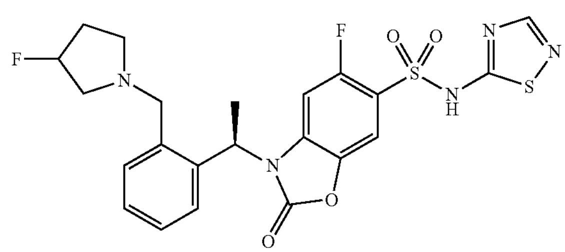 [SMILES: C[C@H](c1ccccc1CN1CCC(F)C1)n1c(=O)oc2cc(S(=O)(=O)Nc3ncns3)c(F)cc21] | 5-fluoro-3-[(1R)-1-{2-[(3-fluoropyrrolidin-1-yl)methyl]phenyl}ethyl]-2-oxo-N-1,2,4-thiadiazol-5-yl-2,3-dihydro-1,3-benzoxazole-6-sulfonamide | Calc'd 522.1076, found 522.1051 |
| 18-5 | 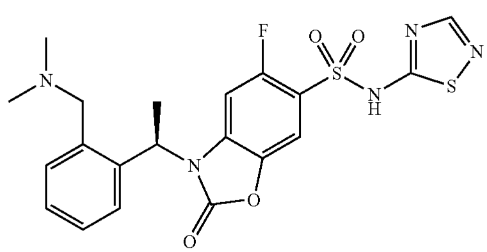 [SMILES: C[C@H](c1ccccc1CN(C)C)n1c(=O)oc2cc(S(=O)(=O)Nc3ncns3)c(F)cc21] | 3-[(1R)-1-{2-[(dimethylamino)methyl]phenyl}ethyl]-5-fluoro-2-oxo-N-1,2,4-thiadiazol-5-yl-2,3-dihydro-1,3-benzoxazole-6-sulfonamide | Calc'd 478.1014, found 478.1001 |

Example 16

Preparation of 3-((7-(3,3-difluoroazetidin-1-yl)-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide hydrochloride (19-6)

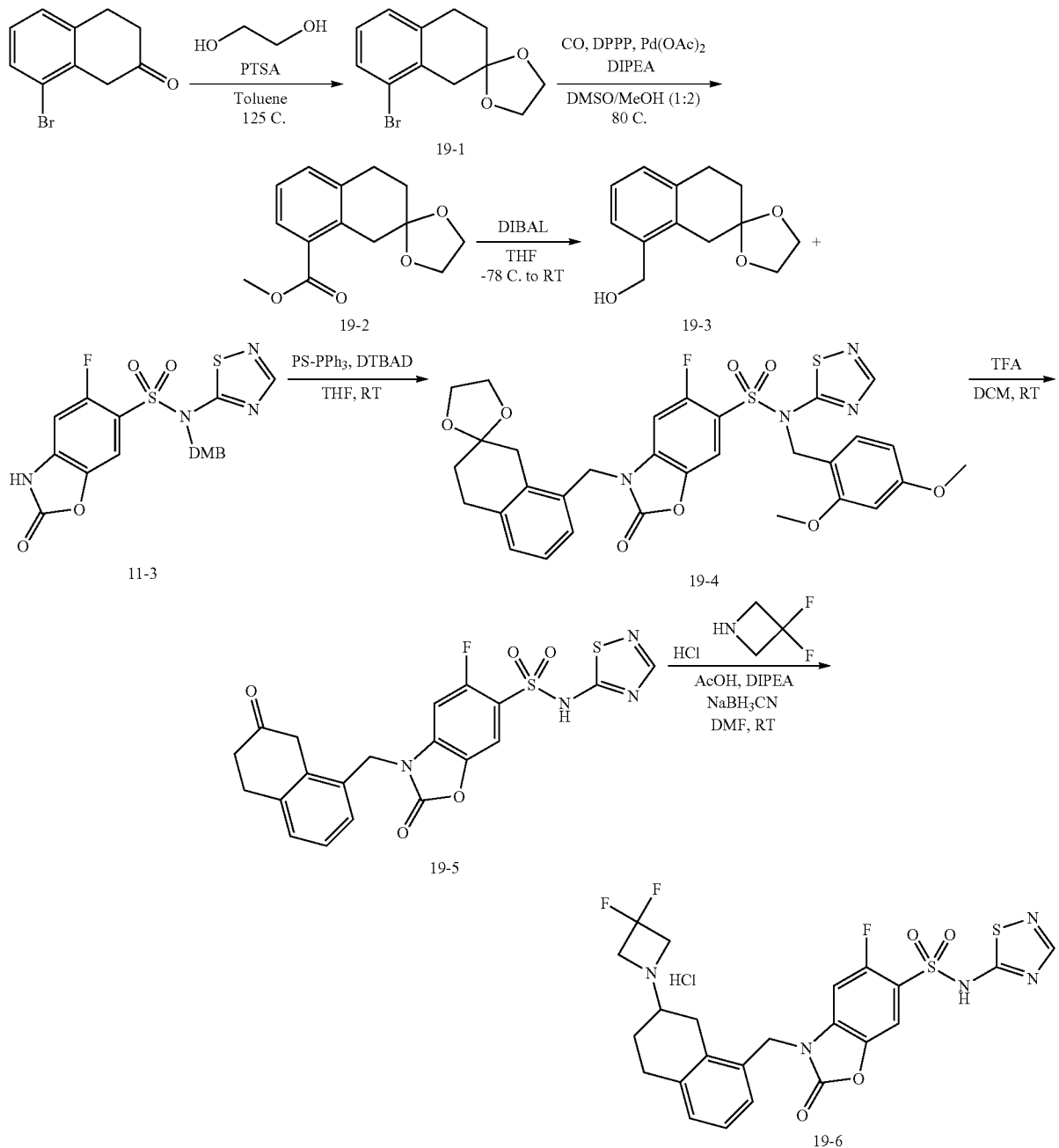

Scheme 19

Preparation of 8'-Bromo-3',4'-dihydro-1'H-spiro[[1,3]dioxolane-2,2'-naphthalene] (19-1)

To a flask containing 8-BROMO-2-TETRALONE (4.11 g, 18.26 mmol) was added P-TOLUENESULFONIC ACID MONOHYDRATE (0.590 g, 3.10 mmol), followed by Toluene (50 ml) then ETHYLENE GLYCOL (1.725 ml, 30.9 mmol). The reaction mixture was then heated to 125 C while stirring in a hot oil bath in the hood overnight with a dean stark trap attached under an atmosphere of nitrogen. Followed by LC/MS. The next morning the reaction mixture was cooled to room temperature then suspended in EtOAc, washed with saturated NaHCO3, then H2O, then brine; dried over Na2SO4, filtered & concentrated. Purification by silica gel chromatography (0-50% EtOAc/Hex; 330 g ISCO); desired fractions concentrated to yield 8'-bromo-3',4'-dihydro-1'H-spiro[[1,3]dioxolane-2,2'-naphthalene](19-1).

Preparation of Methyl 3',4'-dihydro-1'H-spiro[[1,3]dioxolane-2,2'-naphthalene]-8'-carboxylate (19-2)

To a flask containing 8'-bromo-3',4'-dihydro-1'H-spiro[[1,3]dioxolane-2,2'-naphthalene](19-1) (3.04 g, 11.30 mmol) was added anhydrous MeOH (40 ml), & anhydrous DMSO (20 ml), followed by TRIETHYLAMINE (7 ml, 50.5 mmol). The reaction mixture was degassed with CARBON MONOXIDE (6.33 g, 226 mmol) for 5 minutes at room temperature (bubbled CO gas through solution with a vent needle). 1,3-BIS(DIPHENYLPHOSPHINO)PROPANE (0.961 g, 2.330 mmol) & PALLADIUM(II) ACETATE (0.549 g, 2.445 mmol) were then added in one portion as solids, then attached a water cooled reflux condenser & a balloon containing CARBON MONOXIDE (6.33 g, 226 mmol), then purged (3× vacuum/CO). The reaction mixture (clear brown solution became darker/black with heat) was then heated to 80 C while stirring under an atmosphere of CO at 80 C in a hot oil bath overnight (~16 hours). Followed by LC/MS. The reaction mixture was cooled to room temperature, then was suspended in EtOAc & saturated NaHCO3, filtered through celite, then separated layers, the organics were washed with saturated NaHCO3, then H2O, then brine; dried over Na2SO4, filtered & concentrated. Purification by silica gel chromatography (0-40% EtOAc/Hex; 120 g ISCO); desired fractions concentrated to yield methyl 3',4'-dihydro-1'H-spiro[[1,3]dioxolane-2,2'-naphthalene]-8'-carboxylate (19-2).

Preparation of (3',4'-Dihydro-1'H-spiro[[1,3]dioxolane-2,2'-naphthalen]-8'-yl)methanol (19-3)

To a round bottom flask containing methyl 3',4'-dihydro-1'H-spiro[[1,3]dioxolane-2,2'-naphthalene]-8'-carboxylate (19-2) (1.88 g, 7.57 mmol) was added anhydrous THF (15 ml). The reaction mixture was then cooled to 0 C (ice water bath) while stirring under N2. Then added DIBAL-H (24 mL, 24.00 mmol) dropwise over 10 minutes with stirring. Stirred at 0 C for 10 minutes, then permitted to warm to room temperature. Followed by LC/MS. Stirred overnight at room temperature, noticed there was still some starting material so cooled back to 0 C, then added additional DIBAL-H (19 mL, 19.00 mmol) & after 10 minutes warmed to room temperature. The reaction mixture was cooled to 0 C (ice water bath), then quenched by slow dropwise addition of saturated Rochelle's Salt (Na+/K+ Tartrate) (lots of bubbling so add slowly), then stirred for an hour to help break up/solubilize the emulsion; then suspended in EtOAc, filtered emulsion (gooey material, very little desired product by LC/MS); organics separated, then washed with saturated Rochelle's salt again then washed with saturated NH4Cl, then with saturated NaHCO3, then H2O, then brine; organics dried over sodium sulfate, filtered & concentrated. Purification by silica gel chromatography (30-100% EtOAc/Hex; 80 g ISCO); desired fractions concentrated to yield (3',4'-dihydro-1'H-spiro[[1,3]dioxolane-2,2'-naphthalen]-8'-yl)methanol (19-3). HRMS [M+Na] calculated; 243.0992, observed; 243.0990.

Preparation of 3-((3',4'-Dihydro-1'H-spiro[[1,3]dioxolane-2,2'-naphthalen]-8'-yl)methyl)-N-(2,4-dimethoxybenzyl)-5-fluoro-2-oxo-N-(1,2,4-thiadiazol-5-yl)-2,3-dihydrobenzo[d]oxazole-6-sulfonamide (19-4)

To a flask containing N-(2,4-Dimethoxybenzyl)-5-fluoro-2-oxo-N-(1,2,4-thiadiazol-5-yl)-2,3-dihydro-1,3-benzoxazole-6-sulfonamide (11-3) (2.13 g, 4.57 mmol), resin bound (PS) TRIPHENYLPHOSPHINE (5.27 g, 9.70 mmol) & DTBAD (2.187 g, 9.50 mmol) & (3',4'-dihydro-1'H-spiro[[1,3]dioxolane-2,2'-naphthalen]-8'-yl)methanol (19-3) (1.162 g, 5.28 mmol) was added anhydrous THF (40 ml). The reaction mixture was then capped (not under N2) & stirred at room temperature for ~16 hours (overnight). Followed by LC/MS. The reaction mixture was diluted with DCM/EtOAc, filtered (to remove the resin), it was noticed that the filtrate was cloudy white so it was filtered to yield 3-((3',4'-dihydro-1'H-spiro[[1,3]dioxolane-2,2'-naphthalen]-8'-yl)methyl)-N-(2,4-dimethoxybenzyl)-5-fluoro-2-oxo-N-(1,2,4-thiadiazol-5-yl)-2,3-dihydrobenzo[d]oxazole-6-sulfonamide (19-4).

Preparation of 5-Fluoro-2-oxo-3-((7-oxo-5,6,7,8-tetrahydronaphthalen-1-yl)methyl)-N-(1,2,4-thiadiazol-5-yl)-2,3-dihydrobenzo[d]oxazole-6-sulfonamide (19-5)

To a flask containing 3-((3',4'-dihydro-1'H-spiro[[1,3]dioxolane-2,2'-naphthalen]-8'-yl)methyl)-N-(2,4-dimethoxybenzyl)-5-fluoro-2-oxo-N-(1,2,4-thiadiazol-5-yl)-2,3-dihydrobenzo[d]oxazole-6-sulfonamide (19-4) (1.65 g, 2.467 mmol) in DCM (10 ml) was added TFA (8 ml, 104 mmol). The reaction mixture (clear pink/purple with R2 addition) was then capped (not under N2) & stirred at room temperature. Followed by LC/MS . . . added 3 additional portions of TFA then after several hours at room temperature the reaction mixture was diluted with DMSO/MeOH, then concentrated (to remove DCM), then filtered to yield a portion of 5-fluoro-2-oxo-3-((7-oxo-5,6,7,8-tetrahydronaphthalen-1-yl)methyl)-N-(1,2,4-thiadiazazol-5-yl)-2,3-dihydrobenzo[d]oxazole-6-sulfonamide (19-5). The filtrate was then purified by reverse phase chromatography (5-75% MeCN/H2O; 0.1% TFA in AQ; 20 min gradient; Waters 30×150 mm Sunfire 5 micron C18 column); desired fractions concentrated (GENEVAC), then dissolved in MeOH/DCM & concentrated to yield another portion of 5-fluoro-2-oxo-3-((7-oxo-5,6,7,8-tetrahydronaphthalen-1-yl)methyl)-N-(1,2,4-thiadiazol-5-yl)-2,3-dihydrobenzo[d]oxazole-6-sulfonamide (19-5). HRMS [M+H] calculated; 475.0541, observed; 475.0528.

Preparation of 3-((7-(3,3-Difluoroazetidin-1-yl)-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide hydrochloride (19-6)

To a vial was added 5-fluoro-2-oxo-3-((7-oxo-5,6,7,8-tetrahydronaphthalen-1-yl)methyl)-N-(1,2,4-thiadiazol-5-yl)-2,3-dihydrobenzo[d]oxazole-6-sulfonamide (19-5) (41 mg, 0.086 mmol), then DMF (0.6 mL) followed by 3,3-DIFLUOROAZETIDINE HYDROCHLORIDE (38 mg, 0.293 mmol), then DIPEA (100 µL, 0.573 mmol). The reaction mixture was then permitted to stir at room temperature for 20 minutes, then added ACETIC ACID (150 µL, 2.62 mmol). The reaction mixture was then permitted to stir at room temperature for 2 hrs (capped, but not under N2). Followed by LC/MS. After 2 hours at room temperature added SODIUM CYANOBOROHYDRIDE (33 mg, 0.525 mmol) in one portion to the reaction mixture at room temperature. After another hour at room temperature; the reaction mixture was diluted with MeOH/DMSO/drops TFA/drops H2O, stirred for ~10 minutes, then filtered (syringe filter), then purified (without workup) by reverse phase chromatography (5-65% MeCN/H2O; 0.1% TFA in AQ; 20 min gradient; Waters 30×150 mm Sunfire 5 micron C18 column); desired fractions concentrated (GENEVAC), then dissolved in MeOH/DCM & added a saturated solution of HCl in EtOAc (~4N) & concentrated to yield 3-((7-(3,3-difluoroazetidin-1-yl)-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide hydrochloride (19-6). HRMS [M+H] calculated; 552.0982, observed; 552.0982. $^1$H NMR (400 MHz, CD$_3$ OD): δ 8.21 (s, 1H); 7.79 (d, J=5.5 Hz, 1H); 7.24-7.18 (m, 3H); 7.01 (d, J=9.3 Hz, 1H); 5.18-5.01 (m, 2H); 4.99-4.88 (m, 4H); 3.83-3.74 (m, 1H); 3.44-3.40 (m, 1H); 3.03-2.94 (m, 2H); 2.69-2.59 (m, 1H); 2.29-2.22 (m, 1H); 1.79-1.67 (m, 1H).

Example 17

Preparation of 3-((7-amino-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide (20-4) and derivatives of 20-4 and 19-5 bubbling/gas evolution). The reaction mixture was then warmed to room temperature, then suspended in EtOAc, separated, the organics were then washed with saturated NaHCO3, then H2O, then brine; dried over Na2SO4, filtered & concentrated. The resulting residue was purified by silica gel chromatography (0-50% EtOAc/Hex; 80 g ISCO); desired fractions concentrated to yield tert-butyl (8-(hydroxymethyl)-1,2,3,4-tetrahydronaphthalen-2-yl)carbamate (20-2).

Preparation of 3-((7-Amino-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide ((+/−)-20-4)

3-((7-amino-5,6,7,8-tetrahydronaphthalen-1-yl)methyl)-5-fluoro-2-oxo-N-(1,2,4-thiadiazol-5-yl)-2,3-dihydrobenzo

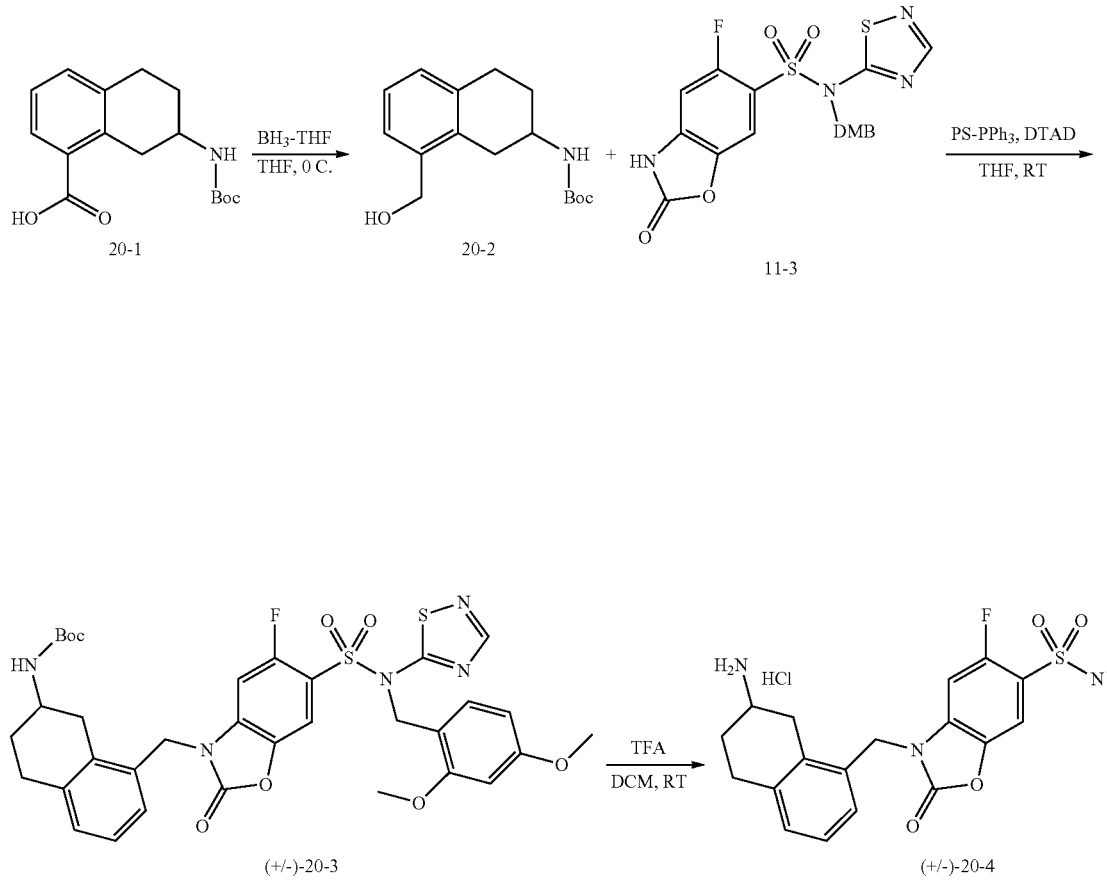

Scheme 20

Preparation of tert-butyl (8-(hydroxymethyl)-1,2,3,4-tetrahydronaphthalen-2-yl)carbamate (20-2)

To a flask was added 7-((tert-butoxycarbonyl)amino)-5,6,7,8-tetrahydro-naphthalene-1-carboxylic acid (20-1) (2.02 g, 6.93 mmol), then anhydrous THF (20 mL). The reaction mixture was cooled to 0 C (ice water bath) while stirring under an atmosphere of nitrogen. Then a 1M solution of BORANE TETRAHYDROFURAN COMPLEX (30 mL, 30.0 mmol) was added dropwise while stirring. The reaction mixture was stirred at 0 C for 1.5 hours. Followed by LC/MS. The reaction mixture was then uncapped (always at 0 C), then quenched by dropwise addition of saturated NH4Cl (lots of

[d]oxazole-6-sulfonamide ((+/−)-20-4) was prepared from a sequence analogous to that for (19-5) presented in Scheme 19 to yield 3-((7-amino-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide ((+/−)-20-4). HRMS [M+H] calculated; 476.0857, observed; 476.0869. $^1$H NMR (400 MHz, CD$_3$ OD): δ 8.21 (s, 1H); 7.80 (d, J=5.5 Hz, 1H); 7.24-7.12 (m, 3H); 6.88 (d, J=9.4 Hz, 1H); 5.17-4.98 (m, 2H); 3.62-3.53 (m, 1H); 3.27-3.23 (m, 1H); 3.00-2.95 (m, 2H); 2.70-2.61 (m, 1H); 2.23-2.16 (m, 1H); 1.84-1.76 (m, 1H).

Scheme 21

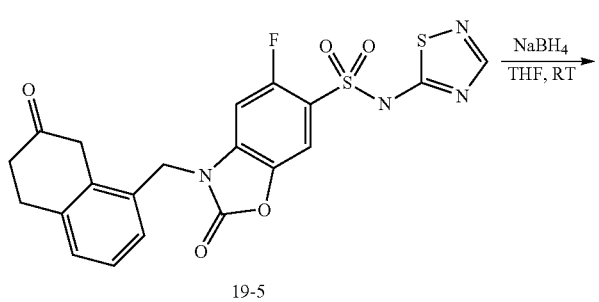

19-5

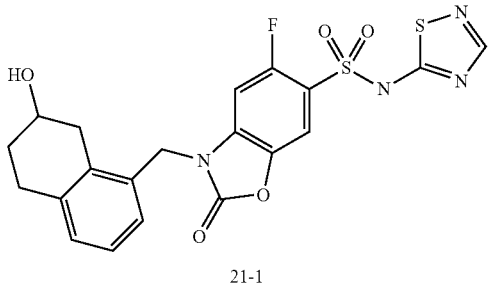

21-1

Preparation of 5-fluoro-3-((7-hydroxy-5,6,7,8-tet-rahydronaphthalen-1-yl)methyl)-2-oxo-N-(1,2,4-thiadiazol-5-yl)-2,3-dihydrobenzo[d]oxazole-6-sulfonamide (21-1)

In a vial was added 5-fluoro-2-oxo-3-((7-oxo-5,6,7,8-tetrahydronaphthalen-1-yl)methyl)-N-(1,2,4-thiadiazol-5-yl)-2,3-dihydrobenzo[d]oxazole-6-sulfonamide (19-5) (29 mg, 0.061 mmol), followed by anhydrous THF (1 mL), then NaBH4 (8 mg, 0.211 mmol). The reaction mixture was then capped (not under N2) & stirred at room temperature. Followed by LC/MS. The reaction mixture was diluted with MeOH/drops of H2O/DMSO/TFA (lot of bubbling), filtered (syringe filter), then purified (without workup) by reverse phase chromatography (5-75% MeCN/H2O; 0.1% TFA in AQ; 20 min gradient; Waters 30×150 mm Sunfire 5 micron C18 column); desired fractions concentrated (GENEVAC), then dissolved in MeOH/DCM & concentrated to yield 5-fluoro-3-((7-hydroxy-5,6,7,8-tetrahydronaphthalen-1-yl)methyl)-2-oxo-N-(1,2,4-thiadiazol-5-yl)-2,3-dihydrobenzo[d]oxazole-6-sulfonamide (21-1). HRMS [M+H] calculated; 477.0697, observed; 477.0705. $^1$H NMR (499 MHz, DMSO): δ 8.49 (s, 1H); 7.79 (d, J=5.5 Hz, 1H); 7.29 (d, J=9.6 Hz, 1H); 7.05-7.02 (m, 2H); 6.87-6.83 (m, 1H); 5.75 (s, 2H); 5.01-4.95 (m, 1H); 4.02-3.92 (m, 1H); 2.99-2.92 (m, 1H); 2.91-2.83 (m, 1H); 2.77-2.68 (m, 1H); 1.91-1.84 (m, 2H); 1.66-1.57 (m, 1H).

Scheme 22

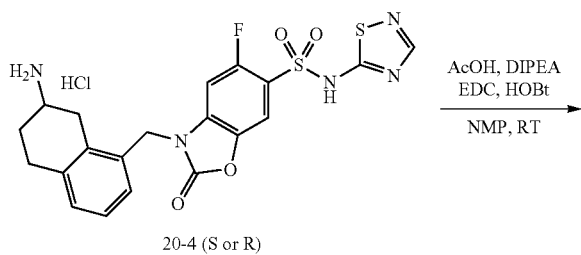

20-4 (S or R)

-continued

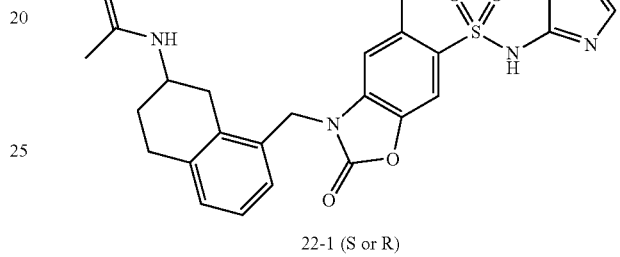

22-1 (S or R)

Preparation of N-(8-((6-(N-(1,2,4-thiadiazol-5-yl)sulfamoyl)-5-fluoro-2-oxobenzo[d]oxazol-3(2H)-yl)methyl)-1,2,3,4-tetrahydronaphthalen-2-yl)acetamide (22-1)

To a flask was added a single enantiomer (S or R) of 3-((7-amino-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide (obtained through chiral separation of racemic 20-4) (15 mg, 0.029 mmol), then anhydrous HOBT (5.15 mg, 0.038 mmol), EDC (7.30 mg, 0.038 mmol), followed by NMP (1 ml), then ACETIC ACID (2.180 µl, 0.038 mmol) then DIPEA (0.025 ml, 0.143 mmol). The reaction mixture was stirred at room temperature (capped but not under N2) & followed by LC/MS for the disappearance of starting amine. The reaction mixture was diluted with MeOH/drops of H2O, was filtered (syringe filter), concentrated to desired volume (blow station) & submitted downstairs for mass guided reverse phase purification (TFA modifier); desired fractions concentrated to yield N-(8-((6-(N-(1,2,4-thiadiazol-5-yl)sulfamoyl)-5-fluoro-2-oxobenzo[d]oxazol-3(2H)-yl)methyl)-1,2,3,4-tetrahydronaphthalen-2-yl)acetamide (22-1, S or R). HRMS [M+H] calculated; 518.0963, observed; 518.0937. $^1$H NMR (499 MHz, DMSO): presaturation at 3.35 ppm: δ 8.49 (s, 1H); 7.96 (d, J=7.5 Hz, 1H); 7.80 (d, J=5.4 Hz, 1H); 7.29 (d, J=9.6 Hz, 1H); 7.06 (d, J=4.5 Hz, 2H); 6.85-6.81 (m, 1H); 5.02-4.91 (m, 2H); 4.06-3.95 (m, 1H); 3.05-2.99 (m, 1H); 2.86-2.80 (m, 2H); 2.53-2.48 (m, 1H); 1.95-1.85 (m, 1H); 1.82 (s, 3H); 1.68-1.58 (m, 1H).

Scheme 23

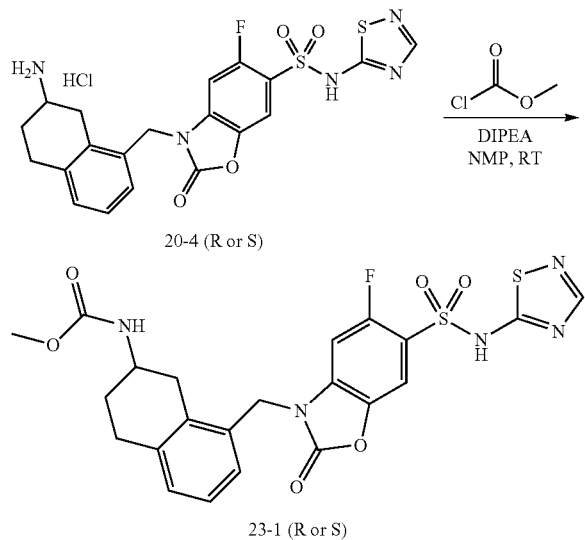

Preparation of methyl (8-((6-(N-(1,2,4-thiadiazol-5-yl)sulfamoyl)-5-fluoro-2-oxobenzo[d]oxazol-3(2H)-yl)methyl)-1,2,3,4-tetrahydronaphthalen-2-yl)carbamate (23-1)

To a vial was added a single enantiomer (R or S) of 3-((7-amino-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide (20-4) (19 mg, 0.037 mmol), then NMP (0.6 ml), DIPEA (30 µL, 0.172 mmol), and finally METHYL CHLOROFORMATE (12.30 µL, 0.159 mmol). The reaction mixture was then capped (not under N2) & stirred at room temperature. Followed by LC/MS. After 10 min at room temperature the reaction mixture was diluted with MeOH/drops of H2O/DMSO, then purified (without workup) by reverse phase chromatography (5-95% MeCN/H2O; 0.1% TFA in AQ; 20 min gradient; Waters 30×150 mm Sunfire 5 micron C18 column); desired fractions concentrated (GENEVAC), then dissolved in MeOH/DCM & concentrated to yield methyl (8-((6-(N-(1,2,4-thiadiazol-5-yl)sulfamoyl)-5-fluoro-2-oxobenzo[d]oxazol-3(2H)-yl)methyl)-1,2,3,4-tetrahydronaphthalen-2-yl)carbamate (23-1). HRMS [M+H] calculated; 534.0912, observed; 534.0918. $^1$H NMR (499 MHz, DMSO): δ 8.48 (s, 1H); 7.79 (d, J=5.5 Hz, 1H); 7.33-7.23 (m, 2H); 7.08-7.03 (m, 2H); 6.88-6.82 (m, 1H); 5.75 (s, 1H); 5.03-4.91 (m, 2H); 3.81-3.71 (m, 2H); 3.55 (s, 3H); 3.06-2.99 (m, 1H); 2.87-2.80 (m, 2H); 1.95-1.88 (m, 1H); 1.68-1.57 (m, 1H).

The following compounds in Table 12 can be prepared using methods presented in Schemes 20, 22 and 23 from the appropriate starting materials:

TABLE 12

| # | Structure | Name | Exact Mass [M + H]+ |
|---|-----------|------|---------------------|
| 23-2 | 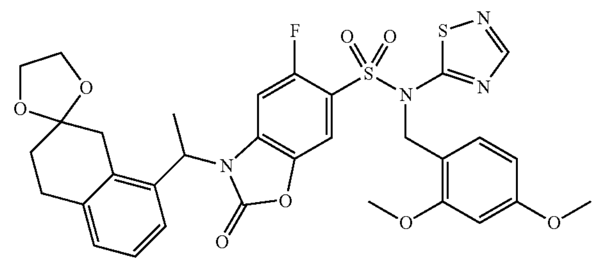 [SMILES: COc1ccc(CN(c2ncns2)S(=O)(=O)c2cc3oc(=O)n(C(C)c4cccc5c4CC4(CC5)OCCO4)c3cc2F)c(OC)c1] | (+/−)-3-[1-(3',4'-dihydro-1'H-spiro[1,3-dioxolane-2,2'-naphthalen]-8'-yl)ethyl]-N-(2,4-dimethoxybenzyl)-5-fluoro-2-oxo-N-1,2,4-thiadiazol-5-yl-2,3-dihydro-1,3-benzoxazole-6-sulfonamide | Calc'd 683.1640, found 683.1623 |
| 23-3 | 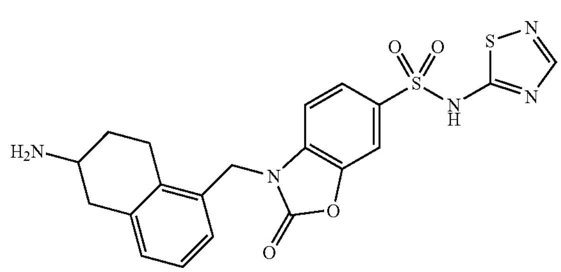 [SMILES: NC1CCc2c(cccc2Cn2c(=O)oc3cc(S(=O)(=O)Nc4ncns4)ccc32)C1] | (+/−)-3-[(6-amino-5,6,7,8-tetrahydronaphthalen-1-yl)methyl]-2-oxo-N-1,2,4-thiadiazol-5-yl-2,3-dihydro-1,3-benzoxazole-6-sulfonamide | Calc'd 458.0951, found 458.0939 |

TABLE 12-continued

| # | Structure | Name | Exact Mass [M + H]+ |
|---|---|---|---|
| 23-4 | 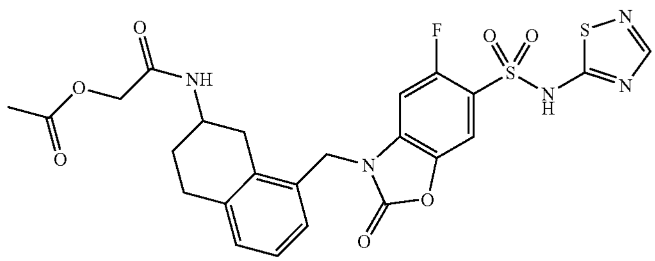 [SMILES: CC(=O)OCC(=O)NC1CCc2cccc(Cn3c(=O)oc4cc(S(=O)(=O)Nc5ncns5)c(F)cc43)c2C1] | (R or S)-2-[(8-{[5-fluoro-2-oxo-6-(1,2,4-thiadiazol-5-ylsulfamoyl)-1,3-benzoxazol-3(2H)-yl]methyl}-1,2,3,4-tetrahydronaphthalen-2-yl)amino]-2-oxoethyl acetate | Calc'd 576.1017, found 576.1020 |
| 23-5 | 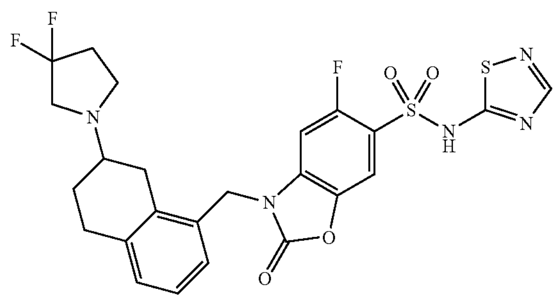 [SMILES: O=c1oc2cc(S(=O)(=O)Nc3ncns3)c(F)cc2n1Cc1cccc2c1CC(N1CCC(F)(F)C1)CC2] | (+/−)-3-{[7-(3,3-difluoropyrrolidin-1-yl)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide | Calc'd 566.1138, found 566.1151 |
| 23-6 | 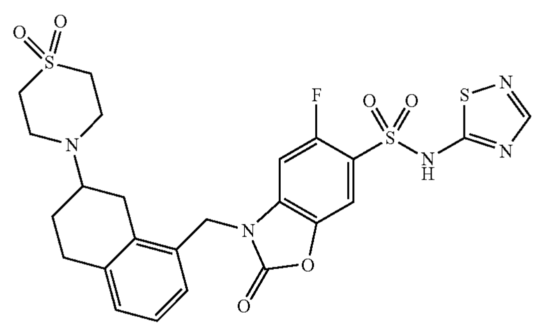 [SMILES: O=c1oc2cc(S(=O)(=O)Nc3ncns3)c(F)cc2n1Cc1cccc2c1CC(N1CCS(=O)(=O)CC1)CC2] | (R or S)-3-{[7-(1,1-dioxidothiomorpholin-4-yl)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide | Calc'd 594.0946, found 594.0958 |
| 23-7 | 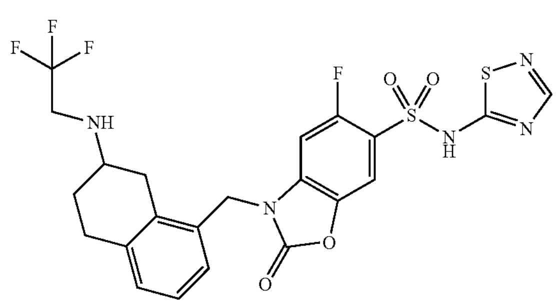 [SMILES: O=c1oc2cc(S(=O)(=O)Nc3ncns3)c(F)cc2n1Cc1cccc2c1CC(NCC(F)(F)F)CC2] | (+/−)-5-fluoro-2-oxo-N-1,2,4-thiadiazol-5-yl-3-({7-[(2,2,2-trifluoroethyl)amino]-5,6,7,8-tetrahydronaphthalen-1-yl}methyl)-2,3-dihydro-1,3-benzoxazole-6-sulfonamide | Calc'd 558.0887, found 558.0891 |
| 23-8 | 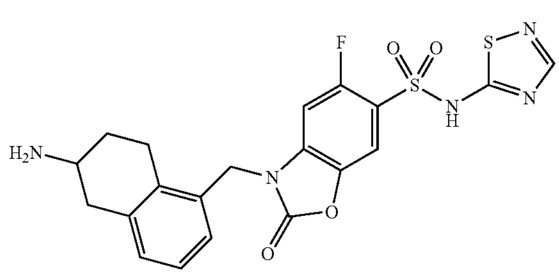 [SMILES: NC1CCc2c(cccc2Cn2c(=O)oc3cc(S(=O)(=O)Nc4ncns4)c(F)cc32)C1] | (+/−)-3-[(6-amino-5,6,7,8-tetrahydronaphthalen-1-yl)methyl]-5-fluoro-2-oxo-N-1,2,4-thiadiazol-5-yl-2,3-dihydro-1,3-benzoxazole-6-sulfonamide | Calc'd 476.0857, found 476.0841 |

TABLE 12-continued

| # | Structure | Name | Exact Mass [M + H]+ |
|---|---|---|---|
| 23-9 | 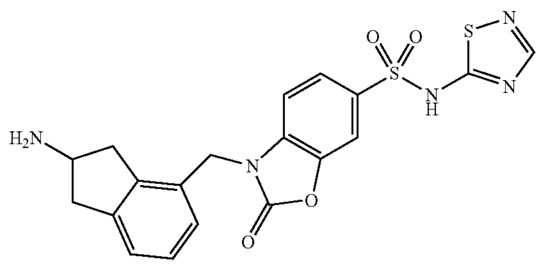 [SMILES: NC1Cc2cccc(Cn3c(=O)oc4cc(S(=O)(=O)Nc5ncns5)ccc43)c2C1] | (+/−)-3-[(2-amino-2,3-dihydro-1H-inden-4-yl)methyl]-2-oxo-N-1,2,4-thiadiazol-5-yl-2,3-dihydro-1,3-benzoxazole-6-sulfonamide | Calc'd 444.0795, found 444.0784 |
| 23-10 | 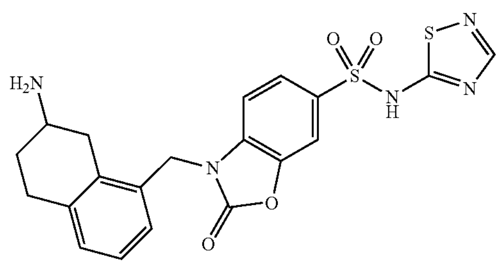 [SMILES: NC1CCc2cccc(Cn3c(=O)oc4cc(S(=O)(=O)Nc5ncns5)ccc43)c2C1] | (R or S)-3-[(7-amino-5,6,7,8-tetrahydronaphthalen-1-yl)methyl]-2-oxo-N-1,2,4-thiadiazol-5-yl-2,3-dihydro-1,3-benzoxazole-6-sulfonamide | Calc'd 458.0951, found 458.0967 |
| 23-11 | 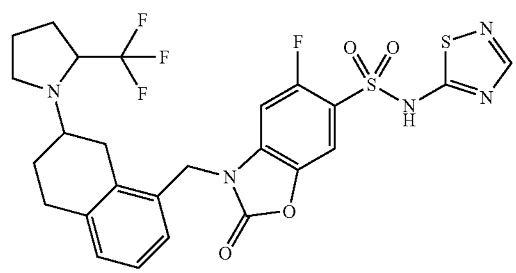 [SMILES: O=c1oc2cc(S(=O)(=O)Nc3ncns3)c(F)cc2n1Cc1cccc2c1CC(N1CCCC1C(F)(F)F)CC2] | (+/−)-5-fluoro-2-oxo-N-1,2,4-thiadiazol-5-yl-3-({7-[2-(trifluoromethyl)pyrrolidin-1-yl]-5,6,7,8-tetrahydronaphthalen-1-yl}methyl)-2,3-dihydro-1,3-benzoxazole-6-sulfonamide | Calc'd 598.1200, found 598.1194 |
| 23-12 | 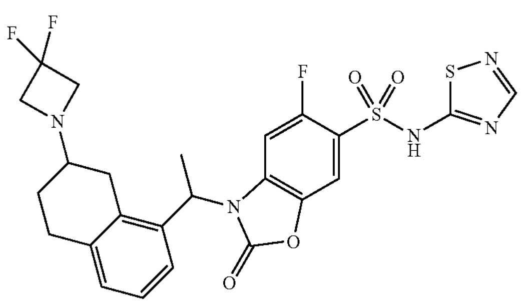 [SMILES: CC(c1cccc2c1CC(N1CC(F)(F)C1)CC2)n1c(=O)oc2cc(S(=O)(=O)Nc3ncns3)c(F)cc21] | (+/−)-3-{1-[7-(3,3-difluoroazetidin-1-yl)-5,6,7,8-tetrahydronaphthalen-1-yl]ethyl}-5-fluoro-2-oxo-N-1,2,4-thiadiazol-5-yl-2,3-dihydro-1,3-benzoxazole-6-sulfonamide | Calc'd 566.1138, found 566.1117 |
| 23-13 | 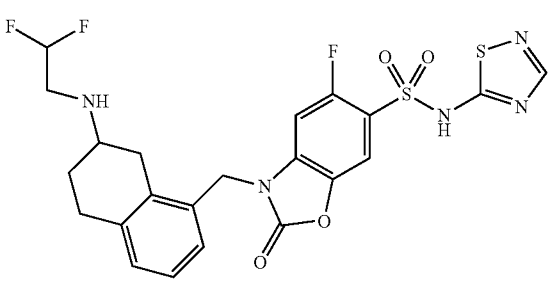 [SMILES: O=c1oc2cc(S(=O)(=O)Nc3ncns3)c(F)cc2n1Cc1cccc2c1CC(NCC(F)F)CC2] | (+/−)-3-({7-[(2,2-difluoroethyl)amino]-5,6,7,8-tetrahydronaphthalen-1-yl}methyl)-5-fluoro-2-oxo-N-1,2,4-thiadiazol-5-yl-2,3-dihydro-1,3-benzoxazole-6-sulfonamide | Calc'd 540.0982, found 540.0974 |

TABLE 12-continued

| # | Structure | Name | Exact Mass [M + H]+ |
|---|---|---|---|
| 23-14 | 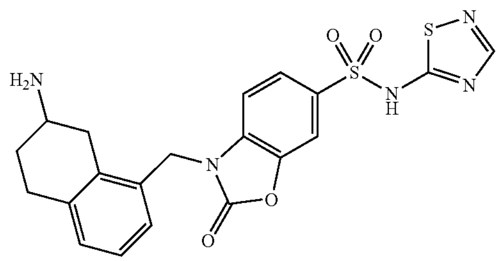 [SMILES: NC1CCc2cccc(Cn3c(=O)oc4cc(S(=O)(=O)Nc5ncns5)ccc43)c2C1] | (S or R)-3-[(7-amino-5,6,7,8-tetrahydronaphthalen-1-yl)methyl]-2-oxo-N-1,2,4-thiadiazol-5-yl-2,3-dihydro-1,3-benzoxazole-6-sulfonamide | Calc'd 458.0951, found 458.0965 |
| 23-15 | 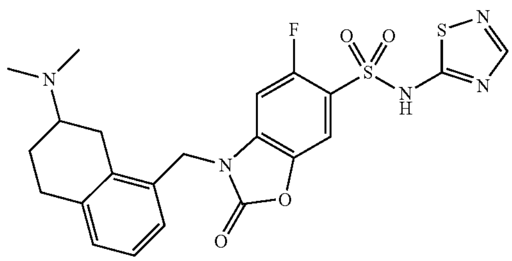 [SMILES: CN(C)C1CCc2cccc(Cn3c(=O)oc4cc(S(=O)(=O)Nc5ncns5)c(F)cc43)c2C1] | (+/−)-3-{[7-(dimethylamino)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide | Calc'd 504.1170, found 504.1194 |
| 23-16 | 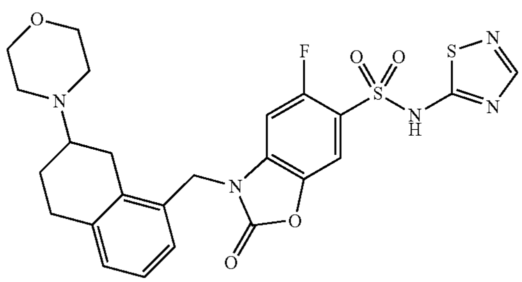 [SMILES: O=c1oc2cc(S(=O)(=O)Nc3ncns3)c(F)cc2n1Cc1cccc2c1CC(N1CCOCC1)CC2] | (+/−)-5-fluoro-3-[(7-morpholin-4-yl-5,6,7,8-tetrahydronaphthalen-1-yl)methyl]-2-oxo-N-1,2,4-thiadiazol-5-yl-2,3-dihydro-1,3-benzoxazole-6-sulfonamide | Calc'd 546.1276, found 546.1281 |
| 23-17 | 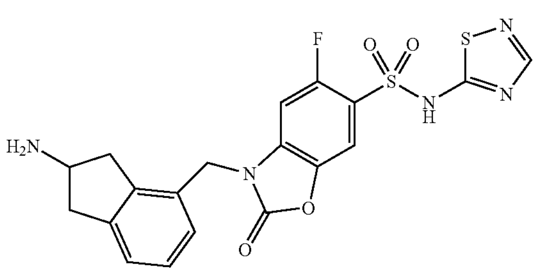 [SMILES: NC1Cc2cccc(Cn3c(=O)oc4cc(S(=O)(=O)Nc5ncns5)c(F)cc43)c2C1] | (+/−)-3-[(2-amino-2,3-dihydro-1H-inden-4-yl)methyl]-5-fluoro-2-oxo-N-1,2,4-thiadiazol-5-yl-2,3-dihydro-1,3-benzoxazole-6-sulfonamide | Calc'd 462.0701, found 462.0684 |
| 23-18 | 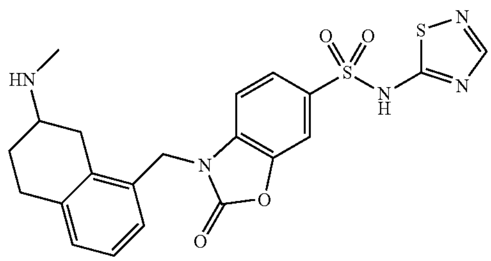 [SMILES: CNC1CCc2cccc(Cn3c(=O)oc4cc(S(=O)(=O)Nc5ncns5)ccc43)c2C1] | (+/−)-3-{[7-(methylamino)-5,6,7,8-tetrahydronaphthalen-1-yl]methyl}-2-oxo-N-1,2,4-thiadiazol-5-yl-2,3-dihydro-1,3-benzoxazole-6-sulfonamide | Calc'd 472.1108, found 472.1116 |

TABLE 12-continued

| # | Structure | Name | Exact Mass [M + H]+ |
|---|-----------|------|---------------------|
| 23-19 | 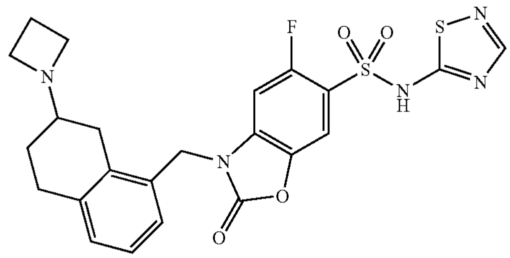 [SMILES: O=c1oc2cc(S(=O)(=O)Nc3ncns3)c(F)cc2n1Cc1cccc2c1CC(N1CCC1)CC2] | (+/−)-3-[(7-azetidin-1-yl-5,6,7,8-tetrahydronaphthalen-1-yl)methyl]-5-fluoro-2-oxo-N-1,2,4-thiadiazol-5-yl-2,3-dihydro-1,3-benzoxazole-6-sulfonamide | Calc'd 516.1170, found 516.1152 |
| 23-20 | 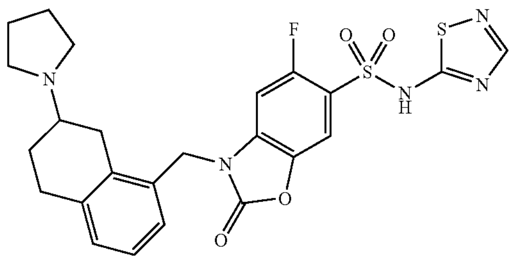 [SMILES: O=c1oc2cc(S(=O)(=O)Nc3ncns3)c(F)cc2n1Cc1cccc2c1CC(N1CCCC1)CC2] | (+/−)-5-fluoro-2-oxo-3-[(7-pyrrolidin-1-yl-5,6,7,8-tetrahydronaphthalen-1-yl)methyl]-N-1,2,4-thiadiazol-5-yl-2,3-dihydro-1,3-benzoxazole-6-sulfonamide | Calc'd 530.1327, found 530.1340 |
| 23-21 | 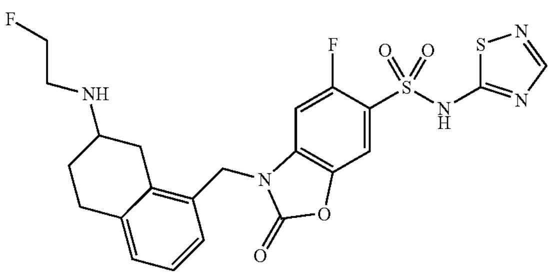 [SMILES: O=c1oc2cc(S(=O)(=O)Nc3ncns3)c(F)cc2n1Cc1cccc2c1CC(NCCF)CC2] | (+/−)-5-fluoro-3-({7-[(2-fluoroethyl)amino]-5,6,7,8-tetrahydronaphthalen-1-yl}methyl)-2-oxo-N-1,2,4-thiadiazol-5-yl-2,3-dihydro-1,3-benzoxazole-6-sulfonamide | Calc'd 522.1076, found 522.1061 |
| 23-22 | 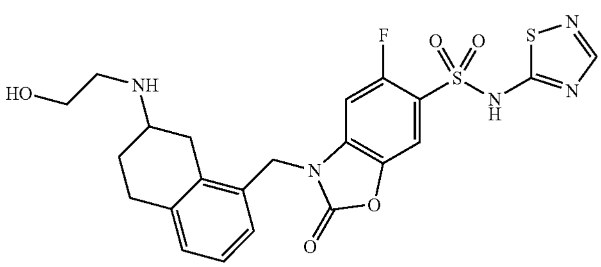 [SMILES: O=c1oc2cc(S(=O)(=O)Nc3ncns3)c(F)cc2n1Cc1cccc2c1CC(NCCO)CC2] | (+/−)-5-fluoro-3-({7-[(2-hydroxyethyl)amino]-5,6,7,8-tetrahydronaphthalen-1-yl}methyl)-2-oxo-N-1,2,4-thiadiazol-5-yl-2,3-dihydro-1,3-benzoxazole-6-sulfonamide | Calc'd 520.1, found 520.1 |
| 23-23 | 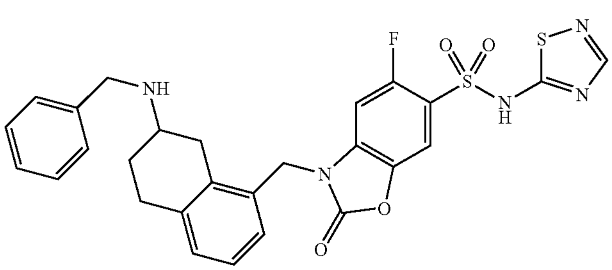 [SMILES: O=c1oc2cc(S(=O)(=O)Nc3ncns3)c(F)cc2n1Cc1cccc2c1CC(NCc1ccccc1)CC2] | (+/−)-3-{[7-(benzylamino)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide | Calc'd 566.1327, found 566.1338 |
| 23-24 | 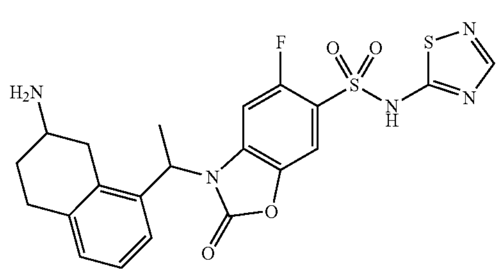 [SMILES: CC(c1cccc2c1CC(N)CC2)n1c(=O)oc2cc(S(=O)(=O)Nc3ncns3)c(F)cc21] | (R,R and S,R) or (R,S and S,S)-3-[1-(7-amino-5,6,7,8-tetrahydronaphthalen-1-yl)ethyl]-5-fluoro-2-oxo-N-1,2,4-thiadiazol-5-yl-2,3-dihydro-1,3-benzoxazole-6-sulfonamide | Calc'd 490.1014, found 490.1010 |

TABLE 12-continued

| # | Structure | Name | Exact Mass [M + H]+ |
|---|-----------|------|---------------------|
| 23-25 | 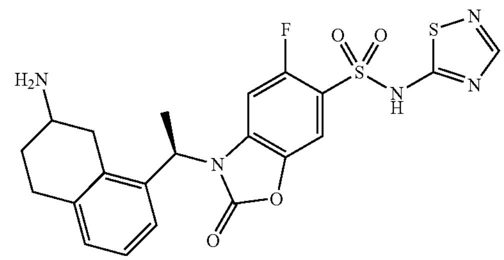 [SMILES: C[C@H](c1cccc2c1CC(N)CC2)n1c(=O)oc2cc(S(=O)(=O)Nc3ncns3)c(F)cc21] | (R or S)-3-[(1R)-1-(7-amino-5,6,7,8-tetrahydronaphthalen-1-yl)ethyl]-5-fluoro-2-oxo-N-1,2,4-thiadiazol-5-yl-2,3-dihydro-1,3-benzoxazole-6-sulfonamide | Calc'd 490.1014, found 490.1010 |
| 23-26 | 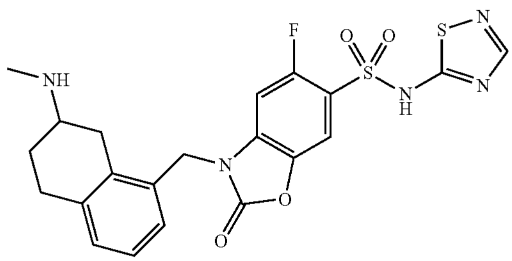 [SMILES: CNC1CCc2cccc(Cn3c(=O)oc4cc(S(=O)(=O)Nc5ncns5)c(F)cc43)c2C1] | (+/−)-5-fluoro-3-{[7-(methylamino)-5,6,7,8-tetrahydronaphthalen-1-yl]methyl}-2-oxo-N-1,2,4-thiadiazol-5-yl-2,3-dihydro-1,3-benzoxazole-6-sulfonamide | Calc'd 490.1014, found 490.1017 |
| 23-27 | 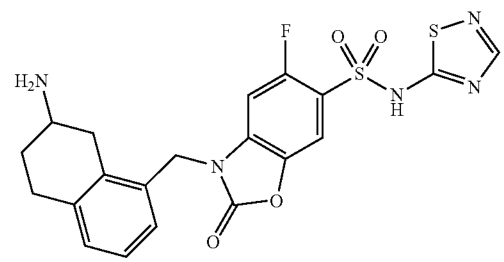 [SMILES: NC1CCc2cccc(Cn3c(=O)oc4cc(S(=O)(=O)Nc5ncns5)c(F)cc43)c2C1] | (S or R)-3-[(7-amino-5,6,7,8-tetrahydronaphthalen-1-yl)methyl]-5-fluoro-2-oxo-N-1,2,4-thiadiazol-5-yl-2,3-dihydro-1,3-benzoxazole-6-sulfonamide | Calc'd 476.057, found 476.0838 |

Example 18

Preparation of 5-fluoro-3-((4-fluoro-1,2,3,4-tetrahydroisoquinolin-8-yl)methyl)-2-oxo-N-(1,2,4-thiadiazol-5-yl)-2,3-dihydrobenzo[d]oxazole-6-sulfonamide hydrochloride (24-9)

Scheme 24

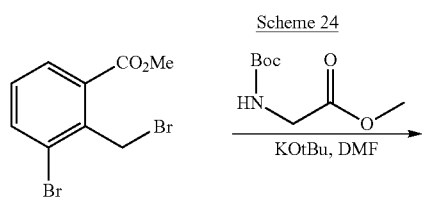

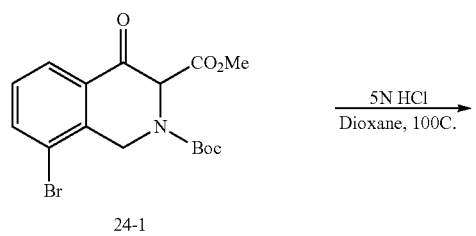

24-1

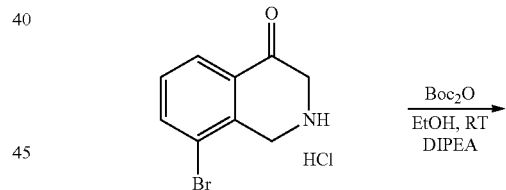

24-2

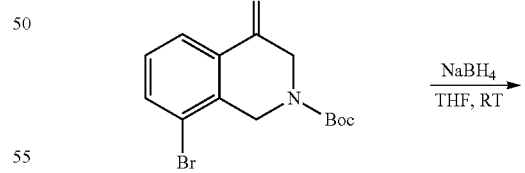

24-3

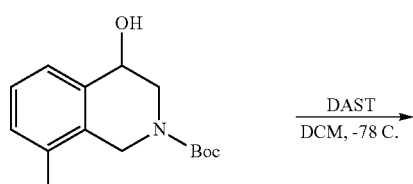

24-4

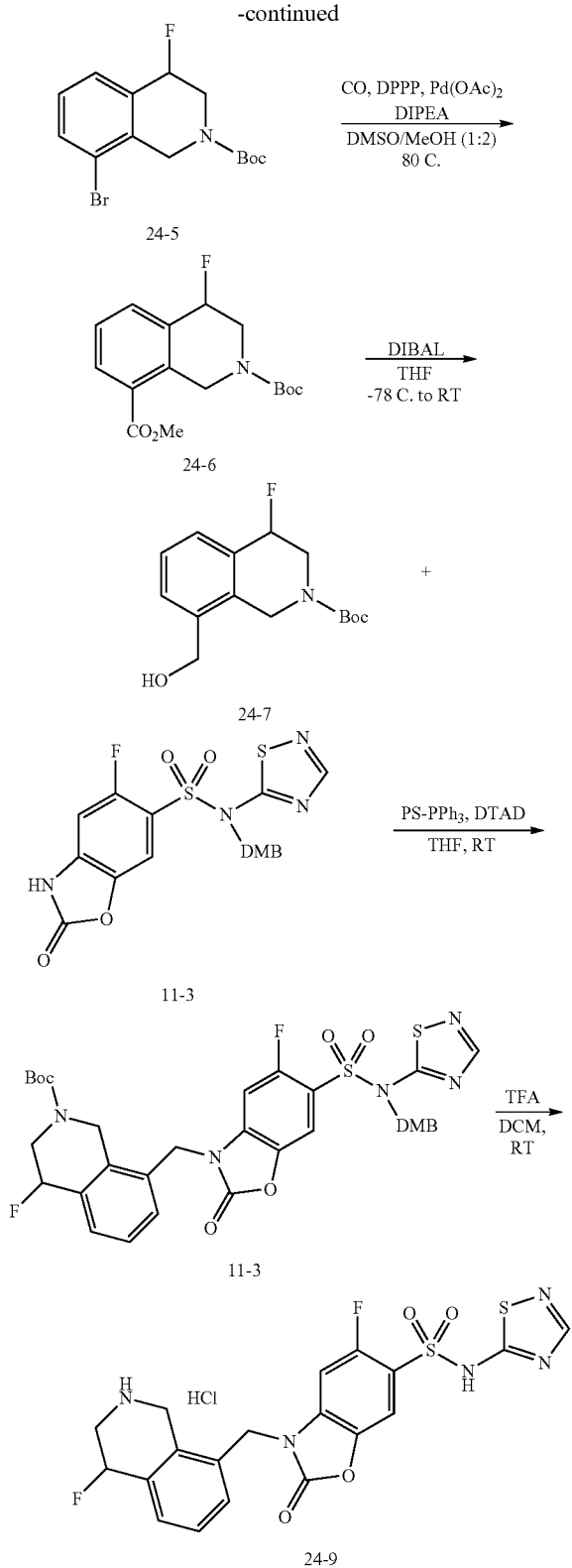

2-tert-Butyl 3-methyl 8-bromo-4-oxo-3,4-dihydroisoquinoline-2,3(1H)-dicarboxylate (24-1)

To a flask containing methyl 2-((tert-butoxycarbonyl)amino)acetate (4.18 g, 22.09 mmol) in anhydrous DMF (50 ml) was added KOtBu (3.99 g, 35.6 mmol) then after 1 min at room temperature added methyl 3-bromo-2-(bromomethyl)benzoate (4.97 g, 16.14 mmol) as a solid in 1 portion. The reaction mixture was then capped (not under N2) & stirred at room temperature for 3 hours. Followed by LC/MS. The reaction mixture was quenched/diluted with sat'd NaHCO3, then suspended in EtOAc, washed with saturated NaHCO3, then H2O, then brine; organics dried over Na2SO4, filtered & concentrated. Purification by silica gel chromatography (0-20% EtOAc/Hex; 220 g ISCO); desired fractions concentrated to yield 2-tert-butyl 3-methyl 8-bromo-4-oxo-3,4-dihydroisoquinoline-2,3 (1H)-dicarboxylate (24-1).

Preparation of 8-Bromo-2,3-dihydroisoquinolin-4(1H)-one hydrochloride (24-2)

To a flask containing 2-tert-butyl 3-methyl 8-bromo-4-oxo-3,4-dihydroisoquinoline-2,3(1H)-dicarboxylate (24-1) (3.44 g, 8.95 mmol) (mixed with impurities) was added was added Dioxane (20 ml), then 5N HCl in H2O (20 ml, 100 mmol). The reaction mixture was then heated to 90 C in the hood overnight. Followed by LC/MS. The next morning another 20 mL of 5N HCl was added and the reaction mixture was heated to 110 C for 3 hours, then was concentrated. The resulting residue was triturated with DCM (hot, then cooled to room temperature) & filtered to yield 8-bromo-2,3-dihydroisoquinolin-4(1H)-one hydrochloride (24-2). HRMS [M+H]: calculated; 225.9862, observed; 225.9860.

Preparation of tert-Butyl 8-bromo-4-oxo-3,4-dihydroisoquinoline-2(1H)-carboxylate (24-3)

To a flask containing 8-bromo-2,3-dihydroisoquinolin-4(1H)-one hydrochloride (24-2) (1.292 g, 4.92 mmol) was added Ethanol (20 ml), then Boc$_2$O, then DIPEA (2 ml, 11.45 mmol). The reaction mixture was then capped (not under N2) & stirred at room temperature. Followed by LC/MS. After 45 minutes the reaction mixture was suspended in EtOAc, washed with saturated NaHCO3, then H2O, then brine; organics dried over Na2SO4, filtered & concentrated. Purification by silica gel chromatography (0-20%, then isocratic @ 10% when 1st peak elutes; EtOAc/Hex; 120 g ISCO); desired fractions concentrated to yield tert-butyl 8-bromo-4-oxo-3,4-dihydroisoquinoline-2(1H)-carboxylate (24-3).

Preparation of tert-Butyl 8-bromo-4-hydroxy-3,4-dihydroisoquinoline-2(1H)-carboxylate (24-4)

To a flask containing tert-butyl 8-bromo-4-oxo-3,4-dihydroisoquinoline-2(1H)-carboxylate (24-3) (644 mg, 1.974 mmol) was added anhydrous THF (5 ml), followed by NaBH4 (399 mg, 10.55 mmol). The reaction mixture was then capped (not under N2) & stirred at room temperature. Followed by LC/MS. After 10 minutes the reaction mixture was quenched with saturated NaHCO3, then suspended in EtOAc, washed with saturated NaHCO3, then H2O, then brine; organics dried over Na2SO4, filtered & concentrated. Purification by silica gel chromatography (0-50% EtOAc/Hex; 40 g ISCO); desired fractions concentrated to yield tert-butyl 8-bromo-4-hydroxy-3,4-dihydroisoquinoline-2 (1H)-carboxylate (24-4). HRMS [M+H]: calculated; 328.0543, observed; 328.0537.

Preparation of tert-Butyl 8-bromo-4-fluoro-3,4-dihydroisoquinoline-2(1H)-carboxylate (24-5)

To a flask containing tert-butyl 8-bromo-4-hydroxy-3,4-dihydroisoquinoline-2(1H)-carboxylate (24-4) (622 mg, 1.895 mmol) was added anhydrous DCM (10 ml). The reaction mixture was then capped & cooled to −78 C (dry ice/acetone bath) while stirring under N2. Then added DAST (1.4 ml, 10.60 mmol) at −78 C. The reaction mixture was then stirred at −78 C. Followed by LC/MS. After 5 minutes at −78 C the reaction was quenched by dropwise addition of a saturated solution of NaHCO3 in water at −78 C (with a vent needle), then permitted to warm to room temperature, then the reaction mixture was suspended in EtOAc, washed with saturated NaHCO3, then H2O, then brine; organics dried over Na2SO4, filtered & concentrated to yield. Purification by silica gel chromatography (0-15% EtOAc/Hex; 40 g ISCO); desired fractions concentrated to yield tert-butyl 8-bromo-4-fluoro-3,4-dihydroisoquinoline-2(1H)-carboxylate (24-5).

Preparation of 2-tert-Butyl 8-methyl 4-fluoro-3,4-dihydroisoquinoline-2,8(1H)-dicarboxylate (24-6)

To a flask containing tert-butyl 8-bromo-4-fluoro-3,4-dihydroisoquinoline-2(1H)-carboxylate (24-5) (316 mg, 0.957 mmol) was added TRIETHYLAMINE (0.6 mL, 4.30 mmol), followed by degassed anhydrous MeOH (6 mL) & DMSO (3 mL). This mixture was then degassed by bubbling N2 through with a vent needle while stirring for ~5 minutes. Then added PdOAc2 (57 mg, 0.254 mmol) & DPPP (83 mg, 0.201 mmol) as solids in 1 portion. A balloon containing CARBON MONOXIDE (536 mg, 19.14 mmol) was then attached and the reaction was purged 3× (vacuum/CO), then the reaction mixture (clear tan, became darker with heat) was heated to 80 C while stirring in a hot oil bath in the hood under an atmosphere of CO. Followed by LC/MS. After 22 hours, the reaction mixture was suspended in EtOAc, washed with saturated NaHCO3, then H2O, then brine; organics dried over Na2SO4, filtered & concentrated. Purification by silica gel chromatography (0-40% EtOAc/Hex; 40 g ISCO); desired fractions concentrated to yield 2-tert-butyl 8-methyl 4-fluoro-3,4-dihydroisoquinoline-2,8(1H)-dicarboxylate (24-6). HRMS [M+H]: calculated; 310.1449, observed; 310.1439.

Preparation of tert-Butyl 4-fluoro-8-(hydroxymethyl)-3,4-dihydroisoquinoline-2(1H)-carboxylate (24-7)

To a flask containing 2-tert-butyl 8-methyl 4-fluoro-3,4-dihydroisoquinoline-2,8(1H)-dicarboxylate (24-6) (214 mg, 0.692 mmol), was added anhydrous THF (3.5 ml) then cooled to −78 C (dry ice/acetone bath) while stirring under an atmosphere of N2. Then added DIBAL-H (2.4 ml, 2.400 mmol) dropwise. The reaction mixture was then stirred at −78 C for ~20 minutes, then warmed to room temperature. Followed by LC/MS. After 10 minutes at room temperature quenched by dropwise addition of saturated solution of Rochelle's Salt (Na+/K+ Tartrate) in water, then suspended in EtOAc, washed with saturated NaHCO3, then H2O, then brine; organics dried over Na2SO4, filtered & concentrated. Purification by silica gel chromatography (0-40%; isocratic @ 30% EtOAc/Hex; 24 g ISCO); desired fractions concentrated to yield tert-butyl 4-fluoro-8-(hydroxymethyl)-3,4-dihydroisoquinoline-2(1H)-carboxylate (24-7). HRMS [M+H]; calculated; 282.1500, observed; 282.1491.

Preparation of tert-Butyl 8-((6-(N-(2,4-dimethoxybenzyl)-N-(1,2,4-thiadiazol-5-yl)sulfamoyl)-5-fluoro-2-oxobenzo[d]oxazol-3(2H)-yl)methyl)-4-fluoro-3,4-dihydroisoquinoline-2(1H)-carboxylate (24-8)

To a flask containing N-(2,4-dimethoxybenzyl)-5-fluoro-2-oxo-N-(1,2,4-thiadiazol-5-yl)-2,3-dihydrobenzo[d]oxazole-6-sulfonamide (11-3) (87 mg, 0.187 mmol), resin bound (PS) TRIPHENYLPHOSPHINE (159 mg, 0.350 mmol), tert-butyl 4-fluoro-8-(hydroxymethyl)-3,4-dihydroisoquinoline-2(1H)-carboxylate (24-7) (89 mg, 0.316 mmol) & DI-TERT-BUTYL AZODICARBOXYLATE (97 mg, 0.421 mmol) was added THF (2 mL). The reaction mixture was then capped (not under N2) & agitated at room temperature. Followed by LC/MS. After ~10 min at room temp rxn mixture (clear tan & resin), filtered (to remove resin), then concentrated. Purification by silica gel chromatography (0-50%; EtOAc/Hex; 24 g ISCO); desired fractions concentrated, then the resulting residue was repurified by reverse phase chromatography (10-100% MeCN/H2O; 0.1% TFA in AQ; 20 min gradient; Waters 30×150 mm Sunfire 5 micron C18 column); desired fractions free based (suspended in EtOAc, washed with saturated NaHCO3, then H2O, then brine; organics dried over Na2SO4, filtered & concentrated) to yield tert-butyl 8-((6-(N-(2,4-dimethoxybenzyl)-N-(1,2,4-thiadiazol-5-yl)sulfamoyl)-5-fluoro-2-oxobenzo[d]oxazol-3(2H)-yl)methyl)-4-fluoro-3,4-dihydroisoquinoline-2(1H)-carboxylate (24-8).

Preparation of 5-Fluoro-3-((4-fluoro-1,2,3,4-tetrahydroisoquinolin-8-yl)methyl)-2-oxo-N-(1,2,4-thiadiazol-5-yl)-2,3-dihydrobenzo[d]oxazole-6-sulfonamide hydrochloride (24-9)

To a flask containing tert-butyl 8-((6-(N-(2,4-dimethoxybenzyl)-N-(1,2,4-thiadiazol-5-yl)sulfamoyl)-5-fluoro-2-oxobenzo[d]oxazol-3(2H)-yl)methyl)-4-fluoro-3,4-dihydroisoquinoline-2(1H)-carboxylate (24-8) (48 mg, 0.066 mmol) in DCM (3 ml) was added TFA (0.5 ml, 6.49 mmol). The reaction mixture was then stirred at room temperature. Followed by LC/MS . . . after ~20 minutes the reaction mixture was diluted/quenched with DMSO, then MeOH, then filtered (syringe filter) then concentrated (to remove DCM), then diluted with MeOH/DMSO & purified (without workup) by reverse phase chromatography (5-75% MeCN/H2O; 0.1% TFA in AQ; 20 min gradient; Waters 30×150 mm Sunfire 5 micron C18 column); desired fractions concentrated (GENEVAC), then dissolved in MeOH/DCM & added saturated HCl in EtOAc (~4N) & concentrated to yield 5-fluoro-3-((4-fluoro-1,2,3,4-tetrahydroisoquinolin-8-yl)methyl)-2-oxo-N-(1,2,4-thiadiazol-5-yl)-2,3-dihydrobenzo[d]oxazole-6-sulfonamide hydrochloride (24-9). HRMS [M+H]: calculated; 480.0606, observed; 480.0587. $^1$H NMR (400 MHz, CD$_3$OD): δ 8.22 (s, 1H); 7.80 (d, J=5.5 Hz, 1H); 7.63-7.57 (m, 1H); 7.57-7.48 (m, 2H); 7.11 (d, J=9.3 Hz, 1H); 5.81 (d, J=48.5 Hz, 1H); 5.16-5.10 (m, 2H); 4.74-4.66 (m, 1H); 4.47-4.39 (m, 1H); 4.02-3.92 (m, 1H); 3.71-3.55 (m, 1H);

Example 19

Preparation of 3-((3-chloroisoquinolin-8-yl)methyl)-5-fluoro-2-oxo-N-(1,2,4-thiadiazol-5-yl)-2,3-dihydrobenzo[d]oxazole-6-sulfonamide (25-2) and 3-((3-Aminoisoquinolin-5-yl)methyl)-5-fluoro-2-oxo-N-(1,2,4-thiadiazol-5-yl)-2,3-dihydrobenzo[d]oxazole-6-sulfonamide (26-5)

Scheme 25

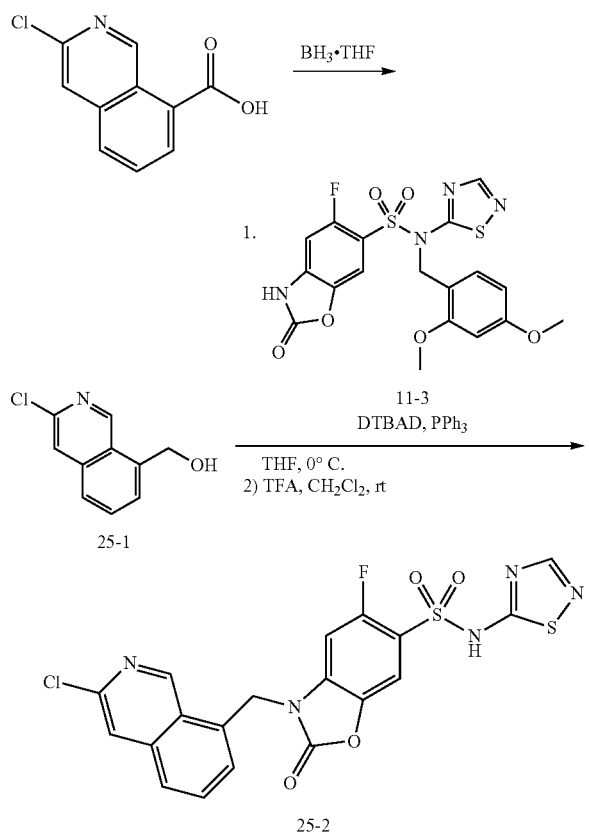

Preparation of (3-Chloroisoquinolin-8-yl)methanol (25-1)

A solution of 3-chloroisoquinoline-8-carboxylic acid (0.5 g, 1.803 mmol) in THF (18.03 ml) at 0° C. was treated with BH$_3$.THF (5.41 ml, 5.41 mmol). After stirring for 2 hours at 0° C., 1N NaOH was added. The reaction was stirred for 30 minutes then diluted with EtOAc and the layers were separated. Aqueous layer was washed with EtOAc three times. All combined organic layers were washed with brine, then dried with sodium sulfate. Filtered and concentrated in vacuo. Purified by silica gel chromatography (0-100% EtOAc in hexane) to yield (3-chloroisoquinolin-8-yl)methanol.

Preparation of 3-((3-Chloroisoquinolin-8-yl)methyl)-5-fluoro-2-oxo-N-(1,2,4-thiadiazol-5-yl)-2,3-dihydrobenzo[d]oxazole-6-sulfonamide (25-2)

A solution of N-(2,4-dimethoxybenzyl)-5-fluoro-2-oxo-N-(1,2,4-thiadiazol-5-yl)-2,3-dihydrobenzo[d]oxazole-6-sulfonamide (11-3) and (3-chloroisoquinolin-8-yl)methanol in THF (697 μl) at 0° C. was treated with ps-triphenylphosphine (73.1 mg, 0.279 mmol) (152 mg resin-bound PPh$_3$, 1.84 mmol PPh$_3$/g of resin), then (E)-di-tert-butyl diazene-1,2-dicarboxylate (64.2 mg, 0.279 mmol). Reaction mixtured was monitored at 0° C. After stirring at 0° C. for 2 h, the reaction was filtered and concentrated in vacuo. Residue was dissolved in 1 mL of DCM and treated with 0.25 mL of TFA. After stirring at RT for 30 minutes, the solvent and TFA were removed in vacuo. Purified by reverse phase chromatography (10-95% MeCN in water w/0.1% TFA, C18 column) to yield 25-2. $^1$H NMR δ (ppm)(CH$_3$OH-d$_4$): 9.48 (1H, s), 8.20 (1H, s), 7.96 (1H, s), 7.90 (1H, d, J=8.36 Hz), 7.81 (1H, d, J=5.48 Hz), 7.75 (1H, t, J=7.75 Hz), 7.57 (1H, d, J=7.08 Hz), 7.12 (1H, d, J=9.32 Hz), 5.69 (2H, s). HRMS [M+H] C$_{19}$H$_{11}$ClFN$_5$O$_4$S$_2$ calc'd 491.9998. Found 492.0001.

Scheme 26

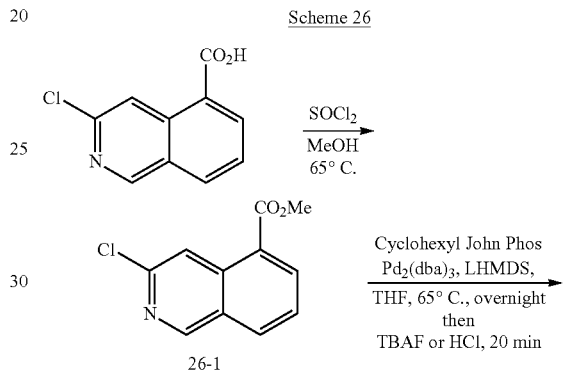

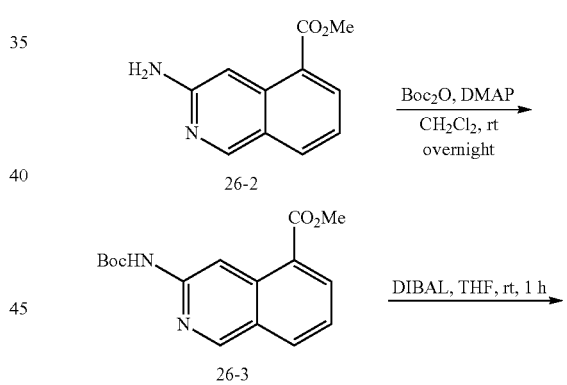

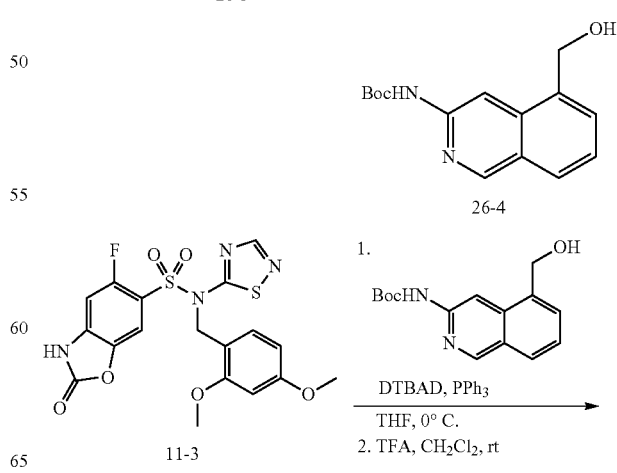

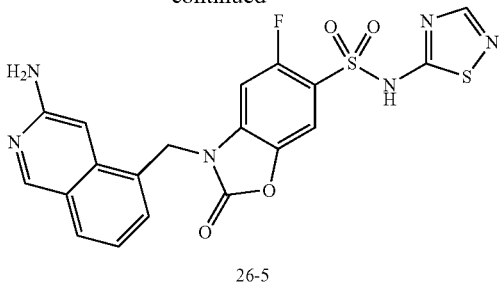

26-5

Preparation of Methyl 3-chloroisoquinoline-5-carboxylate (26-1)

A 20 mL microwave vial was charged with 3-chloroisoquinoline-5-carboxylic acid (1 g, 4.82 mmol) in 5 mL of MeOH and then was added with thionyl chloride (0.703 mL, 9.63 mmol). Stirred at 65° C. overnight and then concentrated in vacuo. Purified by silica gel chromatography (0-50% EtOAc in hexane) yielded Methyl 3-chloroisoquinoline-5-carboxylate (26-1).

Preparation of Methyl 3-aminoisoquinoline-5-carboxylate (26-2)

A 20 mL microwave vial was charged with methyl 3-chloroisoquinoline-5-carboxylate (0.36 g, 1.63 mmol), [1,1'-biphenyl]-2-yldicyclohexylphosphine (57 mg, 0.163 mmol), LHMDS (1.96 mL, 1.96 mmol) and $Pd_2(dba)_3$ (75 mg, 0.082 mmol) and then with 8 mL of THF. Reaction mixture was capped and stirred at 65° C. overnight. Then 2M HCl (4.08 mL, 8.17 mmol) was added and stirred at rt for 20 min. The reaction mixture was filtered and added with sat $NaHCO_3$. Extracted with EtOAc. Combined organic layer was dried, filtered, concentrated in vacuo. Purified by silica gel chromatography (0-50% EtOAc in hexane) yielded 58% Methyl 3-aminoisoquinoline-5-carboxylate (26-2).

Preparation of Methyl 3-((tert-butoxycarbonyl)amino)isoquinoline-5-carboxylate (26-3)

A 10 mL round bottom flask was charged with methyl 3-aminoisoquinoline-5-carboxylate (0.19 g, 0.94 mmol), di-tert-butyl dicarbonate (0.226 g, 1.034 mmol), DMAP (11 mg, 0.094 mmol) and anhydrous DCM (4.7 mL). The reaction mixture was stirred at rt overnight and then concentrated in vacuo. Purified by silica gel chromatography (0-50% EtOAc in hexane) yielded 35% methyl 3-((tert-butoxycarbonyl)amino)isoquinoline-5-carboxylate (26-3).

Preparation of tert-Butyl (5-(hydroxymethyl)isoquinolin-3-yl)carbamate (26-4)

A 10 mL round bottom flask with methyl 3-((tert-butoxycarbonyl)amino)isoquinoline-5-carboxylate (0.2 g, 0.662 mmol) in 6 mL THF was charged with DIBAL (3.3 mL, 3.31 mmol), The reaction mixture was stirred at rt. After stirring for 2 h, the reaction mixture was added with Rochelle's salt and stirred for 1 h and then extracted with EtOAc (3×20 mL). Combined organic layer was dried, filtered and then concentrated in vacuo. Purified by silica gel chromatography (0-100% EtOAc in hexane) yielded tert-butyl (5-(hydroxymethyl)isoquinolin-3-yl)carbamate (26-4).

Preparation of 3-((3-Aminoisoquinolin-5-yl)methyl)-5-fluoro-2-oxo-N-(1,2,4-thiadiazol-5-yl)-2,3-dihydrobenzo[d]oxazole-6-sulfonamide (26-5)

N-(2,4-dimethoxybenzyl)-5-fluoro-2-oxo-N-(1,2,4-thiadiazol-5-yl)-2,3-dihydrobenzo[d]oxazole-6-sulfonamide (50 mg, 0.107 mmol), (E)-di-tert-butyl diazene-1,2-dicarboxylate (49.4 mg, 0.214 mmol) and triphenylphosphine (56.2 mg, 0.214 mmol) were added to a 5 mL RB flask. Then THF was added and rxn mixture was stirred at 0° C. for 10 min before addition of tert-butyl (5-(hydroxymethyl)isoquinolin-3-yl)carbamate (29.4 mg, 0.107 mmol) in THF. After stirring at 0° C. for 2 h, the reaction was filtered and concentrated in vacuo. Residue was dissolved in 1 mL of DCM and treated with 0.25 mL of TFA. After stirring at RT for 30 minutes, the solvent and TFA were removed in vacuo. Purified by reverse phase chromatography (10-95% MeCN in water w/0.1% TFA, C18 column) to yield 26-5. $^1$H NMR δ (ppm)($CH_3$ OH-$d_4$): 9.02 (1H, s), 8.38 (1H, s), 7.95 (2H, d, J=8.72 Hz), 7.76 (1H, d, J=5.33 Hz), 7.55 (1H, d, J=7.15 Hz), 7.43 (1H, t, J=7.69 Hz), 7.01 (1H, d, J=9.05 Hz), 5.47 (2H, s). HRMS [M+H] $C_{19}H_{13}FN_6O_4S_2$ calc'd 473.0496. Found 473.0500.

Example 20

Preparation of 3-((3-aminoisoquinolin-8-yl)methyl)-5-fluoro-2-oxo-N-(1,2,4-thiadiazol-5-yl)-2,3-dihydrobenzo[d]oxazole-6-sulfonamide (27-5)

Scheme 27

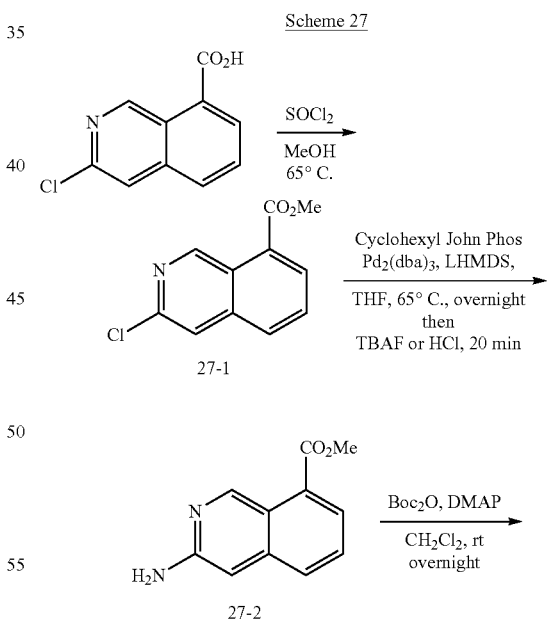

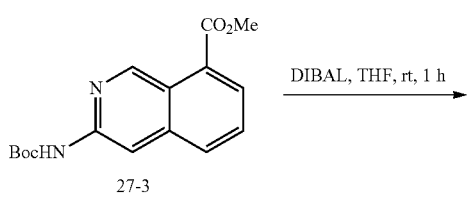

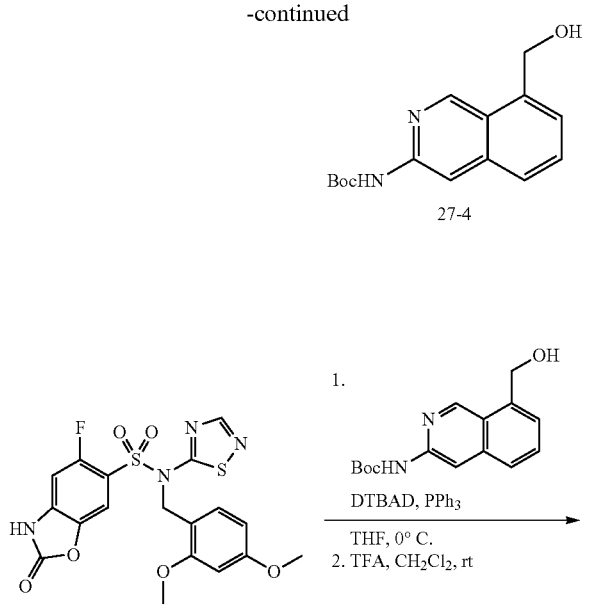

Preparation of Methyl 3-chloroisoquinoline-8-carboxylate (27-1)

A 20 mL microwave vial was charged with 3-chloroisoquinoline-8-carboxylic acid (1 g, 4.82 mmol) in 5 mL of MeOH and then was added with thionyl chloride (0.703 mL, 9.63 mmol). Stirred at 65° C. overnight and then concentrated in vacuo. Purified by silica gel chromatography (0-50% EtOAc in hexane) yielded Methyl 3-chloroisoquinoline-8-carboxylate (27-1).

Preparation of Methyl 3-aminoisoquinoline-8-carboxylate (27-2)

A 20 mL microwave vial was charged with methyl 3-chloroisoquinoline-8-carboxylate (0.56 g, 2.57 mmol), [1,1'-biphenyl]-2-yldicyclohexylphosphine (90 mg, 0.257 mmol), LHMDS (3.0 mL, 3.08 mmol) and $Pd_2(dba)_3$ (118 mg, 0.125 mmol) and then with 12 mL of THF. Reaction mixture was capped and stirred at 65° C. overnight. Then 2M HCl (1.2 mL, 2.57 mmol) was added and stirred at rt for 20 min. The reaction mixture was filtered and added with sat bi carb. Extracted with EtOAc. Combined organic layer was dried, filtered, concentrated in vacuo. Purified by silica gel chromatography (0-50% EtOAc in hexane) yielded 90% Methyl 3-aminoisoquinoline-8-carboxylate (27-2).

Preparation of Methyl 3-((tert-butoxycarbonyl)amino)isoquinoline-8-carboxylate (27-3)

A 10 mL round bottom flask was charged with methyl 3-aminoisoquinoline-8-carboxylate (0.469 g, 2.31 mmol), di-tert-butyl dicarbonate (0.557 g, 2.55 mmol), DMAP (28 mg, 0.232 mmol) and anhydrous DCM (11.6 mL). The reaction mixture was stirred at rt overnight and then concentrated in vacuo. Purified by silica gel chromatography (0-50% EtOAc in hexane) yielded 90% methyl 3-((tert-butoxycarbonyl)amino)isoquinoline-8-carboxylate (27-3).

Preparation of tert-Butyl (8-(hydroxymethyl)isoquinolin-3-yl)carbamate (27-4)

A 10 mL round bottom flask with methyl 3-((tert-butoxycarbonyl)amino)isoquinoline-5-carboxylate (0.473 g, 1.56 mmol) in 15 mL THF was charged with DIBAL (7.8 mL, 7.83 mmol), The reaction mixture was stirred at rt. After stirring for 2 h, the reaction mixture was added with Rochelle's salt and stirred for 1 h and then extracted with EtOAc (3×20 mL). Combined organic layer was dried, filtered and then concentrated in vacuo. Purified by silica gel chromatography (0-100% EtOAc in hexane) yielded tert-butyl (8-(hydroxymethyl)isoquinolin-3-yl)carbamate (27-4).

Preparation of 3-((3-Aminoisoquinolin-8-yl)methyl)-5-fluoro-2-oxo-N-(1,2,4-thiadiazol-5-yl)-2,3-dihydrobenzo[d]oxazole-6-sulfonamide (27-5)

N-(2,4-dimethoxybenzyl)-5-fluoro-2-oxo-N-(1,2,4-thiadiazol-5-yl)-2,3-dihydrobenzo[d]oxazole-6-sulfonamide (11-3, 50 mg, 0.107 mmol), (E)-di-tert-butyl diazene-1,2-dicarboxylate (49.4 mg, 0.214 mmol) and triphenylphosphine (56.2 mg, 0.214 mmol) were added to a 5 mL RB flask. Then THF was added and rxn mixture was stirred at 0° C. for 10 min before addition of tert-butyl (8-(hydroxymethyl)isoquinolin-3-yl)carbamate (29.4 mg, 0.107 mmol) in THF. After stirring at 0° C. for 2 h, the reaction was filtered and concentrated in vacuo. Residue was dissolved in 1 mL of DCM and treated with 0.25 mL of TFA. After stirring at RT for 30 minutes, the solvent and TFA were removed in vacuo. Purified by reverse phase chromatography (10-95% MeCN in water w/0.1% TFA, C18 column) to yield 27-5. $^1$H NMR δ (ppm)(DMSO-$d_6$): 9.08 (1H, s), 7.65 (1H, d, J=5.39 Hz), 7.47 (1H, d, J=8.47 Hz), 7.34-7.26 (2H, m), 6.92 (1H, d, J=7.03 Hz), 6.65 (1H, s), 5.50 (2H, s). HRMS [M+H] $C_{19}H_{13}FN_6O_4S_2$ calc'd 473.0496. Found 473.0499.

The following compounds were prepared from 1-5 and the appropriate alcohol by a synthetic sequence analogous to that illustrated in Scheme 27:

TABLE 13
| # | Structure | Name | HRMS |
|---|---|---|---|
| 27-6 | 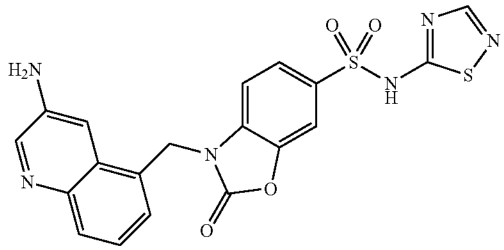 [SMILES: Nc1cnc2cccc(Cn3c(=O)oc4cc(S(=O)(=O)Nc5ncns5)ccc43)c2c1] | 3-[(3-aminoisoquinolin-5-yl)methyl]-2-oxo-N-1,2,4-thiadiazol-5-yl-2,3-dihydro-1,3-benzoxazole-6-sulfonamide | Calc'd 455.0591, found 455.057 |
| 27-7 | 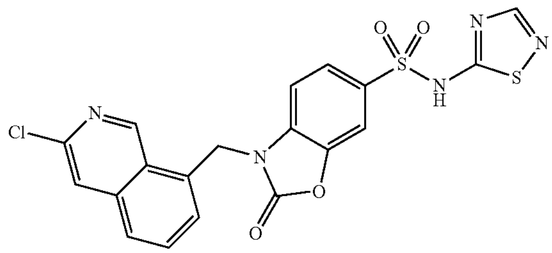 [SMILES: O=c1oc2cc(S(=O)(=O)Nc3ncns3)ccc2n1Cc1cccc2cc(Cl)ncc12] | 3-[(3-chloroisoquinolin-8-yl)methyl]-2-oxo-N-1,2,4-thiadiazol-5-yl-2,3-dihydro-1,3-benzoxazole | Calc'd 474.01, found 474.0082 |
Example 21
Preparation of (R)-3-(1-(3-(1-methyl-1H-pyrazol-3-yl)phenyl)ethyl)-2-oxo-N-(1,2,4-thiadiazol-5-yl)-2,3-dihydrobenzo[d]oxazole-6-sulfonamide (28-3)
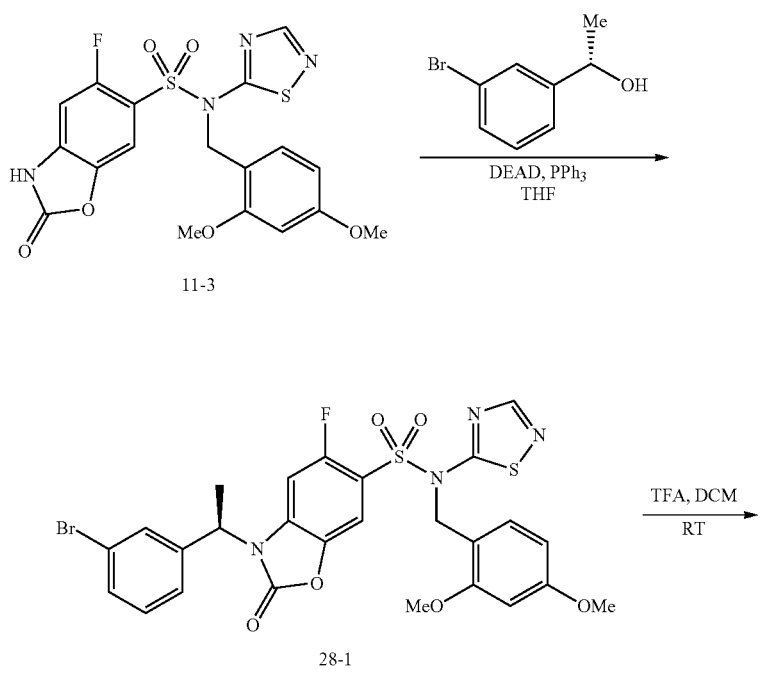
Scheme 28

-continued

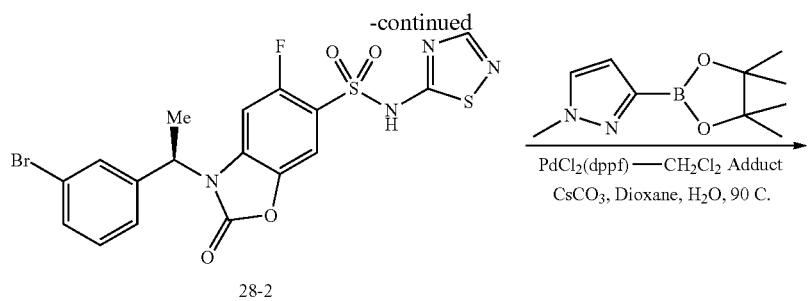

28-2

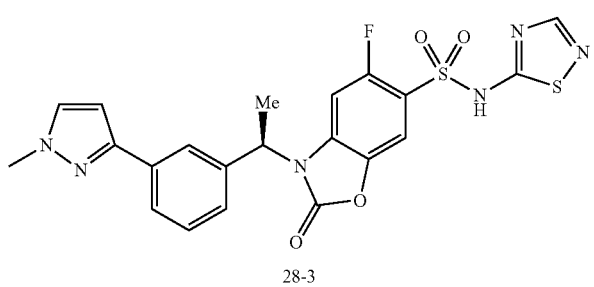

28-3

Preparation of (R)-3-(1-(3-Bromophenyl)ethyl)-N-(2,4-dimethoxybenzyl)-5-fluoro-2-oxo-N-(1,2,4-thiadiazol-5-yl)-2,3-dihydrobenzo[d]oxazole-6-sulfonamide (28-1)

Accordingly, the compound of Formula 28-1 ((R)-3-(1-(3-bromophenyl)ethyl)-N-(2,4-dimethoxybenzyl)-2-oxo-N-(1,2,4-thiadiazol-5-yl)-2,3-dihydrobenzo[d]oxazole-6-sulfonamide) was prepared from a solution provided by dissolving 2 g of the compound of Formula 11-3 (4.29 mmol, prepared as described above) and 0.862 g of (S)-1-(3-bromophenyl)ethanol (4.29 mmol) in 10 mL of THF. This solution was cooled to 0° C. and treated with triphenylphosphine (2.25 g, 8.58 mmol) followed by DEAD (1.36 mL, 8.58 mmol). After stirring at 0° C. for 120 min, the reaction mixture was diluted with EtOAc (50 mL) and sat'd sodium bicarbonate (10 mL), the aqueous layer was extracted with EtOAc (2×20 mL). The combined organics were washed with brine (10 mL), dried over sodium sulfate, filtered, and concentrated in vacuo. Purification by normal phase chromatography (10-80% EtOAc in hexane) yielded the compound of Formula 28-1 as a solid which was used as isolated.

Preparation of (R)-3-(1-(3-Bromophenyl)ethyl)-5-fluoro-2-oxo-N-(1,2,4-thiadiazol-5-yl)-2,3-dihydrobenzo[d]oxazole-6-sulfonamide (28-2)

A solution of the compound of Formula 28-2 was prepared by dissolving the compound of Formula 1 (2.2 g, 3.39 mmol) in 10 mL dichloromethane, and treating the resulting solution with trifluoroacetic acid (1.5 mL). After stirring for 30 minutes at RT, the solution was concentrated and purified by reverse phase HPLC (20-100% MeCN in water with 0.1% TFA, C18 column) to yield the compound of Formula 28-2 as the a white solid.

Preparation of (R)-5-Fluoro-3-(1-(3-(1-methyl-1H-pyrazol-3-yl)phenyl)ethyl)-2-oxo-N-(1,2,4-thiadiazol-5-yl)-2,3-dihydrobenzo[d]oxazole-6-sulfonamide (28-3)

In a sealed vial, compound of Formula 28-2 (45 mg, 0.090 mmol), 1-methyl-3-(4,4,5,5-tetramethyl-1,3,2-dioxaborolan-2-yl)-1H-pyrazole (21 mg, 0.10 mmol), PdCl2(dppf)-CH2Cl2 adduct (7.3 mg, 0.009 mmol), and cesium carbonate (88 mg, 0.270 mmol) were combined in dioxane (1 mL) and water (0.14 mL). The mixture was heated at 90° C. for 24 hours. The mixture was diluted with dioxane (4 mL), filtered through a celite pad, and the filtrate was concentrated. The resulting residue was purified by reverse phase HPLC (20-100% MeCN in water with 0.1% TFA, C18 column) to yield 28-3 as a white solid. $^1$H NMR δ (ppm)(DMSO-d): 8.50 (s, 1H); 7.74 (d, J=5.6 Hz, 1H); 7.63 (s, 1H); 7.52-7.46 (m, 5H); 7.41 (d, J=9.8 Hz, 1H); 6.40 (d, J=1.9 Hz, 1H); 5.65 (q, J=7.2 Hz, 1H); 3.79 (s, 3H); 1.91 (d, J=7.2 Hz, 3H). LRMS C21H18FN6O4S2 [M+H] calc 501.08, obs 501.0.

The compounds of Table 14 were prepared from 28-2 and the appropriate boronic ester in accordance with the process described in Scheme 28

TABLE 14

| No. | Structure | Name | Exact Mass [M + H]+ |
|---|---|---|---|
| 28-4 | 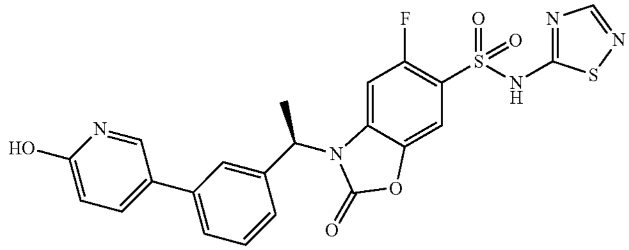 [SMILES: C[C@H](c1cccc(-c2ccc(O)nc2)c1)n1c(=O)oc2cc(S(=O)(=O)Nc3ncns3)c(F)cc21] | 5-fluoro-3-{(1R)-1-[3-(6-hydroxypyridin-3-yl)phenyl]ethyl}-2-oxo-N-1,2,4-thiadiazol-5-yl-2,3-dihydro-1,3-benzoxazole-6-sulfonamide | Calc'd 514.1, found 514.0 |
| 28-5 | 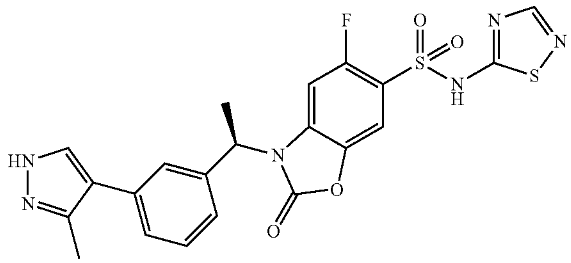 [SMILES: Cc1n[nH]cc1-c1cccc([C@@H](C)n2c(=O)oc3cc(S(=O)(=O)Nc4ncns4)c(F)cc32)c1] | 5-fluoro-3-{(1R)-1-[3-(3-methyl-1H-pyrazol-4-yl)phenyl]ethyl}-2-oxo-N-1,2,4-thiadiazol-5-yl-2,3-dihydro-1,3-benzoxazole-6-sulfonamide | Calc'd 501.1, found 501.0 |

Example 22

Preparation of 5-fluoro-3-(1-{3-[2-(hydroxymethyl) pyridin-4-yl]phenyl}ethyl)-2-oxo-N-1,2,4-thiadiazol-5-yl-2,3-dihydro-1,3-benzoxazole-6-sulfonamide (29-3)

Scheme 29

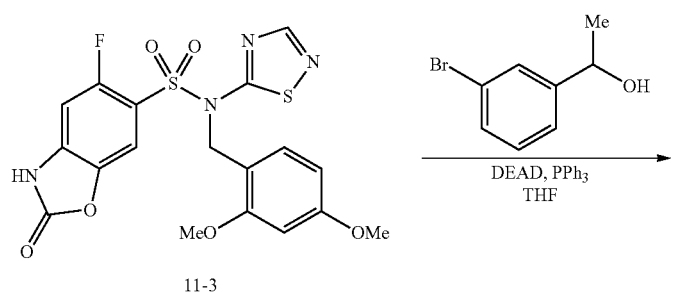

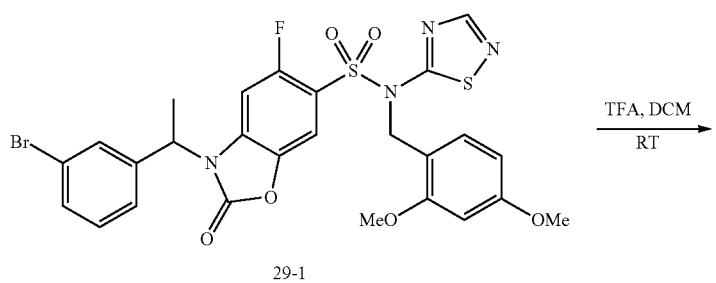

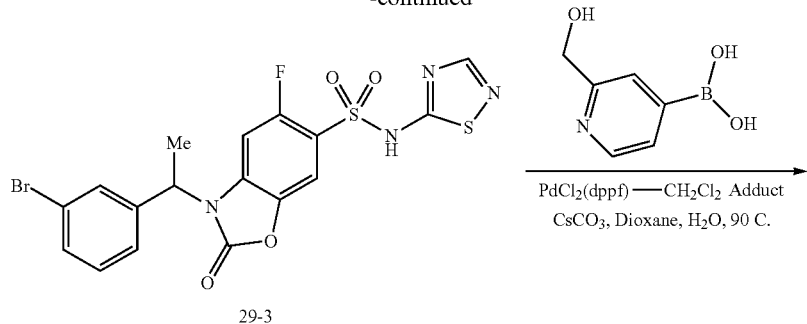

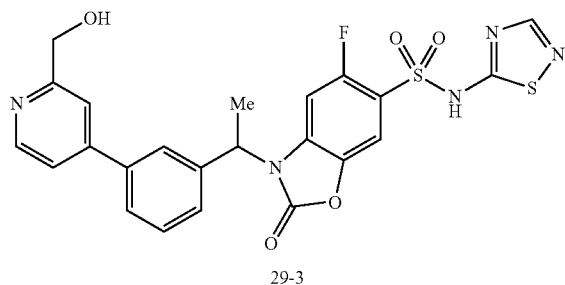

5-Fluoro-3-(1-{3-[2-(hydroxymethyl)pyridin-4-yl]phenyl}ethyl)-2-oxo-N-1,2,4-thiadiazol-5-yl-2,3-dihydro-1,3-benzoxazole-6-sulfonamide (29-3) was prepared from 1-(3-bromophenyl)ethanol and 11-3 in accordance with the experimental processes described in Scheme 28. $^1$H NMR δ (ppm)(Methanol-d): 8.68 (d, J=6.0 Hz, 1H); 8.28-8.24 (m, 3H); 8.00 (s, 1H); 7.92 (d, J=8.0 Hz, 1H); 7.77-7.64 (m, 3H); 7.02 (d, J=10.0 Hz, 1H); 5.72 (q, J=7.2 Hz, 1H); 5.02 (s, 3H); 2.00 (d, J=7.2 Hz, 3H). HRMS C23H19FN5O5S2 [M+H] calc 528.0808, obs 528.0820

The following compound was prepared from 11-3 by a reaction sequence analogous to that illustrated in Scheme 29:

TABLE 15

| # | Structure | Name | Exact Mass [M + H]+ |
|---|-----------|------|---------------------|
| 29-4 | 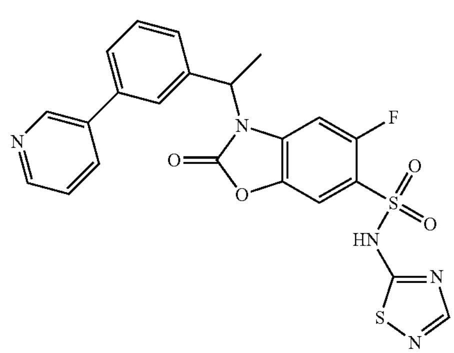 [SMILES: CC(c1cccc(-c2cccnc2)c1)n1c(=O)oc2cc(S(=O)(=O)Nc3ncns3)c(F)cc21] | 5-fluoro-2-oxo-3-[1-(3-pyridin-3-ylphenyl)ethyl]-N-1,2,4-thiadiazol-5-yl-2,3-dihydro-1,3-benzoxazole-6-sulfonamide | Calc'd 498.0701, found 498.0715 |

Example 23

Preparation of (R)-3-(1-(3-(3-aminoprop-1-yn-1-yl)phenyl)ethyl)-5-fluoro-2-oxo-N-(1,2,4-thiadiazol-5-yl)-2,3-dihydrobenzo[d]oxazole-6-sulfonamide (30-3)

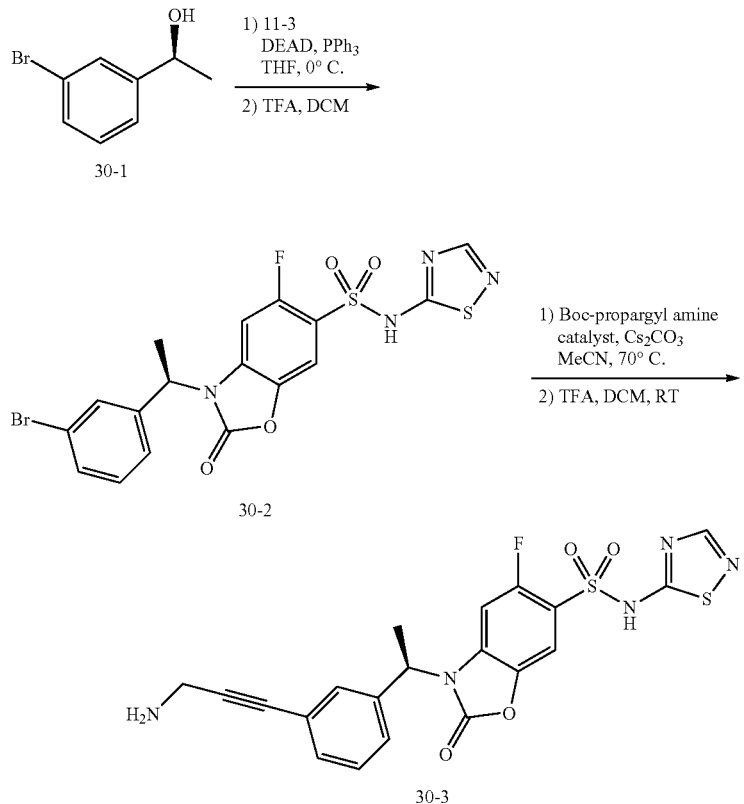

Scheme 30

Preparation of (R)-3-(1-(3-bromophenyl)ethyl)-5-fluoro-2-oxo-N-(1,2,4-thiadiazol-5-yl)-2,3-dihydrobenzo[d]oxazole-6-sulfonamide (30-2)

A solution of 11-3 and triphenylphosphine (2.59 g, 9.86 mmol) in THF (49.3 ml) was treated with DEAD (1.561 ml, 9.86 mmol) then cooled to 0° C. in an ice bath. Commercial (S)-1-(3-bromophenyl)ethanol (30-1, 0.991 g, 4.93 mmol) was added slowly as a solution in THF (5 ml). Stirred for 2 hours at 0° C., then concentrated in vacuo. Purified by normal phase chromatography (0-40% EtOAc in hexane). Isolated material was then deprotected with 30 mL of DCM and 5 mL of TFA at RT. After stirring for 30 minutes at RT, the solvent and TFA were removed in vacuo. Purified by reverse phase chromatography (10-80% MeCN in water w/0.1% TFA, C18 column) to yield 30-2 as a solid.

Preparation of (R)-3-(1-(3-(3-aminoprop-1-yn-1-yl)phenyl)ethyl)-5-fluoro-2-oxo-N-(1,2,4-thiadiazol-5-yl)-2,3-dihydrobenzo[d]oxazole-6-sulfonamide (30-3)

A solution of 30-2 (20 mg, 0.040 mmol), tert-butyl prop-2-yn-1-ylcarbamate (6.84 mg, 0.044 mmol), $Cs_2CO_3$ (39.2 mg, 0.120 mmol), and (2-DICYCLOHEXYLPHOSPHINO-2',4',6'-TRIISOPROPYL-1,1'-BIPHENYL)[2-(2-AMINOETHYL)PHENYL]PALLADIUM(II) CHLORIDE (2.96 mg, 4.01 µmol) in degassed MeCN (401 µl) was heated to 70° C. for 10 hours. Upon cooling to RT, the reaction was filtered and concentrated in vacuo. Residue was dissolved in 1 mL of DCM and treated with 0.2 mL of TFA. After stirring for 1 hour at RT, the solvent and TFA were removed in vacuo. Purified by reverse phase chromatography (5-70% MeCN in water w/0.1% TFA, C18 column) to yield 30-3 (TFA salt) as a tan solid. $^1$H NMR δ (ppm)(DMSO-$d_6$): 8.45 (1H, s), 8.25 (3H, s), 7.75 (1H, d, J=5.50 Hz), 7.56 (1H, d, J=7.39 Hz), 7.49 (1H, s), 7.46-7.36 (3H, m), 5.63-5.59 (1H, m), 4.01-3.95 (2H, m), 1.86 (3H, d, J=7.16 Hz). HRMS C20H16FN5O4S2 [M+H] calc: 474.0701, obs: 474.0700.

The following compound was prepared from 30-2 and the appropriate acetylene by a synthetic sequence analogous to that illustrated in Scheme 30:

TABLE 16

| # | Structure | Name | Exact Mass [M + H]+ |
|---|---|---|---|
| 30-4 | 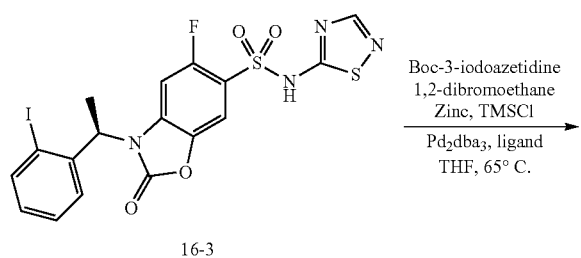 | 3-[(1R)-1-{3-[(1-aminocyclohexyl)ethynyl]phenyl}ethyl]-5-fluoro-2-oxo-N-1,2,4-thiadiazol-5-yl-2,3-dihydro-1,3-benzoxazole-6-sulfonamide | Calc'd 542.1, found 542.2 |

Example 24

Preparation of (R)-3-(1-(2-(azetidin-3-yl)phenyl)ethyl)-5-fluoro-2-oxo-N-(1,2,4-thiadiazol-5-yl)-2,3-dihydrobenzo[d]oxazole-6-sulfonamide (31-1)

Scheme 31

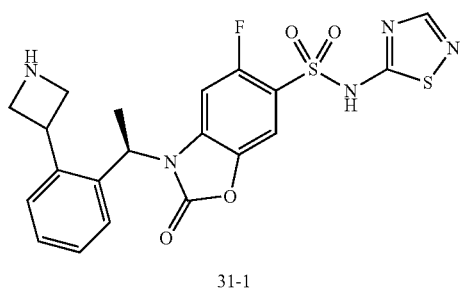

To a flask containing a suspension of zinc metal (1.594 g, 24.39 mmol) in 10 mL of THF was added 1,2-dibromoethane (0.210 ml, 2.439 mmol). Heated to 65° C. in a preheated oil bath. After 10 minutes at 65° C., the reaction was allowed to cool to room temperature. TMS-Cl (0.312 ml, 2.439 mmol) was added and reaction was stirred at room temperature for 30 minutes. tert-butyl 3-iodoazetidine-1-carboxylate (6.56 g, 23.17 mmol) in 6.5 mL of THF was added and the reaction was stirred at room temperature for 45 minutes. 1 ml of the prepared solution above was then added to a prepared solution of 16-3 (20 mg, 0.037 mmol), tri(2-furyl)phosphine (3.40 mg, 0.015 mmol) and $Pd_2dba_3$ (3.35 mg, 3.66 mol) in THF (366 µl) under a nitrogen atmosphere. Heated overnight at 65° C. under nitrogen in a sealed tube. Upon cooling to RT, reaction was quenched with water (0.5 mL) and extracted into EtOAc (3×5 mL). Combined organic layers were dried over sodium sulfate, filtered and concentrated in vacuo. Dissolved residue in 1 mL of DCM and treated with 0.2 mL of TFA at RT. After stirring at RT for 30 minutes, the solvent and TFA were removed in vacuo. Purified by reverse phase chromatography (5-70% MeCN in water w/0.1% TFA, C18 column) to yield 31-1 (TFA salt) as an off-white solid. $^1H$ NMR δ (ppm)(DMSO-$d_6$): 8.91 (1H, s), 8.58 (1H, s), 8.46 (1H, s), 7.77-7.73 (2H, m), 7.64 (1H, d, J 7.74 Hz), 7.51 (1H, t, J=7.53 Hz), 7.44 (1H, t, J=7.58 Hz), 7.01 (1H, d, J=9.84 Hz), 5.60-5.53 (1H, m), 4.35-4.22 (2H, m), 4.18-4.10 (1H, m), 3.99-3.87 (2H, m), 1.79 (3H, d, J=6.97 Hz). HRMS C20H18FN5O4S2 [M+H] calc: 476.0857, obs: 476.0843.

Example 25

Preparation of (R)-5-fluoro-3-(1-(2-(3-hydroxyazetidin-3-yl)phenyl)ethyl)-2-oxo-N-(1,2,4-thiadiazol-5-yl)-2,3-dihydrobenzo[d]oxazole-6-sulfonamide (32-4) and (R)-5-Fluoro-3-(1-(2-(3-fluoroazetidin-3-yl)phenyl)ethyl)-2-oxo-N-(1,2,4-thiadiazol-5-yl)-2,3-dihydrobenzo[d]oxazole-6-sulfonamide (32-6)

Scheme 32

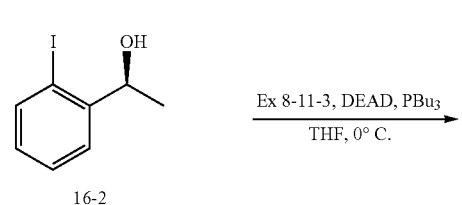

Ex 8-11-3, DEAD, $PBu_3$
THF, 0° C.

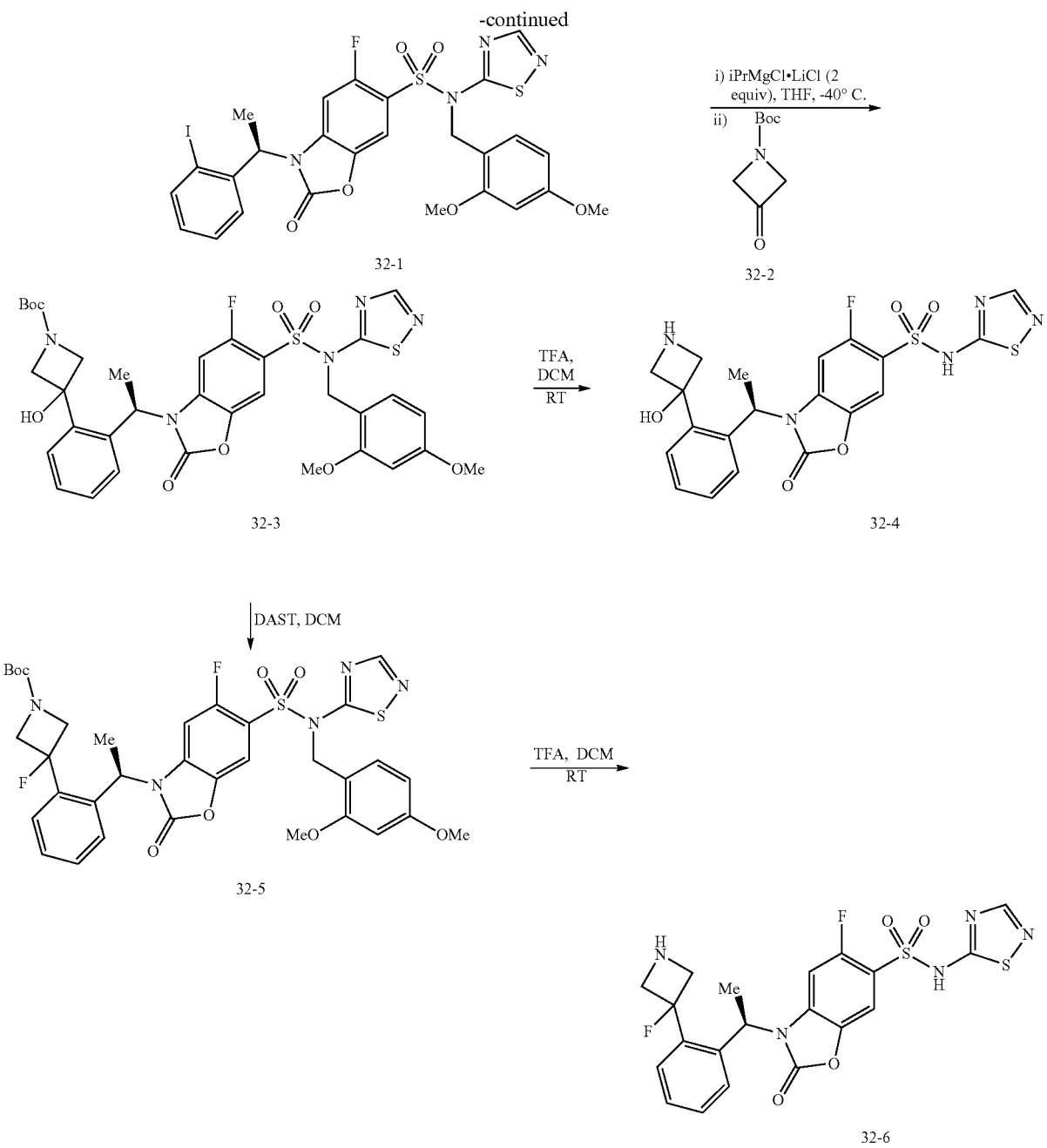

Preparation of (R)—N-(2,4-Dimethoxybenzyl)-5-fluoro-3-(1-(2-iodophenyl)ethyl)-2-oxo-N-(1,2,4-thiadiazol-5-yl)-2,3-dihydrobenzo[d]oxazole-6-sulfonamide (32-1)

Added N-(2,4-dimethoxybenzyl)-5-fluoro-2-oxo-N-(1,2,4-thiadiazol-5-yl)-2,3-dihydrobenzo[d]oxazole-6-sulfonamide (11-3, 2 g, 4.29 mmol) to THF (21.44 ml). Added tri-n-butylphosphine (2.116 ml, 8.58 mmol) and DEAD (1.358 ml, 8.58 mmol) and cooled to 0° C. Was a clear orange solution. Added (S)-1-(2-iodophenyl)ethanol (16-2, 1.064 g, 4.29 mmol). After 24 h at 0° C., concentrated in vacuo, dissolved in 5 mL DCM and purified by normal-phase HPLC (80 g ISCO column, 0-50% EtOAc:Hex) to give 32-1 as a white solid.

Preparation of (R)-tert-Butyl 3-(2-(1-(6-(N-(2,4-dimethoxybenzyl)-N-(1,2,4-thiadiazol-5-yl)sulfamoyl)-5-fluoro-2-oxobenzo[d]oxazol-3(2H)-yl)ethyl)phenyl)-3-hydroxyazetidine-1-carboxylate (32-3)

In an oven-dried 25 mL RB flask, added (R)—N-(2,4-dimethoxybenzyl)-5-fluoro-3-(1-(2-iodophenyl)ethyl)-2-oxo-N-(1,2,4-thiadiazol-5-yl)-2,3-dihydrobenzo[d]oxazole-6-sulfonamide (32-1, 400 mg, 0.574 mmol) to THF (2154 μl) and cooled to −40° C. Was a suspension. Added isopropylmagnesium chloride-lithium chloride complex (1325 μl, 1.723 mmol) dropwise, stirred at −40° C. for 20 min—became a dark orange solution. Following this duration, added tert-butyl 3-oxoazetidine-1-carboxylate (32-2, 295 mg, 1.723 mmol) in THF (718 μl) dropwise via syringe. Solution turned yellow in color. After 60 min at −40° C., partitioned between 10 mL saturated NH₄Cl+15 mL EtOAc, separated layers. Back-extracted aqueous with 2×10 mL EtOAc. Dried combined organics over Na₂SO₄, filtered, concentrated to give a yellow oil. Dissolved in 2 mL DMSO, purified by reverse-phase HPLC (C18 column, 10-90% (0.1% TFA/CH₃CN: 0.1% TFA/H₂O) to give 32-3 as a white solid.

Preparation of (R)-5-Fluoro-3-(1-(2-(3-hydroxyazetidin-3-yl)phenyl)ethyl)-2-oxo-N-(1,2,4-thiadiazol-5-yl)-2,3-dihydrobenzo[d]oxazole-6-sulfonamide (32-4)

In a 1 dram vial, added (R)-tert-butyl 3-(2-(1-(6-(N-(2,4-dimethoxybenzyl)-N-(1,2,4-thiadiazol-5-yl)sulfamoyl)-5-fluoro-2-oxobenzo[d]oxazol-3(2H)-yl)ethyl)phenyl)-3-hydroxyazetidine-1-carboxylate (32-3, 60 mg, 0.081 mmol) to DCM (647 μl) and TFA (162 μl). After 15 min, diluted with 1 mL MeOH, filtered through Celite, purified by reverse-phase HPLC (20 min run, 5-60% 0.1% TFA/CH₃CN:0.1% TFA/H₂O) to give 32-4 as a white solid. ¹H NMR δ (ppm) (CH₃OH-d₄): 8.21 (1H, s), 7.83 (1H, d, J=7.64 Hz), 7.71 (1H, d, J=5.61 Hz), 7.54-7.41 (2H, m), 7.27 (1H, d, J=7.61 Hz), 7.00 (1H, d, J=10.04 Hz), 5.52 (1H, dt, J=13.86, 6.77 Hz), 4.42 (2H, dd, J=10.60, 3.89 Hz), 4.14 (2H, dd, J=10.77, 3.87 Hz), 1.95 (3H, d, J=6.97 Hz). HRMS C20H19FN5O5S2 [M+H] calc: 492.0806, obs: 492.0796.

Preparation of (R)-tert-Butyl 3-(2-(1-(6-(N-(2,4-dimethoxybenzyl)-N-(1,2,4-thiadiazol-5-yl)sulfamoyl)-5-fluoro-2-oxobenzo[d]oxazol-3(2H)-yl)ethyl)phenyl)-3-fluoroazetidine-1-carboxylate (32-5)

In an oven-dried 2 dram vial under N₂, added (R)-tert-butyl 3-(2-(1-(6-(N-(2,4-dimethoxybenzyl)-N-(1,2,4-thiadiazol-5-yl)sulfamoyl)-5-fluoro-2-oxobenzo[d]oxazol-3(2H)-yl)ethyl)phenyl)-3-hydroxyazetidine-1-carboxylate (32-3, 55.8 mg, 0.075 mmol) to DCM (376 μl) and cooled to −78° C. Added DAST (19.88 μl, 0.150 mmol) dropwise. After 30 min at −78° C., removed from bath and allowed to slowly warm to RT. After 20 min, LCMS showed complete consumption of SM to desired product. Cooled reaction to 0° C., slowly quenched with 3 mL H₂O. Diluted with 5 mL DCM, separated layers, back-extracted aqueous with 1×5 mL DCM. Washed combined organics with 1×5 mL H₂O, 1×5 mL brine. Dried combined organics over Na₂SO₄, filtered, concentrated to give 32-5 as a white solid. Carried crude material forward to subsequent step.

Preparation of (R)-5-Fluoro-3-(1-(2-(3-fluoroazetidin-3-yl)phenyl)ethyl)-2-oxo-N-(1,2,4-thiadiazol-5-yl)-2,3-dihydrobenzo[d]oxazole-6-sulfonamide (32-6)

In a 1 dram vial, added crude (R)-tert-butyl 3-(2-(1-(6-(N-(2,4-dimethoxybenzyl)-N-(1,2,4-thiadiazol-5-yl)sulfamoyl)-5-fluoro-2-oxobenzo[d]oxazol-3(2H)-yl)ethyl)phenyl)-3-fluoroazetidine-1-carboxylate (32-5, 25.8 mg, 0.035 mmol) to DCM (277 μl) and TFA (69.4 μl). After 15 min, diluted with 1 mL MeOH, filtered through Celite and concentrated in vacuo. Dissolved in 2 mL DMSO and purified by reverse-phase HPLC (C18 column, 5-60% 0.1% TFA/CH₃CN:0.1% TFA/H₂O) to give 32-6 as a white solid. ¹H NMR δ (ppm) (CH₃OH-d₄): 8.22 (1H, s), 7.80 (1H, d, J=7.86 Hz), 7.75 (1H, d, J=5.61 Hz), 7.62 (1H, t, J=7.61 Hz), 7.56-7.44 (2H, m), 7.06 (1H, d, J=9.97 Hz), 5.49 (1H, d, J=6.64 Hz), 5.12-4.90 (2H, m), 4.81-4.61 (2H, m), 1.95 (3H, d, J=7.03 Hz). HRMS C20H18F2N5O4S2 [M+H] calc: 494.0763, obs: 494.0754.

Example 26

Preparation of (R)-3-(1-(2-(3-Aminopropyl)phenyl)ethyl)-5-fluoro-2-oxo-N-(1,2,4-thiadiazol-5-yl)-2,3-dihydrobenzo[d]oxazole-6-sulfonamide (33-7)

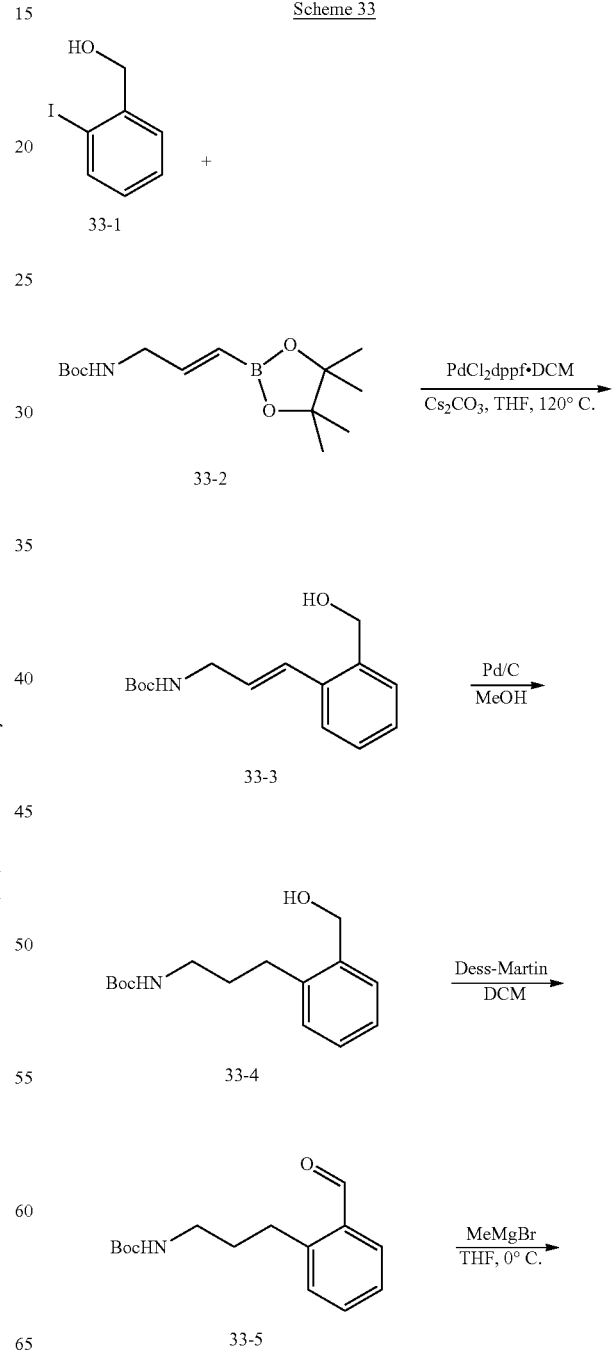

Scheme 33

-continued

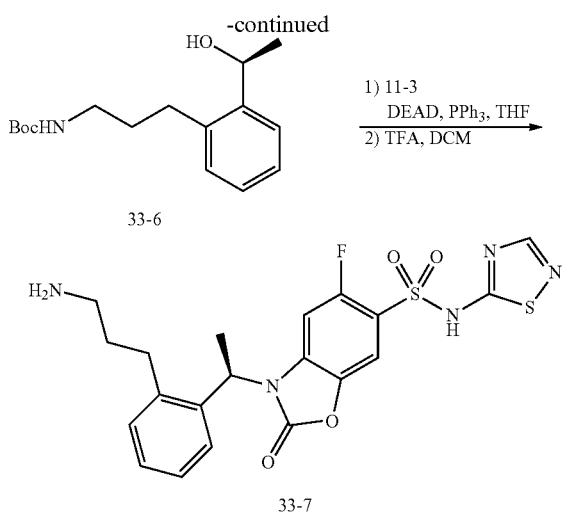

Preparation of (E)-tert-Butyl (3-(2-(hydroxymethyl)phenyl)allyl)carbamate (33-3)

A solution of 33-1 (1 g, 4.27 mmol), 33-2 (2.420 g, 8.55 mmol), Cs$_2$CO$_3$ (6.41 ml, 6.41 mmol), and PdCl$_2$(dppf)-dichloromethane adduct (0.349 g, 0.427 mmol) in degassed THF (21 ml) was heated to 120° C. for 4 hours under an atmosphere of nitrogen in a sealed tube. Upon cooling to RT, the reaction was diluted with 150 mL of EtOAc, then washed with 50 mL of water and brine. Organic layer was dried over Sodium sulfate, filtered and concentrated in vacuo. Purified by normal phase column chromatography (0-40% EtOAc in hexane) to yield 33-3.

Preparation of tert-Butyl (3-(2-(hydroxymethyl)phenyl)propyl)carbamate (33-4)

A solution of 33-3 (0.987 g, 3.19 mmol) in MeOH (32 ml) was treated with Pd/C (0.339 g, 0.319 mmol) under an atmosphere of nitrogen in a three-necked round bottomed flask. The vessel was then briefly evacuated, then backfilled with a balloon containing Hydrogen gas. The reaction was stirred at RT for 2 hours, then filtered through celite, washed with MeOH, followed by dichloromethane. Filtrate was concentrated in vacuo and purified by reverse phase chromatography (C18 column, 5-95% MeCN in water with 0.1% TFA) to yield 33-4.

Preparation of tert-Butyl (3-(2-formylphenyl)propyl)carbamate (33-5)

A solution of 33-4 (0.5 g, 1.884 mmol) in dichloromethane (32 ml) was cooled to 0° C. in an ice bath. Dess-Martin Periodinane (1.199 g, 2.83 mmol) was then added in four portions over 20 minutes. After 1 hour, ether was added and the reaction was quenched with 30 mL of 1N NaOH (aq) followed by vigorous stirring for 30 minutes. The layers were then separated. The organic layer was dried over Sodium sulfate, filtered and concentrated in vacuo. The crude material was purified by silica gel column chromatography (0-30% EtOAc in hexane) to yield 33-5.

Preparation of (S)-tert-Butyl (3-(2-(1-hydroxyethyl)phenyl)propyl)carbamate (33-6)

A solution of 33-5 (0.385 g, 1.462 mmol) in was treated with methylmagnesium bromide (5.1 ml, 15.3 mmol, 3M in diethylether) at 0° C. After stirring overnight at RT, the reaction was quenched with NH$_4$Cl solution. Extracted with Ethyl acetate, washed with brine and dried over sodium sulfate. Material was purified by reverse phase column chromatography (C18 column, 5-95% MeCN in water with 0.1% TFA) to yield a white solid. Racemic material was separated by chiral chromatography (ChiralTech IC column) to yield 33-6.

Preparation of (R)-3-(1-(2-(3-Aminopropyl)phenyl)ethyl)-5-fluoro-2-oxo-N-(1,2,4-thiadiazol-5-yl)-2,3-dihydrobenzo[d]oxazole-6-sulfonamide (33-7)

A solution of 11-3 (42 mg, 0.090 mmol) in THF (0.9 mL) was treated with DEAD (28.5 µl, 0.180 mmol) followed by triphenylphosphine (47.2 mg, 0.180 mmol). Cooled to 0° C., then added 33-6 (25.2 mg, 0.090 mmol). After stirring at RT for 18 hours, the reaction was concentrated in vacuo. Residue was taken up in 1 mL of dichloromethane and treated with 0.25 mL of TFA. After stirring for 30 minutes at RT, the solvent and TFA were removed in vacuo and the reaction was filtered and purified by reverse phase column chromatography (C18 column, 5-95% MeCN in water with 0.1% TFA) to yield 33-7 as the TFA salt. $^1$H NMR δ (ppm)(DMSO-d$_6$): 8.44 (1H, s), 7.76-7.64 (4H, m), 7.35-7.31 (2H, m), 7.25-7.20 (1H, m), 7.07 (1H, d, J=9.90 Hz), 5.74-5.65 (1H, m), 2.83-2.71 (2H, m), 2.71-2.60 (1H, m), 2.6-2.52 (1H, m), 1.82 (3H, d, J=7.07 Hz), 1.77-1.68 (1H, m), 1.67-1.55 (1H, m). HRMS [M+H] calc: 478.1014, obs: 478.1015.

The following compound was prepared from 11-3 and ent-33-6 by a reaction sequence analogous to that described in Scheme 33:

TABLE 16

| # | Structure | Name | Exact Mass [M + H]+ |
|---|---|---|---|
| 33-8 | 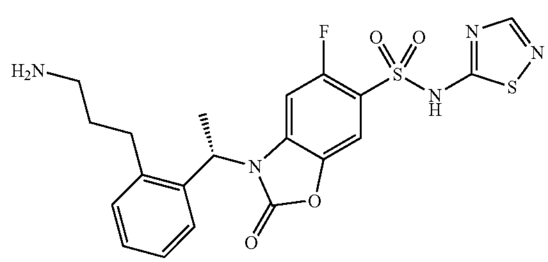 [SMILES: C[C@@H](c1ccccc1CCCN)n1c(=O)oc2cc(S(=O)(=O)Nc3ncns3)c(F)cc21] | 3-{(1S)-1-[2-(3-aminopropyl)phenyl]ethyl}-5-fluoro-2-oxo-N-1,2,4-thiadiazol-5-yl-2,3-dihydro-1,3-benzoxazole-6-sulfonamide | Calc'd 478.1014, found 478.1017 |

Example 27

Preparation of (R)-5-chloro-2-oxo-3-(1-(2-(1,2,3,6-tetrahydropyridin-4-yl)phenyl)ethyl)-N-(1,2,4-thiadiazol-5-yl)-2,3-dihydrobenzo[d]oxazole-6-sulfonamide hydrochloride (34-6)

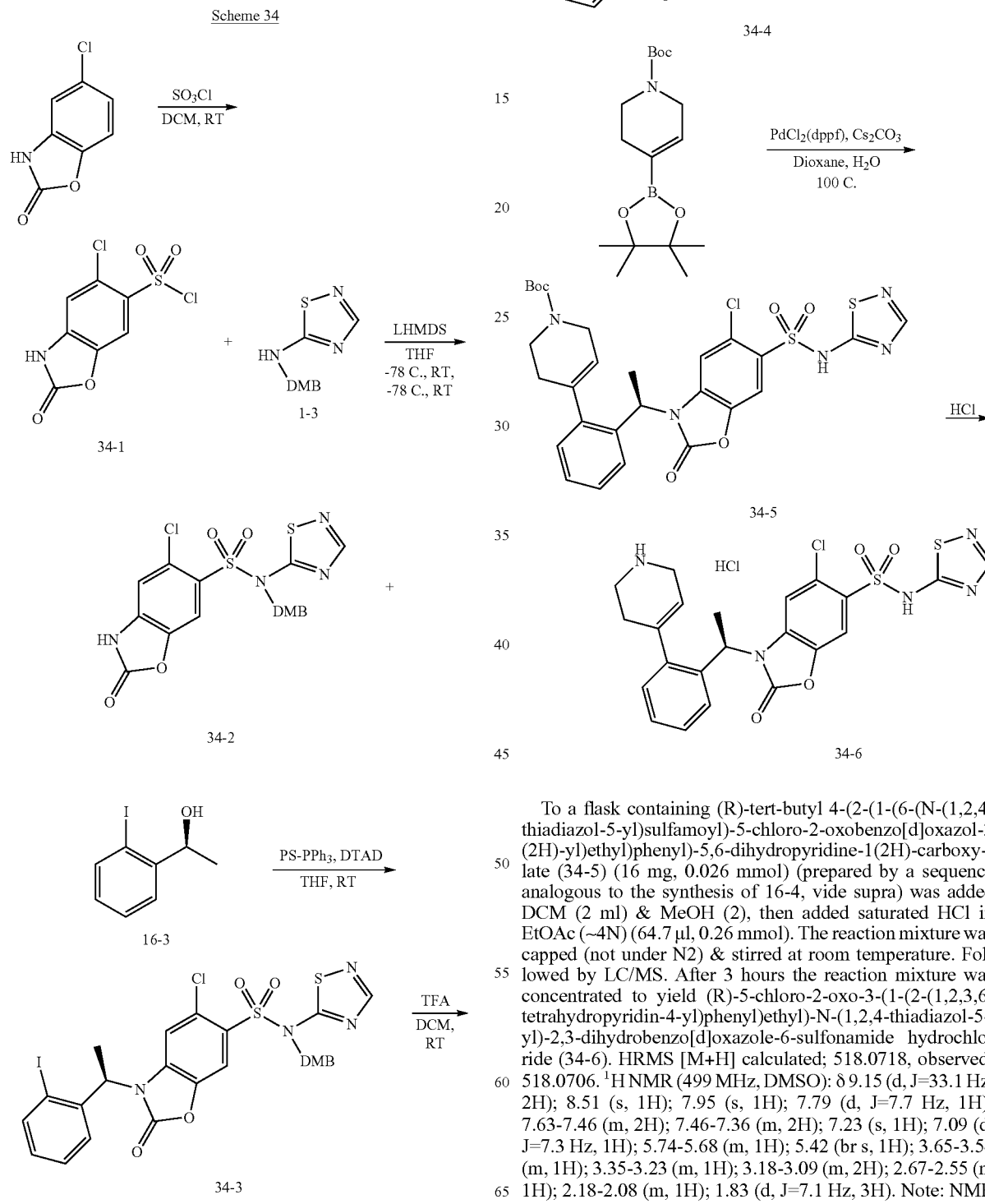

To a flask containing (R)-tert-butyl 4-(2-(1-(6-(N-(1,2,4-thiadiazol-5-yl)sulfamoyl)-5-chloro-2-oxobenzo[d]oxazol-3(2H)-yl)ethyl)phenyl)-5,6-dihydropyridine-1(2H)-carboxylate (34-5) (16 mg, 0.026 mmol) (prepared by a sequence analogous to the synthesis of 16-4, vide supra) was added DCM (2 ml) & MeOH (2), then added saturated HCl in EtOAc (~4N) (64.7 μl, 0.26 mmol). The reaction mixture was capped (not under N2) & stirred at room temperature. Followed by LC/MS. After 3 hours the reaction mixture was concentrated to yield (R)-5-chloro-2-oxo-3-(1-(2-(1,2,3,6-tetrahydropyridin-4-yl)phenyl)ethyl)-N-(1,2,4-thiadiazol-5-yl)-2,3-dihydrobenzo[d]oxazole-6-sulfonamide hydrochloride (34-6). HRMS [M+H] calculated; 518.0718, observed; 518.0706. $^1$H NMR (499 MHz, DMSO): δ 9.15 (d, J=33.1 Hz, 2H); 8.51 (s, 1H); 7.95 (s, 1H); 7.79 (d, J=7.7 Hz, 1H); 7.63-7.46 (m, 2H); 7.46-7.36 (m, 2H); 7.23 (s, 1H); 7.09 (d, J=7.3 Hz, 1H); 5.74-5.68 (m, 1H); 5.42 (br s, 1H); 3.65-3.54 (m, 1H); 3.35-3.23 (m, 1H); 3.18-3.09 (m, 2H); 2.67-2.55 (m 1H); 2.18-2.08 (m, 1H); 1.83 (d, J=7.1 Hz, 3H). Note: NMR peaks overlapping with solvent or water could not be accurately accounted for.

The following compounds can be prepared from 34-2 using previously-described synthetic sequences presented herein:

TABLE 17

| # | Structure | Name | Exact Mass [M + H]+ |
|---|---|---|---|
| 34-7 | 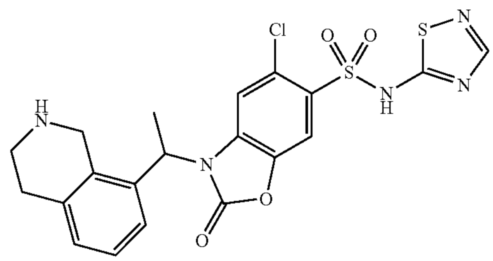 [SMILES: CC(c1cccc2c1CNCC2)n1c(=O)oc2cc(S(=O)(=O)Nc3ncns3)c(Cl)cc21] | (+/−)-5-chloro-2-oxo-3-[1-(1,2,3,4-tetrahydroisoquinolin-8-yl)ethyl]-N-1,2,4-thiadiazol-5-yl-2,3-dihydro-1,3-benzoxazole-6-sulfonamide | Calc'd 492.0562, found 492.0541 |
| 34-8 | 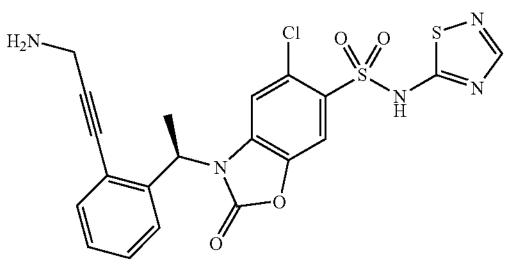 [SMILES: C[C@H](c1ccccc1C#CCN)n1c(=O)oc2cc(S(=O)(=O)Nc3ncns3)c(Cl)cc21] | 3-{(1R)-1-[2-(3-aminoprop-1-yn-1-yl)phenyl]ethyl}-5-chloro-2-oxo-N-1,2,4-thiadiazol-5-yl-2,3-dihydro-1,3-benzoxazole-6-sulfonamide | Calc'd 490.0405, found 490.0389 |

Example 28

Preparation of (R)-5-bromo-2-oxo-3-(1-(1,2,3,4-tetrahydroisoquinolin-8-yl)ethyl)-N-(1,2,4-thiadiazol-5-yl)-2,3-dihydrobenzo[d]oxazole-6-sulfonamide (35-5)

Scheme 35

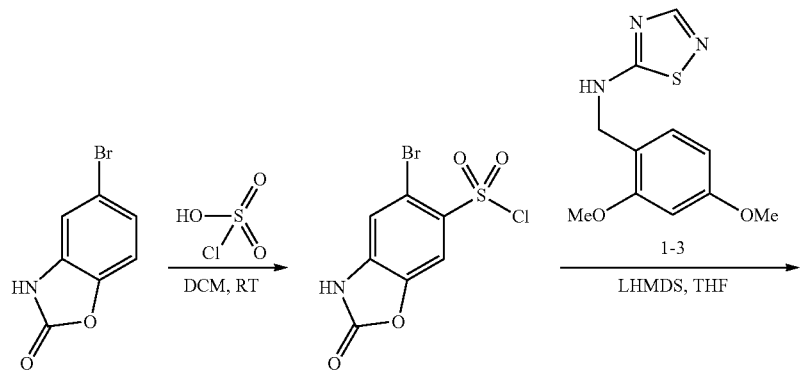

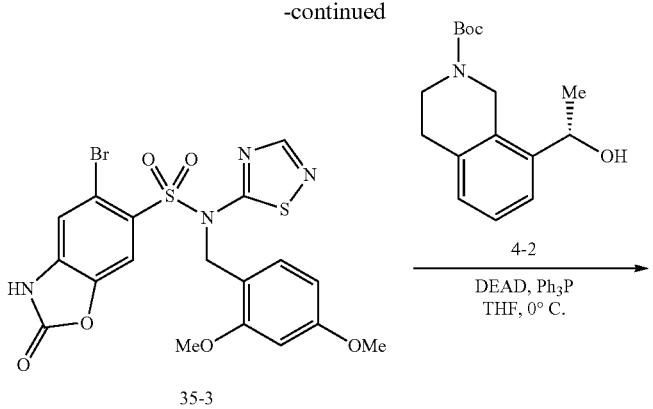

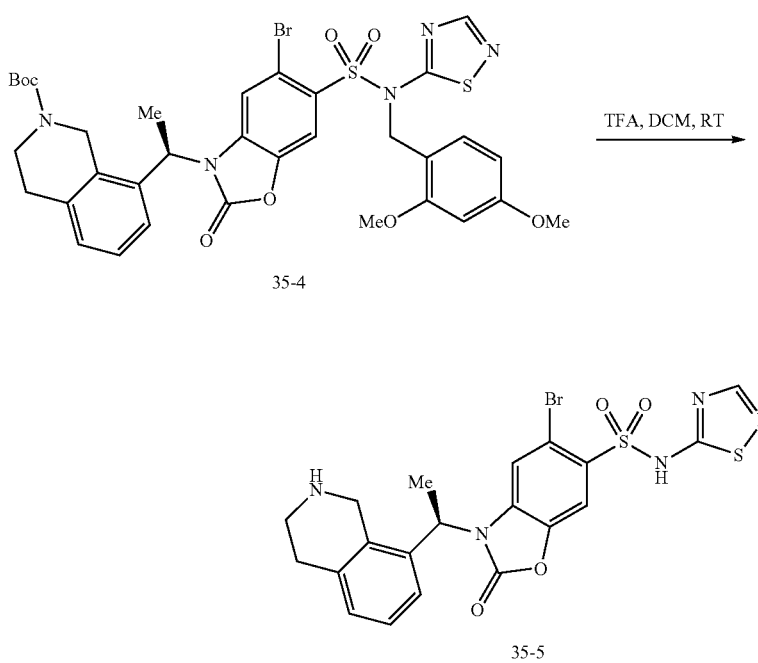

Preparation of 5-Bromo-2-oxo-2,3-dihydrobenzo[d]oxazole-6-sulfonyl chloride (35-2)

To a mixture of commercially-available 5-bromobenzo[d]oxazol-2(3H)-one (35-1, 500 mg, 2.336 mmol) in DCM (23 mL1) at RT was added chlorosulfonic acid (1565 µl, 23.36 mmol). The mixture became a solution that was stirred at RT. After 18 h, The solution was cooled to 0° C. and carefully quenched with ice chips and then partitioned between water (15 mL) and EtOAc (150 mL). The aqueous layer was extracted with 3×30 mL DCM. The combined organics were dried over $Na_2SO_4$, filtered, concentrated to give 35-2 as a white solid, which was carried forward without further purification.

Preparation of 5-Bromo-N-(2,4-dimethoxybenzyl)-2-oxo-N-(1,2,4-thiadiazol-5-yl)-2,3-dihydrobenzo[d]oxazole-6-sulfonamide (35-3)

Added LHMDS (1603 µl, 1.603 mmol, 1M in THF) to 1-3 (422 mg, 1.679 mmol) in THF (1908 µl) at −78° C. Removed cooling bath and stirred at RT for 30 min. Cooled back to −78 C and slowly added the 35-2 (159 mg, 0.509 mmol) in THF (636 µl). The resulting reaction mixture was allowed to slowly warm to RT while remaining in bath. After 2 h, quenched with 5 mL saturated $NH_4Cl$ and diluted with 10 mL EtOAc. Separated layers, back-extracted aqueous with 3×5 mL EtOAc. Dried over $Na_2SO_4$, filtered, concentrated to give a clear, orange oil. Purified by normal-phase HPLC (40 g ISCO column, 0-50% EtOAc:Hex) to give 35-3 as a white solid.

Preparation of (R)-tert-Butyl 8-(1-(5-bromo-6-(N-(2,4-dimethoxybenzyl)-N-(1,2,4-thiadiazol-5-yl)sulfamoyl)-2-oxobenzo[d]oxazol-3(2H)-yl)ethyl)-3,4-dihydroisoquinoline-2(1H)-carboxylate (35-4)

Added 35-3 to THF (765 µl) at RT followed by DEAD (48.5 µl, 0.306 mmol) to give a clear, orange solution. Added triphenylphosphine (80 mg, 0.306 mmol) followed by 4-2 (42.4 mg, 0.153 mmol). After 1 h, 50 min, concentrated to give a yellow/orange oil. Purification by normal-phase HPLC (12 g ISCO column, 0-50% EtOAc:Hex) afforded 35-4 as a white solid.

Preparation of (R)-5-bromo-2-oxo-3-(1-(1,2,3,4-tetrahydroisoquinolin-8-yl)ethyl)-N-(1,2,4-thiadiazol-5-yl)-2,3-dihydrobenzo[d]oxazole-6-sulfonamide (35-5)

Added 35-4 (120 mg, 0.153 mmol) to DCM (610 µl) and TFA (306 µl). After 90 min, diluted with 1 mL MeOH, filtered through Celite, washed with MeOH. Concentrated filtrate in vacuo and dissolved in 2 mL DMSO. Purified by reverse-phase HPLC (C18 column, 2-60% 0.1% TFA/CH₃CN:0.1% TFA/H₂O) to give 35-5 as a white solid The following compound was prepared from 35-3 by a reaction sequence analogous to that described in Scheme 17:

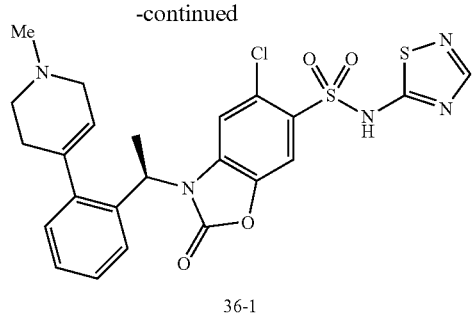

36-1

To round bottom flask was added (R)-5-chloro-2-oxo-3-(1-(2-(1,2,3,6-tetrahydropyridin-4-yl)phenyl)ethyl)-N-(1,2,4-thiadiazol-5-yl)-2,3-dihydrobenzo[d]oxazole-6-sulfona-

TABLE 18

| # | Structure | Name | Exact Mass [M + H]+ |
|---|---|---|---|
| 35-6 | (structure shown) | 3-{(1R)-1-[2-(3-aminoprop-1-yn-1-yl)phenyl]ethyl}-5-bromo-2-oxo-N-1,2,4-thiadiazol-5-yl-2,3-dihydro-1,3-benzoxazole-6-sulfonamide | Calc'd 533.9900, found 533.9881 |

Example 29

Preparation of (R)-5-chloro-3-(1-(2-(1-(methylsulfonyl)-1,2,3,6-tetrahydropyridin-4-yl)phenyl)ethyl)-2-oxo-N-(1,2,4-thiadiazol-5-yl)-2,3-dihydrobenzo[d]oxazole-6-sulfonamide (36-1)

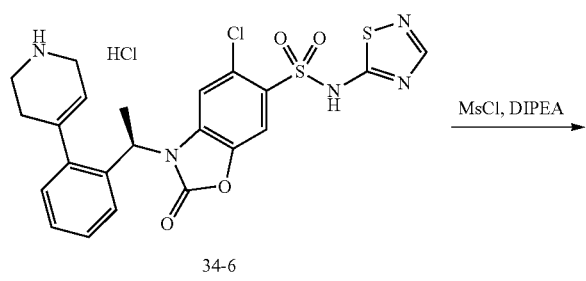

Scheme 36

34-6 → MsCl, DIPEA mide hydrochloride (34-6) (10 mg, 0.018 mmol), followed by NMP (1 ml), then DIPEA (50 µl, 0.286 mmol), followed by METHANESULFONYL CHLORIDE (6.80 µl, 0.087 mmol). The reaction mixture was then capped (not under N2) & stirred at room temperature. Followed by LC/MS. After 2 minutes; the reaction mixture was diluted with H2O, then MeOH, & purified (without workup) by reverse phase chromatography (5-75% MeCN/H2O; 0.1% TFA in AQ; 20 min gradient; Waters 30×150 mm Sunfire 5 micron C18 column); desired fractions concentrated (GENEVAC), then dissolved in MeOH/DCM & concentrated to yield (R)-5-chloro-2-oxo-3-(1-(2-(1,2,3,6-tetrahydropyridin-4-yl)phenyl)ethyl)-N-(1,2,4-thiadiazol-5-yl)-2,3-dihydrobenzo-[d]oxazole-6-sulfonamide hydrochloride (36-1). MS [M+H] calculated; 596.1 observed; 596.0. ¹H NMR (499 MHz, DMSO): δ 8.47 (s, 1H); 7.94 (s, 1H); 7.73 (d, J=7.8 Hz, 1H); 7.37 (d, J=7.6 Hz, 2H); 7.13 (d, J=9.8 Hz, 2H); 5.77-5.73 (m, 2H); 5.46 (s, 1H); 3.75-3.51 (m, 3H); 3.04-2.95 (m, 1H); 2.89 (s, 3H); 1.89-1.74 (m, 4H). Note: Peaks overlapping with water or solvent can not be accurately accounted for.

The compounds of Table 19 were prepared in accordance with Example 29:

TABLE 19

| # | Structure | Name | Exact Mass [M + H]+ |
|---|---|---|---|
| 36-2 | 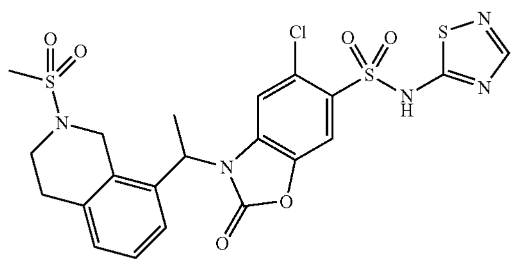 [SMILES: CC(c1cccc2c1CN(S(C)(=O)=O)CC2)n1c(=O)oc2cc(S(=O)(=O)Nc3ncns3)c(Cl)cc21] | (+/−)-5-chloro-3-{1-[2-(methylsulfonyl)-1,2,3,4-tetrahydroisoquinolin-8-yl]ethyl}-2-oxo-N-1,2,4-thiadiazol-5-yl-2,3-dihydro-1,3-benzoxazole-6-sulfonamide | Calc'd 570.0337, found 570.0330 |
| 36-3 | 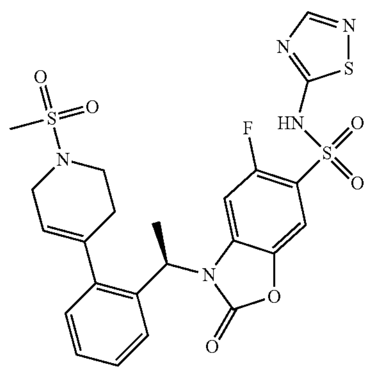 [SMILES: C[C@H](c1ccccc1C1=CCN(S(C)(=O)=O)CC1)n1c(=O)oc2cc(S(=O)(=O)Nc3ncns3)c(F)cc21] | 5-fluoro-3-[(1R)-1-{2-[1-(methylsulfonyl)-1,2,3,6-tetrahydropyridin-4-yl]phenyl}ethyl]-2-oxo-N-1,2,4-thiadiazol-5-yl-2,3-dihydro-1,3-benzoxazole-6-sulfonamide | Calc'd 580.0789, found 580.0765 |
| 36-4 | 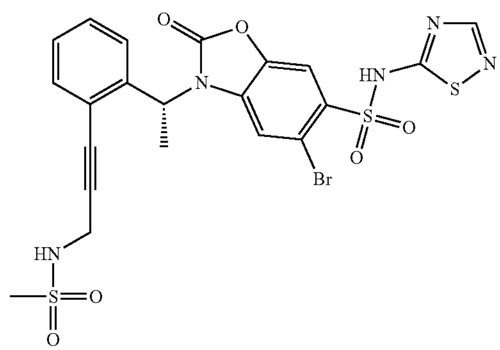 [SMILES: C[C@H](c1ccccc1C#CCNS(C)(=O)=O)n1c(=O)oc2cc(S(=O)(=O)Nc3ncns3)c(Br)cc21] | 5-bromo-3-[(1R)-1-(2-{3-[(methylsulfonyl)amino]prop-1-yn-1-yl}phenyl)ethyl]-2-oxo-N-1,2,4-thiadiazol-5-yl-2,3-dihydro-1,3-benzoxazole-6-sulfonamide | Calc'd 611.9675, found 611.9661 |
| 36-5 | 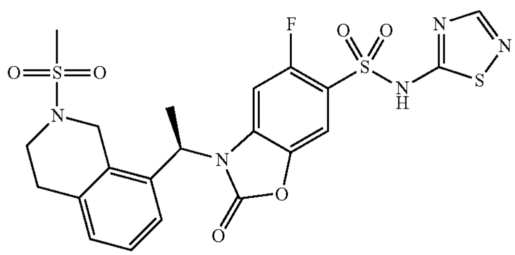 [SMILES: C[C@H](c1cccc2c1CN(S(C)(=O)=O)CC2)n1c(=O)oc2cc(S(=O)(=O)Nc3ncns3)c(F)cc21] | 5-fluoro-3-{(1R)-1-[2-(methylsulfonyl)-1,2,3,4-tetrahydroisoquinolin-8-yl]ethyl}-2-oxo-N-1,2,4-thiadiazol-5-yl-2,3-dihydro-1,3-benzoxazole-6-sulfonamide | Calc'd 554.0633, found 554.0622 |
| 36-6 | 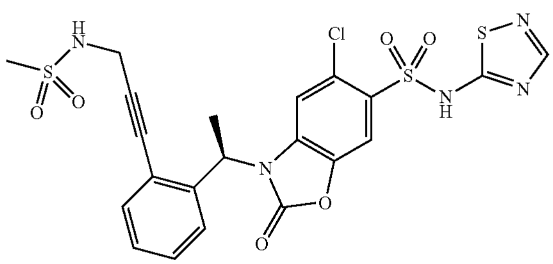 [SMILES: C[C@H](c1ccccc1C#CCNS(C)(=O)=O)n1c(=O)oc2cc(S(=O)(=O)Nc3ncns3)c(Cl)cc21] | 5-chloro-3-[(1R)-1-(2-{3-[(methylsulfonyl)amino]prop-1-yn-1-yl}phenyl)ethyl]-2-oxo-N-1,2,4-thiadiazol-5-yl-2,3-dihydro-1,3-benzoxazole-6-sulfonamide | Calc'd 568.0181, found 568.0181 |

TABLE 19-continued

| # | Structure | Name | Exact Mass [M + H]+ |
|---|---|---|---|
| 36-7 | 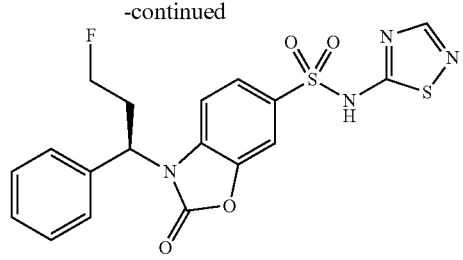 | 5-fluoro-3-[(1R)-1-{7-[(methylsulfonyl)amino]-5,6,7,8-tetrahydronaphthalen-1-yl)ethyl]-2-oxo-N-1,2,4-thiadiazol-5-yl-2,3-dihydro-1,3-benzoxazole-6-sulfonamide | Calc'd 568.0789, found 568.0774 |

Example 30

Preparation of (R)-3-(3-Fluoro-1-phenylpropyl)-2-oxo-N-(1,2,4-thiadiazol-5-yl)-2,3-dihydrobenzo[d]oxazole-6-sulfonamide (37-3)

Scheme 37

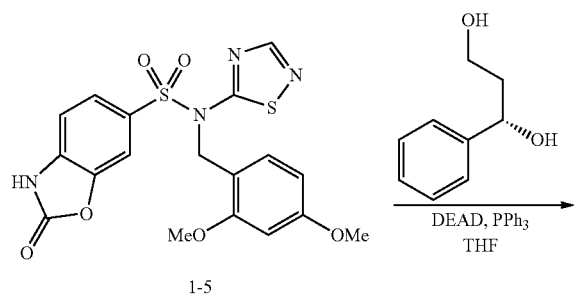

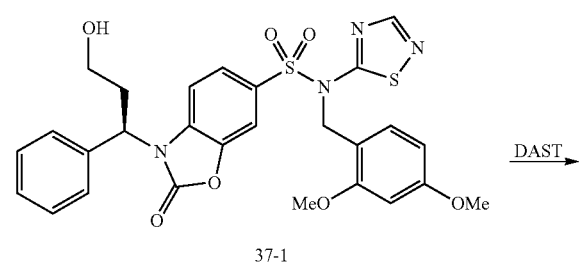

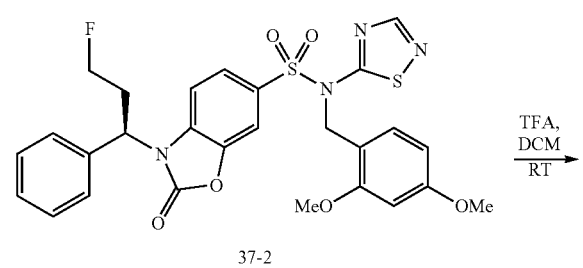

Preparation of (R)—N-(2,4-Dimethoxybenzyl)-3-(3-hydroxy-1-phenylpropyl)-2-oxo-N-(1,2,4-thiadiazol-5-yl)-2,3-dihydrobenzo[d]oxazole-6-sulfonamide (37-1)

Accordingly, the compound of Formula 37-1 (N-(2,4-dimethoxybenzyl)-3-[(1R)-3-hydroxy-1-phenylpropyl]-2-oxo-N-(1,2,4-thiadiazol-5-yl)-2,3-dihydro-1,3-benzoxazole-6-sulfonamide) was prepared from a solution provided by dissolving 200 mg of the compound of Formula 1-5 (0.429 mmol, prepared as described above) and (S)-1-phenylpropane-1,3-diol (65.3 mg, 0.429 mmol) (0.429 mmol) in 2 mL of THF. This solution was cooled to 0° C. and treated with triphenylphosphine (0.225 g, 0.858 mmol) followed by DEAD (0.136 mL, 0.858 mmol). After stirring at 0° C. for 120 min, the reaction mixture was diluted with EtOAc (50 mL) and saturated sodium bicarbonate (5 mL). The organic layer was washed with brine (10 mL), dried over sodium sulfate, filtered, and concentrated in vacuo. Purification by normal phase chromatography (10-80% EtOAc in hexane) yielded the compound of Formula 37-1 as a yellow oil which was used as isolated.

Preparation of (R)—N-(2,4-dimethoxybenzyl)-3-(3-fluoro-1-phenylpropyl)-2-oxo-N-(1,2,4-thiadiazol-5-yl)-2,3-dihydrobenzo[d]oxazole-6-sulfonamide (37-2)

A solution of the compound of Formula 37-2 was prepared by dissolving the compound of Formula 1 (60 mg, 0.100 mmol) in DCM (1 ml). The solution was cooled to 0° C., DAST (0.026 ml, 0.200 mmol) was added. After stirring at 0° C. for 120 min, the reaction mixture was diluted with EtOAc (40 mL) and saturated sodium bicarbonate (4 mL). The organic layer was washed with brine (10 mL), dried over sodium sulfate, filtered, and concentrated in vacuo to yield the compound of Formula 37-2 which was used as isolated.

Preparation of (R)-3-(3-Fluoro-1-phenylpropyl)-2-oxo-N-(1,2,4-thiadiazol-5-yl)-2,3-dihydrobenzo[d]oxazole-6-sulfonamide (37-3)

A solution of the compound of Formula 37-3 was prepared by dissolving the compound of Formula 37-2 (crude from previous step) in dichloromethane (1 mL), and treating the resulting solution with trifluoroacetic acid (0.2 mL). After stirring for 30 minutes at RT, the solution was concentrated and purified by reverse phase HPLC (20-100% MeCN in water with 0.1% TFA, C18 column) to yield the compound of Formula 37-3 as the a white solid. $^1$H NMR δ (ppm)(Methanol-d): 8.20 (s, 1H); 7.74 (m, 1H); 7.51 (m, 2H); 7.42-7.42 (m, 3H); 7.12 (m, 1H); 5.60 (m, 1H); 4.65-4.37 (m, 2H); 3.01-2.65 (m, 2H). HRMS C18H15F2N4O4S2 [M+H] calc 453.0425, obs 453.0497.

Example 31

Preparation of 5-ethyl-2-oxo-3-[(1R)-1-phenylethyl]-N-1,2,4-thiadiazol-5-yl-2,3-dihydro-1,3-benzoxazole-6-sulfonamide (38-2)

Into a solution of (R)-5-bromo-2-oxo-3-(1-phenylethyl)-N-(1,2,4-thiadiazol-5-yl)-2,3-dihydrobenzo[d]oxazole-6-sulfonamide (38-1, 80 mg, 0.166 mmol, prepared from 35-3 by a reaction sequence analogous to that described herein) in NMP (831 ul) was added diethylzinc (1M in hexanes, 0.499 mmol) followed by chloro(2-dicyclohexylphosphino-2',4',6'-triisopropyl-1,1'-biphenyl)[2-(2'-amino-1,1'-biphenyl)]palladium(II) (7 mg, 8.9 umol). The reaction vessel was sealed and heated to 120° C. for 12 h, cooled to rt, diluted with 1 ml of H$_2$O and 3 ml of EtOAc, filtered through celite, concentrated and purified by reversed phase HPLC (2 cm×5 cm C18, acetonitrile-water gradient, 0.05% TFA added) to yield 5-ethyl-2-oxo-3-[(1R)-1-phenylethyl]-N-1,2,4-thiadiazol-5-yl-2,3-dihydro-1,3-benzoxazole-6-sulfonamide (38-2). $^1$H NMR (499 MHz, DMSO): δ 8.44 (s, 1H); 7.75 (s, 1H); 7.46 (d, J=7.7 Hz, 2H); 7.36-7.38 (m, 3H); 7.06 (s, 1H); 5.63 (d, J=7.3 Hz, 1H); 2.92-2.94 (m, 2H); 1.88 (d, J=7.1 Hz, 3H); 1.09 (t, J=7.4 Hz, 3H). LRMS C19H18N4O4S2 [M+H] calc 431.1, obs 431.0.

The following compound was prepared from 38-1 by a reaction sequence analogous to that illustrated in Scheme 38:

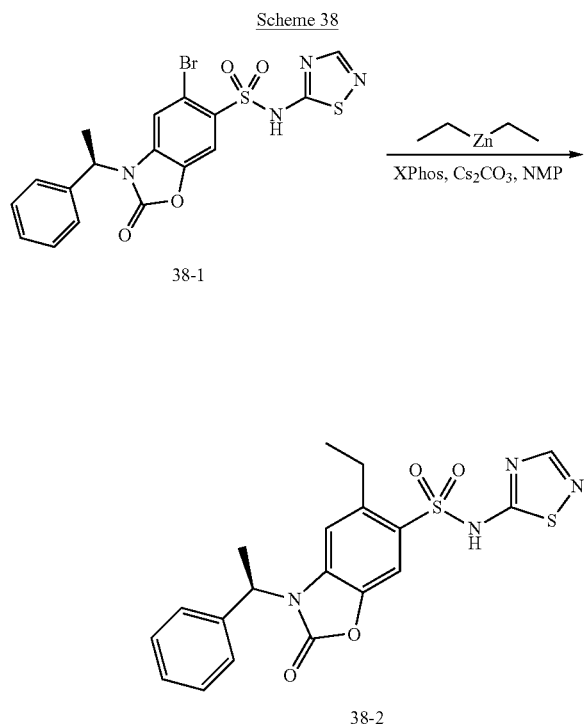

TABLE 20

| # | Structure | Name | Exact Mass [M + H]+ |
|---|---|---|---|
| 38-3 | 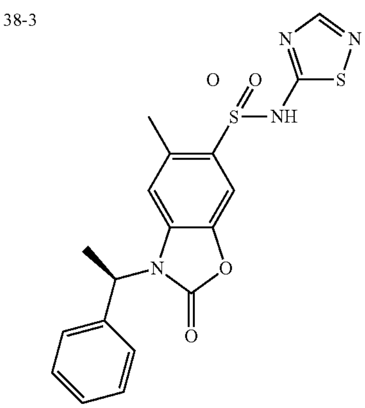 | 5-methyl-2-oxo-3-[(1R)-1-phenylethyl]-N-1,2,4-thiadiazol-5-yl-2,3-dihydro-1,3-benzoxazole-6-sulfonamide | Calc'd 417.1, found 417.3 |

Example 32

Preparation of 3-(7-amino-1,2,3,4-tetrahydronaphthalen-1-yl)-2-oxo-N-(1,2,4-thiadiazol-5-yl)-2,3-dihydrobenzo[d]oxazole-6-sulfonamide (39-3)

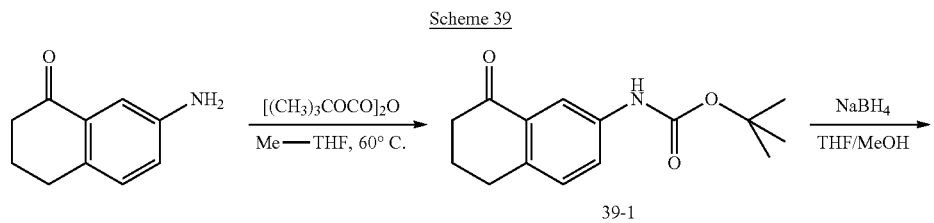

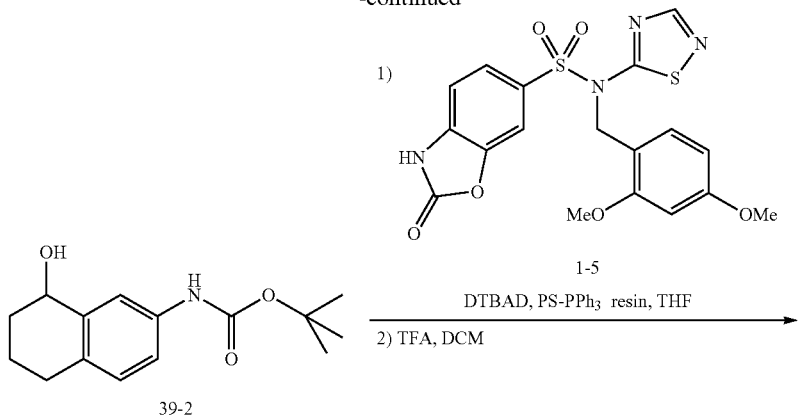

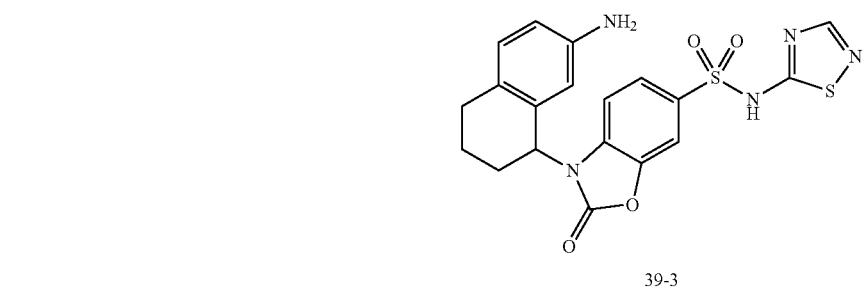

Preparation of tert-Butyl (8-oxo-5,6,7,8-tetrahydronaphthalen-2-yl)carbamate (39-1)

To a solution of 7-amino-3,4-dihydronaphthalen-1(2H)-one (500 mg, 3.10 mmol) in Me-THF (15 mL) was added Di-t-butyl dicarbonate (812 mg, 3.72 mmol) and warmed to 60° C. for 16 hours. Reaction is concentrated in vacuo and the resulting residue is purified by normal phase chromatography (10-30% EtOAc in hexane) to yield the compound of Formula 39-1 as a solid.

Preparation of tert-Butyl (8-hydroxy-5,6,7,8-tetrahydronaphthalen-2-yl)carbamate (39-2)

To a solution of the compound of Formula 39-1 (740 mg, 2.83 mmol) in THF (5 mL)/MeOH (5 mL) was added sodium borohydride (107 mg, 2.83 mmol) while cooled at 0° C. The solution was stirred for 1 hour and concentrated to volume in vacuo. The residue was diluted with EtOAc (40 mL) and washed with sat'd sodium bicarbonate (2×10 mL) and brine (10 mL). Organics were dried over sodium sulfate, filtered, and concentrated in vacuo to yield the compound of Formula 39-2 as a solid.

Preparation of 3-(7-Amino-1,2,3,4-tetrahydronaphthalen-1-yl)-2-oxo-N-(1,2,4-thiadiazol-5-yl)-2,3-dihydrobenzo[d]oxazole-6-sulfonamide (39-3)

In a sealed tube, combined the compound of Formula 1-5 (80 mg, 0.172 mmol), the compound of Formula 39-2 (90 mg, 0.343 mmol), PS-PPh$_3$ resin(161 mg, 0.515 mmol), di-t-butyl azodicarboxylate (118 mg, 0.515 mmol), and THF (2 mL). The resulting slurry was sonicated for 16 h and then filtered over celite and washed the pad with EtOAc (30 mL). The filtrate is washed with sat'd sodium bicarbonate (20 mL), brine (10 mL), dried organics over sodium sulfate, filtered, and concentrated in vacuo. The resulting residue is purified by normal phase chromatography (15-80% EtOAc in hexane) to yield the intermediate as an oil. The oil is dissolved in dichloromethane (0.5 mL), and treated the resulting solution with trifluoroacetic acid (0.5 mL). After stirring for 30 minutes at RT, the solution was concentrated and purified by reverse phase HPLC (20-100% MeCN in water with 0.1% TFA, C18 column) to yield the compound of Formula 39-3 as a white solid. $^1$H NMR δ (ppm)(DMSO-d): 8.47 (1H, s), 7.81 (1H, d, J=5.48 Hz), 7.17 (1H, d, J=8.18 Hz), 6.92 (1H, d, J=8.13 Hz), 6.81 (1H, s), 6.67 (1H, s), 5.53 (1H, t, J=7.80 Hz), 3.38 (1H, q, J=6.99 Hz), 2.90 (1H, m), 2.74 (1H, m), 2.21-2.10 (2H, m), 1.97 (1H, d, J=13.43 Hz), 1.81 (1H, d, J=13.29 Hz), 1.09 (2H, t, J=6.99 Hz). LRMS C19H17FN5O4S2 [M+H] calc 462.07, obs 462.50.

The compounds of Table 21 were prepared by reacting the compound of 11-3 with the appropriate alcohol in accordance with the process described in Scheme 39:

TABLE 21

| # | Structure | Name | Exact Mass [M + H]+ |
|---|---|---|---|
| 39-4 | 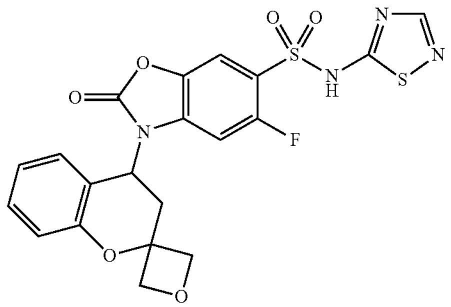 [SMILES: O=c1oc2cc(S(=O)(=O)Nc3ncns3)c(F)cc2n1C1CC2(COC2)Oc2ccccc21] | 3-(3,4-dihydrospiro[chromene-2,3'-oxetan]-4-yl)-5-fluoro-2-oxo-N-1,2,4-thiadiazol-5-yl-2,3-dihydro-1,3-benzoxazole-6-sulfonamide | Calc'd 491.0, found 491.3 |
| 39-5 | 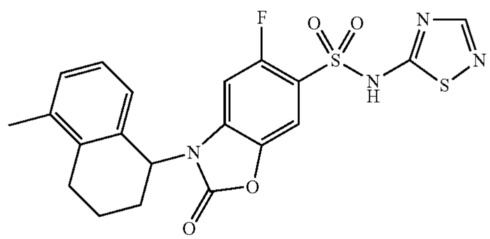 [SMILES: Cc1cccc2c1CCCC2n1c(=O)oc2cc(S(=O)(=O)Nc3ncns3)c(F)cc21] | 5-fluoro-3-(5-methyl-1,2,3,4-tetrahydronaphthalen-1-yl)-2-oxo-N-1,2,4-thiadiazol-5-yl-2,3-dihydro-1,3-benzoxazole-6-sulfonamide | Calc'd 461.5, found 460.9 |
| 39-6 | 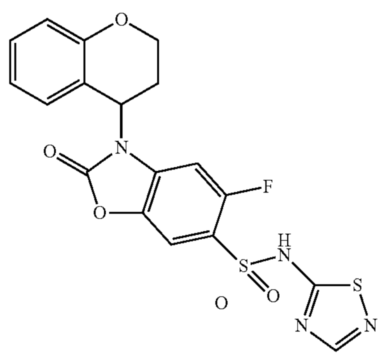 | 3-(3,4-dihydro-2H-chromen-4-yl)-5-fluoro-2-oxo-N-1,2,4-thiadiazol-5-yl-2,3-dihydro-1,3-benzoxazole-6-sulfonamide | Calc'd 449.0, found 449.0 |
| 39-7 | 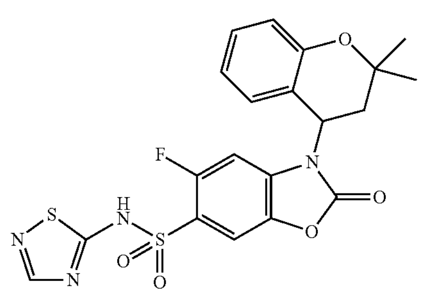 [SMILES: CC1(C)CC(n2c(=O)oc3cc(S(=O)(=O)Nc4ncns4)c(F)cc32)c2ccccc2O1] | 3-(2,2-dimethyl-3,4-dihydro-2H-chromen-4-yl)-5-fluoro-2-oxo-N-1,2,4-thiadiazol-5-yl-2,3-dihydro-1,3-benzoxazole-6-sulfonamide | Calc'd 477.1, found 477.0 |
| 39-8 | 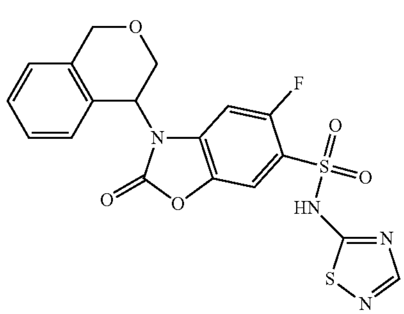 [SMILES: O=c1oc2cc(S(=O)(=O)Nc3ncns3)c(F)cc2n1C1COCc2ccccc21] | 3-(3,4-dihydro-1H-isochromen-4-yl)-5-fluoro-2-oxo-N-1,2,4-thiadiazol-5-yl-2,3-dihydro-1,3-benzoxazole-6-sulfonamide | Calc'd 449.0, found 449.2 |

TABLE 21-continued

| # | Structure | Name | Exact Mass [M + H]+ |
|---|---|---|---|
| 39-9 | 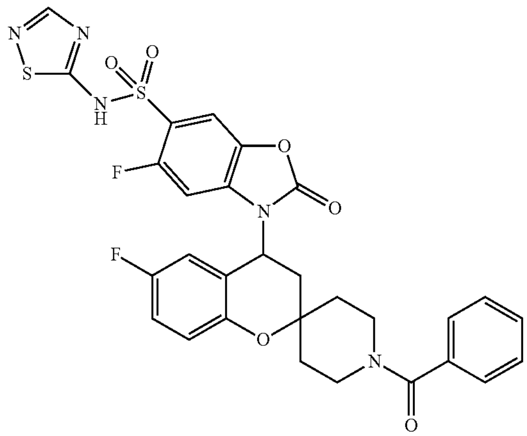 [SMILES: O=C(c1ccccc1)N1CCC2(CC1)CC(n1c(=O)oc3cc(S(=O)(=O)Nc4ncns4)c(F)cc31)c1cc(F)ccc1O2] | 5-fluoro-3-[6-fluoro-1'-(phenylcarbonyl)-3,4-dihydrospiro[chromene-2,4'-piperidin]-4-yl]-2-oxo-N-1,2,4-thiadiazol-5-yl-2,3-dihydro-1,3-benzoxazole-6-sulfonamide | Calc'd 640.1, found 640.1 |
| 39-10 | 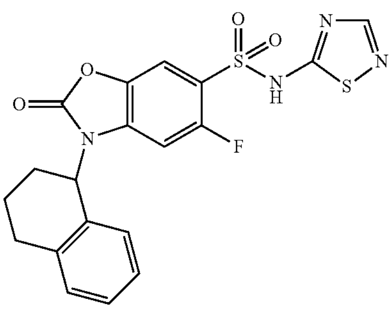 [SMILES: O=c1oc2cc(S(=O)(=O)Nc3ncns3)c(F)cc2n1C1CCCc2ccccc21] | 5-fluoro-2-oxo-3-(1,2,3,4-tetrahydronaphthalen-1-yl)-N-1,2,4-thiadiazol-5-yl-2,3-dihydro-1,3-benzoxazole-6-sulfonamide | Calc'd 447.1, found 447.0 |
| 39-11 | 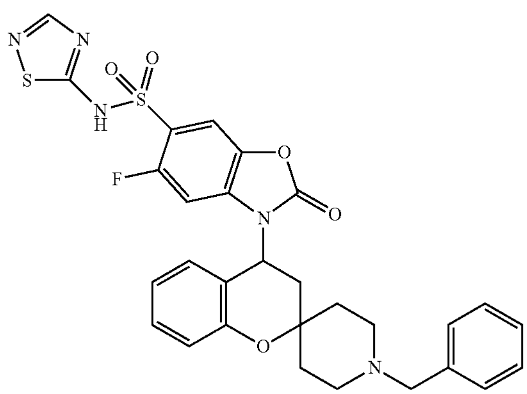 [SMILES: O=c1oc2cc(S(=O)(=O)Nc3ncns3)c(F)cc2n1C1CC2(CCN(Cc3ccccc3)CC2)Oc2ccccc21] | 3-(1'-benzyl-3,4-dihydrospiro[chromene-2,4'-piperidin]-4-yl)-5-fluoro-2-oxo-N-1,2,4-thiadiazol-5-yl-2,3-dihydro-1,3-benzoxazole-6-sulfonamide | Calc'd 608.1, found 608.1 |
| 39-12 | 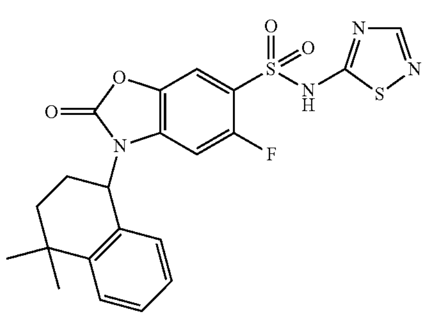 [SMILES: CC1(C)CCC(n2c(=O)oc3cc(S(=O)(=O)Nc4ncns4)c(F)cc32)c2ccccc21] | 3-(4,4-dimethyl-1,2,3,4-tetrahydronaphthalen-1-yl)-5-fluoro-2-oxo-N-1,2,4-thiadiazol-5-yl-2,3-dihydro-1,3-benzoxazole-6-sulfonamide | Calc'd 475.1, found 475.0 |

TABLE 21-continued

| # | Structure | Name | Exact Mass [M + H]+ |
|---|---|---|---|
| 39-13 | 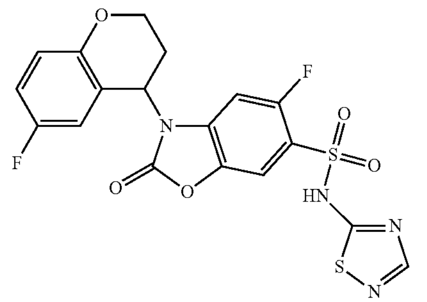 [SMILES: O=c1oc2cc(S(=O)(=O)Nc3ncns3)c(F)cc2n1C1CCOc2ccc(F)cc21] | 5-fluoro-3-(6-fluoro-3,4-dihydro-2H-chromen-4-yl)-2-oxo-N-1,2,4-thiadiazol-5-yl-2,3-dihydro-1,3-benzoxazole-6-sulfonamide | Calc'd 467.0290, found 467.0293 |
| 39-14 | 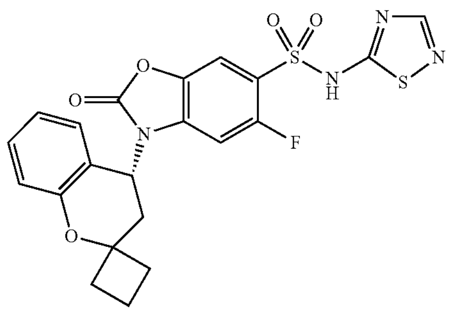 [SMILES: O=c1oc2cc(S(=O)(=O)Nc3ncns3)c(F)cc2n1[C@@H]1CC2(CCC2)Oc2ccccc21] | 3-[(4R)-3,4-dihydrospiro[chromene-2,1'-cyclobutan]-4-yl]-5-fluoro-2-oxo-N-1,2,4-thiadiazol-5-yl-2,3-dihydro-1,3-benzoxazole-6-sulfonamide | Calc'd 489.0, found 489.0 |
| 39-15 | 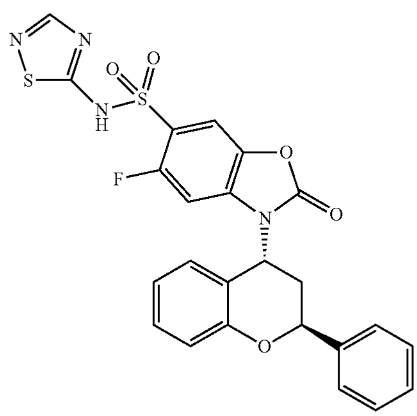 [SMILES: O=c1oc2cc(S(=O)(=O)Nc3ncns3)c(F)cc2n1[C@@H]1C[C@@H](c2ccccc2)Oc2ccccc21] | 5-fluoro-2-oxo-3-[(2S,4R)-2-phenyl-3,4-dihydro-2H-chromen-4-yl]-N-1,2,4-thiadiazol-5-yl-2,3-dihydro-1,3-benzoxazole-6-sulfonamide | Calc'd 525.1, found 525.0 |
| 39-16 | 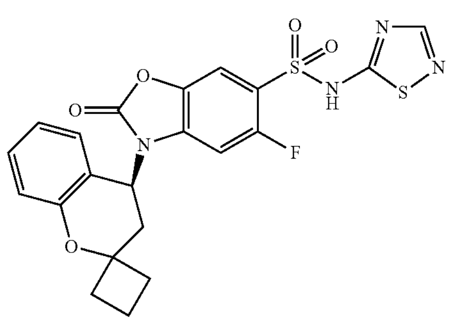 [SMILES: O=c1oc2cc(S(=O)(=O)Nc3ncns3)c(F)cc2n1[C@H]1CC2(CCC2)Oc2ccccc21] | 3-[(4S)-3,4-dihydrospiro[chromene-2,1'-cyclobutan]-4-yl]-5-fluoro-2-oxo-N-1,2,4-thiadiazol-5-yl-2,3-dihydro-1,3-benzoxazole-6-sulfonamide | Calc'd 489.1, found 489.0 |

TABLE 21-continued

| # | Structure | Name | Exact Mass [M + H]+ |
|---|---|---|---|
| 39-17 | 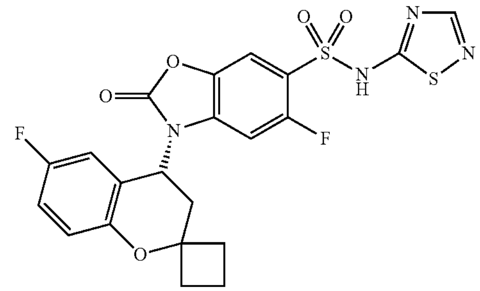 | 5-fluoro-3-[(4S)-6-fluoro-3,4-dihydrospiro[chromene-2,1'-cyclobutan]-4-yl]-2-oxo-N-1,2,4-thiadiazol-5-yl-2,3-dihydro-1,3-benzoxazole-6-sulfonamide | Calc'd 507.1, found 507.0 |

Example 33

Preparation of N-(4-methyl-1,3-thiazol-2-yl)-2-oxo-3-(1-phenylethyl)-2,3-dihydro-1,3-benzoxazole-6-sulfonamide (40-5)

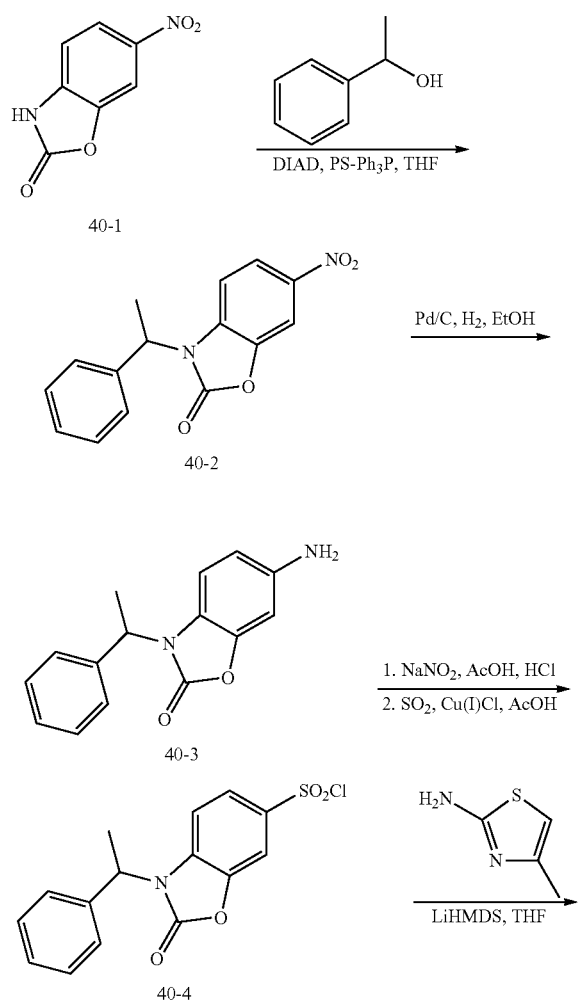

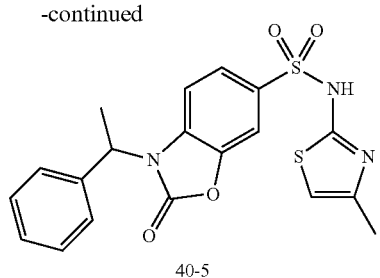

Preparation of 6-Nitro-3-(1-phenylethyl)benzo[d]oxazol-2(3H)-one (40-2)

Into a solution of 6-nitrobenzo[d]oxazol-2(3H)-one (40-1, 5 g, 27.8 mmol) in THF (139 ml) was added α-methylbenzylalcohol (3.7 g, 30.5 mmol), polymer-bound triphenylphosphine (27.7 g, 83 mmol), and DIAD (11.2 g, 55.5 mmol). The reaction was shaken for 1 h at rt, filtered, and concentrated to yield 6-nitro-3-(1-phenylethyl)benzo[d]oxazol-2(3H)-one (7.89 g, 27.8 mmol) which was taken on to the next step without further purification. LRMS C15H14N2O2 [M−79] calc 205.1, obs 205.4.

Preparation of 6-Amino-3-(1-phenylethyl)benzo[d]oxazol-2(3H)-one (40-3)

Into a solution of 6-nitro-3-(1-phenylethyl)benzo[d]oxazol-2(3H)-one (40-2, 7.89 g, 27.8 mmol) in EtOH (139 ml) was added Pd/C (295 mg, 2.78 mmol). The reaction was stirred under 1 atm of H₂ for 2 h, filtered through celite, concentrated and purified using a 50 g SCX column (eluting with 2 N NH₃ in MeOH) to yield 6-amino-3-(1-phenylethyl)benzo[d]oxazol-2(3H)-one (4.4 g, 17.3 mmol). LRMS C15H14N2O2 [M+H] calc 255.1, obs 255.4.

Preparation of 2-Oxo-3-(1-phenylethyl)-2,3-dihydrobenzo[d]oxazole-6-sulfonyl chloride (40-4)

AcOH (8 ml) and HCl (27 ml) were added to a round bottom flask containing 6-amino-3-(1-phenylethyl)benzo[d]oxazol-2(3H)-one (40-3, 4.4 g, 17.3 mmol). The slurry was cooled to −5° C. at which point a solution of sodium nitrite (10 M in H₂O, 1.9 ml) was added dropwise over 10 min. After stirring at −5° C. for 30 min the mixture was added to a SO₂ saturated solution of Cu(I)Cl (425 mg, 4.3 mmol) in AcOH (17 ml) at 0° C. The reaction was allowed to warm to rt, and stirred for 1 h, diluted with 100 ml of water, extracted 3× with 30 ml of EtOAc, washed with satd NaHCO₃ until neutral, dried, filtered, and concentrated to yield 2-oxo-3-(1-phenylethyl)-2,3-dihydrobenzo[d]oxazole-6-sulfonyl chloride (4 g, 11.8 mmol) which was used without further purification. LRMS C15H12ClNO4S [M–99] calc 238.8, obs 238.4.

Preparation of N-(4-methyl-1,3-thiazol-2-yl)-2-oxo-3-(1-phenylethyl)-2,3-dihydro-1,3-benzoxazole-6-sulfonamide (40-5)

Into a solution of 2-amino-4-methylthiazole (17 mg, 0.149 mmol) in THF (740 ul) was added LiHMDS (1M in THF, 0.444 mmol). After 5 min, 2-oxo-3-(1-phenylethyl)-2,3-dihydrobenzo[d]oxazole-6-sulfonyl chloride (50 mg, 0.148 mmol) was added. The reaction was stirred for 10 min, diluted with 1 ml of H₂O and 3 ml of EtOAc, filtered through celite, concentrated and purified by reversed phase HPLC (2 cm×5 cm C18, acetonitrile-water gradient, 0.05% TFA added) to yield N-(4-methyl-1,3-thiazol-2-yl)-2-oxo-3-(1-phenylethyl)-2,3-dihydro-1,3-benzoxazole-6-sulfonamide TFA salt (7.2 mg, 0.014 mmol). ¹H NMR (499 MHz, DMSO): δ 7.67 (s, 1H); 7.57 (d, J=8.4 Hz, 1H); 7.41 (dd, J=23.5, 7.5 Hz, 4H); 7.35 (d, J=13.9 Hz, 1H); 7.32 (s, 1H); 7.16 (d, J=8.4 Hz, 1H); 6.39 (s, 1H); 5.60-5.62 (m, 1H); 2.07 (s, 3H); 1.86 (d, J=7.2 Hz, 3H). HRMS C19H17N3O4S2 [M+H] calc 416.0733, obs 416.0723.

Example 34

Preparation of (R)-2-oxo-3-(1-phenylethyl)-N-(thiazol-2-yl)-2,3-dihydrobenzo[d]oxazole-6-sulfonamide (41-4)

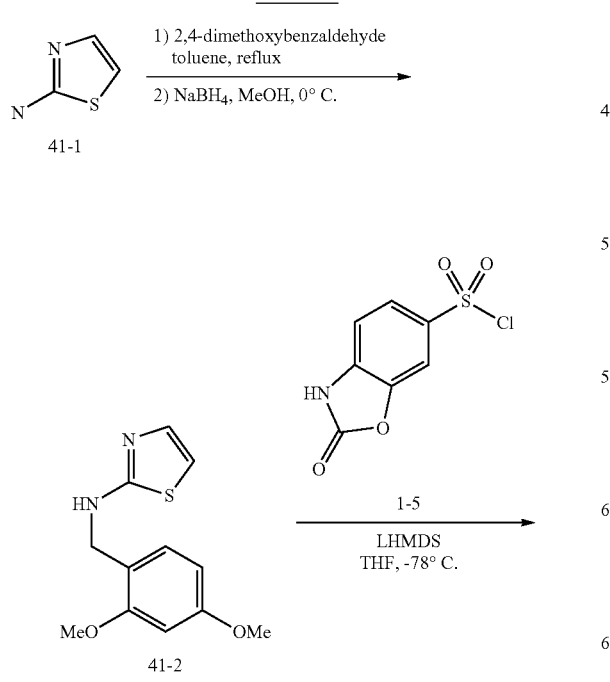

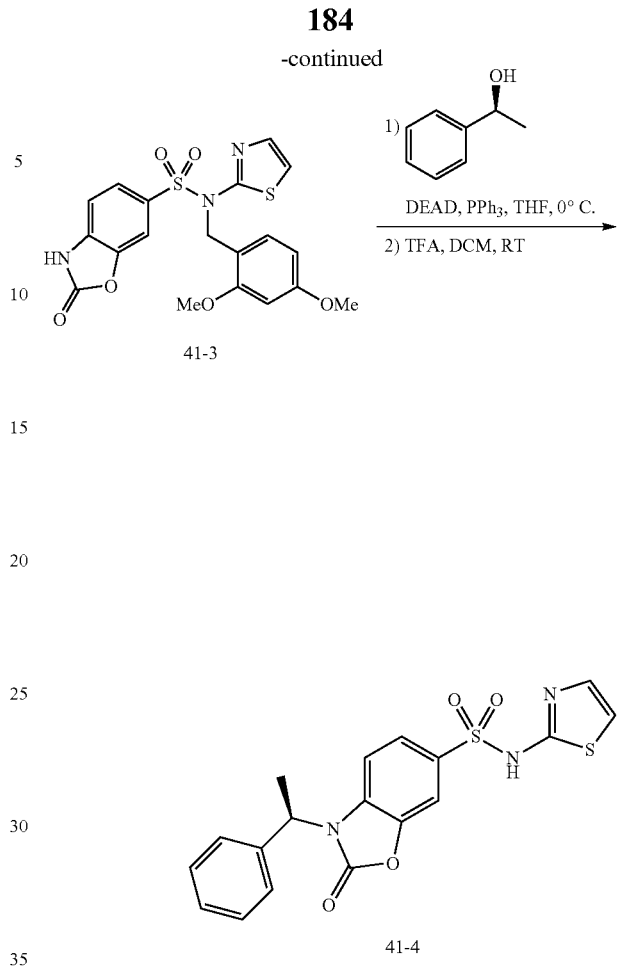

Preparation of N-(2,4-Dimethoxybenzyl)thiazol-2-amine (41-2)

A solution of 41-1 (5 g, 49.9 mmol) and 2,4-dimethoxybenzaldehyde (9.13 g, 54.9 mmol) in toluene (151 ml) was refluxed under Dean-Stark conditions for 10 hours. Upon cooling to ambient temperature (RT, about 25° C.), the reaction was concentrated under reduced pressure to yield the corresponding imine, which was subsequently dissolved in methanol (125 mL) and cooled to 0° C. The reaction mixture was then treated with NaBH₄ (2.83 g, 74.9 mmol) portion wise. After stirring for 1 hour at 0° C., the reaction was quenched with 100 ml of water and diluted with 200 mL of ethyl acetate. The layers were separated and the aqueous layer was back-extracted with EtOAc (2×200 mL). The combined organic layers were concentrated and purified by normal phase chromatography (0-60% EtOAc in hexane) to yield 41-2.

Preparation of N-(2,4-Dimethoxybenzyl)-2-oxo-N-(thiazol-2-yl)-2,3-dihydrobenzo[d]oxazole-6-sulfonamide (41-3)

A solution of 41-2 (2.79 g, 11.13 mmol) in THF (71 mL) was cooled to –78° C. Lithium hexamethyldisilizane (LHMDS, 21.4 ml, 21.4 mmol, 1.0M in THF) was added and the reaction was allowed to warm to RT and stir for 30 minutes. Commercially-available, solid 1-5 (4 g, 17.12 mmol) was then added in portions, maintaining the temperature of the reaction mixture at −78° C. The reaction was allowed to slowly warm to RT. After reaching RT, the reaction was quenched with saturated ammonium chloride solution at 0° C. and extracted into EtOAc (3×150 mL). The combined organic layers were washed with brine, dried over sodium sulfate, filtered and concentrated. Purification by normal phase chromatography (0-60% EtOAc in hexane) yielded 41-3 as a solid.

Preparation of (R)-2-Oxo-3-(1-phenylethyl)-N-(thiazol-2-yl)-2,3-dihydrobenzo[d]oxazole-6-sulfonamide (41-4)

A solution of 41-3 (170 mg, 0.380 mmol) in THF (1.9 ml) was treated with DEAD (120 μl, 0.760 mmol), then triphenylphosphine (199 mg, 0.760 mmol). Cooled to 0° C., then added commercial (S)-phenethyl alcohol (51.1 mg, 0.418 mmol). After stirring overnight at RT, the reaction was concentrated in vacuo. Purified by normal phase chromatography (0-50% EtOAc in hexane). Isolated material was dissolved in 2 mL of DCM and treated with 0.5 mL TFA. After stirring for 30 minutes at RT, the solvent and TFA were removed in vacuo. Purified by reverse phase chromatography (5-75% MeCN in water with 0.1% TFA, C18 column) to yield 41-4 as a solid. $^1$H NMR δ (ppm)(DMSO-d$_6$): 7.68 (1H, d, J=1.67 Hz), 7.58 (1H, dd, J=8.31, 1.71 Hz), 7.45-7.40 (2H, m), 7.40-7.34 (2H, m), 7.33-7.28 (1H, m), 7.24 (1H, d, J=4.62 Hz), 7.16 (1H, d, J=8.33 Hz), 6.83 (1H, d, J=4.58 Hz), 5.64-5.58 (1H, m), 1.86 (3H, d, J=7.19 Hz).

HRMS C18H15N3O4S2 [M+H] calc: 402.0577, obs: 402.0567.

The following compounds were prepared from 41-3 and the appropriate alcohol by a synthetic sequence analogous to that illustrated in Scheme 41:

TABLE 22

| # | Structure | Name | Exact Mass [M + H]+ |
|---|---|---|---|
| 41-5 | 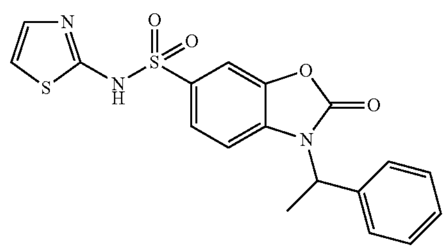 [SMILES: CC(c1ccccc1)n1c(=O)oc2cc(S(=O)(=O)Nc3nccs3)ccc21] | 2-oxo-3-(1-phenylethyl)-N-1,3-thiazol-2-yl-2,3-dihydro-1,3-benzoxazole-6-sulfonamide | Calc'd 402.0577, found 402.0567 |
| 41-6 | 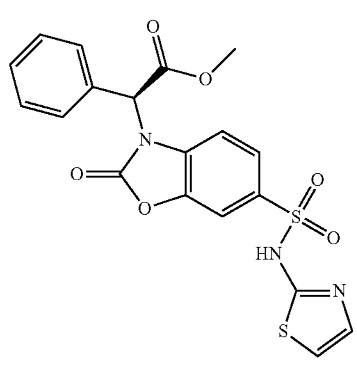 [SMILES: COC(=O)[C@H](c1ccccc1)n1c(=O)oc2cc(S(=O)(=O)Nc3nccs3)ccc21] | methyl (2S)-[2-oxo-6-(1,3-thiazol-2-ylsulfamoyl)-1,3-benzoxazol-3(2H)-yl](phenyl)ethanoate | Calc'd 446.0475, found 446.0468 |

Example 35

Preparation of (R)-2-oxo-3-(1-(1,2,3,4-tetrahydroisoquinolin-8-yl)ethyl)-N-(thiazol-2-yl)-2,3-dihydrobenzo[d]oxazole-6-sulfonamide (42-1)

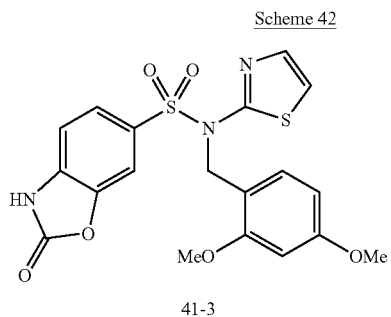

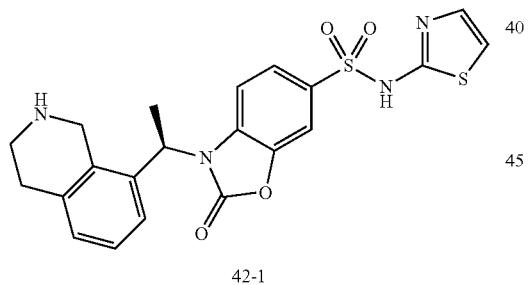

A solution of 41-3 (170 mg, 0.380 mmol) in THF (1.9 ml) was treated with DEAD (120 μl, 0.760 mmol), then triphenylphosphine (199 mg, 0.760 mmol). Cooled to 0° C., then added 4-2 (105 mg, 0.380 mmol). Stirred overnight at RT. Purified by normal phase column chromatography (0-50% EtOAc in hexane) Isolated material was dissolved in 5 mL of DCM and treated with 1 mL TFA. After stirring for 30 minutes at RT, the solvent and TFA was removed in vacuo. Purified by reverse phase chromatography (5-70% MeCN in water with 0.1% TFA, C18) to yield 42-1 as the TFA salt. $^1$H NMR δ (ppm)(DMSO-d$_6$): 12.74 (1H, s), 8.96 (2H, s), 7.71-7.66 (2H, m), 7.57 (1H, dd, J=8.31, 1.79 Hz), 7.41 (1H, t, J=7.69 Hz), 7.29-7.23 (2H, m), 7.19 (1H, d, J=8.34 Hz), 6.83 (1H, d, J=4.58 Hz), 5.66-5.59 (1H, m), 4.45-4.32 (1H, m), 4.15-4.01 (1H, m), 3.34-3.22 (2H, m), 3.07-2.90 (2H, m), 1.81 (3H, d, J=6.90 Hz). HRMS C21H20N4O4S2 [M+H] calc: 457.0999, obs: 457.0987.

Example 36

Preparation of (R)-5-fluoro-2-oxo-3-(1-phenylethyl)-N-(thiazol-2-yl)-2,3-dihydrobenzo[d]oxazole-6-sulfonamide (43-2)

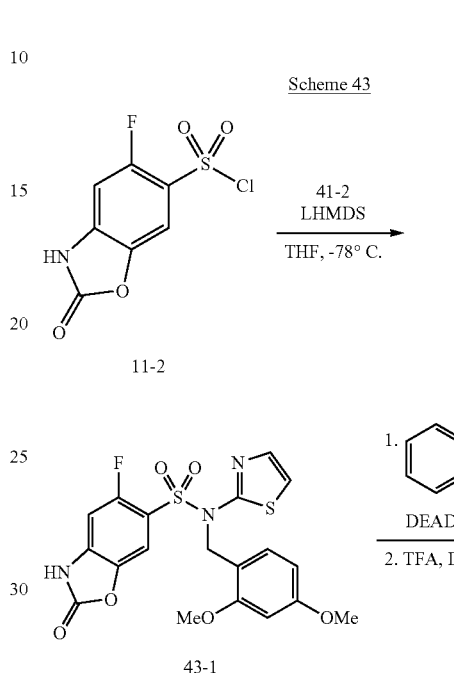

Preparation of N-(2,4-dimethoxybenzyl)-5-fluoro-2-oxo-N-(thiazol-2-yl)-2,3-dihydrobenzo[d]oxazole-6-sulfonamide (43-1)

A solution of 41-2 (2.328 g, 9.30 mmol) in THF (59.6 ml) was cooled to −78° C. LHMDS (17.88 ml, 17.88 mmol) was added and the reaction was allowed to warm to RT and stir for 30 minutes. 11-2 (1.8 g, 7.15 mmol) was then added as a solid at −78° C. Reaction was slowly allowed to each RT and was stirred for 4 hours. Quenched with 20 ml of saturated aqueous NH$_4$Cl solution. Extracted in EtOAc (3×150 ml). Combined organic layers were washed with brine, then dried with Sodium sulfate, filtered and concentrated in vacuo. Purified by normal phase chromatography (0-60% EtOAc in hexane) to yield 43-1 as a solid.

Preparation of (R)-5-Fuoro-2-oxo-3-(1-phenylethyl)-N-(thiazol-2-yl)-2,3-dihydrobenzo[d]oxazole-6-sulfonamide (43-2)

A solution of 43-1 (150 mg, 0.322 mmol) in THF (1.6 ml) was treated with DEAD (102 μl, 0.645 mmol), then triphenylphosphine (169 mg, 0.645 mmol). Cooled to 0° C. in an ice bath, then added (S)-1-phenylethanol (39.4 mg, 0.322 mmol). Reaction concentrated in vacuo after stirring overnight at RT. Purified by silica gel chromatography (0-50% EtOAc in hexane). Isolated material was dissolved in 1 ml of DCM and treated with 0.25 ml TFA. After stirring for 30 minutes at RT, the solvent and TFA was removed in vacuo. Purified by reverse phase chromatography (5-65% MeCN in water with 0.1% TFA, C18) to yield 43-2 as a solid. $^1$H NMR δ (ppm)(DMSO-$d_6$): 7.71 (1H, d, J=5.60 Hz), 7.45 (2H, d, J=7.65 Hz), 7.41-7.35 (2H, m), 7.35-7.31 (1H, m), 7.28 (1H, d, J=4.60 Hz), 7.22 (1H, d, J=9.74 Hz), 6.87 (1H, d, J=4.58 Hz), 5.62-5.56 (1H, m), 1.86 (3H, d, J=7.20 Hz). HRMS C18H14FN3O4S2 [M+H] calc: 420.0483, obs: 420.0483.

The following compounds were prepared from 43-1 and the appropriate alcohol by a synthetic sequence analogous to that depicted in Scheme 43:

TABLE 23

| # | Structure | Name | Exact Mass [M + H]+ |
|---|-----------|------|---------------------|
| 43-3 | 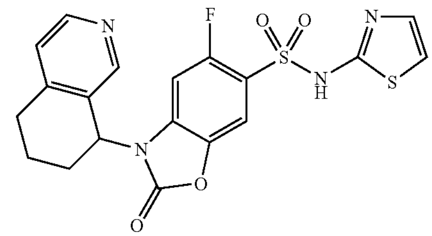 [SMILES: O=c1oc2cc(S(=O)(=O)Nc3nccs3)c(F)cc2n1C1CCCc2ccncc21] | 5-fluoro-2-oxo-3-(5,6,7,8-tetrahydroisoquinolin-8-yl)-N-1,3-thiazol-2-yl-2,3-dihydro-1,3-benzoxazole-6-sulfonamide | Calc'd 447.1, found 446.9 |
| 43-4 | 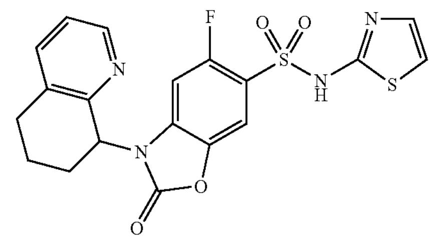 [SMILES: O=c1oc2cc(S(=O)(=O)Nc3nccs3)c(F)cc2n1C1CCCc2cccnc21] | 5-fluoro-2-oxo-3-(5,6,7,8-tetrahydroquinolin-8-yl)-N-1,3-thiazol-2-yl-2,3-dihydro-1,3-benzoxazole-6-sulfonamide | Calc'd 447.1, found 446.9 |
| 43-5 | 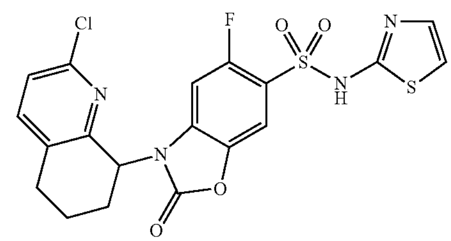 [SMILES: O=c1oc2cc(S(=O)(=O)Nc3nccs3)c(F)cc2n1C1CCCc2ccc(Cl)nc21] | 3-(2-chloro-5,6,7,8-tetrahydroquinolin-8-yl)-5-fluoro-2-oxo-N-1,3-thiazol-2-yl-2,3-dihydro-1,3-benzoxazole-6-sulfonamide | Calc'd 481.0, found 480.8 |
| 43-6 | 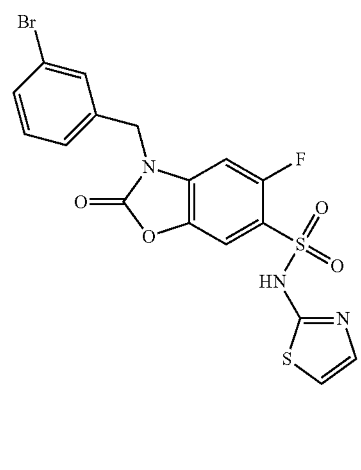 [SMILES: O=c1oc2cc(S(=O)(=O)Nc3nccs3)c(F)cc2n1Cc1cccc(Br)c1] | 3-(3-bromobenzyl)-5-fluoro-2-oxo-N-1,3-thiazol-2-yl-2,3-dihydro-1,3-benzoxazole-6-sulfonamide | Calc'd 483.9, found 485.8 |

TABLE 23-continued

| # | Structure | Name | Exact Mass [M + H]+ |
|---|---|---|---|
| 43-7 | 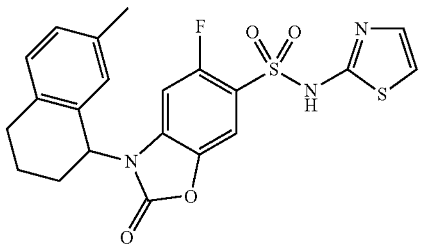 [SMILES: Cc1ccc2c(c1)C(n1c(=O)oc3cc(S(=O)(=O)Nc4nccs4)c(F)cc31)CCC2] | 5-fluoro-3-(7-methyl-1,2,3,4-tetrahydronaphthalen-1-yl)-2-oxo-N-1,3-thiazol-2-yl-2,3-dihydro-1,3-benzoxazole-6-sulfonamide | Calc'd 460.1, found 459.9 |
| 43-8 | 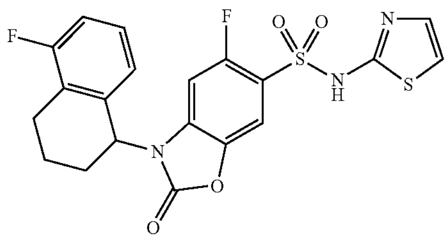 [SMILES: O=c1oc2cc(S(=O)(=O)Nc3nccs3)c(F)cc2n1C1CCCc2c(F)cccc21] | 5-fluoro-3-(5-fluoro-1,2,3,4-tetrahydronaphthalen-1-yl)-2-oxo-N-1,3-thiazol-2-yl-2,3-dihydro-1,3-benzoxazole-6-sulfonamide | Calc'd 464.1, found 463.9 |
| 43-9 | 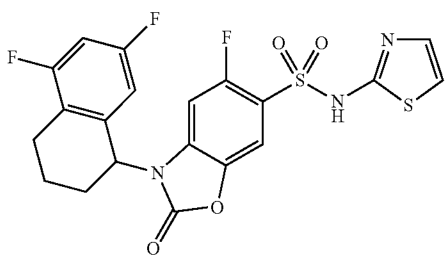 [SMILES: O=c1oc2cc(S(=O)(=O)Nc3nccs3)c(F)cc2n1C1CCCc2c(F)cc(F)cc21] | 3-(5,7-difluoro-1,2,3,4-tetrahydronaphthalen-1-yl)-5-fluoro-2-oxo-N-1,3-thiazol-2-yl-2,3-dihydro-1,3-benzoxazole-6-sulfonamide | Calc'd 482.0, found 481.9 |
| 43-10 | 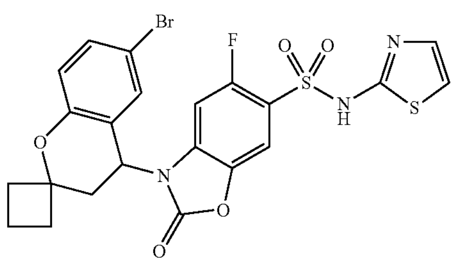 [SMILES: O=c1oc2cc(S(=O)(=O)Nc3nccs3)c(F)cc2n1C1CC2(CCC2)Oc2ccc(Br)cc21] | 3-(6-bromo-3,4-dihydrospiro[chromene-2,1'-cyclobutan]-4-yl)-5-fluoro-2-oxo-N-1,3-thiazol-2-yl-2,3-dihydro-1,3-benzoxazole-6-sulfonamide | Calc'd 566.0, found 565.8 |
| 43-11 | 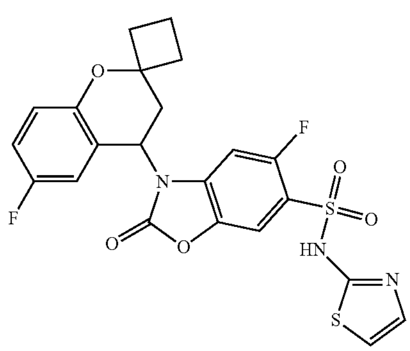 [SMILES: O=c1oc2cc(S(=O)(=O)Nc3nccs3)c(F)cc2n1C1CC2(CCC2)Oc2ccc(F)cc21] | 5-fluoro-3-(6-fluoro-3,4-dihydrospiro[chromene-2,1'-cyclobutan]-4-yl)-2-oxo-N-1,3-thiazol-2-yl-2,3-dihydro-1,3-benzoxazole-6-sulfonamide | Calc'd 506.1, found 507.0 |

TABLE 23-continued

| # | Structure | Name | Exact Mass [M + H]+ |
|---|---|---|---|
| 43-12 | 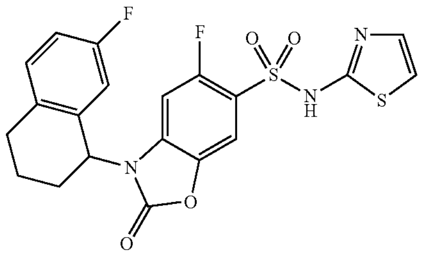 [SMILES: O=c1oc2cc(S(=O)(=O)Nc3nccs3)c(F)cc2n1C1CCCc2ccc(F)cc21] | 5-fluoro-3-(7-fluoro-1,2,3,4-tetrahydronaphthalen-1-yl)-2-oxo-N-1,3-thiazol-2-yl-2,3-dihydro-1,3-benzoxazole-6-sulfonamide | Calc'd 464.1, found 463.9 |

The following compounds were prepared from 43-1 and the appropriate alcohol by the synthetic sequence depicted in Scheme 42:

TABLE 24

| # | Structure | Name | Exact Mass [M + H]+ |
|---|---|---|---|
| 43-13 | 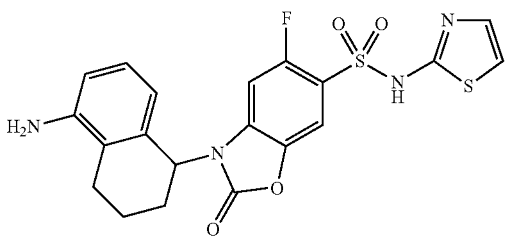 [SMILES: Nc1cccc2c1CCCC2n1c(=O)oc2cc(S(=O)(=O)Nc3nccs3)c(F)cc21] | 3-(5-amino-1,2,3,4-tetrahydronaphthalen-1-yl)-5-fluoro-2-oxo-N-1,3-thiazol-2-yl-2,3-dihydro-1,3-benzoxazole-6-sulfonamide | Calc'd 461.1, found 460.9 |
| 43-14 | 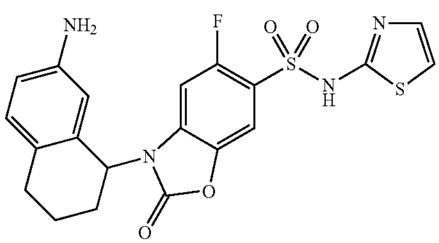 [SMILES: Nc1ccc2c(c1)C(n1c(=O)oc3cc(S(=O)(=O)Nc4nccs4)c(F)cc31)CCC2] | 3-(7-amino-1,2,3,4-tetrahydronaphthalen-1-yl)-5-fluoro-2-oxo-N-1,3-thiazol-2-yl-2,3-dihydro-1,3-benzoxazole-6-sulfonamide | Calc'd 461.1, found 460.9 |
| 43-15 | 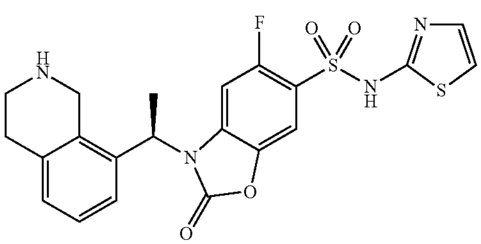 [SMILES: C[C@H](c1cccc2c1CNCC2)n1c(=O)oc2cc(S(=O)(=O)Nc3nccs3)c(F)cc21] | 5-fluoro-2-oxo-3-[(1R)-1-(1,2,3,4-tetrahydroisoquinolin-8-yl)ethyl]-N-1,3-thiazol-2-yl-2,3-dihydro-1,3-benzoxazole-6-sulfonamide | Calc'd 475.1, found 475.2 |
| 43-16 | 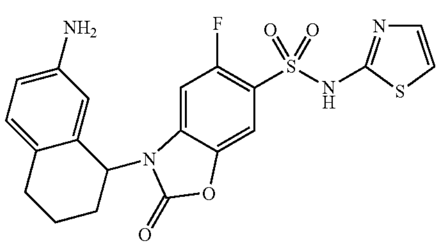 [SMILES: Nc1ccc2c(c1)C(n1c(=O)oc3cc(S(=O)(=O)Nc4nccs4)c(F)cc31)CCC2] | 3-(7-amino-1,2,3,4-tetrahydronaphthalen-1-yl)-5-fluoro-2-oxo-N-1,3-thiazol-2-yl-2,3-dihydro-1,3-benzoxazole-6-sulfonamide | Calc'd 461.1, found 460.9 |

The following compounds were prepared from 43-1 and alcohols 15-2 and ent-15-2 by analogy to the sequence depicted in Scheme 15:

TABLE 25

| # | Structure | Name | Exact Mass [M + H]+ |
|---|---|---|---|
| 43-17 | 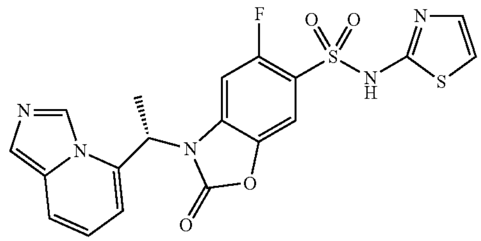 [SMILES: C[C@@H](c1cccc2cncn12)n1c(=O)oc2cc(S(=O)(=O)Nc3nccs3)c(F)cc21] | 5-fluoro-3-[(1S)-1-imidazo[1,5-a]pyridin-5-ylethyl]-2-oxo-N-1,3-thiazol-2-yl-2,3-dihydro-1,3-benzoxazole-6-sulfonamide | Calc'd 460.0544, found 460.0535 |
| 43-18 | 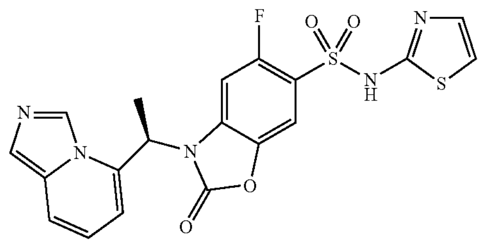 [SMILES: C[C@H](c1cccc2cncn12)n1c(=O)oc2cc(S(=O)(=O)Nc3nccs3)c(F)cc21] | 5-fluoro-3-[(1R)-1-imidazo[1,5-a]pyridin-5-ylethyl]-2-oxo-N-1,3-thiazol-2-yl-2,3-dihydro-1,3-benzoxazole-6-sulfonamide | Calc'd 460.0544, found 460.0534 |

The following compound was prepared from 43-1 and propargyl amine by analogy to the sequence depicted in Scheme 17:

TABLE 26

| # | Structure | Name | Exact Mass [M + H]+ |
|---|---|---|---|
| 43-19 | 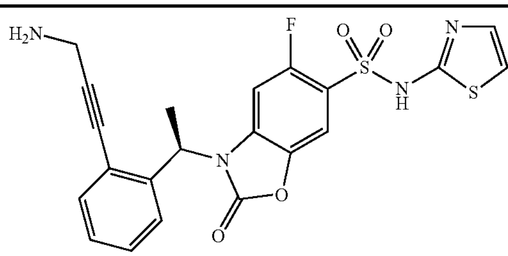 | 3-{(1R)-1-[2-(3-aminoprop-1-yn-1-yl)phenyl]ethyl}-5-fluoro-2-oxo-N-1,3-thiazol-2-yl-2,3-dihydro-1,3-benzoxazole-6-sulfonamide | Calc'd 473.0748, found 473.0731 |

The following compounds were prepared from 43-1 by analogy to the sequence depicted in Scheme 31:

TABLE 27

| # | Structure | Name | Exact Mass [M + H]+ |
|---|---|---|---|
| 43-20 | 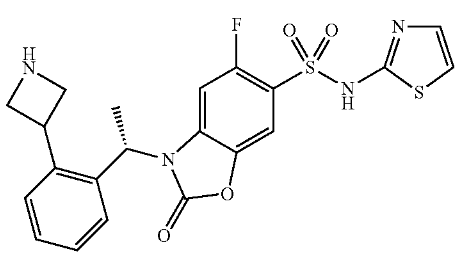 [SMILES: C[C@@H](c1ccccc1C1CNC1)n1c(=O)oc2cc(S(=O)(=O)Nc3nccs3)c(F)cc21] | 3-[(1S)-1-(2-azetidin-3-ylphenyl)ethyl]-5-fluoro-2-oxo-N-1,3-thiazol-2-yl-2,3-dihydro-1,3-benzoxazole-6-sulfonamide | Calc'd 475.0905, found 475.0899 |

TABLE 27-continued

| # | Structure | Name | Exact Mass [M + H]+ |
|---|---|---|---|
| 43-21 | 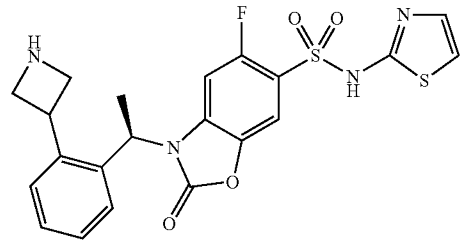 [SMILES: C[C@H](c1ccccc1C1CNC1)n1c(=O)oc2cc(S(=O)(=O)Nc3nccs3)c(F)cc21] | 3-[(1R)-1-(2-azetidin-3-ylphenyl)ethyl]-5-fluoro-2-oxo-N-1,3-thiazol-2-yl-2,3-dihydro-1,3-benzoxazole-6-sulfonamide | Calc'd 475.0905, found 475.0892 |

The following compounds were prepared from 43-1 by analogy to the reaction sequence illustrated in Scheme 32:

TABLE 28

| # | Structure | Name | Exact Mass [M + H]+ |
|---|---|---|---|
| 42-22 | 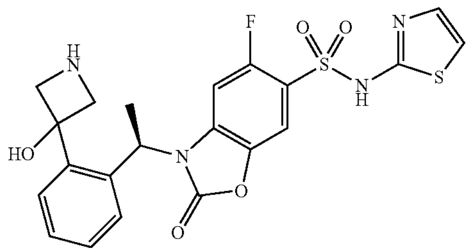 [SMILES: C[C@H](c1ccccc1C1(O)CNC1)n1c(=O)oc2cc(S(=O)(=O)Nc3nccs3)c(F)cc21] | 5-fluoro-3-{(1R)-1-[2-(3-hydroxyazetidin-3-yl)phenyl]ethyl}-2-oxo-N-1,3-thiazol-2-yl-2,3-dihydro-1,3-benzoxazole-6-sulfonamide | Calc'd 491.0854, found 491.0838 |
| 43-23 | 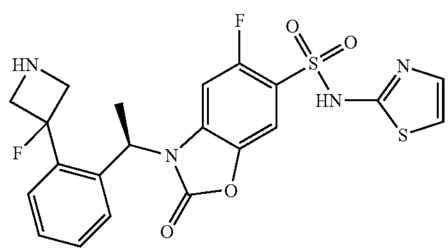 [SMILES: C[C@H](c1ccccc1C1(F)CNC1)n1c(=O)oc2cc(S(=O)(=O)Nc3nccs3)c(F)cc21] | 5-fluoro-3-{(1R)-1-[2-(3-fluoroazetidin-3-yl)phenyl]ethyl}-2-oxo-N-1,3-thiazol-2-yl-2,3-dihydro-1,3-benzoxazole-6-sulfonamide | Calc'd 493.0810, found 493.0793 |

The following compounds were prepared from 43-1 by analogy to the sequence depicted in Scheme 28:

TABLE 29

| # | Structure | Name | Exact Mass [M + H]+ |
|---|---|---|---|
| 43-24 | 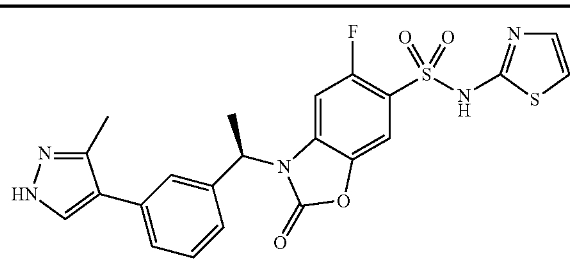 | 5-fluoro-3-{(1R)-1-[3-(3-methyl-1H-pyrazol-4-yl)phenyl]ethyl}-2-oxo-N-1,3-thiazol-2-yl-2,3-dihydro-1,3-benzoxazole-6-sulfonamide | Calc'd 500.1, found 499.9 |

TABLE 29-continued

| # | Structure | Name | Exact Mass [M + H]+ |
|---|---|---|---|
| 43-25 | 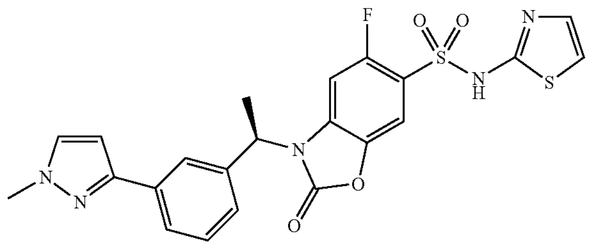 [SMILES: C[C@H](c1cccc(-c2ccn(C)n2)c1)n1c(=O)oc2cc(S(=O)(=O)Nc3nccs3)c(F)cc21] | 5-fluoro-3-{(1R)-1-[3-(1-methyl-1H-pyrazol-3-yl)phenyl]ethyl}-2-oxo-N-1,3-thiazol-2-yl-2,3-dihydro-1,3-benzoxazole-6-sulfonamide | Calc'd 500.1, found 499.9 |

The following compounds were prepared from 43-1 by analogy to the sequence depicted in Scheme 24:

TABLE 30

| # | Structure | Name | Exact Mass [M + H]+ |
|---|---|---|---|
| 43-26 | 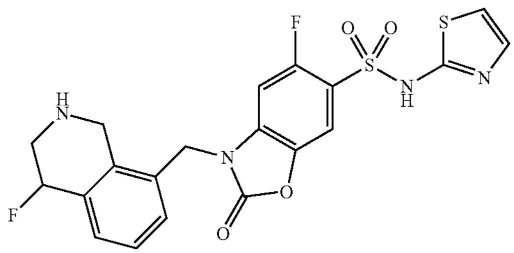 [SMILES: O=c1oc2cc(S(=O)(=O)Nc3nccs3)c(F)cc2n1Cc1cccc2c1CNCC2F] | (+/-)-5-fluoro-3-[(4-fluoro-1,2,3,4-tetrahydroisoquinolin-8-yl)methyl]-2-oxo-N-1,3-thiazol-2-yl-2,3-dihydro-1,3-benzoxazole-6-sulfonamide | Calc'd 479.0654, found 479.0637 |
| 43-27 | 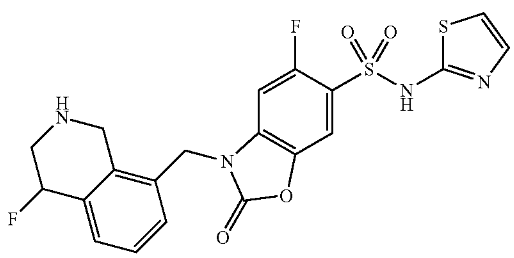 [SMILES: O=c1oc2cc(S(=O)(=O)Nc3nccs3)c(F)cc2n1Cc1cccc2c1CNCC2F] | (R or S)-5-fluoro-3-[(4-fluoro-1,2,3,4-tetrahydroisoquinolin-8-yl)methyl]-2-oxo-N-1,3-thiazol-2-yl-2,3-dihydro-1,3-benzoxazole-6-sulfonamide | Calc'd 479.0654, found 479.0647 |
| 43-28 | 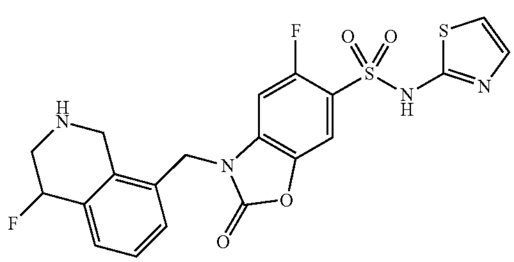 [SMILES: O=c1oc2cc(S(=O)(=O)Nc3nccs3)c(F)cc2n1Cc1cccc2c1CNCC2F] | (S or R)-5-fluoro-3-[(4-fluoro-1,2,3,4-tetrahydroisoquinolin-8-yl)methyl]-2-oxo-N-1,3-thiazol-2-yl-2,3-dihydro-1,3-benzoxazole-6-sulfonamide | Calc'd 479.0654, found 479.0646 |

Example 37

Preparation of 3-((4,4-Difluoro-1,2,3,4-tetrahydroisoquinolin-8-yl)methyl)-5-fluoro-2-oxo-N-(thiazol-2-yl)-2,3-dihydrobenzo[d]oxazole-6-sulfonamide

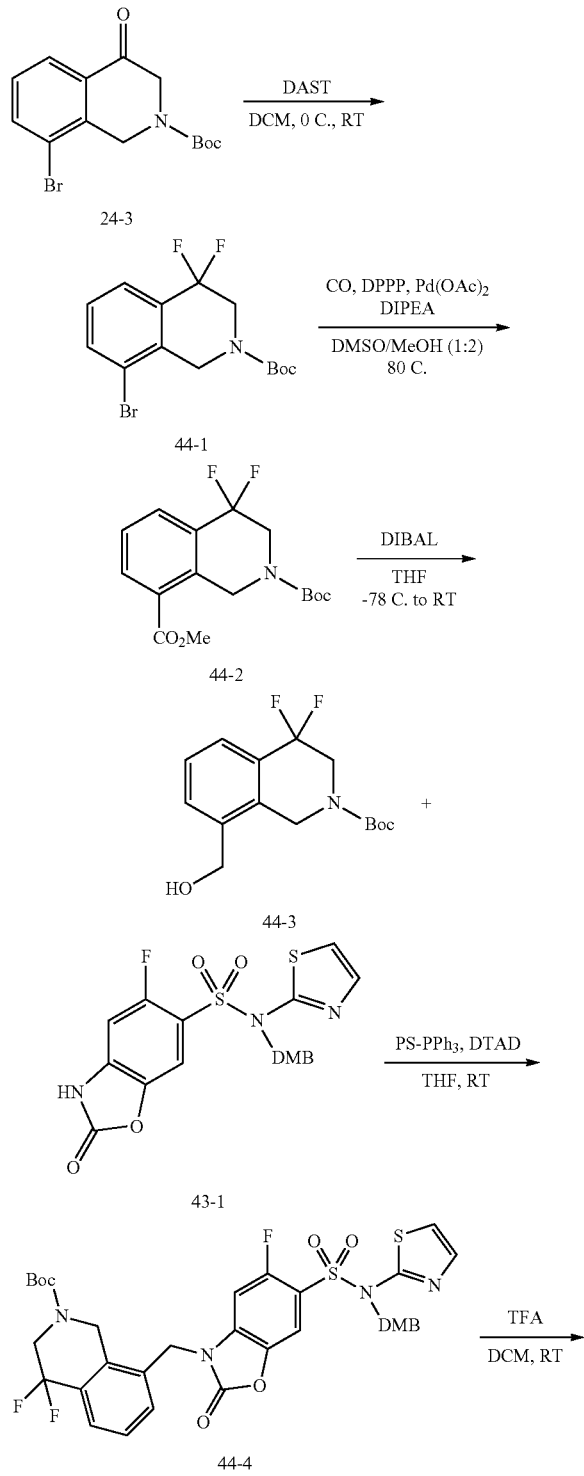

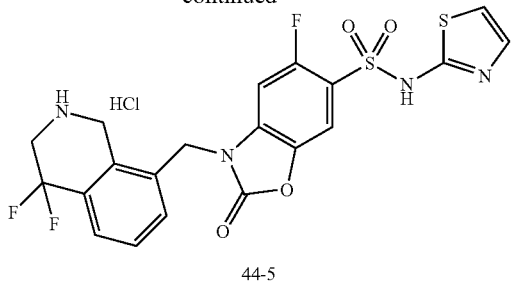

Preparation of tert-Butyl 8-bromo-4,4-difluoro-3,4-dihydroisoquinoline-2(1H)-carboxylate (44-1)

To a flask containing tert-butyl 8-bromo-4-oxo-3,4-dihydroisoquinoline-2(1H)-carboxylate (24-3) (1.3 g, 3.99 mmol) was added DCM (6 ml), then cooled to 0 C (ice water bath) while stirring under N2. Then added DAST (3 ml, 22.71 mmol). The reaction mixture was then stirred at 0 C for 15 minutes, then warmed to room temperature. Followed by LC/MS. After 3 days at room temperature an additional portion of DAST (3 ml, 22.71 mmol) was added, then stirred an additional 4 days at room temperature, then the reaction mixture was cooled back to 0 C (ice water bath), then uncapped & slowly quenched by addition of saturated NaHCO3, then suspended in EtOAc, washed with saturated NaHCO3, then H2O, then brine; organics dried over Na2SO4, filtered & concentrated. Purification by silica gel chromatography (0-15% EtOAc/Hex; 120 g ISCO) desired fractions concentrated to yield tert-butyl 8-bromo-4,4-difluoro-3,4-dihydroisoquinoline-2(1H)-carboxylate (44-1).

Preparation of 3-((4,4-Difluoro-1,2,3,4-tetrahydroisoquinolin-8-yl)methyl)-5-fluoro-2-oxo-N-(thiazol-2-yl)-2,3-dihydrobenzo[d]oxazole-6-sulfonamide hydrochloride (44-5)

To a flask containing tert-butyl 8-(((6-(N-(2,4-dimethoxybenzyl)-N-(thiazol-2-yl)sulfamoyl)-5-fluoro-2-oxobenzo[d]oxazol-3(2H)-yl)methyl)-4,4-difluoro-3,4-dihydroisoquinoline-2(1H)-carboxylate (44-4) (45 mg, 0.060 mmol) (prepared from 43-1 by a sequence analogous to that presented herein) in DCM (3 ml) was added TFA (300 µl, 3.89 mmol). The reaction mixture was then stirred at room temperature. Followed by LC/MS. After 20 minutes the reaction mixture was diluted/quenched with DMSO, then MeOH then filtered (syringe filter) then concentrated (to remove DCM), then diluted with MeOH/DMSO & filtered. The filtrate was purified (without workup) by reverse phase chromatography (5-75% MeCN/H2O; 0.1% TFA in AQ; 20 min gradient; Waters 30×150 mm Sunfire 5 micron C18 column); desired fractions concentrated (GENEVAC), then dissolved in MeOH/DCM & added saturated HCl in EtOAc (~4N) & concentrated to yield 3-((4,4-difluoro-1,2,3,4-tetrahydroisoquinolin-8-yl)methyl)-5-fluoro-2-oxo-N-(thiazol-2-yl)-2,3-dihydrobenzo[d]oxazole-6-sulfonamide hydrochloride (44-5). HRMS [M+H]: calculated; 497.0560, observed; 497.0556. $^1$H NMR (499 MHz, DMSO): δ 7.77 (d, J=5.5 Hz, 1H); 7.73 (d, J=7.5 Hz, 1H); 7.58-7.50 (m, 2H); 7.39 (d, J=9.4 Hz, 1H); 7.29 (d, J=4.6 Hz, 1H); 6.88 (d, J=4.6 Hz, 1H); 5.13 (s, 2H); 4.52 (s, 2H); 3.99 (t, J=11.8 Hz, 2H).

Cell Based Assays for Na$_v$1.7 and Na$_v$1.5 Activity

Compounds were tested on human Nav1.7 and Nav1.5 channels stably expressed in HEK 293 cells. Sodium current measurements on IonWorks Quattro: An automated patch-clamp assay on the IonWorks Quattro platform (Molecular Devices) was used to measure state-dependent inhibition of human Nav1.7 and 1.5 channels. Cells were sealed on a planar substrate using the Population Patch Plate (PPC) technology. Electrical access was obtained using both nystatin and amphotericin. A double-pulse protocol was used for the determination of IC$_{50}$ values for inactivated state block. Nav1.7 and Nav1.5 expressing cells were voltage clamped at −100 mV and −110 mV, respectively. A depolarizing prepulse to −10 mV (Nav1.7) or −30 mV (Nav1.5) for 1000 ms followed by a 10 ms repolarization to −100 mV (Nav1.7) or −110 mV (Nav1.5) was given to generate fractional channel inactivation of ~50%, followed by a 10 ms test pulse to −10 mV (Nav1.7) or −30 mV (Nav1.5) to measure peak current in control conditions and after compound addition. The following recording solutions were used (mM). External: 150 NaCl, 2 CaCl$_2$, 5 KCl, 1 Mg Cl$_2$, 10 HEPES, 12 Dextrose; internal: 120 CsF, 30 CsCl, 10 EGTA, 5 HEPES, 5 NaF, 2 MgCl$_2$.

Sodium Current Measurements on the PatchXpress 7000®:

To measure state and use-dependent sodium channel inhibition, test compounds were further characterized in an automated PatchXpress® assay (Molecular Devices). Two voltage-clamp protocols were used. 1) Use-dependent protocol: Cells were held at a membrane potential 20 mV negative to the potential at which ~50% of the channels are inactivated (V$_{0.5\ inact}$). A train of 30 ms depolarizations to −20 mV was applied to the cells expressing Nav1.7 at a frequency of 10 Hz. A train of 200 ms depolarizations to −20 mV was applied to cells expressing Nav1.5 at a frequency of 3 Hz. Data was collected in the absence and presence of drug, and after drug washout. 2) A double-pulse protocol was used to measure inactivated state block. Cells were held at a potential 20 mV negative to V$_{0.5\ inact}$. A 8000 ms pre-pulse 7 mV positive to V$_{0.5\ inact}$ was given followed by a hyperpolarizing 2 ms pulse to −120 mV and a 20 ms test pulse to −20 mV. Protocol was applied to cells in the absence, presence of compound and after washout. The temperature of PatchXpress instruments was maintained at 22° C. The following recording solutions were used. Internal solution (mM): 30 CsCl, 5 HEPES, 10 EGTA, 120 CsF, 5 NaF, 2MgCl$_2$, pH=7.3 with CsOH, 324 mosmo. External solution (mM): 120 NMDG, 40 NaCl, 1 KCl, 0.5 MgCl$_2$, 5 HEPES, 2.7 CaCl$_2$, pH=7.5 with NMDG-OH.

Sodium Current Measurements Using the Manual Whole-Cell Patch Clamp Technique

The following assay protocols were used to measure inactivated state block and use-dependent block. 1) Inactivated state block: Cells were held at −120 mV. Current inhibition by test compounds was measured during a 20 ms test pulse to 0 mV following a prepulse to V$_{0.5\ inact}$ for 8000 ms. 2) Use-dependent inhibition: Cells expressing Nav1.7 were held at −120 mV and depolarized to 0 mV for 50 ms at a frequency of 10 Hz. Cells expressing Nav1.5 were held at 20 mV negative to V$_{0.5\ inact}$. 200 ms testpulses to −20 mV were given at a frequency of 3 Hz. All recordings were performed at room temperature (22° C.) with either an Axopatch 200B or Multiclamp700A amplifiers controlled by pClamp 9 software (Axon Instruments, Burlingame, Calif.). The following recording solutions were used. External solution (in mM): 120 NMDG, 40 NaCl, 1 KCl, 5 HEPES, 2.7 mM CaCl$_2$, and 0.5 MgCl$_2$, pH 7.4 with NaOH. Pipettes were filled with internal solution (in mM): 30 CsCl, 5 HEPES, 10 EGTA, 120 CsF, 5 NaF, 2 MgCl$_2$, pH 7.3 with CsOH. Compounds or vehicle solutions were applied to the cells via continuous bath perfusion.

For all electrophysiology experiments, offline analysis was used to correct for current rundown and to determine percent inhibition as a function of drug concentration. IC$_{50}$ values were determined by fitting to the Hill equation.

The various compounds exemplified above were assayed for activity and selectivity using the foregoing IonWorks® technique. The results are reported in the following paragraph in a format expressing the identification of the compound with reference to Scheme and compound (e.g. 3-3 is Scheme 3, compound 3) followed by the observed potency in nM and the ratio of Na$_v$1.7 potency:Na$_v$1.5 potency as described here. Thus, 3-3: 1.7=216/ratio=65 identifies compound Scheme 3, Compound 3 as having 216 nM potency for the Nav 1.7 sodium ion channel (as measured by IonWorks®) and a ratio of 65 Nav 1.5:Nav 1.7 potency, determined by IonWorks® measurement. The following results are reported:

1-8: 1.7=423/ratio=>78; 1-10: 1.7=803/ratio=>41; 1-11: 1.7=360/ratio=59; 1-12: 1.7=408/ratio=67; 1-13: 1.7=976/ratio=>34; 1-14: 1.7=265/ratio=>125; 1-15: 1.7=605/ratio=>55; 1-16: 1.7=1693/ratio=>19; 1-17: 1.7=216/ratio=65; 3-3: 1.7=216/ratio=65; 3-4: 1.7=158/ratio=>209; 3-5: 1.7=248/ratio=>133; 3-6: 1.7=287/ratio=>115; 3-7: 1.7=292/ratio=>113; 3-8: 1.7=321/ratio=>103; 3-9: 1.7=563/ratio=>59; 3-10: 1.7=1744/ratio=>19; 3-11: 1.7=596/ratio=>56; 3-12: 1.7=287/ratio=>115; 3-13: 1.7=395/ratio=>83; 3-14: 1.7=430/ratio=35; 3-15: 1.7=646/ratio=>51; 3:16: 1.7=759/ratio=>43; 3-17: 1.7=827/ratio=>40; 3-18: 1.7=1330/ratio=>25; 4-4: 1.7=5/ratio=4494; 4-6: 1.7=954/ratio=>35; 4-7: 1.7=670/ratio=28; 4-8: 1.7=1483/ratio=>22; 4-9: 1.7=1138/ratio=22; 4-10: 1.7=1326/ratio=>25; 4-11: 1.7=1733/ratio=9; 4-12: 1.7=1040/ratio=>32; 4-13: 1.7=272/ratio=NA; 4-14: 1.7=25/ratio=>1338; 4-15: 1.7=73/ratio=>451; 6-1: 1.7=366/ratio=88; 6-2: 1.7=336/ratio=>98; 6-3: 1.7=642/ratio=>51; 6-4: 1.7=464/ratio=54; 8-4 1.7=526/ratio=20; 9-1 1.7=638/ratio=35; 10-1 1.7=666/ratio=>50; 11-5: 1.7=101/ratio=182; 11-6: 1.7=576/ratio=57; 12-3: 1.7=5/ratio=6084; 13-2: 1.7=4/ratio=2604; 13-3: 1.7=21/ratio=418; 13-4: 1.7=157/ratio=78; 13-5: 1.7=110/ratio=>300; 13-6: 1.7=65/ratio=>511.

The various compounds exemplified above were assayed for activity and selectivity using the foregoing PatchXpress® technique. The results are reported in the following paragraph in a format expressing the identification of the compound with reference to Scheme and compound (e.g. 3-3 is Scheme 3, compound 3) followed by the observed potency in nM and the ratio of Na$_v$1.7 potency:Na$_v$1.5 potency as described here. Thus, 3-3: 1.7=336/ratio=>89 identifies compound Scheme 3, Compound 3 as having 336 nM potency for the Nav 1.7 sodium ion channel (as measured by PatchXpress®) and a ratio of >89 Nav 1.5:Nav 1.7 potency, determined by PatchXpress® measurement. The following results are reported:

1-8: 1.7=190/ratio=>158; 1-10: 1.7=486/ratio=>62; 1-11: 1.7=360/ratio=59; 1-12: 1.7=408/ratio=67; 1-13: 1.7=976/ratio=>34; 1-14: 1.7=365/ratio=45; 1-16: 1.7=3205/ratio=>9; 3-3: 1.7=336/ratio=>89; 3-4: 1.7=110/ratio=>272; 3-5: 1.7=111/ratio=>271; 3-6: 1.7=329/ratio=>91; 3-7: 1.7=137/ratio=>219; 3-8: 1.7=278/ratio=>108; 3-11: 1.7=219/ratio=87; 3-12: 1.7=545/ratio=55; 4-4: 1.7=26/ratio=>1153; 4-6: 1.7=342/ratio=>88; 4-7: 1.7=74/ratio=287; 4-9: 1.7=2636/ratio=>11; 4-10: 1.7=643/ratio=>47; 4-11:

1.7=1772/ratio=>17; 4-13: 1.7=88/ratio=177; 4-14: 1.7=61/ratio=>495; 4-15: 1.7=343/ratio=>87; 6-1: 1.7=869/ratio=>35; 6-2: 1.7=234/ratio=71; 6-4: 1.7=626/ratio=37; 8-4: 1.7=254/ratio=>1180; 9-1: 1.7=530/ratio=>57; 10-1: 1.7=598/ratio=14; 11-5: 1.7=69/ratio=139; 11-6: 1.7=322/ratio=>93; 11-7: 1.7=545/ratio=55; 11-9: 1.7=301/ratio=56; 11-10: 1.7=44/ratio=123; 11-11: 1.7=490/ratio=81; 11-12: 1.7=81/ratio=368; 11-13: 1.7=49/ratio=50; 12-3: 1.7=27/ratio=1096; 13-2: 1.7=26/ratio=357; 13-3: 1.7=42/ratio=162; 13-4: 1.7=167/ratio=27; 13-5: 1.7=145/ratio=>30; 13-10: 1.7=63/ratio=256; 13-12: 1.7=422/ratio=>71; 14-7: 1.7=40/ratio=749; 14-8: 1.7=71/ratio=114; 14-9: 1.7=808/ratio=37; 14-10: 1.7=779/ratio=27; 15-3: 1.7=134/ratio=122; 15-4: 1.7=235/ratio=60; 16-3: 1.7=69/ratio=272; 16-4: 1.7=28/ratio=296; 16-5: 1.7=46/ratio=646; 16-6: 1.7=18/ratio=1692; 17-1: 1.7=96/ratio=313; 17-2: 1.7=332/ratio=90; 17-3: 1.7=172/ratio=97; 17-4: 1.7=147/ratio=360; 17-5: 1.7=122/ratio=246; 17-6: 1.7=104/ratio=91; 17-7: 1.7=78/ratio=1257; 17-8: 1.7=64/ratio=27; 17-9: 1.7=58/ratio=45; 17-10: 1.7=56/ratio=534; 17-11: 1.7=51/ratio=589; 17-12: 1.7=37/ratio=262; 17-13: 1.7=34/ratio=789; 17-14: 1.7=34/ratio=1055; 17-15: 1.7=32/ratio=1566; 17-16: 1.7=31/ratio=973; 17-17: 1.7=29/ratio=1034; 17-18: 1.7=28/ratio=1085; 17-19: 1.7=22/ratio=1390; 17-20: 1.7=13/ratio=2324; 17-21: 1.7=13/ratio=2344; 17-22: 1.7=13/ratio=1456; 17-23: 1.7=12/ratio=2477; 18-2: 1.7=24/ratio=446; 18-3: 1.7=768/ratio=15; 18-4: 1.7=132/ratio=82; 18-5: 1.7=13/ratio=525; 19-6: 1.7=118/ratio=103; 20-4: 1.7=179/ratio=167; 21-1: 1.7=121/ratio=113; 22-1: 1.7=175/ratio=172; 23-1: 1.7=122/ratio=71; 23-2: 1.7=1650/ratio=18; 23-3: 1.7=342/ratio=88; 23-4: 1.7=310/ratio=97; 23-5: 1.7=278/ratio=78; 23-6: 1.7=206/ratio=146; 23-7: 1.7=206/ratio=146; 23-8: 1.7=186/ratio=161; 23-9: 1.7=180/ratio=167; 23-10: 1.7=179/ratio=167; 23-11: 1.7=115/ratio=73; 23-12: 1.7=109/ratio=46; 23-13: 1.7=84/ratio=121; 23-14: 1.7=75/ratio=393; 23-15: 1.7=72/ratio=207; 23-16: 1.7=70/ratio=431; 23-17: 1.7=50/ratio=321; 23-18: 1.7=47/ratio=642; 23-19: 1.7=32/ratio=499; 23-20: 1.7=30/ratio=802; 23-21: 1.7=28/ratio=920; 23-22: 1.7=26/ratio=221; 23-23: 1.7=24/ratio=502; 23-24: 1.7=15/ratio=1119; 23-25: 1.7=15/ratio=203; Ex 23-26: 1.7=12/ratio=2451; 23-27: 1.7 6/ratio=29; 24-9: 1.7=183/ratio=704; 23-2: 1.7=116/ratio=260; 26-5: 1.7=67/ratio=450; 27-5: 1.7=67/ratio=450; 27-6: 1.7=492/ratio=61; 27-7: 1.7=182/ratio=144; 28-3: 1.7=306/ratio=86; 28-4: 1.7=107/ratio=181; 28-5: 1.7=48/ratio=64; 29-3: 1.7=216/ratio=61; 29-4: 1.7=162/ratio=57; 30-3: 1.7=28/ratio=289; 30-4: 1.7=10/ratio=309; 31-1: 1.7=15/ratio=603; 32-4: 1.7=34/ratio=110; 32-6: 1.7=18/ratio=1333; 33-7: 1.7=51/ratio=166; 33-8: 1.7=168/ratio=179; 34-6: 1.7=25/ratio=1200; 34-7: 1.7=565/ratio=129; 34-8: 1.7=40/ratio=40; 35-5: 1.7=16/ratio=932; 35-6: 1.7=27/ratio=334; 36-1: 1.7=527/ratio=54; 36-2: 1.7=334/ratio=13; 36-3: 1.7=255/ratio=88; 36-4: 1.7=169/ratio=36; 36-5: 1.7=155/ratio=35; 36-6: 1.7=121/ratio=175; 36-7: 1.7=27/ratio=107; 37-3: 1.7=132/ratio=39; 38-2: 1.7=94/ratio=17; 38-3: 1.7=43/ratio=37; 39-3: 1.7=41/ratio=1196; 39-4: 1.7=312/ratio=58; 39-5: 1.7=261/ratio=14; 39-6: 1.7=221/ratio=110; 39-7: 1.7=218/ratio=137; 39-8: 1.7=204/ratio=29; 39-9: 1.7=168/ratio=54; 39-10: 1.7=168/ratio=199; 39-11: 1.7=166/ratio=114; 39-12: 1.7=159/ratio=38; 39-13: 1.7=112/ratio=295; 39-14: 1.7=60/ratio=99; 39-15: 1.7=54/ratio=36; 39-16: 1.7=53/ratio=149; 39-17: 1.7=53/ratio=115; 40-5: 1.7=1190/ratio=25; 41-4: 1.7=161/ratio=187; 41-6: 1.7=553/ratio=54; 42-1: 1.7=30/ratio=1017; 43-2: 1.7=68/ratio=88; 43-3: 1.7=550/ratio=91; 43-4: 1.7=424/ratio=71; 43-5: 1.7=416/ratio=202; 43-6: 1.7=162/ratio=80; 43-7: 1.7=111/ratio=137; 43-8: 1.7=71/ratio=75; 43-9: 1.7=67/ratio=95; 43-10: 1.7=58/ratio=29; 43-11: 1.7=41/ratio=196; 43-12: 1.7=30/ratio=145; 43-13: 1.7=405/ratio=74; 43-14: 1.7=140/ratio=724; 43-15: 1.7=80/ratio=147; 43-16: 1.7=211/ratio=329; 43-17: 1.7=621/ratio=48; 43-18: 1.7=215/ratio=139; 43-19: 1.7=29/ratio=1267; 43-20: 1.7=621/ratio=48; 43-21: 1.7=18/ratio=1164; 43-22: 1.7=61/ratio=703; 43-23: 1.7=4/ratio=5541; 43-24: 1.7=103/ratio=33; 43-25: 1.7=306/ratio=86; 43-26: 1.7=141/ratio=150; 43-27: 1.7=106/ratio=282; 43-28: 1.7=120/ratio=684; 44-5: 1.7=181/ratio=151.

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound of the formula:

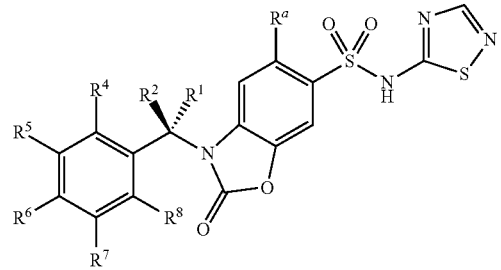

wherein:
a) $R^1$ and $R^2$ are independently: (i) —H; (ii) $C_{1-8}$ alkyl, wherein the alkyl moiety is optionally substituted with, independently for each occurrence, one or more: hydroxyl; halogen; —(C=O)—O—($C_{1-6}$-alkyl); or $C_{3-6}$ cycloalkyl moiety; (iii) $C_{1-4}$ alkenyl; or (iv) a five or six member heteroaryl moiety;
b) $R^4$ and $R^5$ are independently: (i) $C_{1-4}$ alkyl, optionally substituted by one or more: (a) halogen atoms; (b) —$NH_2$, or (c) —$NR'^a_2$, wherein $R'^a$ is independently for each occurrence: linear or cyclic —$(Y^a)_x$-alkyl, wherein, x=0, 1, and if present (x=1), $Y^a$ is: —$SO_2$—; —C(O)—; or —(C=O)O—, and the alkyl portion of the moiety is $C_{1-6}$-linear alkyl or $C_{3-6}$-cycloalkyl; (ii) $C_{1-4}$ alkenyl, optionally substituted by one or more: (a) halogen atoms; (b) —$NH_2$, or (c) —$NR'^a{}_2$, wherein $R'^a$ is independently for each occurrence: linear or cyclic —$(Y^a)_x$-alkyl, wherein, x=0, 1, and if present (x=1), $Y^a$ is: —$SO_2$—; —C(O)—; or —(C=O)O—; (iii) a piperidine moiety which is bonded to the aryl ring through any of the atoms of the piperidine ring; (iv) a dihydropyridine, bonded through any of the atoms of the pyridine ring; (v) a tetrahydropyridine moiety bonded through any of the atoms of the pyridine ring; (vi) a pyridine moiety bonded to the aryl ring through any of the atoms of the pyridine ring, wherein the pyridine is optionally substituted on any other available ring atom with a heterocycle or an —$C_{1-3}$-alkyl-N-heterocycle, wherein preferably said heterocycle portion of the moiety is piperidine; (vii) an aryl moiety which is optionally substituted with a heterocycle moiety bonded to any available carbon atom of the aryl ring through any atom of the heterocycle ring; (viii) a tetrahydroquinoline moiety bonded through any of the carbon atoms of the aromatic ring optionally substituted on any available carbon atom with halogen, —CN, $C_{1-6}$-alkyl or $C_{1-6}$-alkoxy; (ix) a tetrahydroisoquinoline moiety bonded through any of the carbon atoms of the aromatic ring optionally substituted on any available carbon atom with halogen, —CN, $C_{1-6}$-alkyl, or $C_{1-6}$-alkoxy, and where the N-moiety in said isoquinoline is optionally substituted with —$SO_2$—$C_{1-6}$-alkyl; (x) an azabicyclo-moiety of the structure:

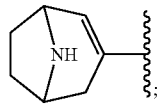 [SMILES: *C1=CC2CCC(C1)N2]

(xi) —$C_{1-4}$-alkynyl optionally substituted with one or more of: $C_{1-4}$-alkyl; amino; or halogen moieties; or (xii) heteroaryl; or $R^4$ and $R^5$ together with the aryl ring to which they are bonded form a 10 to 12-member heteroaryl-aryl or heteroalkyl-aryl bicyclic moiety; and c) $R^6$, $R^7$, and $R^8$ are independently for each occurrence: —CN; $C_{1-6}$-alkyl; $C_{1-6}$-alkoxy-; —H or halogen.

2. A compound of the Formula

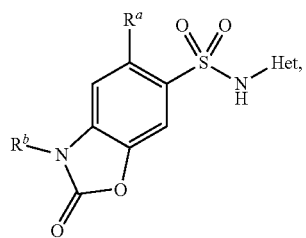

or a salt thereof,
wherein:
$R^a$ is —H, $C_{1-6}$ alkyl, $C_{1-6}$ alkoxy, —CN, or halogen; and when selected to be a halogen is preferably —F;
Het is a 5 member heteroaryl moiety comprising up to three heteroatoms selected from N, S, and O, bonded through any ring-atom of the aryl moiety available for bonding and optionally substituted with one or more alkyl, aryl, heteroaryl, aralkyl, alkylaryl, aralkenyl, heteroaralkyl, alkylheteroaryl, heteroaralkenyl, hydroxyl, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N$—, $R^{60}R^{65}N$-alkyl-, $R^{60}R^{65}NC(O)$— and $R^{60}R^{65}NSO_2$—, wherein $R^{60}$ and $R^{65}$ are each independently: hydrogen, alkyl, aryl, and aralkyl; and
$R^b$ is a moiety of Formula AE-1:

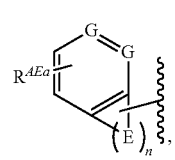

Formula AE-1 wherein:
one of G is —HC= and the other is —HC= or —N=;
$R^{AEa}$ is independently for each occurrence:
(a) $C_{1-6}$-alkyl which is optionally substituted with halogen, hydroxy, alkoxy or $N(R^{AGd})_2$, wherein $R^{AGd}$ is independently —H, $C_{1-6}$-alkyl-C(O)—, $C_{1-6}$-alkyl-C(O)—O—, $C_{1-6}$-alkyl-$SO_2$—, or $C_{1-6}$-alkyl, which alkyl is optionally substituted by one or more halogen, hydroxyl or alkoxy moiety or two $R^{AHd}$ together form a $C_{1-6}$-cycloalkyl moiety which is optionally substituted on any suitable carbon atom thereof b a halogen, alkoxy, hydroxy or alkyl moiety;
(b) $N(R^{AHd})_2$, wherein $R^{AHd}$ is independently —H, $C_{1-6}$-alkyl-C(O)—, $C_{1-6}$-alkyl-C(O)—O—, $C_{1-6}$-alkyl-$SO_2$—, or $C_{1-6}$-alkyl, which alkyl is optionally substituted by one or more halogen, hydroxyl or alkoxy moiety or two $R^{AHd}$ together form a $C_{1-6}$-cycloalkyl moiety which is optionally substituted on any suitable carbon atom thereof by a halogen, alkoxy, hydroxy or alkyl moiety;
(c) halogen;
(d) —H; or
(e) a 4 to 6-member heterocycle moiety which may optionally be substituted with $C_{1-4}$-alkyl, said moiety comprising one or more heteroatoms which are: (i) —O—; (ii) —$N(R^{AJa})$—, wherein $R^{AJa}$ is independently for each occurrence —H or $C_{1-4}$-alkyl; or (iii) —N=;
n is an integer of 3 to 6; and
E is independently for each occurrence:
(a) —$C(R^{AEb})_2$—, wherein $R^{AEb}$ is independently: (i) —H; (ii) halogen; (iii) $C_{1-6}$-alkyl; (iv) $N(R^{AEd})_2$, wherein $R^{AEd}$ is independently —H, $C_{1-6}$-alkyl-C(O)—, $C_{1-6}$-alkyl-C(O)—O—, $C_{1-6}$-alkyl-$SO_2$—, $C_{1-6}$-alkyl, which alkyl is optionally substituted by one or more halogen, hydroxyl or alkoxy moiety; or two $R^{AEd}$ together form a $C_{2-6}$-cycloalkyl moiety or a $C_{2-6}$-heterocyclo-alkyl moiety comprising additionally 1 to 3 heteroatoms which is optionally substituted on any suitable carbon atom thereof by a halogen, alkoxy, hydroxy or alkyl moiety; (v) two $R^{AEb}$ together form a $C_{1-6}$-cycloalkyl moiety which is optionally substituted on any suitable carbon atom thereof by a halogen, alkoxy, hydroxy or alkyl moiety;
(b) —O—; or
(c) —N($R^{AEc}$)—, wherein $R^{AEc}$ is: (i) —H; or (ii) $C_{1-6}$-alkyl-SO2-; or (iii) $C_{1-6}$-alkyl;
and wherein the nitrogen of the benzoxazolinone portion of the compound may be bonded to said moiety through any of E which is a suitable carbon atom for bonding.

3. A compound of the Formula

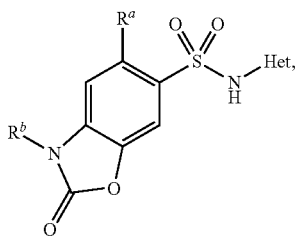

or a salt thereof,
wherein:
$R^a$ is —H, $C_{1-6}$ alkyl, $C_{1-6}$ alkoxy, —CN, or halogen; and when selected to be a halogen is preferably —F;
Het is a 5 member heteroaryl moiety comprising up to three heteroatoms selected from N, S, and O, bonded through any ring-atom of the aryl moiety available for bonding and optionally substituted with one or more alkyl, aryl, heteroaryl, aralkyl, alkylaryl, aralkenyl, heteroaralkyl, alkylheteroaryl, heteroaralkenyl, hydroxyl, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N$—, $R^{60}R^{65}N$-alkyl-, $R^{60}R^{65}NC(O)$— and $R^{60}R^{65}NSO_2$—, wherein $R^{60}$ and $R^{65}$ are each independently: hydrogen, alkyl, aryl, and aralkyl; and
$R^b$ is a moiety of Formula AF-1:

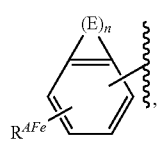

Formula AF-1 wherein: $R^{AFe}$ independently for each occurrence:
(a) $C_{1-6}$-alkyl which is optionally substituted with halogen, hydroxy, alkoxy or $N(R^{AGd})_2$, wherein $R^{AGd}$ is independently —H, $C_{1-6}$-alkyl-C(O)—, $C_{1-6}$-alkyl-C(O)—O—, $C_{1-6}$-alkyl-SO_2—, or $C_{1-6}$-alkyl, which alkyl is optionally substituted by one or more halogen, hydroxyl or alkoxy moiety or two $R^{AGd}$ together form a $C_{1-6}$-cycloalkyl moiety which is optionally substituted on any suitable carbon atom thereof by a halogen, alkoxy, hydroxy or alkyl moiety;
(b) $N(R^{AHd})_2$, wherein $R^{AHd}$ is independently —H, $C_{1-6}$-alkyl-C(O)—, $C_{1-6}$-alkyl-C(O)—O—, $C_{1-6}$-alkyl-SO_2—, or $C_{1-6}$-alkyl, which alkyl is optionally substituted by one or more halogen, hydroxyl or alkoxy moiety or two $R^{AHd}$ together form a $C_{1-6}$-cycloalkyl moiety which is optionally substituted on any suitable carbon atom thereof by a halogen, alkoxy, hydroxy or alkyl moiety;
(c) halogen;
(d) —H; or
(e) a 4 to 6-member heterocycle moiety which may optionally be substituted with $C_{1-4}$-alkyl, said moiety comprising one or more heteroatoms which are: (i) —O—; (ii) —N($R^{AJa}$)—, wherein $R^{AJa}$ is independently for each occurrence —H or $C^{1-4}$-alkyl; or (iii) —N═;

n is an integer of 3 to 6; and

E is independently for each occurrence:
(a) —C($R^{AFb}$)_2—, wherein $R^{AFb}$ is independently: (i) —H; (ii) halogen; (iii) $C_{1-6}$-alkyl; (iv) $N(R^{AFd})_2$, wherein $R^{AFd}$ is independently —H, $C_{1-6}$-alkyl-C(O)—, $C_{1-6}$-alkyl-C(O)—O—, $C_{1-6}$-alkyl, which alkyl is optionally substituted by one or more halogen, hydroxyl or alkoxy moiety; or two $R^{AF}$ together form a $C_{1-6}$-cycloalkyl moiety which is optionally substituted on any suitable carbon atom thereof by a halogen, alkoxy, hydroxy or alkyl moiety; (v) two $R^{AFb}$ together form a $C_{1-6}$-cycloalkyl moiety which is optionally substituted on any suitable carbon atom thereof by a halogen, alkoxy, hydroxy or alkyl moiety;
(b) —O—; or
(c) —N($R^{AFc}$)—, wherein $R^{AFc}$ is: (i) —H; (ii) $C_{1-6}$-alkyl-SO2-; or (iii) $C_{1-6}$-alkyl;
and wherein the nitrogen of the benzoxazolinone portion of the compound may be bonded to the aryl portion of said moiety through available carbon atom on the ring in place of a hydrogen atom otherwise residing there.

4. A compound of claim 3 wherein Het is:
(i) a moiety of Formula AD1-a:

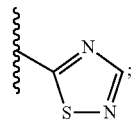

Formula AD1-a (ii) a moiety of Formula AD1-b:

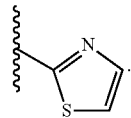

Formula AD1-b

5. A compound of claim 4 having Formula CC:

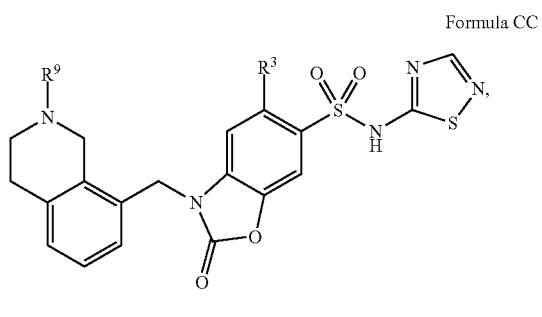

Formula CC or a salt thereof,
wherein:
(a) R³ is —F or —H; and
(b) R⁹ is: (i) —H; (ii) $C_{1-3}$-linear alkyl; (iii) $C_{3-5}$ cycloalkyl; (iv) $C_{1-3}$-alkylcarbonyl-; or (v) $C_{1-7}$-alkylsulfonyl-.

6. A compound of claim 1 having Formula CD:

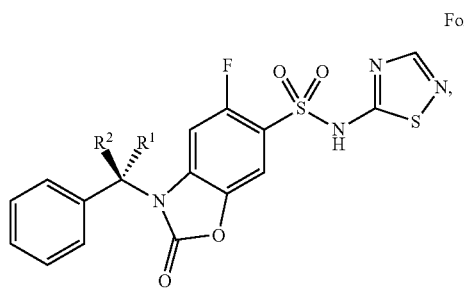

Formula CD or a salt thereof,
wherein one of R¹ and R² is —H and the other of R¹ and R² is —H or $C_{1-3}$ alkyl.

7. A compound of claim 1 having Formula CE:

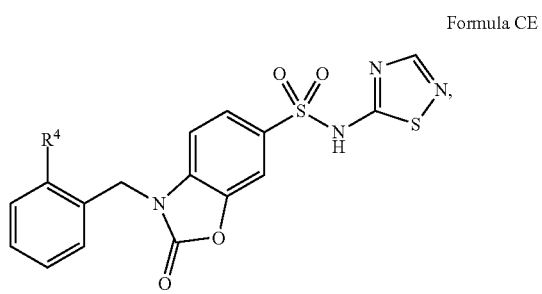

Formula CE or a salt thereof,
wherein R⁴ is:
(i) hydrogen;
(ii) tetrahydroquinoline bonded to the aryl ring in the compound of Formula CE through any carbon of the aryl ring in the tetrahydroquinoline;
(iii) tetrahydroisoquinoline bonded to the aryl ring in the compound of Formula E through any carbon of the aryl ring in the tetrahydroisoquinoline;
(iv) tetrahydropyridine bonded to the aryl ring in the compound of Formula E through any carbon atom of the tetrahydropyridine; or
(v) alkylamino bonded to the aryl ring of the compound of Formula E via a $C_{1-3}$ alkyl chain terminated with amino.

8. A compound of claim 1 having Formula CI:

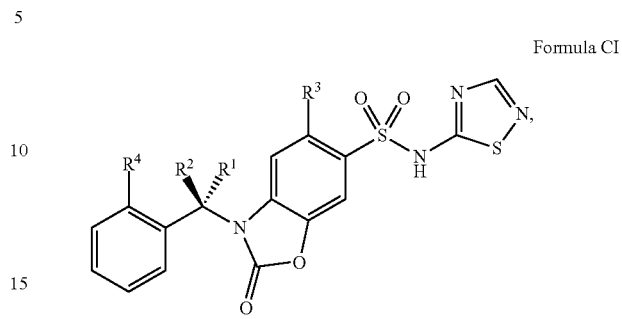

Formula CI or a salt thereof,
wherein R¹, R², R³, and R⁴ are defined in Table Ic, TABLE Ic

| R¹ | R² | R³ | R⁴ |
|---|---|---|---|
| —CH₃ | —H | —F | —H |
| —H | —CH₃ | —F | —H |
| —H | —H | —F | —H |
| Racemic —H and -isopropyl | | —F | —H |
| —H | —H | —F | H₂N—CH₂CH=CH— |
| Racemic —H and —CH₂CH=CH₂ | | —H | —H |
| —H | —CH₃ | —H | —H |
| Racemic —H and —CH₃, | | —H | —H |
| Racemic —H and -isopropyl | | —H | —H |
| Racemic —H and —CH₃ | | —H | —CF₃ |
| Racemic —H and 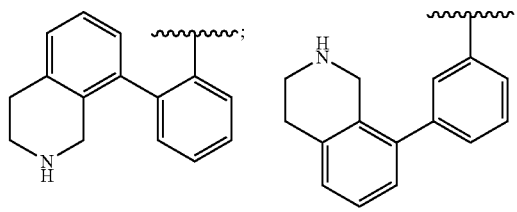 | | —H | —H |
| —CH₃ | —H | —H | —H. |

9. A compound of Formula CII:

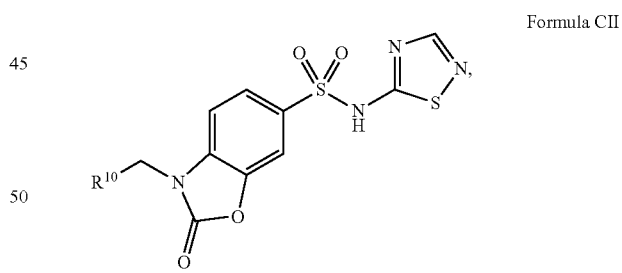

Formula CII or a salt thereof,
wherein R¹⁰ is:

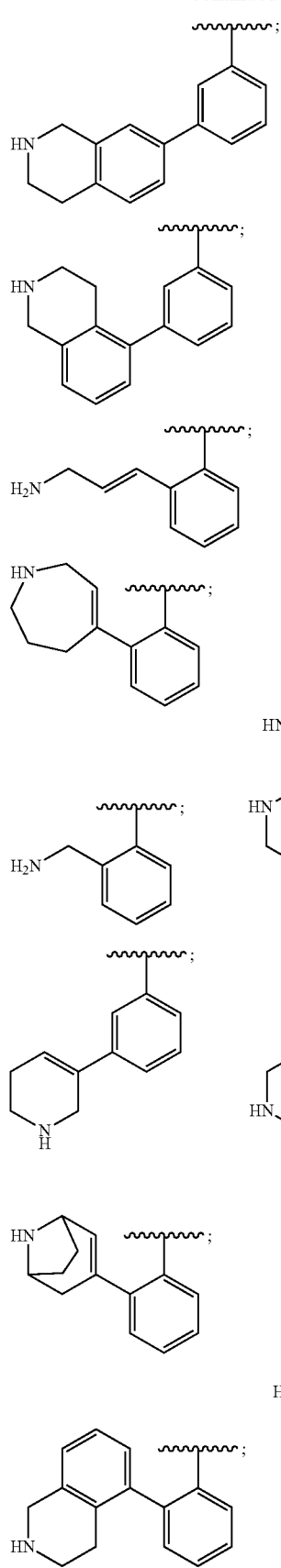
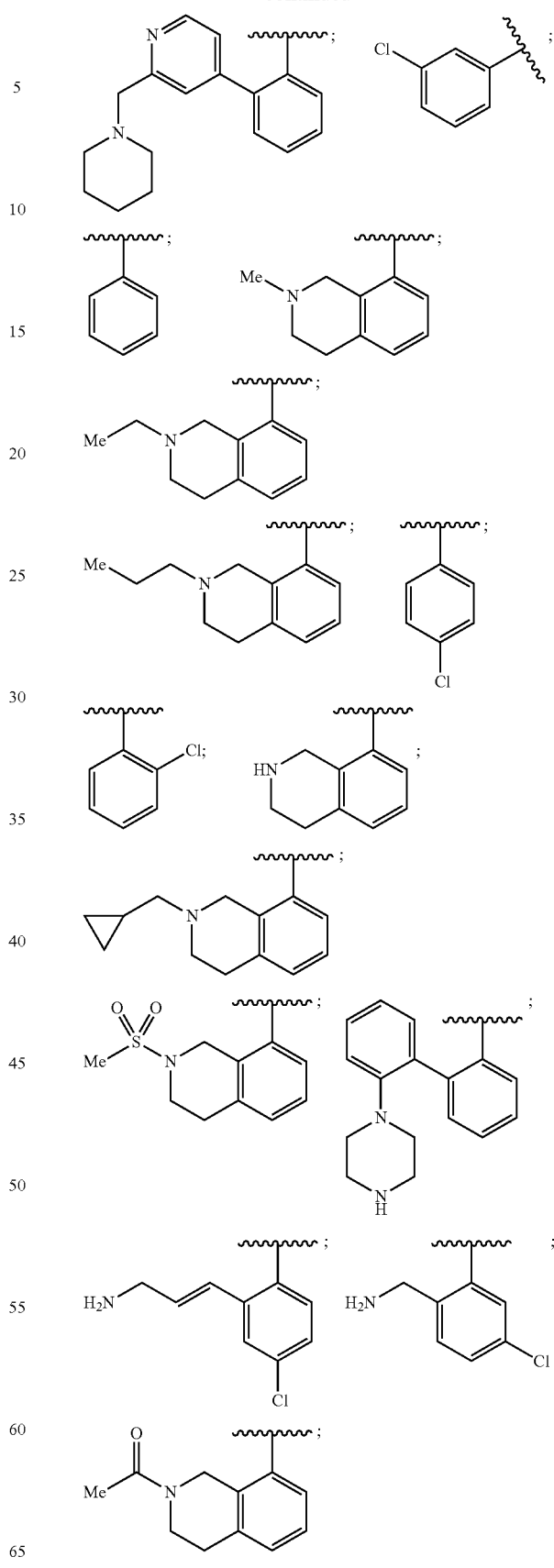

10. A compound of Formula CIIIa:

Formula CIIIa or a salt thereof,
wherein R¹⁰ is:

11. A compound of Formula CIIIb:

Formula CIIIb or a salt thereof,
wherein R¹⁰ᵃ is:

12. The following compounds
[2-Oxo-3-(1,2,3,4-tetrahydroisoquinolin-8-ylmethyl)-N-(1,2,4-thiadiazol-5-yl)-2,3-dihydro-1,3-benzoxazole-6-sulfonamide;
3-[2-(aminomethyl)benzyl]-2-oxo-N-1,2,4-thiadiazol-5-yl-2,3-dihydro-1,3-benzoxazole-6-sulfonamide;
2-oxo-3-[2-(1,2,3,4-tetrahydroisoquinolin-8-yl)benzyl]-N-1,2,4-thiadiazol-5-yl-2,3-dihydro-1,3-benzoxazole-6-sulfonamide;
2-oxo-3-[2-(2,5,6,7-tetrahydro-1H-azepin-4-yl)benzyl]-N-1,2,4-thiadiazol-5-yl-2,3-dihydro-1,3-benzoxazole-6-sulfonamide;
2-oxo-3-[2-(1,2,5,6-tetrahydropyridin-3-yl)benzyl]-N-1,2,4-thiadiazol-5-yl-2,3-dihydro-1,3-benzoxazole-6-sulfonamide;
3-[2-(8-azabicyclo[3.2.1]oct-2-en-3-yl)benzyl]-2-oxo-N-1,2,4-thiadiazol-5-yl-2,3-dihydro-1,3-benzoxazole-6-sulfonamide;
2-oxo-3-[2-(1,2,3,4-tetrahydroisoquinolin-5-yl)benzyl]-N-1,2,4-thiadiazol-5-yl-2,3-dihydro-1,3-benzoxazole-6-sulfonamide;
2-oxo-3-[3-(1,2,3,4-tetrahydroisoquinolin-7-yl)benzyl]-N-1,2,4-thiadiazol-5-yl-2,3-dihydro-1,3-benzoxazole-6-sulfonamide;
2-Oxo-3-[(1R)-1-(1,2,3,4-tetrahydroisoquinolin-8-yl)ethyl]-N-(1,2,4-thiadiazazol-5-yl)-2,3-dihydro-1,3-benzoxazole-6-sulfonamide;
2-oxo-3-[(1R)-1-phenylethyl]-N-1,2,4-thiadiazol-5-yl-2,3-dihydro-1,3-benzoxazole-6-sulfonamide;
2-oxo-3-(1-phenylbut-3-en-1-yl)-N-1,2,4-thiadiazol-5-yl-2,3-dihydro-1,3-benzoxazole-6-sulfonamide;
2-oxo-3-[1-(1,2,3,4-tetrahydroisoquinolin-8-yl)ethyl]-N-1,2,4-thiadiazol-5-yl-2,3-dihydro-1,3-benzoxazole-6-sulfonamide;
2-oxo-3-[(1S)-1-(1,2,3,4-tetrahydroisoquinolin-8-yl)ethyl]-N-1,2,4-thiadiazol-5-yl-2,3-dihydro-1,3-benzoxazole-6-sulfonamide;
3-{[2-(Methylsulfonyl)-1,2,3,4-tetrahydroisoquinolin-8-yl]methyl}-2-oxo-N-(1,2,4-thiadiazol-5-yl)-2,3-dihydro-1,3-benzoxazole-6-sulfonamide;
5-Fluoro-2-oxo-3-(1,2,3,4-tetrahydroisoquinolin-8-ylmethyl)-N-(1,2,4-thiadiazol-5-yl)-2,3-dihydro-1,3-benzoxazole-6-sulfonamide;
3-{2-[(1E)-3-Aminoprop-1-en-1-yl]benzyl}-5-fluoro-2-oxo-N-(1,2,4-thiadiazol-5-yl)-2,3-dihydro-1,3-benzoxazole-6-sulfonamide;

5-Fluoro-2-oxo-3-[(1R)-1-(1,2,3,4-tetrahydroisoquinolin-8-yl)ethyl]-N-(1,2,4-thiadiazol-5-yl)-2,3-dihydro-1,3-benzoxazole-6-sulfonamide;
5-fluoro-2-oxo-3-[(1R)-1-phenylethyl]-N-1,2,4-thiadiazol-5-yl-2,3-dihydro-1,3-benzoxazole-6-sulfonamide;
3-[cyclopropyl(phenyl)methyl]-5-fluoro-2-oxo-N-1,2,4-thiadiazol-5-yl-2,3-dihydro-1,3-benzoxazole-6-sulfonamide; or
5-fluoro-2-oxo-3-[(1S)-1-(1,2,3,4-tetrahydroisoquinolin-8-yl)ethyl]-N-1,2,4-thiadiazol-5-yl-2,3-dihydro-1,3-benzoxazole-6-sulfonamide,
or a pharmaceutically acceptable salt of any thereof.

13. The following compounds, or a pharmaceutically acceptable salt of any thereof:

[2-Oxo-3-(1,2,3,4-tetrahydroisoquinolin-8-ylmethyl)-N-(1,2,4-thiadiazol-5-yl)-2,3-dihydro-1,3-benzoxazole-6-sulfonamide;
3-benzyl-2-oxo-N-1,2,4-thiadiazol-5-yl-2,3-dihydro-1,3-benzoxazole-6-sulfonamide;
3-(3-chlorobenzyl)-2-oxo-N-1,2,4-thiadiazol-5-yl-2,3-dihydro-1,3-benzoxazole-6-sulfonamide;
3-(2-chlorobenzyl)-2-oxo-N-1,2,4-thiadiazol-5-yl-2,3-dihydro-1,3-benzoxazole-6-sulfonamide;
3-(4-chlorobenzyl)-2-oxo-N-1,2,4-thiadiazol-5-yl-2,3-dihydro-1,3-benzoxazole-6-sulfonamide;
3-[2-(aminomethyl)benzyl]-2-oxo-N-1,2,4-thiadiazol-5-yl-2,3-dihydro-1,3-benzoxazole-6-sulfonamide;
3-[2-(aminomethyl)-5-chlorobenzyl]-2-oxo-N-1,2,4-thiadiazol-5-yl-2,3-dihydro-1,3-benzoxazole-6-sulfonamide;
2-oxo-3-(1,2,3,4-tetrahydroisoquinolin-5-ylmethyl)-N-1,2,4-thiadiazol-5-yl-2,3-dihydro-1,3-benzoxazole-6-sulfonamide;
3-{2-[(1E)-3-Aminoprop-1-en-1-yl]benzyl}-2-oxo-N-(1,2,4-thiadiazol-5-yl)-2,3-dihydro-1,3-benzoxazole-6-sulfonamide;
2-oxo-3-[2-(1,2,3,4-tetrahydroisoquinolin-8-yl)benzyl]-N-1,2,4-thiadiazol-5-yl-2,3-dihydro-1,3-benzoxazole-6-sulfonamide;
2-oxo-3-[2-(2,5,6,7-tetrahydro-1H-azepin-4-yl)benzyl]-N-1,2,4-thiadiazol-5-yl-2,3-dihydro-1,3-benzoxazole-6-sulfonamide;
2-oxo-3-[2-(1,2,5,6-tetrahydropyridin-3-yl)benzyl]-N-1,2,4-thiadiazol-5-yl-2,3-dihydro-1,3-benzoxazole-6-sulfonamide;
3-[2-(8-azabicyclo[3.2.1]oct-2-en-3-yl)benzyl]-2-oxo-N-1,2,4-thiadiazol-5-yl-2,3-dihydro-1,3-benzoxazole-6-sulfonamide;
2-oxo-3-[2-(1,2,3,4-tetrahydroisoquinolin-5-yl)benzyl]-N-1,2,4-thiadiazol-5-yl-2,3-dihydro-1,3-benzoxazole-6-sulfonamide;
2-oxo-3-[(2'-piperazin-1-ylbiphenyl-2-yl)methyl]-N-1,2,4-thiadiazol-5-yl-2,3-dihydro-1,3-benzoxazole-6-sulfonamide;
2-oxo-3-{2-[2-(piperidin-1-ylmethyl)pyridin-4-yl]benzyl}-N-1,2,4-thiadiazol-5-yl-2,3-dihydro-1,3-benzoxazole-6-sulfonamide;
3-{2-[(1E)-3-aminoprop-1-en-1-yl]-4-chlorobenzyl}-2-oxo-N-1,2,4-thiadiazol-5-yl-2,3-dihydro-1,3-benzoxazole-6-sulfonamide;
2-oxo-3-[3-(1,2,3,4-tetrahydroisoquinolin-7-yl)benzyl]-N-1,2,4-thiadiazol-5-yl-2,3-dihydro-1,3-benzoxazole-6-sulfonamide;
2-oxo-3-[3-(1,2,3,4-tetrahydroisoquinolin-8-yl)benzyl]-N-1,2,4-thiadiazol-5-yl-2,3-dihydro-1,3-benzoxazole-6-sulfonamide;
2-oxo-3-[3-(1,2,3,4-tetrahydroisoquinolin-5-yl)benzyl]-N-1,2,4-thiadiazol-5-yl-2,3-dihydro-1,3-benzoxazole-6-sulfonamide;
2-oxo-3-[3-(1,2,5,6-tetrahydropyridin-3-yl)benzyl]-N-1,2,4-thiadiazol-5-yl-2,3-dihydro-1,3-benzoxazole-6-sulfonamide;
2-oxo-3-[3-(1,2,3,6-tetrahydropyridin-4-yl)benzyl]-N-1,2,4-thiadiazol-5-yl-2,3-dihydro-1,3-benzoxazole-6-sulfonamide;
2-oxo-3-[3-(2,5,6,7-tetrahydro-1H-azepin-4-yl)benzyl]-N-1,2,4-thiadiazol-5-yl-2,3-dihydro-1,3-benzoxazole-6-sulfonamide;
3-[3-(8-azabicyclo[3.2.1]oct-2-en-3-yl)benzyl]-2-oxo-N-1,2,4-thiadiazol-5-yl-2,3-dihydro-1,3-benzoxazole-6-sulfonamide;
2-Oxo-3-[(1R)-1-(1,2,3,4-tetrahydroisoquinolin-8-yl)ethyl]-N-(1,2,4-thiadiazol-5-yl)-2,3-dihydro-1,3-benzoxazole-6-sulfonamide;
2-oxo-3-(1-phenylethyl)-N-1,2,4-thiadiazol-5-yl-2,3-dihydro-1,3-benzoxazole-6-sulfonamide;
2-oxo-3-[(1R)-1-phenylethyl]-N-1,2,4-thiadiazol-5-yl-2,3-dihydro-1,3-benzoxazole-6-sulfonamide;
2-oxo-3-[(1S)-1-phenylethyl]-N-1,2,4-thiadiazol-5-yl-2,3-dihydro-1,3-benzoxazole-6-sulfonamide;
2-oxo-N-1,2,4-thiadiazol-5-yl-3-{1-[2-(trifluoromethyl)phenyl]ethyl}-2,3-dihydro-1,3-benzoxazole-6-sulfonamide;
3-[1,3-oxazol-2-yl(phenyl)methyl]-2-oxo-N-1,2,4-thiadiazol-5-yl-2,3-dihydro-1,3-benzoxazole-6-sulfonamide;
3-(1-methyl-3-phenylpropyl)-2-oxo-N-1,2,4-thiadiazol-5-yl-2,3-dihydro-1,3-benzoxazole-6-sulfonamide;
3-[cyclopropyl(phenyl)methyl]-2-oxo-N-1,2,4-thiadiazol-5-yl-2,3-dihydro-1,3-benzoxazole-6-sulfonamide;
2-oxo-3-(1-phenylbut-3-en-1-yl)-N-1,2,4-thiadiazol-5-yl-2,3-dihydro-1,3-benzoxazole-6-sulfonamide;
2-oxo-3-[1-(1,2,3,4-tetrahydroisoquinolin-8-yl)ethyl]-N-1,2,4-thiadiazol-5-yl-2,3-dihydro-1,3-benzoxazole-6-sulfonamide;
2-oxo-3-[(1S)-1-(1,2,3,4-tetrahydroisoquinolin-8-yl)ethyl]-N-1,2,4-thiadiazol-5-yl-2,3-dihydro-1,3-benzoxazole-6-sulfonamide;
3-[(2-Methyl-1,2,3,4-tetrahydroisoquinolin-8-yl)methyl]-2-oxo-N-(1,2,4-thiadiazol-5-yl)-2,3-dihydro-1,3-benzoxazole-6-sulfonamide;
3-[(2-ethyl-1,2,3,4-tetrahydroisoquinolin-8-yl)methyl]-2-oxo-N-1,2,4-thiadiazol-5-yl-2,3-dihydro-1,3-benzoxazole-6-sulfonamide;
2-oxo-3-[(2-propyl-1,2,3,4-tetrahydroisoquinolin-8-yl)methyl]-N-1,2,4-thiadiazol-5-yl-2,3-dihydro-1,3-benzoxazole-6-sulfonamide;
3-{[2-(cyclopropylmethyl)-1,2,3,4-tetrahydroisoquinolin-8-yl]methyl}-2-oxo-N-1,2,4-thiadiazol-5-yl-2,3-dihydro-1,3-benzoxazole-6-sulfonamide;
3-{[2-(Methylsulfonyl)-1,2,3,4-tetrahydroisoquinolin-8-yl]methyl}-2-oxo-N-(1,2,4-thiadiazol-5-yl)-2,3-dihydro-1,3-benzoxazole-6-sulfonamide;
3-[(2-Acetyl-1,2,3,4-tetrahydroisoquinolin-8-yl)methyl]-2-oxo-N-(1,2,4-thiadiazol-5-yl)-2,3-dihydro-1,3-benzoxazole-6-sulfonamide;
3-{[2-(Cyclopropylcarbonyl)-1,2,3,4-tetrahydroisoquinolin-8-yl]methyl}-2-oxo-N-1,2,4-thiadiazol-5-yl-2,3-dihydro-1,3-benzoxazole-6-sulfonamide;
5-Fluoro-2-oxo-3-(1,2,3,4-tetrahydroisoquinolin-8-ylmethyl)-N-(1,2,4-thiadiazol-5-yl)-2,3-dihydro-1,3-benzoxazole-6-sulfonamide;

3-benzyl-5-fluoro-2-oxo-N-1,2,4-thiadiazol-5-yl-2,3-dihydro-1,3-benzoxazole-6-sulfonamide;

3-{2-[(1E)-3-Aminoprop-1-en-1-yl]benzyl}-5-fluoro-2-oxo-N-(1,2,4-thiadiazol-5-yl)-2,3-dihydro-1,3-benzoxazole-6-sulfonamide;

5-Fluoro-2-oxo-3-[(1R)-1-(1,2,3,4-tetrahydroisoquinolin-8-yl)ethyl]-N-(1,2,4-thiadiazol-5-yl)-2,3-dihydro-1,3-benzoxazole-6-sulfonamide;

5-fluoro-2-oxo-3-[(1R)-1-phenylethyl]-N-1,2,4-thiadiazol-5-yl-2,3-dihydro-1,3-benzoxazole-6-sulfonamide;

5-fluoro-2-oxo-3-[(1S)-1-phenylethyl]-N-1,2,4-thiadiazol-5-yl-2,3-dihydro-1,3-benzoxazole-6-sulfonamide;

3-[cyclopropyl(phenyl)methyl]-5-fluoro-2-oxo-N-1,2,4-thiadiazol-5-yl-2,3-dihydro-1,3-benzoxazole-6-sulfonamide; or 5-fluoro-2-oxo-3-[(1S)-1-(1,2,3,4-tetrahydroisoquinolin-8-yl)ethyl]-N-1,2,4-thiadiazol-5-yl-2,3-dihydro-1,3-benzoxazole-6-sulfonamide.

14. The following compounds, or a pharmaceutically acceptable salt of any thereof:

3-(isoquinolin-8-ylmethyl)-2-oxo-N-1,2,4-thiadiazol-5-yl-2,3-dihydro-1,3-benzoxazole-6-sulfonamide;

3-(2,3-dihydro-1H-isoindol-4-ylmethyl)-2-oxo-N-1,2,4-thiadiazol-5-yl-2,3-dihydro-1,3-benzoxazole-6-sulfonamide;

3-(diphenylmethyl)-2-oxo-N-1,2,4-thiadiazol-5-yl-2,3-dihydro-1,3-benzoxazole-6-sulfonamide;

2-oxo-3-(1-phenylpropyl)-N-1,2,4-thiadiazol-5-yl-2,3-dihydro-1,3-benzoxazole-6-sulfonamide;

3-benzyl-5-fluoro-2-oxo-N-1,2,4-thiadiazol-5-yl-2,3-dihydro-1,3-benzoxazole-6-sulfonamide;

5-fluoro-3-{[(1R,2S)-2-iodocyclopropyl]methyl}-2-oxo-N-1,2,4-thiadiazol-5-yl-2,3-dihydro-1,3-benzoxazole-6-sulfonamide;

5-fluoro-2-oxo-3-[(2-phenylcyclopropyl)methyl]-N-1,2,4-thiadiazol-5-yl-2,3-dihydro-1,3-benzoxazole-6-sulfonamide;

5-fluoro-3-[(2-methyl-2H-indazol-7-yl)methyl]-2-oxo-N-1,2,4-thiadiazol-5-yl-2,3-dihydro-1,3-benzoxazole-6-sulfonamide;

5-fluoro-3-(imidazo[1,5-a]pyridine-5-ylmethyl)-2-oxo-N-1,2,4-thiadiazol-5-yl-2,3-dihydro-1,3-benzoxazole-6-sulfonamide;

3-(1a,7b-dihydro-1H-cyclopropa[a]naphthalen-7-ylmethyl)-5-fluoro-2-oxo-N-1,2,4-thiadiazol-5-yl-2,3-dihydro-1,3-benzoxazole-6-sulfonamide;

(R)-3-(1-(isoquinolin-8-yl)ethyl)-2-oxo-N-(1,2,4-thiadiazol-5-yl)-2,3-dihydrobenzo[d]oxazole-6-sulfonamide;

5-fluoro-3-[(1R)-1-isoquinolin-8-ylethyl]-2-oxo-N-1,2,4-thiadiazol-5-yl-2,3-dihydro-1,3-benzoxazole-6-sulfonamid;

3-[(1S)-1-isoquinolin-8-ylethyl]-2-oxo-N-1,2,4-thiadiazol-5-yl-2,3-dihydro-1,3-benzoxazole-6-sulfonamide;

5-fluoro-3-[(1S)-1-isoquinolin-8-ylethyl]-2-oxo-N-1,2,4-thiadiazol-5-yl-2,3-dihydro-1,3-benzoxazole-6-sulfonamide;

(R)-5-Fluoro-3-(1-(imidazo[1,5-a]pyridine-5-yl)ethyl)-2-oxo-N-(1,2,4-thiadiazol-5-yl)-2,3-dihydrobenzo[d]oxazole-6-sulfonamide;

5-fluoro-3-[(1S)-1-imidazo[1,5-a]pyridine-5-ylethyl]-2-oxo-N-1,2,4-thiadiazol-5-yl-2,3-dihydro-1,3-benzoxazole-6-sulfonamide;

(R)-5-Fluoro-3-(1-(2-iodophenyl)ethyl)-2-oxo-N-(1,2,4-thiadiazol-5-yl)-2,3-dihydrobenzo[d]oxazole-6-sulfonamide;

(R)-5-Fluoro-2-oxo-3-(1-(2-(1,2,3,6-tetrahydropyridin-4-yl)phenyl)ethyl)-N-(1,2,4-thiadiazol-5-yl)-2,3-dihydrobenzo[d]oxazole-6-sulfonamide;

5-fluoro-2-oxo-3-{(1R)-1-[2-(1,2,5,6-tetrahydropyridin-3-yl)phenyl]ethyl}-N-1,2,4-thiadiazol-5-yl-2,3-dihydro-1,3-benzoxazole-6-sulfonamide;

5-fluoro-2-oxo-3-{(1R)-1-[2-(2,5,6,7-tetrahydro-1H-azepin-4-yl)phenyl]ethyl}-N-1,2,4-thiadiazol-5-yl-2,3-dihydro-1,3-benzoxazole-6-sulfonamide;

(R)-3-(1-(2-((1-aminocyclopropyl)ethynyl)phenyl)ethyl)-5-fluoro-2-oxo-N-(1,2,4-thiadiazol-5-yl)-2,3-dihydrobenzo[d]oxazole-6-sulfonamide;

5-fluoro-3-{(1R)-1-[2-(3-morpholin-4-ylprop-1-yn-1-yl)phenyl]ethyl}-2-oxo-N-1,2,4-thiadiazol-5-yl-2,3-dihydro-1,3-benzoxazole-6-sulfonamide;

5-fluoro-3-[(1R)-1-{2-[(1-hydroxycyclopentyl)ethynyl]phenyl}ethyl]-2-oxo-N-1,2,4-thiadiazol-5-yl-2,3-dihydro-1,3-benzoxazole-6-sulfonamide;

5-fluoro-3-{(1R)-1-[2-(4-hydroxybut-1-yn-1-yl)phenyl]ethyl}-2-oxo-N-1,2,4-thiadiazol-5-yl-2,3-dihydro-1,3-benzoxazole-6-sulfonamide;

3-[(1R)-1-{2-[3-(1,1-dioxidothiomorpholin-4-yl)prop-1-yn-1-yl]phenyl}ethyl]-5-fluoro-2-oxo-N-1,2,4-thiadiazol-5-yl-2,3-dihydro-1,3-benzoxazole-6-sulfonamide;

3-{(1R)-1-[2-(3-ethyl-3-hydroxypent-1-yn-1-yl)phenyl]ethyl}-5-fluoro-2-oxo-N-1,2,4-thiadiazol-5-yl-2,3-dihydro-1,3-benzoxazole-6-sulfonamide;

5-fluoro-3-[(1R)-1-{2-[(3R)-3-hydroxybut-1-yn-1-yl]phenyl}ethyl]-2-oxo-N-1,2,4-thiadiazol-5-yl-2,3-dihydro-1,3-benzoxazole-6-sulfonamide;

5-fluoro-3-[(1R)-1-{2-[(1-methyl-1H-imidazol-5-yl)ethynyl]phenyl}ethyl]-2-oxo-N-1,2,4-thiadiazol-5-yl-2,3-dihydro-1,3-benzoxazole-6-sulfonamide;

5-fluoro-3-{(1R)-1-[2-(3-hydroxyprop-1-yn-1-yl)phenyl]ethyl}-2-oxo-N-1,2,4-thiadiazol-5-yl-2,3-dihydro-1,3-benzoxazole-6-sulfonamide;

3-{(1R)-1-[2-(3-amino-3-methylbut-1-yn-1-yl)phenyl]ethyl}-5-fluoro-2-oxo-N-1,2,4-thiadiazol-5-yl-2,3-dihydro-1,3-benzoxazole-6-sulfonamide;

5-fluoro-3-[(1R)-1-{2-[3-(methylamino)prop-1-yn-1-yl]phenyl}ethyl]-2-oxo-N-1,2,4-thiadiazol-5-yl-2,3-dihydro-1,3-benzoxazole-6-sulfonamide;

5-fluoro-3-[(1R)-1-{2-[(3S)-3-hydroxybut-1-yn-1-yl]phenyl}ethyl]-2-oxo-N-1,2,4-thiadiazol-5-yl-2,3-dihydro-1,3-benzoxazole-6-sulfonamide;

5-fluoro-2-oxo-3-{(1R)-1-[2-(3-pyrrolidin-2-ylprop-1-yn-1-yl)phenyl]ethyl}-N-1,2,4-thiadiazol-5-yl-2,3-dihydro-1,3-benzoxazole-6-sulfonamide;

5-fluoro-2-oxo-3-({(1R)-1-[2-(pyrrolidin-3-ylethynyl)phenyl]ethyl}-N-1,2,4-thiadiazol-5-yl-2,3-dihydro-1,3-benzoxazole-6-sulfonamide;

3-{(1R)-1-[2-(4-amino-4-methylpent-1-yn-1-yl)phenyl]ethyl}-5-fluoro-2-oxo-N-1,2,4-thiadiazol-5-yl-2,3-dihydro-1,3-benzoxazole-6-sulfonamide;

3-{(1R)-1-[2-(azetidin-3-ylethynyl)phenyl]ethyl}-5-fluoro-2-oxo-N-1,2,4-thiadiazol-5-yl-2,3-dihydro-1,3-benzoxazole-6-sulfonamide;

5-fluoro-2-oxo-3-[(1R)-1-{2-[(2S)-pyrrolidin-2-ylethynyl]phenyl}ethyl]-N-1,2,4-thiadiazol-5-yl-2,3-dihydro-1,3-benzoxazole-6-sulfonamide;

3-{(1R)-1-[2-(3-azetidin-1-ylprop-1-yn-1-yl)phenyl]ethyl}-5-fluoro-2-oxo-N-1,2,4-thiadiazol-5-yl-2,3-dihydro-1,3-benzoxazole-6-sulfonamide;

3-{(1R)-1-[2-(3-aminobut-1-yn-1-yl)phenyl]ethyl}-5-fluoro-2-oxo-N-1,2,4-thiadiazol-5-yl-2,3-dihydro-1,3-benzoxazole-6-sulfonamide;

3-{(1R)-1-[2-(3-aminoprop-1-yn-1-yl)phenyl]ethyl}-5-fluoro-2-oxo-N-1,2,4-thiadiazol-5-yl-2,3-dihydro-1,3-benzoxazole-6-sulfonamide;

5-fluoro-2-oxo-3-[(1R)-1-{2-[(2R)-pyrrolidin-2-ylethynyl]phenyl}ethyl]-N-1,2,4-thiadiazol-5-yl-2,3-dihydro-1,3-benzoxazole-6-sulfonamide;

5-fluoro-2-oxo-3-{(1R)-1-[2-(piperidin-2-ylethynyl)phenyl]ethyl}-N-1,2,4-thiadiazol-5-yl-2,3-dihydro-1,3-benzoxazole-6-sulfonamide;

3-[(1R)-1-{2-[(1-aminocyclohexyl)ethynyl]phenyl}ethyl]-5-fluoro-2-oxo-N-1,2,4-thiadiazol-5-yl-2,3-dihydro-1,3-benzoxazole-6-sulfonamide;

(R)-5-fluoro-2-oxo-3-(1-(2-(pyrrolidin-1-ylmethyl)phenyl)ethyl)-N-(1,2,4-thiadiazol-5-yl)-2,3-dihydrobenzo[d]oxazole-6-sulfonamide;

3-[(1R)-1-{2-[(3,3-difluoropyrrolidin-1-yl)methyl]phenyl}ethyl]-5-fluoro-2-oxo-N-1,2,4-thiadiazol-5-yl-2,3-dihydro-1,3-benzoxazole-6-sulfonamide;

5-fluoro-3-[(1R)-1-{2-[(3-fluoropyrrolidin-1-yl)methyl]phenyl}ethyl]-2-oxo-N-1,2,4-thiadiazol-5-yl-2,3-dihydro-1,3-benzoxazole-6-sulfonamide;

3-[(1R)-1-{2-[(dimethylamino)methyl]phenyl}ethyl]-5-fluoro-2-oxo-N-1,2,4-thiadiazol-5-yl-2,3-dihydro-1,3-benzoxazole-6-sulfonamide;

3-((7-(3,3-difluoroazetidin-1-yl)-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide hydrochloride;

3-((7-amino-5,6,7,8-tetrahydronaphthalen-1-yl)methyl)-5-fluoro-2-oxo-N-(1,2,4-thiadiazol-5-yl)-2,3-dihydrobenzo[d]oxazole-6-sulfonamide;

5-fluoro-3-((7-hydroxy-5,6,7,8-tetrahydronaphthalen-1-yl)methyl)-2-oxo-N-(1,2,4-thiadiazol-5-yl)-2,3-dihydrobenzo[d]oxazole-6-sulfonamide;

N-(8-((6-(N-(1,2,4-thiadiazol-5-yl)sulfamoyl)-5-fluoro-2-oxobenzo[d]oxazol-3(2H)-yl)methyl)-1,2,3,4-tetrahydronaphthalen-2-yl)acetamide;

(8-((6-(N-(1,2,4-thiadiazol-5-yl)sufamoyl)-5-fluoro-2-oxobenzo[d]oxazol-3 (2H)-yl)methyl)-1,2,3,4-tetrahydronaphthalen-2-yl)carbamate;

(+/−)-3-[1-(3',4'-dihydro-1'H-spiro[1,3-dioxolane-2,2'-naphthalen]-8'-yl)ethyl]-N-(2,4-dimethoxybenzyl)-5-fluoro-2-oxo-N-1,2,4-thiadiazol-5-yl-2,3-dihydro-1,3-benzoxazole-6-sulfonamide;

(+/−)-3-[(6-amino-5,6,7,8-tetrahydronaphthalen-1-yl)methyl]-2-oxo-N-1,2,4-thiadiazol-5-yl-2,3-dihydro-1,3-benzoxazole-6-sulfonamide;

(S)-2-[(8-{[5-fluoro-2-oxo-6-(1,2,4-thiadiazol-5-ylsulfamoyl)-1,3-benzoxazol-3(2H)-yl]methyl}-1,2,3,4-tetrahydronaphthalen-2-yl)amino]-2-oxoethyl acetate;

(R)-2-[(8-{[5-fluoro-2-oxo-6-(1,2,4-thiadiazol-5-ylsulfamoyl)-1,3-benzoxazol-3(2H)-yl]methyl}-1,2,3,4-tetrahydronaphthalen-2-yl)amino]-2-oxoethyl acetate;

(+/−)-3-{[7-(3,3-difluoropyrrolidin-1-yl)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide;

(S)-3-{[7-(1,1-dioxidothiomorpholin-4-yl)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide;

(R)-3-{[7-(1,1-dioxidothiomorpholin-4-yl)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide;

(+/−)-5-fluoro-2-oxo-N-1,2,4-thiadiazol-5-yl-3-({7-[(2,2,2-trifluoroethyl)amino]-5,6,7,8-tetrahydronaphthalen-1-yl}methyl)-2,3-dihydro-1,3-benzoxazole-6-sulfonamide;

(+/−)-3-[(6-amino-5,6,7,8-tetrahydronaphthalen-1-yl)methyl]-5-fluoro-2-oxo-N-1,2,4-thiadiazol-5-yl-2,3-dihydro-1,3-benzoxazole-6-sulfonamide;

(+/−)-3-[(2-amino-2,3-dihydro-1H-inden-4-yl)methyl]-2-oxo-N-1,2,4-thiadiazol-5-yl-2,3-dihydro-1,3-benzoxazole-6-sulfonamide;

(S)-3-[(7-amino-5,6,7,8-tetrahydronaphthalen-1-yl)methyl]-2-oxo-N-1,2,4-thiadiazol-5-yl-2,3-dihydro-1,3-benzoxazole-6-sulfonamide;

(S)-3-[(7-amino-5,6,7,8-tetrahydronaphthalen-1-yl)methyl]-2-oxo-N-1,2,4-thiadiazol-5-yl-2,3-dihydro-1,3-benzoxazole-6-sulfonamide;

(+/−)-5-fluoro-2-oxo-N-1,2,4-thiadiazol-5-yl-3-({7-[2-(trifluoromethyl)pyrrolidin-1-yl]-5,6,7,8-tetrahydronaphthalen-1-yl}methyl)-2,3-dihydro-1,3-benzoxazole-6-sulfonamide;

(+/−)-3-{1-[7-(3,3-difluoroazetidin-1-yl)-5,6,7,8-tetrahydronaphthalen-1-yl]ethyl}-5-fluoro-2-oxo-N-1,2,4-thiadiazol-5-yl-2,3-dihydro-1,3-benzoxazole-6-sulfonamide;

(+/−)-3-({7-[(2,2-difluoroethyl)amino]-5,6,7,8-tetrahydronaphthalen-1-yl}methyl)-5-fluoro-2-oxo-N-1,2,4-thiadiazol-5-yl-2,3-dihydro-1,3-benzoxazole-6-sulfonamide;

(S or R)-3-[(7-amino-5,6,7,8-tetrahydronaphthalen-1-yl)methyl]-2-oxo-N-1,2,4-thiadiazol-5-yl-2,3-dihydro-1,3-benzoxazole-6-sulfonamide;

(+/−)-3-{[7-(dimethylamino)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide;

(+/−)-5-fluoro-3-[(7-morpholin-4-yl-5,6,7,8-tetrahydronaphthalen-1-yl)methyl]-2-oxo-N-1,2,4-thiadiazol-5-yl-2,3-dihydro-1,3-benzoxazole-6-sulfonamide;

(+/−)-3-[(2-amino-2,3-dihydro-1H-inden-4-yl)methyl]-5-fluoro-2-oxo-N-1,2,4-thiadiazol-5-yl-2,3-dihydro-1,3-benzoxazole-6-sulfonamide;

(+/−)-3-{[7-(methylamino)-5,6,7,8-tetrahydronaphthalen-1-yl]methyl}-2-oxo-N-1,2,4-thiadiazol-5-yl-2,3-dihydro-1,3-benzoxazole-6-sulfonamide;

(+/−)-3-[(7-azetidin-1-yl-5,6,7,8-tetrahydronaphthalen-1-yl)methyl]-5-fluoro-2-oxo-N-1,2,4-thiadiazol-5-yl-2,3-dihydro-1,3-benzoxazole-6-sulfonamide;

(+/−)-5-fluoro-2-oxo-3-[(7-pyrrolidin-1-yl-5,6,7,8-tetrahydronaphthalen-1-yl)methyl]-N-1,2,4-thiadiazol-5-yl-2,3-dihydro-1,3-benzoxazole-6-sulfonamide;

(+/−)-5-fluoro-3-({7-[(2-fluoroethyl)amino]-5,6,7,8-tetrahydronaphthalen-1-yl}methyl)-2-oxo-N-1,2,4-thiadiazol-5-yl-2,3-dihydro-1,3-benzoxazole-6-sulfonamide;

(+/−)-5-fluoro-3-({7-[(2-hydroxyethyl)amino]-5,6,7,8-tetrahydronaphthalen-1-yl}methyl)-2-oxo-N-1,2,4-thiadiazol-5-yl-2,3-dihydro-1,3-benzoxazole-6-sulfonamide;

(+/−)-3-{[7-(benzylamino)-5,6,7,8-tetrahydronaphthalen-1-yl]methyl}-5-fluoro-2-oxo-N-1,2,4-thiadiazol-5-yl-2,3-dihydro-1,3-benzoxazole-6-sulfonamide;

(R,R and S,R) or (R,S and S,S)-3-[1-(7-amino-5,6,7,8-tetrahydronaphthalen-1-yl)ethyl]-5-fluoro-2-oxo-N-1,2,4-thiadiazol-5-yl-2,3-dihydro-1,3-benzoxazole-6-sulfonamide;

(R or S)-3-[(1R)-1-(7-amino-5,6,7,8-tetrahydronaphthalen-1-yl)ethyl]-5-fluoro-2-oxo-N-1,2,4-thiadiazol-5-yl-2,3-dihydro-1,3-benzoxazole-6-sulfonamide;

(+/−)-5-fluoro-3-{[7-(methylamino)-5,6,7,8-tetrahydronaphthalen-1-yl]methyl}-2-oxo-N-1,2,4-thiadiazol-5-yl-2,3-dihydro-1,3-benzoxazole-6-sulfonamide;
(S or R)-3-[(7-amino-5,6,7,8-tetrahydronaphthalen-1-yl)methyl]-5-fluoro-2-oxo-N-1,2,4-thiadiazol-5-yl-2,3-dihydro-1,3-benzoxazole-6-sulfonamide;
5-fluoro-3-((4-fluoro-1,2,3,4-tetrahydroisoquinolin-8-yl)methyl)-2-oxo-N-(1,2,4-thiadiazol-5-yl)-2,3-dihydrobenzo[d]oxazole-6-sulfonamide hydrochloride;
3-((3-chloroisoquinolin-8-yl)methyl)-5-fluoro-2-oxo-N-(1,2,4-thiadiazol-5-yl)-2,3-dihydrobenzo[d]oxazole-6-sulfonamide;
3-((3-Aminoisoquinolin-5-yl)methyl)-5-fluoro-2-oxo-N-(1,2,4-thiadiazol-5-yl)-2,3-dihydrobenzo[d]oxazole-6-sulfonamide;
3-((3-aminoisoquinolin-8-yl)methyl)-5-fluoro-2-oxo-N-(1,2,4-thiadiazol-5-yl)-2,3-dihydrobenzo[d]oxazole-6-sulfonamide;
3-[(3-aminoisoquinolin-5-yl)methyl]-2-oxo-N-1,2,4-thiadiazol-5-yl-2,3-dihydro-1,3-benzoxazole-6-sulfonamide;
3-[(3-chloroisoquinolin-8-yl)methyl]-2-oxo-N-1,2,4-thiadiazol-5-yl-2,3-dihydro-1,3-benzoxazole;
(R)-3-(1-(3-(1-methyl-1H-pyrazol-3-yl)phenyl)ethyl)-2-oxo-N-(1,2,4-thiadiazol-5-yl)-2,3-dihydrobenzo[d]oxazole-6-sulfonamide;
5-fluoro-3-{(1R)-1-[3-(6-hydroxypyridin-3-yl)phenyl]ethyl}-2-oxo-N-1,2,4-thiadiazol-5-yl-2,3-dihydro-1,3-benzoxazole-6-sulfonamide;
5-fluoro-3-{(1R)-1-[3-(3-methyl-1H-pyrazol-4-yl)phenyl]ethyl}-2-oxo-N-1,2,4-thiadiazol-5-yl-2,3-dihydro-1,3-benzoxazole-6-sulfonamide;
5-fluoro-3-(1-{3-[2-(hydroxymethyl)pyridine-4-yl]phenyl}ethyl)-2-oxo-N-1,2,4-thiadiazol-5-yl-2,3-dihydro-1,3-benzoxazole-6-sulfonamide;
5-fluoro-2-oxo-3-[1-(3-pyridin-3-ylphenyl)ethyl]-N-1,2,4-thiadiazol-5-yl-2,3-dihydro-1,3-benzoxazole-6-sulfonamide;
(R)-3-(1-(3-(3-aminoprop-1-yn-1-yl)phenyl)ethyl)-5-fluoro-2-oxo-N-(1,2,4-thiadiazol-5-yl)-2,3-dihydrobenzo[d]oxazole-6-sulfonamide;
3-[(1R)-1-{3-[(1-aminocyclohexyl)ethynyl]phenyl}ethyl]-5-fluoro-2-oxo-N-1,2,4-thiadiazol-5-yl-2,3-dihydro-1,3-benzoxazole-6-sulfonamide;
(R)-3-(1-(2-(azetidin-3-yl)phenyl)ethyl)-5-fluoro-2-oxo-N-(1,2,4-thiadiazol-5-yl)-2,3-dihydrobenzo[d]oxazole-6-sulfonamide;
(R)-5-fluoro-3-(1-(2-(3-hydroxyazetidin-3-yl)phenyl)ethyl)-2-oxo-N-(1,2,4-thiadiazol-5-yl)-2,3-dihydrobenzo[d]oxazole-6-sulfonamide;
(R)-5-Fluoro-3-(1-(2-(3-fluoroazetidin-3-yl)phenyl)ethyl)-2-oxo-N-(1,2,4-thiadiazol-5-yl)-2,3-dihydrobenzo[d]oxazole-6-sulfonamide;
(R)-3-(1-(2-(3-Aminopropyl)phenyl)ethyl)-5-fluoro-2-oxo-N-(1,2,4-thiadiazol-5-yl)-2,3-dihydrobenzo[d]oxazole-6-sulfonamide;
3-{(1S)-1-[2-(3-aminopropyl)phenyl]ethyl}-5-fluoro-2-oxo-N-1,2,4-thiadiazol-5-yl-2,3-dihydro-1,3-benzoxazole-6-sulfonamide;
(R)-5-chloro-2-oxo-3-(1-(2-(1,2,3,6-tetrahydropyridin-4-yl)phenyl)ethyl)-N-(1,2,4-thiadiazol-5-yl)-2,3-dihydrobenzo[d]oxazole-6-sulfonamide hydrochloride;
(+/−)-5-chloro-2-oxo-3-[1-(1,2,3,4-tetrahydroisoquinolin-8-yl)ethyl]-N-1,2,4-thiadiazol-5-yl-2,3-dihydro-1,3-benzoxazole-6-sulfonamide;
3-{(1R)-1-[2-(3-aminoprop-1-yn-1-yl)phenyl]ethyl}-5-chloro-2-oxo-N-1,2,4-thiadiazol-5-yl-2,3-dihydro-1,3-benzoxazole-6-sulfonamide;
(R)-5-bromo-2-oxo-3-(1-(1,2,3,4-tetrahydroisoquinolin-8-yl)ethyl)-N-(1,2,4-thiadiazol-5-yl)-2,3-dihydrobenzo[d]oxazole-6-sulfonamide;
3-{(1R)-1-[2-(3-aminoprop-1-yn-1-yl)phenyl]ethyl}-5-bromo-2-oxo-N-1,2,4-thiadiazol-5-yl-2,3-dihydro-1,3-benzoxazole-6-sulfonamide;
(R)-5-chloro-3-(1-(2-(1-(methylsulfonyl)-1,2,3,6-tetrahydropyridin-4-yl)phenyl)ethyl)-2-oxo-N-(1,2,4-thiadiazol-5-yl)-2,3-dihydrobenzo[d]oxazole-6-sulfonamide;
(+/−)-5-chloro-3-{1-[2-(methylsulfonyl)-1,2,3,4-tetrahydroisoquinolin-8-yl]ethyl}-2-oxo-N-1,2,4-thiadiazol-5-yl-2,3-dihydro-1,3-benzoxazole-6-sulfonamide;
5-fluoro-3-[(1R)-1-{2-[1-(methylsulfonyl)-1,2,3,6-tetrahydropyridin-4-yl]phenyl}ethyl]-2-oxo-N-1,2,4-thiadiazol-5-yl-2,3-dihydro-1,3-benzoxazole-6-sulfonamide;
5-bromo-3-[(1R)-1-(2-{3-[(methylsulfonyl)amino]prop-1-yn-1-yl}phenyl)ethyl]-2-oxo-N-1,2,4-thiadiazol-5-yl-2,3-dihydro-1,3-benzoxazole-6-sulfonamide;
5-fluoro-3-{(1R)-1-[2-(methylsulfonyl)-1,2,3,4-tetrahydroisoquinolin-8-yl]ethyl}-2-oxo-N-1,2,4-thiadiazol-5-yl-2,3-dihydro-1,3-benzoxazole-6-sulfonamide;
5-chloro-3-[(1R)-1-(2-{3-[(methylsulfonyl)amino]prop-1-yn-1-yl}phenyl)ethyl]-2-oxo-N-1,2,4-thiadiazol-5-yl-2,3-dihydro-1,3-benzoxazole-6-sulfonamide;
5-fluoro-3-[(1R)-1-{7-[(methylsulfonyl)amino]-5,6,7,8-tetrahydronaphthalen-1-yl}ethyl]-2-oxo-N-1,2,4-thiadiazol-5-yl-2,3-dihydro-1,3-benzoxazole-6-sulfonamide;
(R)-3-(3-Fluoro-1-phenylpropyl)-2-oxo-N-(1,2,4-thiadiazol-5-yl)-2,3-dihydrobenzo[d]oxazole-6-sulfonamide;
5-ethyl-2-oxo-3-[(1R)-1-phenylethyl]-N-1,2,4-thiadiazol-5-yl-2,3-dihydro-1,3-benzoxazole-6-sulfonamide;
5-methyl-2-oxo-3-[(1R)-1-phenylethyl]-N-1,2,4-thiadiazol-5-yl-2,3-dihydro-1,3-benzoxazole-6-sulfonamide;
3-(7-amino-1,2,3,4-tetrahydronaphthalen-1-yl)-2-oxo-N-(1,2,4-thiadiazol-5-yl)-2,3-dihydrobenzo[d]oxazole-6-sulfonamide;
3-(3,4-dihydrospiro[chromene-2,3'-oxetan]-4-yl)-5-fluoro-2-oxo-N-1,2,4-thiadiazol-5-yl-2,3-dihydro-1,3-benzoxazole-6-sulfonamide;
5-fluoro-3-(5-methyl-1,2,3,4-tetrahydronaphthalen-1-yl)-2-oxo-N-1,2,4-thiadiazol-5-yl-2,3-dihydro-1,3-benzoxazole-6-sulfonamide;
3-(3,4-dihydro-2H-chromen-4-yl)-5-fluoro-2-oxo-N-1,2,4-thiadiazol-5-yl-2,3-dihydro-1,3-benzoxazole-6-sulfonamide;
3-(2,2-dimethyl-3,4-dihydro-2H-chromen-4-yl)-5-fluoro-2-oxo-N-1,2,4-thiadiazol-5-yl-2,3-dihydro-1,3-benzoxazole-6-sulfonamide;
3-(3,4-dihydro-1H-isochromen-4-yl)-5-fluoro-2-oxo-N-1,2,4-thiadiazol-5-yl-2,3-dihydro-1,3-benzoxazole-6-sulfonamide;
5-fluoro-3-[6-fluoro-1'-(phenylcarbonyl)-3,4-dihydrospiro[chromene-2,4'-piperidin]-4-yl]-2-oxo-N-1,2,4-thiadiazol-5-yl-2,3-dihydro-1,3-benzoxazole-6-sulfonamide;
5-fluoro-2-oxo-3-(1,2,3,4-tetrahydronaphthalen-1-yl)-N-1,2,4-thiadiazol-5-yl-2,3-dihydro-1,3-benzoxazole-6-sulfonamide;
3-(1'-benzyl-3,4-dihydrospiro[chromene-2,4'-piperidin]-4-yl)-5-fluoro-2-oxo-N-1,2,4-thiadiazol-5-yl-2,3-dihydro-1,3-benzoxazole-6-sulfonamide;

3-(4,4-dimethyl-1,2,3,4-tetrahydronaphthalen-1-yl)-5-fluoro-2-oxo-N-1,2,4-thiadiazol-5-yl-2,3-dihydro-1,3-benzoxazole-6-sulfonamide;
5-fluoro-3-(6-fluoro-3,4-dihydro-2H-chromen-4-yl)-2-oxo-N-1,2,4-thiadiazol-5-yl-2,3-dihydro-1,3-benzoxazole-6-sulfonamide;
3-[(4R)-3,4-dihydrospiro[chromene-2,1'-cyclobutan]-4-yl]-5-fluoro-2-oxo-N-1,2,4-thiadiazol-5-yl-2,3-dihydro-1,3-benzoxazole-6-sulfonamide;
5-fluoro-2-oxo-3-[(2S,4R)-2-phenyl-3,4-dihydro-2H-chromen-4-yl]-N-1,2,4-thiadiazol-5-yl-2,3-dihydro-1,3-benzoxazole-6-sulfonamide;
3-[(4S)-3,4-dihydrospiro[chromene-2,1'-cyclobutan]-4-yl]-5-fluoro-2-oxo-N-1,2,4-thiadiazol-5-yl-2,3-dihydro-1,3-benzoxazole-6-sulfonamide;
5-fluoro-3-[(4S)-6-fluoro-3,4-dihydrospiro[chromene-2,1'-cyclobutan]-4-yl]-2-oxo-N-1,2,4-thiadiazol-5-yl-2,3-dihydro-1,3-benzoxazole-6-sulfonamide;
N-(4-methyl-1,3-thiazol-2-yl)-2-oxo-3-(1-phenylethyl)-2,3-dihydro-1,3-benzoxazole-6-sulfonamide;
(R)-2-oxo-3-(1-phenylethyl)-N-(thiazol-2-yl)-2,3-dihydrobenzo[d]oxazole-6-sulfonamide;
2-oxo-3-[(1R)-1-phenylethyl]-N-1,3-thiazol-2-yl-2,3-dihydro-1,3-benzoxazole-6-sulfonamide;
2-oxo-3-(1-phenylethyl)-N-1,3-thiazol-2-yl-2,3-dihydro-1,3-benzoxazole-6-sulfonamide;
methyl (2S)-[2-oxo-6-(1,3-thiazol-2-ylsulfamoyl)-1,3-benzoxazol-3(2H)-yl](phenyl)ethanoate;
(R)-2-oxo-3-(1-(1,2,3,4-tetrahydroisoquinolin-8-yl)ethyl)-N-(thiazol-2-yl)-2,3-dihydrobenzo[d]oxazole-6-sulfonamide;
(R)-5-fluoro-2-oxo-3-(1-phenylethyl)-N-(thiazol-2-yl)-2,3-dihydrobenzo[d]oxazole-6-sulfonamide;
5-fluoro-2-oxo-3-(5,6,7,8-tetrahydroisoquinolin-8-yl)-N-1,3-thiazol-2-yl-2,3-dihydro-1,3-benzoxazole-6-sulfonamide;
5-fluoro-2-oxo-3-(5,6,7,8-tetrahydroquinolin-8-yl)-N-1,3-thiazol-2-yl-2,3-dihydro-1,3-benzoxazole-6-sulfonamide;
3-(2-chloro-5,6,7,8-tetrahydroquinolin-8-yl)-5-fluoro-2-oxo-N-1,3-thiazol-2-yl-2,3-dihydro-1,3-benzoxazole-6-sulfonamide;
3-(3-bromobenzyl)-5-fluoro-2-oxo-N-1,3-thiazol-2-yl-2,3-dihydro-1,3-benzoxazole-6-sulfonamide;
5-fluoro-3-(7-methyl-1,2,3,4-tetrahydronaphthalen-1-yl)-2-oxo-N-1,3-thiazol-2-yl-2,3-dihydro-1,3-benzoxazole-6-sulfonamide;
5-fluoro-3-(5-fluoro-1,2,3,4-tetrahydronaphthalen-1-yl)-2-oxo-N-1,3-thiazol-2-yl-2,3-dihydro-1,3-benzoxazole-6-sulfonamide;
5-fluoro-2-oxo-3-[(1R)-1-phenylethyl]-N-1,3-thiazol-2-yl-2,3-dihydro-1,3-benzoxazole-6-sulfonamide;
3-(5,7-difluoro-1,2,3,4-tetrahydronaphthalen-1-yl)-5-fluoro-2-oxo-N-1,3-thiazol-2-yl-2,3-dihydro-1,3-benzoxazole-6-sulfonamide;
3-(6-bromo-3,4-dihydrospiro[chromene-2,1'-cyclobutan]-4-yl)-5-fluoro-2-oxo-N-1,3-thiazol-2-yl-2,3-dihydro-1,3-benzoxazole-6-sulfonamide;
5-fluoro-3-(6-fluoro-3,4-dihydrospiro[chromene-2,1'-cyclobutan]-4-yl)-2-oxo-N-1,3-thiazol-2-yl-2,3-dihydro-1,3-benzoxazole-6-sulfonamide;
5-fluoro-3-(7-fluoro-1,2,3,4-tetrahydronaphthalen-1-yl)-2-oxo-N-1,3-thiazol-2-yl-2,3-dihydro-1,3-benzoxazole-6-sulfonamide;
3-(5-amino-1,2,3,4-tetrahydronaphthalen-1-yl)-5-fluoro-2-oxo-N-1,3-thiazol-2-yl-2,3-dihydro-1,3-benzoxazole-6-sulfonamide;
3-(7-amino-1,2,3,4-tetrahydronaphthalen-1-yl)-5-fluoro-2-oxo-N-1,3-thiazol-2-yl-2,3-dihydro-1,3-benzoxazole-6-sulfonamide;
5-fluoro-2-oxo-3-[(1R)-1-(1,2,3,4-tetrahydroisoquinolin-8-yl)ethyl]-N-1,3-thiazol-2-yl-2,3-dihydro-1,3-benzoxazole-6-sulfonamide;
3-(7-amino-1,2,3,4-tetrahydronaphthalen-1-yl)-5-fluoro-2-oxo-N-1,3-thiazol-2-yl-2,3-dihydro-1,3-benzoxazole-6-sulfonamide;
5-fluoro-3-[(1S)-1-imidazo[1,5-a]pyridine-5-ylethyl]-2-oxo-N-1,3-thiazol-2-yl-2,3-dihydro-1,3-benzoxazole-6-sulfonamide;
5-fluoro-3-[(1R)-1-imidazo[1,5-a]pyridine-5-ylethyl]-2-oxo-N-1,3-thiazol-2-yl-2,3-dihydro-1,3-benzoxazole-6-sulfonamide;
3-{(1R)-1-[2-(3-aminoprop-1-yn-1-yl)phenyl]ethyl}-5-fluoro-2-oxo-N-1,3-thiazol-2-yl-2,3-dihydro-1,3-benzoxazole-6-sulfonamide;
3-[(1S)-1-(2-azetidin-3-ylphenyl)ethyl]-5-fluoro-2-oxo-N-1,3-thiazol-2-yl-2,3-dihydro-1,3-benzoxazole-6-sulfonamide;
3-[(1R)-1-(2-azetidin-3-ylphenyl)ethyl]-5-fluoro-2-oxo-N-1,3-thiazol-2-yl-2,3-dihydro-1,3-benzoxazole-6-sulfonamide;
5-fluoro-3-{(1R)-1-[2-(3-hydroxyazetidin-3-yl)phenyl]ethyl}-2-oxo-N-1,3-thiazol-2-yl-2,3-dihydro-1,3-benzoxazole-6-sulfonamide;
5-fluoro-3-{(1R)-1-[2-(3-fluoroazetidin-3-yl)phenyl]ethyl}-2-oxo-N-1,3-thiazol-2-yl-2,3-dihydro-1,3-benzoxazole-6-sulfonamide;
5-fluoro-3-{(1R)-1-[3-(3-methyl-1H-pyrazol-4-yl)phenyl]ethyl}-2-oxo-N-1,3-thiazol-2-yl-2,3-dihydro-1,3-benzoxazole-6-sulfonamide;
5-fluoro-3-{(1R)-1-[3-(1-methyl-1H-pyrazol-3-yl)phenyl]ethyl}-2-oxo-N-1,3-thiazol-2-yl-2,3-dihydro-1,3-benzoxazole-6-sulfonamide;
(+/−)-5-fluoro-3-[(4-fluoro-1,2,3,4-tetrahydroisoquinolin-8-yl)methyl]-2-oxo-N-1,3-thiazol-2-yl-2,3-dihydro-1,3-benzoxazole-6-sulfonamide;
(R)-5-fluoro-3-[(4-fluoro-1,2,3,4-tetrahydroisoquinolin-8-yl)methyl]-2-oxo-N-1,3-thiazol-2-yl-2,3-dihydro-1,3-benzoxazole-6-sulfonamide;
(S)-5-fluoro-3-[(4-fluoro-1,2,3,4-tetrahydroisoquinolin-8-yl)methyl]-2-oxo-N-1,3-thiazol-2-yl-2,3-dihydro-1,3-benzoxazole-6-sulfonamide
(S or R)-5-fluoro-3-[(4-fluoro-1,2,3,4-tetrahydroisoquinolin-8-yl)methyl]-2-oxo-N-1,3-thiazol-2-yl-2,3-dihydro-1,3-benzoxazole-6-sulfonamide;
3-((4,4-Difluoro-1,2,3,4-tetrahydroisoquinolin-8-yl)methyl)-5-fluoro-2-oxo-N-(thiazol-2-yl)-2,3-dihydrobenzo[d]oxazole-6-sulfonamide hydrochloride;
5-fluoro-2-oxo-3-{[(1S,2S)-2-phenylcyclopropyl]methyl}-N-1,2,4-thiadiazol-5-yl-2,3-dihydro-1,3-benzoxazole-6-sulfonamide;
(R)-5-fluoro-3-(1-(2-(3-hydroxyazetidin-3-yl)phenyl)ethyl)-2-oxo-N-(1,2,4-thiadiazol-5-yl)-2,3-dihydrobenzo[d]oxazole-6-sulfonamide;
5-fluoro-3-(1-(3-(2-(hydroxymethyl)pyridine-4-yl)phenyl)ethyl)-2-oxo-N-(1,2,4-thiadiazol-5-yl)-2,3-dihydrobenzo[d]oxazole-6-sulfonamide;
(R)-5-fluoro-3-(1-(3-(1-methyl-1H-pyrazol-3-yl)phenyl)ethyl)-2-oxo-N-(1,2,4-thiadiazol-5-yl)-2,3-dihydrobenzo[d]oxazole-6-sulfonamide;
(R)-tert-butyl 1-((2-(1-(6-(N-1,2,4-thiadiazol-5-ylsulfamoyl)-5-fluoro-2-oxobenzo[d]oxazol-3 (2H)-yl)ethyl)phenyl)ethynyl)cyclopropylcarbamate;
2-oxo-N-(1,3,4-thiadiazol-2-yl)-3-((2-(2,2,2-trifluoroethyl)-1,2,3,4-tetrahydroisoquinolin-8-yl)methyl)-2,3-dihydrobenzo[d]oxazole-6-sulfonamide;
5-fluoro-3-(2-iodobenzyl)-2-oxo-N-(1,2,4-thiadiazol-5-yl)-2,3-dihydrobenzo[d]oxazole-6-sulfonamide;
(S)-3-(1-(2-iodophenyl)ethyl)-2-oxo-N-(1,2,4-thiadiazol-5-yl)-2,3-dihydrobenzo[d]oxazole-6-sulfonamide;

5-fluoro-2-oxo-3-(1-(pyridine-2-yl)ethyl)-N-(1,2,4-thia-diazol-5-yl)-2,3-dihydrobenzo[d]oxazole-6-sulfonamide;

(R)-tert-butyl 8-(1-(6-(N-1,3,4-thiadiazol-2-ylsulfamoyl)-2-oxobenzo[d]oxazol-3(2H)-yl)ethyl)-3,4-dihydroisoquinoline-2(1H)-carboxylate;

3-(7-amino-1,2,3,4-tetrahydronaphthalen-1-yl)-5-fluoro-2-oxo-N-(thiazol-2-yl)-2,3-dihydrobenzo[d]oxazole-6-sulfonamide;

(R)-2-oxo-3-(1-(1,2,3,4-tetrahydroisoquinolin-8-yl)ethyl)-N-(thiazol-2-yl)-2,3-dihydrobenzo[d]oxazole-6-sulfonamide;

(R)-5-(1-methyl-1H-pyrazol-5-yl)-2-oxo-3-(1-phenylethyl)-N-(1,2,4-thiadiazol-5-yl)-2,3-dihydrobenzo[d]oxazole-6-sulfonamide; or 3-(5-amino-1,2,3,4-tetrahydronaphthalen-1-yl)-5-fluoro-2-oxo-N-(thiazol-2-yl)-2,3-dihydrobenzo[d]oxazole-6-sulfonamide.

15. A compound of Formula B, or a salt thereof:

Formula B wherein:

G is —HC= or —N=;

$R^1$ and $R^2$ are independently: (i) —H; (ii) $C_{1-8}$ alkyl, wherein the alkyl moiety is optionally substituted with hydroxyl, halogen, —(C=O)—O—($C_{1-6}$ alkyl), or $C_{3-6}$ cycloalkyl moiety; (iii) $C_{1-4}$ alkenyl; or (iv) a five or six member heteroaryl moiety;

$R^3$ is —H, $C_{1-6}$ alkyl, $C_{1-6}$ alkoxy, —CN or halogen;

$R^4$ and $R^5$ are independently: (i) $C_{1-4}$ alkyl, optionally substituted by one or more: (a) halogen; (b) —$NH_2$, or (c) —$NR'^a_2$, wherein $R'^a$ is independently for each occurrence: linear or cyclic —$(Y^a)_x$—alkyl, wherein, x=0, 1, and if present (x=1), $Y^a$ is —$SO_2$, —C(O)—, or —(C=O)O—, and the alkyl portion of the moiety is $C_{1-6}$-linear alkyl or $C_{3-6}$-cycloalkyl; (ii) $C_{1-4}$ alkenyl, optionally substituted by one or more: (a) halogen; (b) —$NH_2$, or (c) —$NR'^a_2$, wherein $R'^a$ is independently for each occurrence: linear or cyclic —$(Y^a)_x$-alkyl, wherein, x=0, 1, and if present (x=1), $Y^a$ is —$SO_2$, —C(O)—, or —(C=O)O—; (iii) a piperidine moiety which is bonded to the aryl ring through any of the atoms of the piperidine ring; (iv) a dihydropyridine, bonded through any of the atoms of the pyridine ring; (v) a tetrahydropyridine moiety bonded through any of the atoms of the pyridine ring; (vi) a pyridine moiety bonded to the aryl ring through any of the atoms of the pyridine ring, wherein the pyridine is optionally substituted on any other available ring atom with a heterocycle or a —$C_{1-3}$-alkyl-N-heterocycle; (vii) an aryl moiety which is optionally substituted with a heterocycle moiety bonded to any available carbon atom of the aryl ring through any atom of the heterocycle ring; (viii) a tetrahydroquinoline moiety bonded through any of the carbon atoms of the aromatic ring optionally substituted on any available carbon atom with halogen, —CN, $C_{1-6}$-alkyl or $C_{1-6}$-alkoxy; (ix) a tetrahydroisoquinoline moiety bonded through any of the carbon atoms of the aromatic ring optionally substituted on any available carbon atom with halogen, —CN, $C_{1-6}$-alkyl or $C_{1-6}$-alkoxy and where the N-moiety in said isoquinoline is optionally substituted with —$SO_2$—$C_{1-6}$-alkyl; (x) an azabicyclo-moiety of the structure:

(xi) $C_{2-4}$-alkynyl optionally substituted by alkyl, halogen, or amino; or (xii) heteroaryl; or $R^4$ and $R^5$ together with the aryl ring to which they are bonded form a 10 to 12-member heteroaryl-aryl or heteroalkyl-aryl bicyclic moiety, in some embodiments wherein $R^4$ and $R^5$ together with the aryl moiety to which they are bonded form a heteroalkyl-aryl moiety, preferably they form a tetrahydroquinoline or tetrahydroisoquinoline moiety; and $R^6$, $R^7$, and $R^8$ are independently selected from hydrogen, CN, alkyl, alkoxy or halogen.

16. A pharmaceutical composition comprising a compound of claim 14, or a salt thereof, and at least one excipient.

17. A method of treating a neuropathic pain disorder comprising administering to a patient in need thereof a therapeutically effective amount of a pharmaceutical composition of claim 16.

18. A compound according to claim 14 for use in therapy.

19. A compound according to claim 14 for treating neuropathic pain disorders.

20. A pharmaceutical composition comprising a compound of claim 13 or a salt thereof, and at least one excipient.

21. A pharmaceutical composition comprising a compound of claim 12 or a salt thereof, and at least one excipient.

22. A compound of claim 2 wherein Het is:

(i) a moiety of Formula AD1-a:

Formula AD1-a or (ii) a moiety of Formula AD1-b:

Formula AD1-b

* * * * *